(12) United States Patent
Marx et al.

(10) Patent No.: US 10,233,152 B2
(45) Date of Patent: *Mar. 19, 2019

(54) LSD1 INHIBITORS

(71) Applicant: Mirati Therapeutics, Inc., San Diego, CA (US)

(72) Inventors: Matthew Arnold Marx, San Diego, CA (US); Arkadii Vaisburg, Kirkland (CA); James Gail Christensen, San Diego, CA (US); Robert Anthony Galemmo, Jr., San Francisco, CA (US)

(73) Assignee: MIRATI THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/725,949

(22) Filed: Oct. 5, 2017

(65) Prior Publication Data
US 2018/0127369 A1 May 10, 2018

Related U.S. Application Data

(63) Continuation of application No. 15/343,008, filed on Nov. 3, 2016, now Pat. No. 9,809,541.

(60) Provisional application No. 62/295,369, filed on Feb. 15, 2016, provisional application No. 62/272,082, filed on Dec. 29, 2015.

(51) Int. Cl.
| C07D 211/58 | (2006.01) |
| C07D 205/04 | (2006.01) |
| C07D 211/76 | (2006.01) |
| C07D 211/88 | (2006.01) |
| C07D 221/22 | (2006.01) |
| C07D 401/12 | (2006.01) |
| C07D 413/12 | (2006.01) |
| C07D 413/14 | (2006.01) |
| C07D 417/12 | (2006.01) |
| C07D 265/10 | (2006.01) |
| C07D 213/64 | (2006.01) |

(52) U.S. Cl.
CPC .......... *C07D 211/58* (2013.01); *C07D 205/04* (2013.01); *C07D 211/76* (2013.01); *C07D 211/88* (2013.01); *C07D 213/64* (2013.01); *C07D 221/22* (2013.01); *C07D 265/10* (2013.01); *C07D 401/12* (2013.01); *C07D 413/12* (2013.01); *C07D 413/14* (2013.01); *C07D 417/12* (2013.01)

(58) Field of Classification Search
CPC .................................................. C07D 211/58
See application file for complete search history.

(56) References Cited

U.S. PATENT DOCUMENTS

| 7,244,751 B2 | 7/2007 | Lu et al. |
| 9,149,447 B2 | 10/2015 | Munoz et al. |
| 9,255,097 B2 | 2/2016 | Chen et al. |
| 9,278,931 B2 | 3/2016 | Tomita et al. |
| 9,346,840 B2 | 5/2016 | Johnson et al. |
| 2012/0004262 A1 | 1/2012 | Guibourt et al. |
| 2013/0090386 A1 | 4/2013 | Ortega Munoz et al. |
| 2013/0231342 A1 | 9/2013 | Ortega Munoz et al. |
| 2013/0289076 A1 | 10/2013 | Laria et al. |
| 2013/0303545 A1 | 11/2013 | Maes et al. |
| 2014/0213657 A1 | 7/2014 | Ortega Munoz et al. |
| 2014/0228405 A1 | 8/2014 | Tomita et al. |
| 2015/0025054 A1 | 1/2015 | Ortega Munoz et al. |
| 2015/0119396 A9 | 4/2015 | Ortega Munoz et al. |
| 2015/0191427 A1 | 7/2015 | Holson et al. |
| 2015/0225375 A1 | 8/2015 | Wu et al. |
| 2015/0225379 A1 | 8/2015 | Wu et al. |
| 2015/0225394 A1 | 8/2015 | Wu et al. |
| 2015/0225401 A1 | 8/2015 | Wu et al. |
| 2015/0266881 A1 | 9/2015 | Tomita et al. |
| 2015/0291577 A1 | 10/2015 | Matsumoto et al. |
| 2015/0315187 A1 | 11/2015 | Chen et al. |
| 2016/0039748 A1 | 2/2016 | Suzuki et al. |
| 2016/0108046 A1 | 4/2016 | Chen et al. |
| 2016/0120862 A1 | 5/2016 | Zhang |
| 2016/0152595 A1 | 6/2016 | Chen et al. |

FOREIGN PATENT DOCUMENTS

| WO | 2010/043721 A1 | 4/2010 |
| WO | 2011/035941 A1 | 3/2011 |
| WO | 2011/042217 A1 | 4/2011 |
| WO | 2012/013728 A1 | 2/2012 |
| WO | 2012/107499 A1 | 8/2012 |
| WO | 2012/135113 A2 | 10/2012 |
| WO | 2013/057320 A1 | 4/2013 |
| WO | 2014/086790 A1 | 6/2014 |
| WO | 2014/164867 A1 | 10/2014 |
| WO | 2015/089192 A1 | 6/2015 |
| WO | 2015/123408 A1 | 8/2015 |
| WO | 2015/123437 A1 | 8/2015 |

(Continued)

OTHER PUBLICATIONS

Singh et al., "Preclinical activity of combined HDAC and KDM1A inhibition in glioblastoma," Neuro-Oncology, 2015, 11 pages.

(Continued)

Primary Examiner — Shawquia Jackson
(74) Attorney, Agent, or Firm — McDonnell Boehnen Hulbert & Berghoff LLP

(57) ABSTRACT

The present invention relates to compounds that inhibit LSD1 activity. In particular, the present invention relates to compounds, pharmaceutical compositions and methods of use, such as methods of treating cancer using the compounds and pharmaceutical compositions of the present invention.

23 Claims, No Drawings

(56) References Cited

FOREIGN PATENT DOCUMENTS

| WO | 2016/123387 A1 | 8/2016 |
|---|---|---|
| WO | 2016/130952 A1 | 8/2016 |
| WO | 2016/161282 A1 | 10/2016 |
| WO | 2017/109061 A1 | 6/2017 |

OTHER PUBLICATIONS

Stewart et al., "Altering the course of Small cell lung cancer Targeting cancer stem cells via LSD1 inhibition," Cancer Cell, Jul. 13, 2015, pp. 4-6, vol. 28.
Sugino et al., A novel LSD1 inhibitor NCD38 ameliorates MDS-related leukemia with complex karyotype by attenuating leukemia programs via activating super-enhancers, Leukemia accepted article preview, Feb. 17, 2017, 53 pages, doi: 10.1038/leu.2017.59.
Sun et al., "LncRNA HOXA11-AS promotes proliferation and invasion of gastric cancer by scaffolding the chromatin modification factors PRC2, LSD1 and DNMT1," Cancer Research, 2016, 37 pages.
Takagi et al., "LSD1 inhibitor T-3775440 inhibits SCLC cell proliferation by disrupting LDS1 interactions with SNAG domain proteins INSM1 and GFI1B," Cancer Research, 2017, 36 pages.
Thambyrajah et al., "GFI1 proteins orchestrate the emergence of haematopoietic stem cells through recruitment of LSD1," Nature Cell Biology, 2015, pp. 21-34, vol. 18, No. 1.
Valente et al., "Pure disastereomers of a tranylcypromine-based LSD1 inhibitor enzyme selectivity and in-cell studies," ACS Med Chem,, 2014, pp. 173-177, vol. 6.
Velinder et al., "GFI1 functions in transcriptional control and cell fate determination require SNAG domain methylation to recruit LSD1," Biochemical Journal, 2016, 40 pages.
Wang et al., Design, synthesis and biological evaluation of [1,2,4]triazolo[1,5-a]pyrimidines as potent lysine specific demethylase 1 (LSD1/KDM1A) inhibitors, European Journal of Medicinal Chemistry, 2016, 29 pages, doi: 10.1016/j.ejmech.2016.10.021.
Wang et al., "Inhibition of LSD1 by pargyline inhibited process of EMT and delayed progression of prostate cancer in vivo," BBRC, 2015, pp. 310-315, vol. 467.
Wang et al., "Relationship between LSD1 expression and E-cadherin expression in prostate cancer," Int Urol Nephrol., 2015, pp. 485-490, vol. 47.
Wang et al., The histone demethylase LSD1 is a novel oncogene and therapeutic target in oral cancer, Cancer Letters, 2016, pp. 12-21, vol. 374.
Whyte et al., "Enhancer decommissioning by LSD1 during embryonic stem cell differentiation," Nature, 2012, pp. 221-225, vol. 482.
Wissmann et al., "Cooperative demethylation by JMJD2C and LSD1 promotes androgen receptor-dependent gene expression," Nature Cell Biology, 2007, 12 pages, vol. 9, No. 3.
Zhang et al., "Pluripotent stem cell protien Sox2 confers sensitivity to LSD1 inhibition in cancer cells," Cell, 2013, pp. 445-457, vol. 5.
Zhou et al., "Identification of novel selective LSD1 inhibitors using a pharmacophore based virtual screening combined with docking," Chemical Biology and Drug Design, 2014, 29 pages.
Zhou et al., "Synthesis and biological evaluation of novel (E)-N'-(2,3-dihydro-1H-inden-1-ylidene) benzohydrazides as potent LSD1 inhibitors," Bioorganic Medicinal Chemistry Letters, 2015, 2016, pp. 4552-4557, vol. 26.
Pieroni et al., "Further insights into the SAR of α-substituted cyclopropylamine derivatives as inhibitors of histone demethylase KDM1A," European Journal of Medicinal Chemistry, 2015, pp. 377-386, vol. 92.
Pilotto et al., "Interplay among nucleosomal DNA, histone tails, and corepressor CoREST underlies LSD1-mediated H3 demethylation," PNAS, 2015, pp. 2752-2757, vol. 112, No. 9.
Pilotto et al., "LSD1 KDM1A mutations associated to a newly described form of intellectual disability impair demethylase activity and binding to transcription factors," HMG, 2016, 33 pages.
Prusevich et al., "A Selective Phenelzine Analogue Inhibior of Histone Demethylase LSD1," ACS Chemical Biology and Supplementary Information, 2014, 115 pages.
Przespoleswki et al., "Inhibitors of LSD1 as a potential therapy for acute myeloid leukemia," Expert Opinion on Investigational Drugs, 2016, pp. 771-780, vol. 25, No. 7.
Rudolph et al., "Lysine-specific histone demethylase LSD1 and the dynamic control of chromatin," Biological Chemistry, 2013, pp. 1019-1028, vol. 394, No. 8.
Sartori et al., "Thieno[3,2-b]pyrrole-5-carboxamides as New Reversible Inhibitors of Histone Lysine Demethylase KDM1A-LSD1 Part 1 High Throughput Screening and Preliminary Exploration," JMC, 2017, 80 pages.
Sharma et al., "Growth Inhibition of SCLC Cell Lines by LSD1 Inhibitors is Associated with Modulation of Neuroendocrine and Mesenchymal Pathways," Keystone Conference Poster, 2016, 1 page.
Shin et al., "Molecular Toggle Switch of Histone Demethylase LSD1," Molecular Cell, 2015, 2 pages.
Shixian et al., "Lysine-specific demethylase 1 promotes tumorigenesis and predicts prognosis in gallbladder cancer," Oncotarget, 2015, 12 pages.
Golub et al., "Molecular Classification of Cancer: Class Discovery and Class Prediction by Gene Expression Monitoring", Science, 1999, vol. 286, 531-537.
Peeyush et al., "Role of nitric oxide in tumor progression: Lessons from experimental tumors", Cancer and Metastasis, 1998, 17(1), 91-106.
Cancer [online], (retrieved on Jul. 6, 2007), Retrieved from the internet, URL http://www.nlm.nih.gov./medlineplus/cancer.html, 10 pages.
Binda et al., "Biochemical, Structural and Biological Evaluation of Tranylcypromine Derivatives as Inhibitors of Histone Demethylases LSD1 and LSD2," J. Am. Chem. Soc., 2010, 132, 6827-6833.
Khan et al., "Design, synthesis and biological activity of N-alkylated analogue of NCL1, a selective inhibitor of lysine-specific demethylase 1," Med. Chem. Commun., Royal Society of Chemistry, 2014, 6 pages.
Han et al., "Novel Tranylcypromine/Hydroxylcinnamic Acid Hybrids as Lysine-Specific Demethylase 1 Inhibitors with Potent Antitumor Activity," Chem. Pharm. Bull. 63, 882-889 (2015).
Metzger et al., "LSD1 demethylates repressive histone marks to promote androgen-receptor-dependent transcription," Nature Letters, vol. 437, Sep. 15, 2005, pp. 436-439.
Mimasu et al., Structurally Designed trans-2-Phenylcyclopropylamine Derivatives Potently Inhibit Histone Demethylase LSD1/KDM1, Biochemistry, 2010, 49, 6494-6503.
Mohammad et al., "A DNA Hypomethylation Signature Predicts Antitumor Activity of LSD1 Inhibitors in SCLC," CellPress, Cancer Cell 28, Jul. 13, 2015, 47 pages.
Shi et al., "Histone Demethylation Mediated by the Nuclear Amine Oxidase Homolog LSD1," Cell, vol. 119, 941-953, Dec. 29, 2004.
Suzuki et al., "Lysine Demethylases Inhibitors," J. Med. Chem., 2011, 54, 8236-8250.
Vianello et al., "Discovery of a Novel Inhibitor of Histone Lysine-Specific Demethylase 1A (KDM1A/LSD1) as Orally Active Antitumor Agent," J. Med. Chem. Article, Jul. 31, 2015, 17 pages.
Vianello et al., "Discovery of a Novel Inhibitor of Histone Lysine-Specific Demethylase 1A (KDM1A/LSD1) as Orally Active Antitumor Agent," J. Med. Chem. Article, Dec. 24, 2015, 66 pages.
Adamo et al., "LSD1 regulates the balance between self-renewal and differentiation in human embryonic stem cells," Nature Cell Biology, Jun. 2011, 30 pages.
Amente et al., "LSD1-mediated demethylation of histone H3 lysine 4 triggers Myc-induced transcription," Oncogene, 2010, pp. 3691-3702, vol. 29.
Bennesch et al., "LSD1 engages a corepressor complex for the activation of the estrogen receptor α by estrogen and cAMP," Nucleic Acids Research, 2016, pp. 1-16.
Burg et al., "Lysine-Specific Demethylase 1A (KDM1A/LSD1): Product Recognition and Kinetic Analysis of Full-Length Histones," Biochemistry, 2016, pp. 1652-1662.

(56) References Cited

OTHER PUBLICATIONS

Cao et al., "Functinal interaction of histone deacetylase 5 (HDAC5) and lysine-specific demethylase 1 (LSD1) promotes breast cancer progression," Oncogene, 2016, pp. 1-13.

Chen et al., "Effects of cisplatin on the LSD1-mediated invasion and metastasis of prostate cancer cells," Molecular Medicine Reports, 2016, pp. 2511-2517, vol. 14.

Crunkhorn, Sarah, Nature Reviews Drug Discovery, 2015, p. 602, vol. 14 Published online Sep. 1, 2015.

Derr et al., "High nuclear expression levels of histone-modifying enzymes LSD1, HDAC2 and SIRT1 in tumor cells correlate with decreased survival and increased relapse in breast cancer patients," BMC Cancer, 2014, 20 pages.

Ding et al., "LSD1-mediated epigenetic modification colon cancer," British Journal of Cancer, 2013, pp. 994-1003, vol. 109.

Feng et al., "Phosphorylation of LSD1 at Ser112 is crucial for its function in induction of EMT and metastasis in breast cancer," Breast Cancer Res Treat, 2016, 14 pages.

Fiskus et al., "Corrigendum—Highly effective combination of LSD1 (KDM1A) antagonist and pan-histone deacetylase inhibitor against human AML cells," Leukemia, 2017, 1 page.

Fiskus et al., "Highly effective combination of LSD1 (KDM1A) antagonist and pan-histone deacetylase inhibitor against human AML cells," Leukemia, 2014, pp. 1-10.

Haydn et al., "Concomitant epigenetic targeting of LSD1 and HDAC synergistically induces mitochondrial apoptosis in rhabdomyosarcoma cells," Cell Death and Disease, 2017, 12 pages, vol. 8.

Hayward, D. and Cole, P.A., "LSD1 Histone Demethylase Assays and Inhibition," Methods in Enzymology, 2016, pp. 261-278.

Huang et al., "Lysine-Specific Demethylase 1 (LSD1/KDM1A) Contributes to Colorectal Tumorigenesis via Activation of the Wnt/B-Catenin Pathway by Down-Regulating Dickkopf-1 (DKK1)," PLoS ONE, Jul. 2013, 12 pages, vol. 8, No. 7.

Ishikawa et al., "A novel LSD1 inhibitor T-3775440 disrupts GFI1B-containing complex leading to transdifferentiation and impaired growth of AML cells," Cancer Research; 2016, 49 pages.

Janzer et al, "Lysine-specific demethylase 1 (LSD1) and histone deacetylase 1 (HDAC1) synergistically repress proinflammatory cytokines classical complement pathway components," BBRC, 2012, pp. 665-670, vol. 421.

Jin et al., "LSD1 collaborates with EZH2 to regulate expression of interferon-stimulated genes," Biomedicine & Pharmacotherapy, 2017, pp. 728-737, vol. 88.

Jin et al., "LSD1 knockdown reveals novel histone lysine methylation in human breast cancer MCF-7 cells," Biomedicine and Pharmacotherapy, 2017, pp. 896-904, vol. 92.

Ketscher et al., "LSD1 controls metastasis of androgen-independent prostate cancer cells through PXN and LPAR6, Oncogenesis, 2014, 9 pages, vol. 3.

Kim et al., "LSD1 is essential for oocyte meiotic progression by regulating CDC25B expression in mice," Nature Communications, 2015, pp. 1-12.

Konovalov et al., "Analysis of the levels of lysine-specific demethylase 1 (LSD1) mRNA in human ovarian tumors and the effects of chemical LSD1 inhibitors in ovarian cancer cell lines," Journal of Ovarian Research, 2013, pp. 1-15, vol. 6, No. 1.

Kozono et al., "Dynamic epigenetic regulation of glioblastoma tumorigenicity through LSD1 modulation of MYC expression," PNAS, 2015, 22 pages.

Laurent et al., "Expression, Purification, and biochemical analysis of the LSD1-KDM1A histone demethylase," Methods in Enzymology, 2016, pp. 241-259, vol. 573.

Li et al., "Discovery of [1,2,3]Triazolo[4,5-d]pyrimidine Derivatives as Novel LSD1 Inhibitors," ACS Medicinal Chemistry Letters, 2017, pp. 384-389, vol. 8.

Li et al., "Upregulated long non-coding RNA AGAP2-AS1 represses LATS2 and KLF2 expression through interacting with EZH2 and LSD1 in non-small-cell lung cancer cells," Cell Death and Disease, 2016, 11 pages, vol. 7.

Li et al., "HBXIP and LSD1 scaffolded by lncRNA Hotair mediates transcriptional activation by c-Myc," Cancer Research, 2015, 40 pages.

Lim et al., "Lysine-specific demethylase 1 (LSD1) is highly expressed in ER-negative breast cancers and a biomarker predicting aggressive biology," Carcinogenesis, 2010, pp. 512-520, vol. 31, No. 3.

Luo et al., "MOF Acetylates the Histone Demethylase LSD1 to Suppress Spithelial-to-Mesenchymal Transition," Cell Reports, Jun. 21, 2016, pp. 1-14, vol. 15.

Lv et al., "Over-Expression of LSD1 Promotes Proliferation, Migration and Invasion in Non-Small Cell Lung Cancer," PLoS ONE, Apr. 2012, pp. 1-8, vol. 7, No. 4.

Lynch et al., "CD86 expression as a surogate cellular biomarker for pharmacological inhibition of the histone demethylase lysine-specific demthylase 1," Analytical Biochemistry, 2013, pp. 104-106, vol. 442.

Lynch et al., "LSD1 inhibition a therapeutic strategy in cancer," Expert Opinion on Therapeutic Targets, 2012, pp. 1239-1249.

Ma et al., "Design, synthesis and structure-activity relationship of novel LSD1 inhibitors based on pyrimidine-thiourea hybrids as potent, orally active antitumor agents," J Med Chem., 2015, 36 pages.

Maiques-Diaz et al., "LSD1 biologic roles and therapeutic targeting," Epigenomics, 2016, 14 pages.

Marabelli et al., "The growing structural and functional complexity of the LSD1-KDM1A histone demethylase," Structural Biology, 2016, pp. 135-144, vol. 41.

Marango et al., "The MMSET protein is a histone methyltransferase with characteristics of a transcriptional corepressor," Blood, Mar. 15, 2008, pp. 3145-3154, vol. 111, No. 6.

Mohammad et al., "Antitumor activity of LSD1 inhibitors in lung cancer," Molecular and Cellular Oncology, 2016, 4 pages, vol. 3, No. 2.

Mould et al., "Reversible inhibitors of LSD1 as therapeutics agents in acute myeloid leukemia clinical significance and progress to date," Medicinal Research Reviews, 2015, pp. 586-618.

Nalawansha et al., "LSD1 Substrate Binding and Gene Expression Are Affected by HDAC1-Mediated Deacetylation," ACS Chemical Biology; 2016, pp. A-K.

Niebel et al., "Lysine-specific demethylase 1 (LSD1) in hematopoietic and lymphoid neoplasms," Blood, 2014, pp. 151-152, vol. 124, No. 1.

LSD1 INHIBITORS

CROSS REFERENCE

This application is a continuation of U.S. patent application Ser. No. 15/343,008, filed Nov. 3, 2016, which claims the benefit of U.S. Provisional Application No. 62/272,082, filed Dec. 29, 2015, and U.S. Provisional Application No. 62/295,369, filed Feb. 15, 2016, the entire content of each application is hereby incorporated by reference in their entirety.

FIELD OF THE INVENTION

The present invention relates to compounds that inhibit lysine-specific demethylase one (LSD1). In particular, the present invention relates to compounds that irreversibly inhibit the activity of LSD1, pharmaceutical compositions comprising the compounds and methods of use therefor.

BACKGROUND OF THE INVENTION

Lysine-specific demethylase one ("LSD1"), also known as KDM1A, is a flavin-dependent lysine demethylase that removes methyl groups from mono- and dimethylated lysine4 of the histone H3 protein through flavin adenine dinucleotide (FAD) dependent enzymatic oxidation (e.g., see Shi et al., (2004) Cell 119:941-953). In addition, LSD1 demethylates mono- and dimethylation of histone H3 lysine9 in prostate cancer cell lines and is essential for transcriptional regulation mediated by the androgen receptor (Metzger et al., Nature (2005) 437:436-439). LSD1 also demethylates a number of cellular proteins, such as p53, E2F1 and STAT3 and regulates their function.

LSD1 has been reported to be overexpressed in a wide variety of cancers and tissues, including lung cancer, bladder cancer, neuroblastoma, prostate cancer and breast cancer. LSD1 is thought to play a role in cellular proliferation and cancer cell growth by modulating prosurvival gene expression and p53 transcriptional activity (e.g., see Suzuki and Miyata (2011) J. Med. Chem. 54:8236-8250). LSD1 also plays a role in regulating viral gene transcription, e.g., Herpes Simplex Virus (HSV), by demethylating histone H3 lysine9 required for viral gene expression in the host.

With increasing evidence that LSD1 plays a critical role in a diverse set of cancers and diseases, a variety of LSD1 inhibitors, including irreversible LSD1 inhibitors, have been reported and are in clinical development. Irreversible cyclopropyl amine-containing inhibitors, e.g., reviewed in Suzuki and Miyata, ibid, have been shown to be potent inhibitors of the LSD1 enzyme; however, such compounds tend to lack robust cellular potency, have poor metabolic stability and high clearance in vivo.

SUMMARY OF THE INVENTION

The present inventors recognized a need to develop new LSD1 inhibitors that demonstrate improved cellular potency, efficacy, stability and safety. The compounds and compositions of the present invention advantageously overcome one or more of these shortcomings by providing potent, selective and orally active LSD1 inhibitors.

In one aspect of the invention, compounds are provided that irreversibly inhibit LSD1 activity. In certain embodiments, the compounds are represented by formula (I):

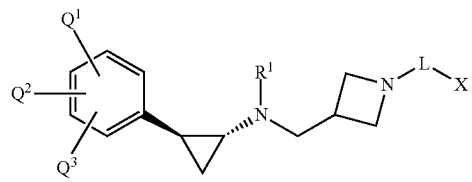

Formula (I)

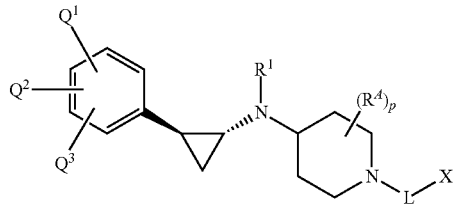

Formula (II)

or a pharmaceutically acceptable salt thereof, $R^1$ is hydrogen, $C_1$-$C_4$ alkyl or $C_1$-$C_4$ acyl;

L is —$(CH_2)_s$—$CR^2R^3$—$(CH_2)_m$—;

$R^2$ and $R^3$ are each independently hydrogen, $C_1$-$C_4$ alkyl, —$OR^4$ or aralkyl;

each $R^4$ is independently hydrogen or $C_1$-$C_4$ alkyl;

X is —W—$R^5$ or Y—$R^6$;

W is —$NR^4$— or —O—;

Y is —C(O)—, —S—, —SO—, —$SO_2$—, —$NR^4SO_2$—, —$SO_2NR^4$— and —$NR^4C(O)$—;

$R^5$ is selected from the group consisting of acyl, $C_1$-$C_4$alkyl, cycloalkyl, heterocyclyl, aryl or heteroaryl, wherein each of said cycloalkyl, heterocyclyl, aryl or heteroaryl is optionally independently substituted with one or more $R^8$;

$R^6$ is $C_1$-$C_6$ alkyl, —$NR^4R^7$ or heterocyclyl optionally independently substituted on one or more carbon atoms with $C_1$-$C_6$ alkyl, halogen, cyano, or haloalkyl, or optionally independently substituted on one or more nitrogen atoms with —C(O)$C_1$-$C_6$ alkyl; —C(O)O$C_1$-$C_6$ alkyl; —C(O)$NR^4C_1$-$C_6$ alkyl, or —S(O)$_2NR^4C_1$-$C_6$ alkyl;

$R^7$ is hydroxyl, alkoxy, —$SO_2C_1$-$C_6$alkyl; —$SO_2$cycloalkyl, or —$SO_2$aryl, wherein the cycloalkyl and aryl of each of the —$SO_2$cycloalkyl and —$SO_2$aryl is optionally independently substituted with one or more $R^8$;

each $R^8$ is independently halogen, hydroxyl, amino, cyano, $C_1$-$C_6$ alkyl, $C_2$-$C_6$ alkenyl, $C_2$-$C_6$ alkynyl, haloalkyl, alkoxy, alkylamino, dialkylamino, cycloalkyl, aryl, heteroaryl, heterocyclyl, aralkyl, heteroarylalkyl, —$(CH_2)_n COOR^4$, —$(CH_2)_n C(O)NR^4OC_1$-$C_6$alkyl, —$(CH_2)_n C(O)NR^4SO_2C_1$-$C_6$alkyl, —$(CH_2)_n C(O)NR^4SO_2$cycloalkyl, —$(CH_2)_n C(O)NR^4SO_2$aryl, —$C_2$-$C_6$ alkenylC(O)$OR^4$, —$C_2$-$C_6$ alkenylC(O)$NR^4SO_2C_1$-$C_4$alkyl, or —$C_2$-$C_6$ alkenylC(O)$NR^4SO_2$aryl, wherein each of the cycloalkyl, aryl, heteroaryl, and heterocyclyl is optionally independently substituted with one or more $C_1$-$C_3$ alkyl.

m is 0 or 1;

s is 0 or 1;

each n is 0, 1, or 2;

each p is 0, 1 or 2;

each $R^4$ is independently oxo or $C_1$-$C_3$ alkyl, or two $R^4$ groups on different ring atoms together form a $C_1$-$C_3$ bridge in which one of the bridge carbons is optionally replaced with —NH—;

each $Q^1$, $Q^2$ and $Q^3$ is independently hydrogen, halogen, haloalkyl, $C_1$-$C_4$-alkyl, or $C_1$-$C_4$-alkoxy.

In another aspect of the invention, pharmaceutical compositions are provided comprising a therapeutically effective amount of a compound of formula (I) or formula (II) and a pharmaceutically acceptable excipient.

In yet another aspect of the invention, methods for inhibiting LSD1 activity in a cell comprising contacting the cell with a compound of formula (I) or formula (II) are provided. Also provided are methods for treating cancer in a patient comprising administering a therapeutically effective amount of a compound of formula (I) or formula (II) or pharmaceutical composition thereof to a patient in need thereof.

DETAILED DESCRIPTION OF THE INVENTION

The present invention relates to LSD1 inhibitors. In particular, the present invention relates to compounds that irreversibly inhibit the activity of LSD1, pharmaceutical compositions comprising a therapeutically effective amount of the compounds, and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference to the extent they are consistent with the present disclosure. Terms and ranges have their generally defined definition unless expressly defined otherwise.

For simplicity, chemical moieties are defined and referred to throughout primarily as univalent chemical moieties (e.g., alkyl, aryl, etc.). Nevertheless, such terms may also be used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for 0, and 2, 4, or 6 for S, depending on the oxidation state of the S).

As used herein, "LSD1" refers to a mammalian lysine-specific demethylase enzyme ("LSD1"), which removes methyl groups from mono- and dimethylated lysine4 and lysine9 of the histone H3 protein.

As used herein, an "LSD1 inhibitor" refers to compounds of the present invention that are represented by formulae (I) or (II) as described herein. These compounds are capable of negatively modulating or inhibiting all or a portion of the enzymatic activity of LSD1. The LSD1 inhibitors of the present invention irreversibly inhibit LSD1 activity by forming a covalent adduct with the flavin ring of FAD in the active site of LSD1 following one electron oxidation and cyclopropyl ring opening.

The term "amino" refers to —$NH_2$.

The term "alkyl" as employed herein refers to straight and branched chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms. As such, "alkynyl" encompasses $C_2$, $C_3$, $C_4$, $C_5$, $C_6$, $C_7$, $C_8$, $C_9$, $C_{10}$, $C_{11}$ and $C_{12}$ groups. Examples alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Examples of alkylene groups include, without limitation, methylene, ethylene, propylene, and butylene. Exemplary alkenylene groups include, without limitation, ethenylene, propenylene, and butenylene. Exemplary alkynylene groups include, without limitation, ethynylene, propynylene, and butynylene.

The term "alkoxy" refers to —$OC_1$-$C_6$ alkyl.
The term "alkylthio" refers to —$SC_1$-$C_6$alkyl.
The term "alkylamino" refers to —$NR^4C_1$-$C_6$alkyl.
The term "alkylsulfonyl" refers to —$SO_2C_1$-$C_6$alkyl.

The term "cycloalkyl" as employed herein is a saturated and partially unsaturated cyclic hydrocarbon group having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are independently replaced O, S, or $NR^4$ wherein $R^4$ is as defined herein.

An "aryl" group is a $C_6$-$C_{14}$ aromatic moiety comprising one to three aromatic rings. As such, "aryl" includes $C_6$, $C_{10}$, $C_{13}$, and $C_{14}$ cyclic hydrocarbon groups. An exemplary the aryl group is a $C_6$-$C_{10}$ aryl group. Particular aryl groups include, without limitation, phenyl, naphthyl, anthracenyl, and fluorenyl.

An "aralkyl" or "arylalkyl" group comprises an aryl group covalently linked to an alkyl group wherein the moiety is linked to another group via the alkyl moiety. An exemplary aralkyl group is —($C_1$-$C_6$)alkyl($C_6$-$C_{10}$)aryl, including, without limitation, benzyl, phenethyl, and naphthylmethyl.

A "heterocyclyl" or "heterocyclic" group is a mono- or bicyclic (fused or spiro) ring structure having from 3 to 12 atoms, (3, 4, 5, 6, 7, 8, 9, 10, 11 or 12 atoms), for example 4 to 8 atoms, wherein one or more ring atoms are independently —C(O)—, $NR^4$, O, or S, and the remainder of the ring atoms are quaternary or carbonyl carbons. Examples of heterocyclic groups include, without limitation, epoxy, azetidinyl, aziridinyl, tetrahydrofuranyl, tetrahydropyranyl, pyrrolidinyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidonyl, thiomorpholinyl, dimethyl-morpholinyl, and morpholinyl. Specifically excluded from the scope of this term are compounds having adjacent ring O and/or S atoms.

The term "heterocyclylalkyl" refers to a heterocyclyl group as defined herein linked to the remaining portion of the molecule via an alkyl linker.

As used herein, the term "heteroaryl" refers to a group having 5 to 14 ring atoms, preferably 5, 6, 10, 13 or 14 ring atoms; having 6, 10, or 14 it electrons shared in a cyclic array; and having, in addition to carbon atoms, from one to three heteroatoms that are each independently N, O, or S. "Heteroaryl" also includes fused multicyclic (e.g., bicyclic) ring systems in which one or more of the fused rings is non-aromatic, provided that at least one ring is aromatic and at least one ring contains an N, O, or S ring atom. Examples of such multicyclic heteroaryl ring systems include 2H-benzo[b][1,4]oxazin-3(4H)-one and 2H-pyrido[3,2-b][1,4]oxazin-3(4H)-one.

Examples of heteroaryl groups include acridinyl, azocinyl, benzimidazolyl, benzofuranyl, benzo[d]oxazol-2(3H)-one, 2H-benzo[b][1,4]oxazin-3(4H)-one, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroaralkyl" or "heteroarylalkyl" group comprises a heteroaryl group covalently linked to another group via an alkyl linker Examples of heteroalkyl groups comprise a $C_1$-$C_6$ alkyl group and a heteroaryl group having 5, 6, 9, or 10 ring atoms. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent ring O and/or S atoms.

An "arylene," "heteroarylene," or "heterocyclylene" group is an bivalent aryl, heteroaryl, or heterocyclyl group, respectively, as defined hereinabove, that is positioned between and serves to connect two other chemical groups.

When a hydrocarbon (e.g., an alkyl or aryl) is described as having a certain range of numbers of carbon atoms (e.g., $C_1$-$C_6$ alkyl), it will be understood that it encompasses hydrocarbons with each number of carbons within that range. So, for example, "$C_1$-$C_6$ alkyl" represents the group "$C_1$ alkyl, $C_2$ alkyl, $C_3$ alkyl, $C_4$ alkyl, $C_5$ alkyl, and $C_6$ alkyl."

As employed herein, when a moiety (e.g., cycloalkyl, hydrocarbyl, aryl, heteroaryl, heterocyclic, urea, etc.) is described as "optionally substituted" without expressly stating the substitutuents it is meant that the group optionally has from one to four, preferably from one to three, more preferably one or two, non-hydrogen substituents. Suitable substituents include, without limitation, halo, hydroxy, oxo (e.g., a ring —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Exemplary substituents, which are themselves not further substituted (unless expressly stated otherwise) are:

for $Q^1$, $Q^2$ and $Q^3$: hydrogen, halogen, particularly F, Cl or Br, halohydrocarbyl, such as $CF_3$, alkyl, such as $C_1$-$C_4$-alkyl, or alkoxy, such as $C_1$-$C_4$-alkoxy.

A moiety that is "optionally independently substituted" with one or more groups is unsubstituted, substituted with one group, or substituted with more than one group wherein each of the groups is selected independently of the others. For example, an alkyl optionally independently substituted with one or more halo, cyano, or —OH groups includes ethyl, trifluromethyl, and 1-chloro,2-hydroxypropyl.

The term "haloalkyl" refers to an alkyl chain in which one or more hydrogens have been replaced by a halogen. Exemplary haloalkyls are trifluoromethyl, difluoromethyl, fluorochloromethyl, and fluoromethyl The term "halogen" or "halo" as employed herein refers to chlorine, bromine, fluorine, or iodine.

As herein employed, the term "acyl" refers to an alkylcarbonyl or arylcarbonyl substituent wherein the alkyl and aryl portions are as defined herein. The term "acylamino" refers to an amide group attached at the nitrogen atom (i.e., R—CO—NH—). The term "carbamoyl" refers to an amide group attached at the carbonyl carbon atom (i.e., $NH_2$—CO—). The term "sulfonamido" refers to a sulfonamide substituent attached by either the sulfur or the nitrogen atom. The term "ureido" as employed herein refers to a substituted or unsubstituted urea moiety.

The term "radical" as used herein means a chemical moiety comprising one or more unpaired electrons.

As used herein, "an effective amount" of a compound is an amount that is sufficient to negatively modulate or inhibit the activity of LSD1.

As used herein, a "therapeutically effective amount" of a compound is an amount that is sufficient to ameliorate or in some manner reduce a symptom or stop or reverse progression of a condition, or negatively modulate or inhibit the activity of LSD1. Such amount may be administered as a single dosage or may be administered according to a regimen, whereby it is effective.

As used herein, "treatment" means any manner in which the symptoms or pathology of a condition, disorder or disease in a patient are ameliorated or otherwise beneficially altered.

As used herein, amelioration of the symptoms of a particular disorder by administration of a particular compound or pharmaceutical composition refers to any lessening, whether permanent or temporary, lasting or transient, that can be attributed to or associated with administration of the composition.

Compounds

In one aspect of the invention, compounds are provided represented by formula (I) or formula (II):

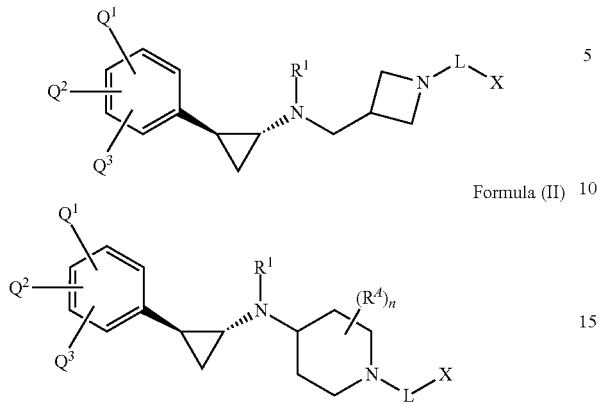

Formula (I)

Formula (II)

or a pharmaceutically acceptable salts thereof.

$R^1$ is hydrogen, $C_1$-$C_4$ alkyl or $C_1$-$C_4$ acyl;

L is —$(CH_2)_s$—$CR^2R^3$—$(CH_2)_m$—;

$R^2$ and $R^3$ are each independently hydrogen, $C_1$-$C_4$ alkyl, —$OR^4$ or aralkyl;

each $R^4$ is independently hydrogen or $C_1$-$C_4$ alkyl;

X is —W—$R^5$ or Y—$R^6$;

W is —$NR^4$— or —O—;

Y is —C(O)—, —S—, —SO—, —$SO_2$—, —$NR^4SO_2$—, —$SO_2NR^4$— and —$NR^4C(O)$—;

$R^5$ is acyl, $C_1$-$C_4$ alkyl, cycloalkyl, heterocyclyl, aryl or heteroaryl, wherein each of said cycloalkyl, heterocyclyl, aryl or heteroaryl is optionally independently substituted with one or more $R^8$;

$R^6$ is $C_1$-$C_6$ alkyl, aryl, —$NR^4R^7$ or heterocyclyl optionally independently substituted on one or more carbon atoms with $C_1$-$C_6$ alkyl, halogen, cyano, or haloalkyl, or optionally independently substituted on one or more nitrogen atoms with —$C(O)C_1$-$C_6$ alkyl; —$C(O)OC_1$-$C_6$ alkyl; —$C(O)NR^4C_1$-$C_6$ alkyl, or —$S(O)_2NR^4C_1$-$C_6$ alkyl;

$R^7$ is hydroxyl, alkoxy, —$SO_2C_1$-$C_6$alkyl; —$SO_2$cycloalkyl, or —$SO_2$aryl, wherein the cycloalkyl and aryl of each of the —$SO_2$cycloalkyl and —$SO_2$aryl is optionally independently substituted with one or more $R^8$;

each $R^8$ is independently halogen, hydroxyl, amino, cyano, $C_1$-$C_6$ alkyl, $C_2$-$C_6$ alkenyl, $C_2$-$C_6$ alkynyl, haloalkyl, alkoxy, alkylamino, dialkylamino, cycloalkyl, aryl, heteroaryl, heterocyclyl, aralkyl, heteroarylalkyl, —$(CH_2)_nCOOR^4$, —$(CH_2)_nC(O)NR^4OC_1$-$C_6$alkyl, —$(CH_2)_nC(O)NR^4SO_2C_1$-$C_6$alkyl, —$(CH_2)_nC(O)NR^4SO_2$cycloalkyl, —$(CH_2)_nC(O)NR^4SO_2$aryl, —$C_2$-$C_6$ alkenylC(O)OR^4$, —$C_2$-$C_6$ alkenylC(O)NR^4SO_2C_1$-$C_4$alkyl, or —$C_2$-$C_6$ alkenylC(O)NR^4SO_2$aryl, wherein each of the cycloalkyl, aryl, heteroaryl, and heterocyclyl is optionally independently substituted with one or more $C_1$-$C_3$ alkyl or —$CH_2NR^4SO_2$aryl.

m is 0 or 1;

s is 0 or 1;

each n is 0, 1, or 2;

each p is 0, 1 or 2;

each $R^A$ is independently oxo or $C_1$-$C_3$ alkyl, or two $R^A$ groups on different ring atoms together form a $C_1$-$C_3$ bridge in which one of the bridge carbons is optionally replaced with —NH—;

each $Q^1$, $Q^2$ and $Q^3$ is independently hydrogen, halogen, haloalkyl, $C_1$-$C_4$-alkyl, or $C_1$-$C_4$-alkoxy.

In one aspect of the invention, X is —W—$R^5$ and W is —O—, s is 1 and m is 0. In certain embodiments of this aspect, $R^5$ is aryl optionally independently substituted with one or more $R^8$. In some these embodiments, the aryl is phenyl optionally independently substituted with one or more $R^8$. In some of these embodiments, each $R^8$ is independently a heterocyclyl optionally independently substituted one or more $C_1$-$C_3$ alkyl or $C_1$-$C_4$ acyl, and the heterocyclyl is azetidinyl, pyrrolidinyl, pyrazolidinyl, piperidinyl, piperazinyl, 4-methyl-piperazinyl, 4-acyl-piperazinyl, tetrahydropyranyl, 1,3-dioxolanyl, 1,4-dioxanyl, morpholinyl, dimethyl-morpholinyl, thiomorpholinyl, 1,4-dithianyl, or 1,3,5-trithianyl. In other of these embodiments, the heterocyclyl is:

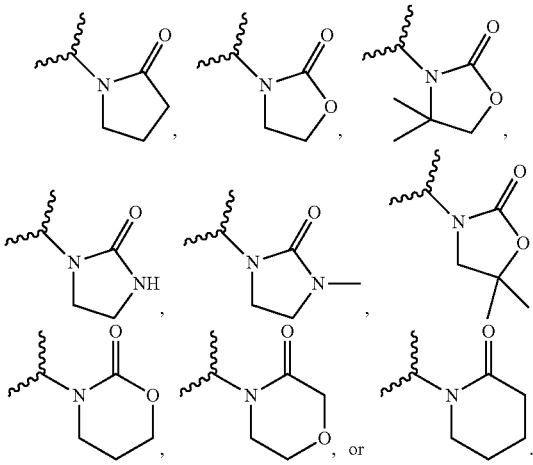

In other embodiments of this aspect, $R^5$ is phenyl optionally independently substituted with one or more $R^8$, wherein each $R^8$ is independently halogen, $C_1$-$C_6$ alkyl, —$(CH_2)_n$COOR^4$, —$(CH_2)_pC(O)NR^4OC_1$-$C_4$alkyl, —$(CH_2)_pC(O)NR^4SO_2C_1$-$C_4$alkyl, —$(CH_2)_nC(O)NR^4SO_2$cycloalkyl, —$(CH_2)_nC(O)NR^4SO_2$aryl, —CH=CHC(O)OR^4, —CH=CHC(O)NR^4SO_2C_1$-$C_4$alkyl, or —CH=CHC(O)NR^4SO_2$aryl. In some of these embodiments, there is a single $R^8$ substitution which is —$(CH_2)_nCOOR^4$.

In further embodiments of this aspect, $R^5$ is heteroaryl optionally independently substituted with one or more $R^8$. In certain embodiments, the heteroaryl optionally independently substituted with one or more $R^8$ is the heteroaryl is pyridyl, 6-methyl-pyridyl, 4-carboxy-pyridyl, dihydroquinolinone, indolinone, quinazolinyl, quinolinyl, pyrimidinyl, 2-methyl-pyrimidinyl, pyridazinyl, 6-methyl-pyridiazinyl, pyrazolyl, 1-methyl-pyrazolyl, 5-methyl-pyrazolyl, 1,3-dimethyl-pyrazolyl, thiazolyl, 5-methyl-thiazolyl, benzo[d]oxazol-2(3H)-one, 2H-benzo[b][1,4]oxazin-3(4H)-one, thiadiazolyl or 5-methyl-thiadiazolyl.

In yet other embodiments, the heteroaryl is pyridyl optionally independently substituted with one or more $R^8$. For some of these embodiments, $R^8$ is heterocyclyl optionally independently substituted with one or more $C_1$-$C_3$ alkyl or $C_1$-$C_4$ acyl. In some embodiments, the heterocyclyl optionally independently substituted with one or more $C_1$-$C_3$ alkyl or $C_1$-$C_4$ acyl is azetidinyl, pyrrolidinyl, pyrazolidinyl, piperidinyl, piperazinyl, 4-methyl-piperazinyl, 4-acyl-piperazinyl, tetrahydropyranyl, 1,3-dioxolanyl, 1,4-dioxanyl, morpholinyl, dimethyl-morpholinyl, thiomorpholinyl, 1,4-dithianyl, or 1,3,5-trithianyl. In other embodiments, the $R^8$ heterocyclyl is:

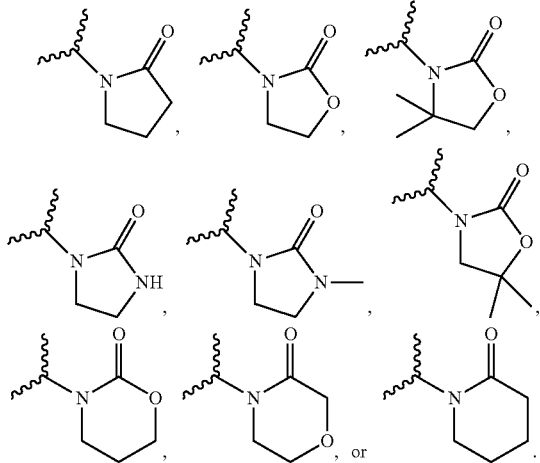

In yet other embodiments of this aspect, $R^8$ is halogen, $C_1$-$C_6$ alkyl, —$(CH_2)_n COOR^4$, —$(CH_2)_p C(O)NR^4 OC_1$-$C_4$alkyl, —$(CH_2)_p C(O)NR^4 SO_2 C_1$-$C_4$alkyl, —$(CH_2)_p C(O)NR^4 SO_2$cycloalkyl, —$(CH_2)_n C(O)NR^4 SO_2$aryl, —CH=CHC(O)OR$^4$, —CH=CHC(O)NR$^4$SO$_2$C$_1$-C$_4$ alkyl, or —CH=CHC(O)NR$^4$SO$_2$aryl.

In other embodiments of this aspect for compounds of formula (II), $R^A$ is Oxo and n is 1 or 2, thereby forming a piperdin-2-one or piperdin-2,6-dione. In alternative embodiments for compounds of formula (II), there are two $R^A$ groups on different piperidine ring atoms that form a $C_1$-$C_3$ bridge in which one of the carbon atoms of the bridge is optionally substituted by —NH—. Examples of piperidine groups with two $R^A$ groups forming a bridge include, but are not limited to, 3-azabicyclo[3.1.1]heptan-3-yl, 1-azabicyclo[2.2.2]octan-3-yl, 1-azabicyclo[2.2.2]octan-4-yl, 1-azabicyclo[3.2.1]octan-6-yl, and 3,7-diazabicyclo[3.3.1]nonanyl.

In certain embodiments of this aspect, $R^1$ is hydrogen, $C_1$-$C_4$ alkyl or $C_1$-$C_4$ acyl and $R^2$ and $R^3$ are each independently hydrogen, $C_1$-$C_4$ alkyl, —$OR^4$ or aralkyl, wherein $R^4$ is hydrogen or alkyl. In certain embodiments, $R^2$ is hydroxyl. In certain embodiments, $R^2$ and $R^3$ are each independently hydrogen, methyl and benzyl. In certain other exemplary embodiments, $R^4$ is hydrogen or methyl.

In certain other embodiments of this aspect, $R^1$ is hydrogen, L is ethylene, W is —O—, $R^5$ is an $R^8$ substituted phenylene, and $R^8$ is heterocyclyl, wherein the heterocyclyl is azetidinyl, pyrrolidinyl, pyrazolidinyl, piperidinyl, piperazinyl, 4-methyl-piperazinyl, 4-acyl-piperazinyl, morpholinyl, dimethyl-morpholinyl, or thiomorpholinyl.

In certain other embodiments of this aspect, $R^1$ is methyl, L is ethylene, W is —O—, $R^5$ is an $R^8$ substituted phenylene, and $R^8$ is heterocyclyl, wherein the heterocyclyl is azetidinyl, pyrrolidinyl, pyrazolidinyl, piperidinyl, piperazinyl, 4-methyl-piperazinyl, 4-acyl-piperazinyl, morpholinyl, dimethyl-morpholinyl, or thiomorpholinyl.

In certain other embodiments of this aspect, $R^1$ is hydrogen, L is ethylene, W is —O—, $R^5$ is an $R^8$ substituted phenylene, and $R^8$ is heterocyclyl, wherein the heterocyclyl is:

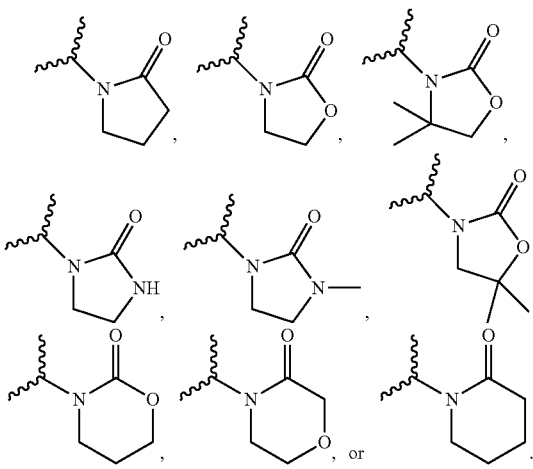

In certain other embodiments of this aspect, $R^1$ is methyl, L is ethylene, W is —O—, $R^5$ is an $R^8$ substituted phenylene, and $R^8$ is heterocyclyl, wherein the heterocyclyl is:

In certain other embodiments of this aspect, $R^1$ is acyl, L is ethylene, W is —O—, $R^5$ is an $R^8$ substituted phenylene, and $R^8$ is heterocyclyl, wherein the heterocyclyl is:

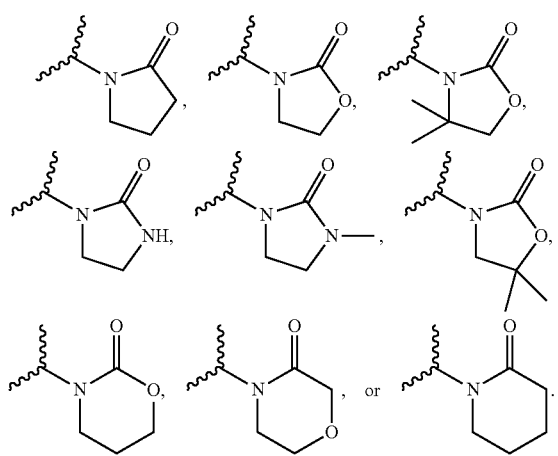

In another aspect of the invention, R¹ is hydrogen, s and m are each one, R² is hydroxyl, R³ is hydrogen, W is —O—, R⁵ is an R⁸ substituted phenylene, and R⁸ is heterocyclyl, wherein the heterocyclyl is:

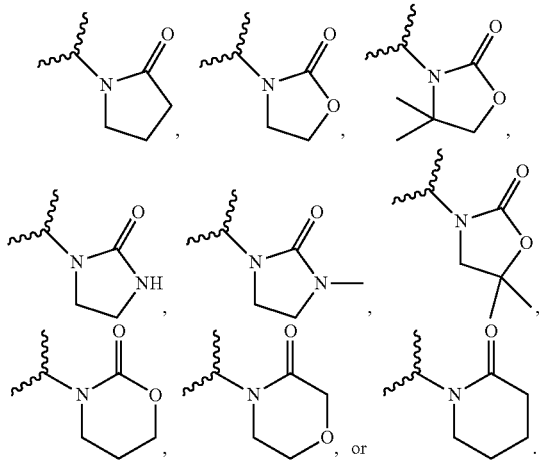

In yet another aspect of the invention, R¹ is hydrogen, L is ethylene, W is —O—, R⁵ is an R⁸ substituted pyridylene, and R⁸ is heterocyclyl, wherein the heterocyclyl is azetidinyl, pyrrolidinyl, pyrazolidinyl, piperidinyl, piperazinyl, 4-methyl-piperazinyl, 4-acyl-piperazinyl, morpholinyl, dimethyl-morpholinyl, or thiomorpholinyl.

In certain other embodiments of this aspect, R¹ is methyl, L is ethylene, W is —O—, R⁵ is an R⁸ substituted pyridylene, and R⁸ is heterocyclyl, wherein the heterocyclyl is azetidinyl, pyrrolidinyl, pyrazolidinyl, piperidinyl, piperazinyl, 4-methyl-piperazinyl, 4-acyl-piperazinyl, morpholinyl, dimethyl-morpholinyl, or thiomorpholinyl.

In certain other embodiments of this aspect, R¹ is hydrogen, L is ethylene, W is —O—, R⁵ is an R⁸ substituted pyridylene, and R⁸ is heterocyclyl, wherein the heterocyclyl is:

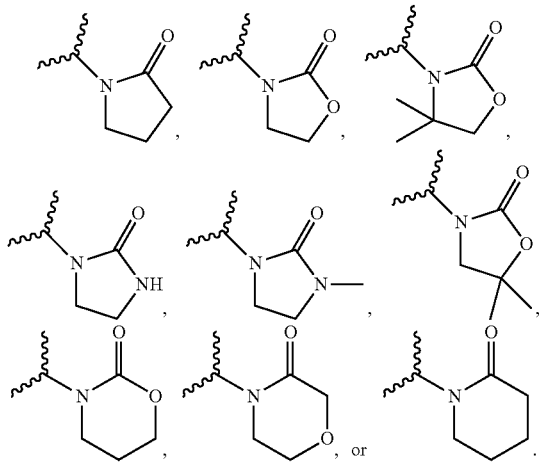

In certain embodiments, compounds of formula (I) and formula (II) wherein W is —O— are
1-phenoxy-3-[4-[[trans-2-phenylcyclopropyl] amino]-1-piperidyl] propan-2-ol;
1-(2-methoxy-3-phenoxy-propyl)-N-[trans-2-phenylcyclopropyl]piperidin-4-amine;
2-methyl-1-phenoxy-3-(4-(((trans)-2-phenylcyclopropyl) amino)piperidin-1-yl)propan-2-ol;
1-phenoxy-3-[3-[[[(trans)-2-phenylcyclopropyl]amino] methyl]azetidin-1-yl]propan-2-ol;
(R)-1-phenoxy-3-(4-(((1S,2R)-2-phenylcyclopropyl)amino) piperidin-1-yl)propan-2-ol;
(S)-1-phenoxy-3-(4-(((1S,2R)-2-phenylcyclopropyl)amino) piperidin-1-yl)propan-2-ol;
1-phenoxy-3-[(1R,5S)-6-[[(trans)-2-phenylcyclopropyl] amino]-3-azabicyclo[3.1.1]heptan-3-yl]propan-2-ol;
(trans)-N-[[1-(2-phenoxyethyl)azetidin-3-yl]methyl]-2-phenyl-cyclopropanamine;
(trans)-N-[[1-(3-phenoxypropyl)azetidin-3-yl]methyl]-2-phenyl-cyclopropanamine;
1-[2-(4-bromophenoxy)ethyl]-N-[(1R,2S)-2-phenylcyclopropyl]piperidin-4-amine;
1-(3-Phenoxypropyl)-N-((trans)-2-phenylcyclopropyl)piperidin-4-amine;
1-(2-Phenoxyethyl)-N-((trans)-2-phenylcyclopropyl)piperidin-4-amine;
2-(4-(2-(4-(((1R,2S)-2-Phenylcyclopropyl)amino)piperidin-1-yl)ethoxy)phenyl)acetic acid;
N-(Methylsulfonyl)-2-(4-(2-(4-(((1R,2S)-2-phenylcyclopropyl)amino)piperidin-1-yl)ethoxy)phenyl)acetamide;
2-(4-(2-(4-(((1R,2S)-2-phenylcyclopropyl)amino)piperidin-1-yl)ethoxy)phenyl)-N-(phenyl sulfonyl)acetamide;
N,N-Dimethyl-2-(4-(2-(4-(((1R,2S)-2-phenylcyclopropyl) amino)piperidin-1-yl)ethoxy)phenyl)acetamide;
N-methoxy-2-(4-(2-(4-(((1R,2S)-2-phenylcyclopropyl) amino)piperidin-1-yl)ethoxy)phenyl)acetamide;
1-[2-(4-morpholinophenoxy)ethyl]-N-[(1R,2S)-2-phenylcyclopropyl]piperidin-4-amine;
1-(2-(4-(4-methylpiperazin-1-yl)phenoxy)ethyl)-N-((1R, 2S)-2-phenylcyclopropyl)piperidin-4-amine;
3-(4-(2-(4-(((1R,2S)-2-phenylcyclopropyl)amino)piperidin-1-yl)ethoxy)phenyl)oxazolidin-2-one;
1-methyl-3-(4-(2-(4-(((1R,2S)-2-phenylcyclopropyl)amino) piperidin-1-yl)ethoxy)phenyl)imidazolidin-2-one;
3-(4-(2-(4-(((1R,2S)-2-phenylcyclopropyl)amino)piperidin-1-yl)ethoxy)phenyl)-1,3-oxazinan-2-one;
4-(4-(2-(4-(((1R,2S)-2-phenylcyclopropyl)amino)piperidin-1-yl)ethoxy)phenyl)morpholin-3-one;
1-(4-(4-(2-(4-(((1R,2S)-2-phenylcyclopropyl)amino)piperidin-1-yl)ethoxy)phenyl)piperazin-1-yl)ethan-1-one;
1-(4-(2-(4-(((1R,2S)-2-phenylcyclopropyl)amino)piperidin-1-yl)ethoxy)phenyl)pyrrolidin-2-one;
1-(4-(2-(4-(((1R,2S)-2-phenylcyclopropyl)amino)piperidin-1-yl)ethoxy)phenyl)piperidin-2-one;
N-((1R,2S)-2-phenylcyclopropyl)-1-(2-(4-(piperidin-1-yl) phenoxy)ethyl)piperidin-4-amine;
2-(4-(2-hydroxy-3-(4-(((1R,2S)-2-phenylcyclopropyl) amino)piperidin-1-yl)propoxy)phenyl)acetic acid;
4-(2-hydroxy-3-(4-(((1R,2S)-2-phenylcyclopropyl)amino) piperidin-1-yl)propoxy)benzoic acid;
(E)-3-(4-(2-hydroxy-3-(4-(((1R,2S)-2-phenylcyclopropyl) amino)piperidin-1-yl)propoxy)phenyl)acrylic acid;
2-(4-(3-(4-(((1R,2S)-2-phenylcyclopropyl)amino)piperidin-1-yl)propoxy)phenyl)acetic acid;
4-(3-(4-(((1R,2S)-2-phenylcyclopropyl)amino)piperidin-1-yl)propoxy)benzoic acid;
(E)-3-(4-(3-(4-(((1R,2S)-2-phenylcyclopropyl)amino)piperidin-1-yl)propoxy)phenyl)acrylic acid;
(1R,2S)—N-((1-(2-(4-bromophenoxy)ethyl)azetidin-3-yl) methyl)-2-phenylcyclopropan-1-amine;
1-(2-(2,4-dichlorophenoxy)ethyl)-N-((1R,2S)-2-phenylcyclopropyl)piperidin-4-amine;

(1R,2S)—N-((1-(2-(2,4-dichlorophenoxy)ethyl)azetidin-3-yl)methyl)-2-phenylcyclopropan-1-amine;
1-(2-(2,4-difluorophenoxy)ethyl)-N-((1R,2S)-2-phenylcyclopropyl)piperidin-4-amine;
(1R,2S)—N-((1-(2-(2,4-difluorophenoxy)ethyl)azetidin-3-yl)methyl)-2-phenylcyclopropan-1-amine;
(E)-3-(4-(2-hydroxy-3-(4-(((1R,2S)-2-phenylcyclopropyl)amino)piperidin-1-yl)propoxy)phenyl)-N-(methylsulfonyl)acrylamide;
1-(2-((2-methylpyridin-4-yl)oxy)ethyl)-N-((1R,2S)-2-phenylcyclopropyl)piperidin-4-amine;
(1R,2S)-2-phenyl-N-((1-(2-(p-tolyloxy)ethyl)azetidin-3-yl)methyl)cyclopropan-1-amine;
(1R,2S)-2-phenyl-N-((1-(2-(pyridin-2-yloxy)ethyl)azetidin-3-yl)methyl)cyclopropan-1-amine;
4-(2-(4-(((1R,2S)-2-phenylcyclopropyl)amino)piperidin-1-yl)ethoxy)benzoic acid;
N-(cyclopropylsulfonyl)-4-(2-(4-(((1R,2S)-2-phenylcyclopropyl)amino)piperidin-1-yl)ethoxy)benzamide;
4-(2-(4-(((1R,2S)-2-phenylcyclopropyl)amino)piperidin-1-yl)ethoxy)-N-(phenyl sulfonyl)benzamide;
(E)-N-(methylsulfonyl)-3-(4-(3-(4-(((1R,2S)-2-phenylcyclopropyl)amino)piperidin-1-yl)propoxy)phenyl)acrylamide;
3-(4-(2-(3-((((1R,2S)-2-phenylcyclopropyl)amino)methyl)azetidin-1-yl)ethoxy)phenyl)-1,3-oxazinan-2-one;
4-(2-(3-((((1R,2S)-2-phenylcyclopropyl)amino)methyl)azetidin-1-yl)ethoxy)phenyl)morpholin-3-one
1-(4-(2-(3-((((1R,2S)-2-phenylcyclopropyl)amino)methyl)azetidin-1-yl)ethoxy)phenyl)piperidin-2-one;
(1R,2S)-2-phenyl-N-((1-(2-(4-(piperazin-1-yl)phenoxy)ethyl)azetidin-3-yl)methyl)cyclopropan-1-amine;
(1R,2S)—N-((1-(2-(4-(4-methylpiperazin-1-yl)phenoxy)ethyl)azetidin-3-yl)methyl)-2-phenylcyclopropan-1-amine;
1-(4-(4-(2-(3-((((1R,2S)-2-phenylcyclopropyl)amino)methyl)azetidin-1-yl)ethoxy)phenyl)piperazin-1-yl)ethan-1-one;
1-(2-((5-methylpyridin-2-yl)oxy)ethyl)-N-((1R,2S)-2-phenylcyclopropyl)piperidin-4-amine;
1-(2-((6-methylpyridin-3-yl)oxy)ethyl)-N-((1R,2S)-2-phenylcyclopropyl)piperidin-4-amine;
N-(methyl sulfonyl)-4-(2-(4-(((1R,2S)-2-phenylcyclopropyl)amino)piperidin-1-yl)ethoxy)benzamide;
N-(ethylsulfonyl)-4-(2-(4-(((1R,2S)-2-phenylcyclopropyl)amino)piperidin-1-yl)ethoxy)benzamide;
(1S,2R)—N-((1-(2-((5-(4-methylpiperazin-1-yl)pyridin-2-yl)oxy)ethyl)azetidin-3-yl)methyl)-2-phenylcyclopropan-1-amine;
2-(4-(2-(3-((((1S,2R)-2-phenylcyclopropyl)amino)methyl)azetidin-1-yl)ethoxy)phenyl)acetic acid;
4-(2-(3-((((1R,2S)-2-phenylcyclopropyl)amino)methyl)azetidin-1-yl)ethoxy)benzoic acid
2-(4'-(2-(3-((((1S,2R)-2-phenylcyclopropyl)amino)methyl)azetidin-1-yl)ethoxy)-[1,1'-biphenyl]-4-yl)-N-(phenylsulfonyl)acetamide;
3-(6-(2-(4-(((1R,2S)-2-phenylcyclopropyl)amino)piperidin-1-yl)ethoxy)pyridin-3-yl)-1,3-oxazinan-2-one;
3-(5-(2-(4-(((1R,2S)-2-phenylcyclopropyl)amino)piperidin-1-yl)ethoxy)pyridin-2-yl)-1,3-oxazinan-2-one;
N-((1R,2S)-2-phenylcyclopropyl)-1-(2-(p-tolyloxy)ethyl)piperidin-4-amine;
3-(4-(2-(4-(methyl((1R,2S)-2-phenylcyclopropyl)amino)piperidin-1-yl)ethoxy)phenyl)-1,3-oxazinan-2-one;
2-(4-(2-(1-methyl-3-((((1R,2S)-2-phenylcyclopropyl)amino)methyl)-λ4-azetidin-1-yl)ethoxy)phenyl)-N-(methylsulfonyl)acetamide;
N-methyl-1-(2-((6-methylpyridin-3-yl)oxy)ethyl)-N-((1R,2S)-2-phenylcyclopropyl)piperidin-4-amine;
(1R,2S)—N-((1-(2-((6-methylpyridin-3-yl)oxy)ethyl)azetidin-3-yl)methyl)-2-phenylcyclopropan-1-amine;
4-(2-(1-methyl-3-((((1R,2S)-2-phenylcyclopropyl)amino)methyl)-λ4-azetidin-1-yl)ethoxy)-N-(methyl sulfonyl)benzamide;
3-(5-(2-3-((((1R,2S)-2-phenylcyclopropyl)amino)methyl)azetidin-1-yl)ethoxy)pyridin-2-yl)-1,3-oxazinan-2-one;
6-(2-(4-(((1R,2S)-2-phenylcyclopropyl)amino)piperidin-1-yl)ethoxy)-3,4-dihydroquinolin-2(1H)-one;
5-(2-(4-(((1R,2S)-2-phenylcyclopropyl)amino)piperidin-1-yl)ethoxy)indolin-2-one;
1-(2-(3-fluoro-4-methylphenoxy)ethyl)-N-((1R,2S)-2-phenylcyclopropyl)piperidin-4-amine;
N-((1R,2S)-2-phenylcyclopropyl)-1-(2-(quinazolin-4-yloxy)ethyl)piperidin-4-amine;
N-((1R,2S)-2-phenylcyclopropyl)-1-(2-(quinolin-4-yloxy)ethyl)piperidin-4-amine;
N-((1R,2S)-2-phenylcyclopropyl)-1-(2-(pyrimidin-5-yloxy)ethyl)piperidin-4-amine;
1-(2-(3,5-difluorophenoxy)ethyl)-N-((1R,2S)-2-phenylcyclopropyl)piperidin-4-amine;
1-(2-(3,5-dichlorophenoxy)ethyl)-N-((1R,2S)-2-phenylcyclopropyl)piperidin-4-amine;
1-(2-((6-methylpyridazin-3-yl)oxy)ethyl)-N-((1R,2S)-2-phenylcyclopropyl)piperidin-4-amine;
(E)-3-(4-(2-(4-(((1R,2S)-2-phenylcyclopropyl)amino)piperidin-1-yl)ethoxy)phenyl)acrylic acid;
1-(2-(3-fluorophenoxy)ethyl)-N-((1R,2S)-2-phenylcyclopropyl)piperidin-4-amine;
1-(2-((6-methylpyridin-2-yl)oxy)ethyl)-N-((1R,2S)-2-phenylcyclopropyl)piperidin-4-amine;
1-(2-((2-methylpyrimidin-5-yl)oxy)ethyl)-N-((1R,2S)-2-phenylcyclopropyl)piperidin-4-amine;
1-(2-(4-bromophenoxy)ethyl)-4-(((1R,2S)-2-phenylcyclopropyl)amino)piperidin-2-one;
2-(4-(((1R,2S)-2-phenylcyclopropyl)amino)piperidin-1-yl)ethan-1-ol;
N-(1-(2-(4-(2-oxo-1,3-oxazinan-3-yl)phenoxy)ethyl)piperidin-4-yl)-N-((1R,2S)-2-phenylcyclopropyl)acetamide;
1-(2-methoxyethyl)-N-((1R,2S)-2-phenylcyclopropyl)piperidin-4-amine;
1-(2-((1,3-dimethyl-1H-pyrazol-5-yl)oxy)ethyl)-N-((1R,2S)-2-phenylcyclopropyl)piperidin-4-amine;
1-(2-((1-methyl-1H-pyrazol-3-yl)oxy)ethyl)-N-((1R,2S)-2-phenylcyclopropyl)piperidin-4-amine;
3-(4-(2-(3-((((1R,2S)-2-phenylcyclopropyl)amino)methyl)azetidin-1-yl)ethoxy)phenyl)-1,3-oxazinan-2-one;
1-(2-isopropoxyethyl)-N-((1R,2S)-2-phenylcyclopropyl)piperidin-4-amine;
2-(2-fluoro-4-(2-(4-(((1R,2S)-2-phenylcyclopropyl)amino)piperidin-1-yl)ethoxy)phenyl)acetic acid;
1-(2-(3,5-difluoro-4-methylphenoxy)ethyl)-N-((1R,2S)-2-phenylcyclopropyl)piperidin-4-amine;
1-(2-((5-methyl-1,3,4-thiadiazol-2-yl)oxy)ethyl)-N-((1R,2S)-2-phenylcyclopropyl)piperidin-4-amine;
2-(2-(4-(((1R,2S)-2-phenylcyclopropyl)amino)piperidin-1-yl)ethoxy)isonicotinic acid;
3-(4-(2-(4-(((1R,2S)-2-phenylcyclopropyl)amino)piperidin-1-yl)ethoxy)phenyl)oxazolidin-2-one;
1-(2-(4-bromophenoxy)ethyl)-4-(((1R,2S)-2-phenylcyclopropyl)amino)piperidine-2,6-dione;
N-((1R,2S)-2-phenylcyclopropyl)-1-(2-(pyridin-3-yloxy)ethyl)piperidin-4-amine;
7-(2-(4-(((1R,2S)-2-phenylcyclopropyl)amino)piperidin-1-yl)ethoxy)-2H-benzo[b][1,4]oxazin-3(4H)-one;

6-(2-(4-(((1R,2S)-2-phenylcyclopropyl)amino)piperidin-1-yl)ethoxy)benzo[d]oxazol-2(3H)-one;

1-(2-((5-methylthiazol-2-yl)oxy)ethyl)-N-((1R,2S)-2-phenylcyclopropyl)piperidin-4-amine;

3-(2-(4-(((1R,2S)-2-phenylcyclopropyl)amino)piperidin-1-yl)ethoxy)isonicotinic acid;

2-(3-chloro-4-(2-(4-(((1R,2S)-2-phenylcyclopropyl)amino)piperidin-1-yl)ethoxy)phenyl)acetic acid;

2-(3-fluoro-4-(2-(4-(((1R,2S)-2-phenylcyclopropyl)amino)piperidin-1-yl)ethoxy)phenyl)acetic acid;

2-(3-methyl-4-(2-(4-(((1R,2S)-2-phenylcyclopropyl)amino)piperidin-1-yl)ethoxy)phenyl)acetic acid;

4-(2-(4-(((1R,2S)-2-(3,4-difluorophenyl)cyclopropyl)amino)piperidin-1-yl)ethoxy)benzoic acid;

and pharmaceutically acceptable salts of the foregoing compounds, including, but not limited to, di-hydrochloride salts.

In another aspect of the invention, X is —W—$R^5$ and W is —$NR^4$—, s is 1 and m is 0. In certain embodiments of this aspect, $R^5$ is aryl optionally independently substituted with one or more $R^8$. In some these embodiments, the aryl optionally independently substituted with one or more $R^8$ is phenyl. In some of these embodiments, each $R^8$ is independently a heterocyclyl optionally independently substituted one or more $C_1$-$C_3$ alkyl or $C_1$-$C_4$ acyl, and the heterocyclyl is azetidinyl, pyrrolidinyl, pyrazolidinyl, piperidinyl, piperazinyl, 4-methyl-piperazinyl, 4-acyl-piperazinyl, tetrahydropyranyl, 1,3-dioxolanyl, 1,4-dioxanyl, morpholinyl, dimethyl-morpholinyl, thiomorpholinyl, 1,4-dithianyl, or 1,3,5-trithianyl. In other of these embodiments, the heterocyclyl is:

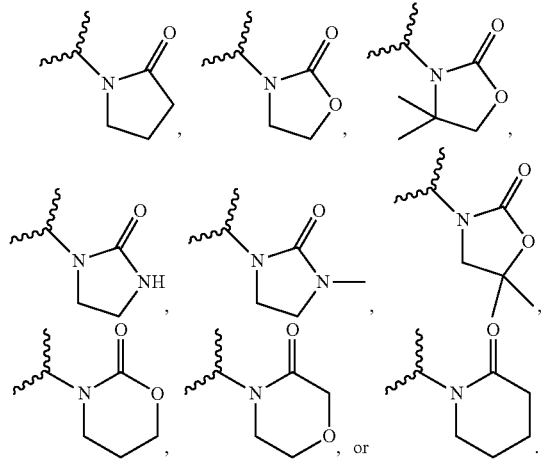

In other embodiments of this aspect, $R^5$ is phenyl optionally independently substituted with one or more $R^8$, wherein each $R^8$ is independently halogen, $C_1$-$C_6$ alkyl, —$(CH_2)_n$COOR$^4$, —$(CH_2)_pC(O)NR^4OC_1$-$C_4$alkyl, —$(CH_2)_nC(O)NR^4SO_2C_1$-$C_4$alkyl, —$(CH_2)_nC(O)NR^4SO_2$cycloalkyl, —$(CH_2)_nC(O)NR^4SO_2$aryl, —CH=CHC(O)OR$^4$, —CH=CHC(O)NR$^4$SO$_2$C$_1$-C$_4$alkyl, or —CH=CHC(O)NR$^4$SO$_2$aryl. In some of these embodiments, there is a single $R^8$ substitution which is —$(CH_2)_n$COOR$^4$.

In further embodiments where W is —$NR^4$—, $R^5$ is heteroaryl optionally independently substituted with one or more $R^8$. In certain embodiments, the heteroaryl optionally independently substituted with one or more $R^8$ is the heteroaryl is pyridyl, 6-methyl-pyridyl, 4-carboxy-pyridyl, dihydroquinolinone, indolinone, quinazolinyl, quinolinyl, pyrimidinyl, 2-methyl-pyrimidinyl, pyridazinyl, 6-methyl-pyridiazinyl, pyrazolyl, 1-methyl-pyrazolyl, 5-methyl-pyrazolyl, 1,3-dimethyl-pyrazolyl, thiazolyl, 5-methyl-thiazolyl, benzo[d]oxazol-2(3H)-one, 2H-benzo[b][1,4]oxazin-3 (4H)-one, thiadiazolyl or 5-methyl-thiadiazolyl. In yet other embodiments, the heteroaryl is pyridyl optionally independently substituted with one or more $R^8$. For certain compounds, $R^8$ is heterocyclyl optionally independently substituted one or more $C_1$-$C_3$ alkyl. In some embodiments, the heterocyclyl optionally independently substituted one or more $C_1$-$C_3$ alkyl is azetidinyl, pyrrolidinyl, pyrazolidinyl, piperidinyl, piperazinyl, 4-methyl-piperazinyl, 4-acyl-piperazinyl, tetrahydropyranyl, 1,3-dioxolanyl, 1,4-dioxanyl, morpholinyl, dimethyl-morpholinyl, thiomorpholinyl, 1,4-dithianyl, or 1,3,5-trithianyl.

In other embodiments, the heterocyclyl optionally independently substituted one or more $C_1$-$C_3$ alkyl is

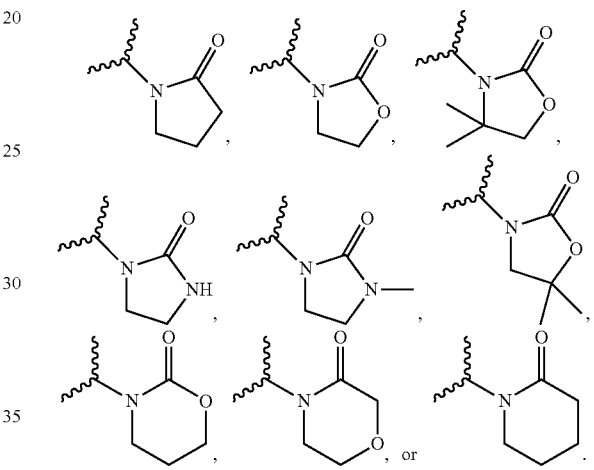

In yet other embodiments of this aspect, $R^5$ is pyridyl and each $R^8$ is independently halogen, alkyl, —$(CH_2)_n$COOR$^4$, —$(CH_2)_pC(O)NR^4OC_1$-$C_4$alkyl, —$(CH_2)_nC(O)NR^4SO_2C_1$-C$_4$alkyl, —$(CH_2)_nC(O)NR^4SO_2$cycloalkyl, —$(CH_2)_nC(O)NR^4SO_2$aryl, —CH=CHC(O)OR$^4$, —CH=CHC(O)NR$^4$SO$_2$C$_1$-C$_4$ alkyl, or —CH=CHC(O)NR$^4$SO$_2$aryl.

In other embodiments of this aspect for compounds of formula (II), there are two $R^4$ on the same carbon forming an oxo and n is 1 or 2, thereby forming a piperdin-2-one or piperdin-2,6-dione. In alternative embodiments for compounds of formula (II), there are two $R^4$ groups on different piperidine ring atoms that form a $C_1$-$C_3$ bridge in which one of the carbon atoms of the bridge is optionally substituted by —NH—. Examples of piperidine groups with two $R^4$ groups forming a bridge include, but are not limited to, 3-azabicyclo[3.1.1]heptan-3-yl, 1-azabicyclo[2.2.2]octan-3-yl, 1-azabicyclo[2.2.2]octan-4-yl, 1-azabicyclo[3.2.1]octan-6-yl, and 3,7-diazabicyclo[3.3.1]nonanyl.

In certain embodiments of this aspect, $R^1$ is hydrogen, $C_1$-$C_4$ alkyl or $C_1$-$C_4$ acyl and $R^2$ and $R^3$ are each independently hydrogen, $C_1$-$C_4$ alkyl, —OR$^4$ or aralkyl, wherein $R^4$ is hydrogen or alkyl. In certain embodiments, $R^2$ is hydroxyl. In certain other embodiments, $R^2$ and $R^3$ are each independently hydrogen, methyl and benzyl. In certain other exemplary embodiments, $R^4$ is hydrogen or methyl.

In certain other embodiments of this aspect, $R^1$ is hydrogen, L is ethylene, W is —$NR^4$—, $R^4$ is hydrogen, $R^5$ is an $R^8$ substituted phenylene, and $R^8$ is heterocyclyl, wherein the heterocyclyl is azetidinyl, pyrrolidinyl, pyrazolidinyl, piperidinyl, piperazinyl, 4-methyl-piperazinyl, 4-acyl-piperazinyl, morpholinyl, dimethyl-morpholinyl, or thiomorpholinyl.

In certain other embodiments of this aspect, $R^1$ is methyl, L is ethylene, W is —$NR^4$—, $R^4$ is hydrogen, $R^5$ is an $R^8$ substituted phenylene, and $R^8$ is heterocyclyl, wherein the heterocyclyl is azetidinyl, pyrrolidinyl, pyrazolidinyl, piperidinyl, piperazinyl, 4-methyl-piperazinyl, 4-acyl-piperazinyl, morpholinyl, dimethyl-morpholinyl, or thiomorpholinyl.

In certain other embodiments of this aspect, $R^1$ is hydrogen, L is ethylene, W is —$NR^4$—, $R^4$ is hydrogen, $R^5$ is an $R^8$ substituted phenylene, and $R^8$ is heterocyclyl, wherein the heterocyclyl is:

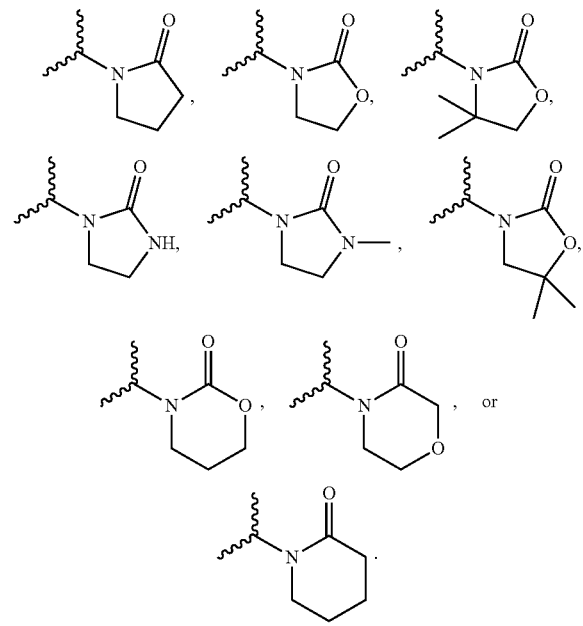

In certain other embodiments of this aspect, $R^1$ is methyl, L is ethylene, W is —$NR^4$—, $R^4$ is hydrogen, $R^5$ is an $R^8$ substituted phenylene, and $R^8$ is heterocyclyl, wherein the heterocyclyl is:

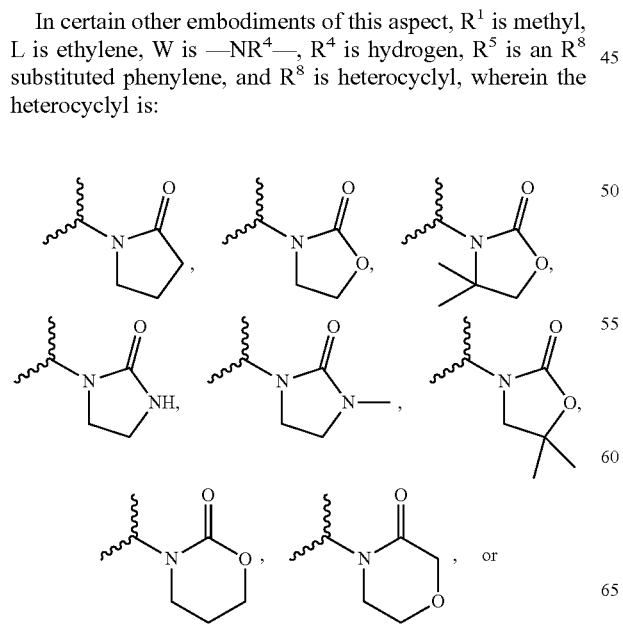

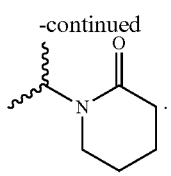

In certain other embodiments of this aspect, $R^1$ is acyl, L is ethylene, W is —$NR^4$—, $R^4$ is hydrogen, $R^5$ is an $R^8$ substituted phenylene, and $R^8$ is heterocyclyl, wherein the heterocyclyl is:

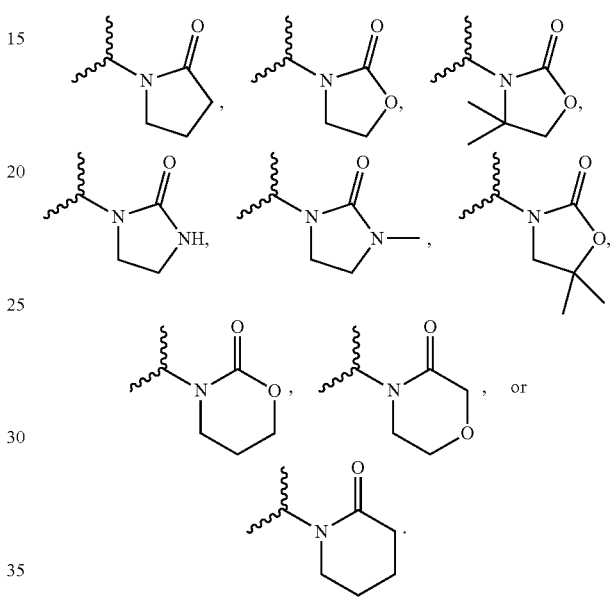

In another aspect of the invention, $R^1$ is hydrogen, s and m are each one, $R^2$ is hydroxyl, $R^3$ is hydrogen, W is —$NR^4$—, $R^4$ is hydrogen, $R^5$ is an $R^8$ substituted phenylene, and $R^8$ is heterocyclyl, wherein the heterocyclyl is:

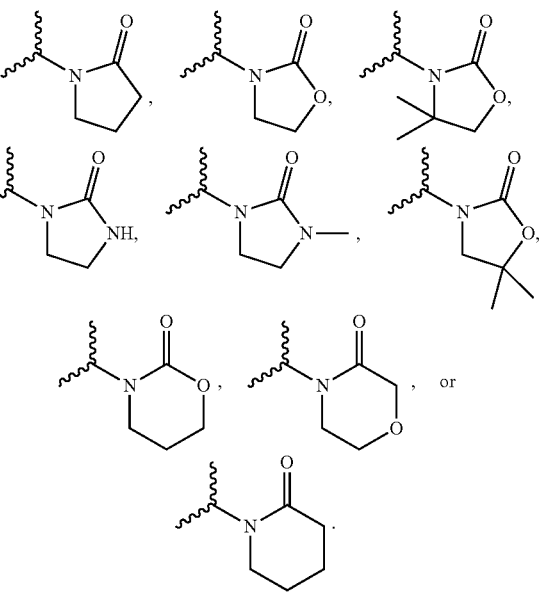

In certain other embodiments of this aspect, $R^1$ is hydrogen, L is ethylene, W is —$NR^4$—, $R^4$ is hydrogen, $R^5$ is an $R^8$ substituted phenylene, and $R^8$ is heteroaryl, wheherein the heteroaryl is pyridyl, dihydroquinolinone, indolinone, quinazolinyl, quinolinyl, pyrimidinyl, pyridazinyl, pyrazolyl, pyrazolyl, 1-methyl-pyrazolyl, 5-methyl-pyrazolyl, thiazolyl, benzo[d]oxazolone, thiazolyl or 5-methyl-thiazolyl.

In yet another aspect of the invention, $R^1$ is hydrogen, L is ethylene, W is —$NR^4$—, $R^4$ is hydrogen, $R^5$ is an $R^8$ substituted pyridylene, and $R^8$ is heterocyclyl, wherein the heterocyclyl is azetidinyl, pyrrolidinyl, pyrazolidinyl, piperidinyl, piperazinyl, 4-methyl-piperazinyl, 4-acyl-piperazinyl, morpholinyl, dimethyl-morpholinyl, or thiomorpholinyl.

In certain other embodiments of this aspect, $R^1$ is methyl, L is ethylene, W is —$NR^4$—, $R^4$ is hydrogen, $R^5$ is an $R^8$ substituted pyridylene, and $R^8$ is heterocyclyl, wherein the heterocyclyl is azetidinyl, pyrrolidinyl, pyrazolidinyl, piperidinyl, piperazinyl, 4-methyl-piperazinyl, 4-acyl-piperazinyl, morpholinyl, dimethyl-morpholinyl or thiomorpholinyl.

In certain other embodiments of this aspect, $R^1$ is hydrogen, L is ethylene, W is —$NR^4$—, $R^4$ is hydrogen, $R^5$ is an $R^8$ substituted pyridylene, and $R^8$ is heterocyclyl, wherein the heterocyclyl is:

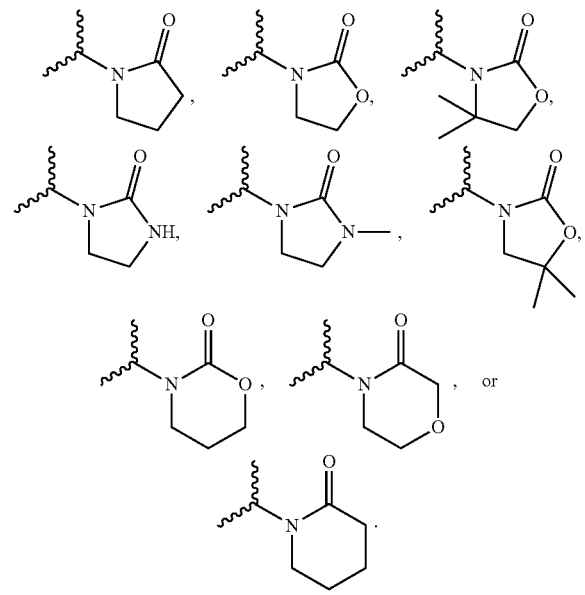

In certain embodiments, compounds of formula (I) and formula (II) wherein W is —$NR^4$— are:
1-anilino-3-[4-[[trans-2-phenylcyclopropyl]amino]-1-piperidyl] propan-2-ol;
1-(N-methylanilino)-3-[4-[[trans-2-phenylcyclopropyl]amino]-1-piperidyl]propan-2-ol;
1-(2-(phenylamino)ethyl)-N-((1R,2S)-2-phenylcyclopropyl)piperidin-4-amine;
1-(2-(methyl(phenyl)amino)ethyl)-N-((1R,2S)-2-phenylcyclopropyl)piperidin-4-amine;
1-(2-((4-bromophenyl)amino)ethyl)-N-((1R,2S)-2-phenylcyclopropyl)piperidin-4-amine;
1-(4-((2-(4-(((1R,2S)-2-phenylcyclopropyl)amino)piperidin-1-yl)ethyl)amino)phenyl)piperidin-2-one;
3-(4-((2-(4-(((1R,2S)-2-phenylcyclopropyl)amino)piperidin-1-yl)ethyl)amino)phenyl)-1,3-oxazinan-2-one;
4-(4-((2-(4-(((1R,2S)-2-phenylcyclopropyl)amino)piperidin-1-yl)ethyl)amino)phenyl)morpholin-3-one;
N-((1R,2S)-2-phenylcyclopropyl)-1-(2-((4-(piperidin-1-yl)phenyl)amino)ethyl)piperidin-4-amine;
1-(2-((4-morpholinophenyl)amino)ethyl)-N-((1R,2S)-2-phenylcyclopropyl)piperidin-4-amine;
1-(2-((4-(4-methylpiperazin-1-yl)phenyl)amino)ethyl)-N-((1R,2S)-2-phenylcyclopropyl)piperidin-4-amine;
1-(4-((2-(4-(((1R,2S)-2-phenylcyclopropyl)amino)piperidin-1-yl)ethyl)amino)phenyl)pyrrolidin-2-one;
3-(4-((2-(4-(((1R,2S)-2-phenylcyclopropyl)amino)piperidin-1-yl)ethyl)amino)phenyl)oxazolidin-2-one;
1-methyl-3-(4-((2-(4-(((1R,2S)-2-phenylcyclopropyl)amino)piperidin-1-yl)ethyl)amino)phenyl)imidazolidin-2-one;
1-(4-(4-((2-(4-(((1R,2S)-2-phenylcyclopropyl)amino)piperidin-1-yl)ethyl)amino)phenyl)piperazin-1-yl)ethan-1-one;
3-(4-((2-(3-((((1R,2S)-2-phenylcyclopropyl)amino)methyl)azetidin-1-yl)ethyl)amino)phenyl)-1,3-oxazinan-2-one;
N,6-dimethyl-N-(2-(4-(((1R,2S)-2-phenylcyclopropyl)amino)piperidin-1-yl)ethyl)pyridin-3-amine;
1-(2-((4-bromophenyl)(methyl)amino)ethyl)-N-((1R,2S)-2-phenylcyclopropyl)piperidin-4-amine;
3-(4-(methyl(2-(4-(((1R,2S)-2-phenylcyclopropyl)amino)piperidin-1-yl)ethyl)amino)phenyl)-1,3-oxazinan-2-one;
1-methyl-3-(2-(4-(((1R,2S)-2-phenylcyclopropyl)amino)piperidin-1-yl)ethyl)urea;
N-methyl-N-(2-(4-(((1R,2S)-2-phenylcyclopropyl)amino)piperidin-1-yl)ethyl)acetamide;
N,2-dimethyl-N-(2-(4-(((1R,2S)-2-phenylcyclopropyl)amino)piperidin-1-yl)ethyl)pyridin-4-amine;
1-(2-(4-bromo-2-fluorophenoxy)ethyl)-N-((1R,2S)-2-phenylcyclopropyl)piperidin-4-amine;
2-((2-(4-(((1R,2S)-2-phenylcyclopropyl)amino)piperidin-1-yl)ethyl)amino)isonicotinic acid; and
3-((2-(4-(((1R,2S)-2-phenylcyclopropyl)amino)piperidin-1-yl)ethyl)amino)isonicotinic acid.

and pharmaceutically acceptable salts of the foregoing compounds, including, but not limited to dihydrochloride salts.

In yet another aspect of the invention, compounds of formula (I) and formula (II) are provided wherein Y is —C(O)—, s is 0, m is 0, $R^2$ is $C_1$-$C_4$ alkyl or aralkyl, and $R^6$ is heterocyclyl, wherein the heterocyclyl is piperazinyl, 4-methyl-piperazinyl, 4-acyl-piperazinyl, morpholinyl dimethyl-morpholinyl, or thiomorpholinyl. In certain embodiments of this aspect, Y is —C(O)—, s is 0, m is 0, $R^2$ is methyl, and $R^6$ is piperazinyl, 4-methyl-piperazinyl, 4-acyl-piperazinyl, morpholinyl, dimethyl-morpholinyl or thiomorpholinyl. In certain other embodiments of this aspect, Y is —C(O)—, s is 0, m is 0, $R^2$ is benzyl, and $R^6$ is piperazinyl, 4-methyl-piperazinyl, 4-acyl-piperazinyl, morpholinyl, dimethyl-morpholinyl or thiomorpholinyl.

In yet another aspect of the invention, compounds of formula (I) and formula (II) are provided wherein Y is —C(O)—, L is ethylene, and $R^6$ is heterocyclyl optionally independently substituted one or more $C_1$-$C_3$ alkyl. In certain embodiments, the heterocyclyl optionally independently substituted one or more $C_1$-$C_3$ alkyl is azetidinyl, pyrrolidinyl, pyrazolidinyl, piperidinyl, piperazinyl, 4-methyl-piperazinyl, 4-acyl-piperazinyl, tetrahydropyranyl, 1,3-dioxolanyl, 1,4-dioxanyl, morpholinyl, dimethyl-morpholinyl, thiomorpholinyl, 1,4-dithianyl, or 1,3,5-trithianyl. In other embodiments, the heterocyclyl is:

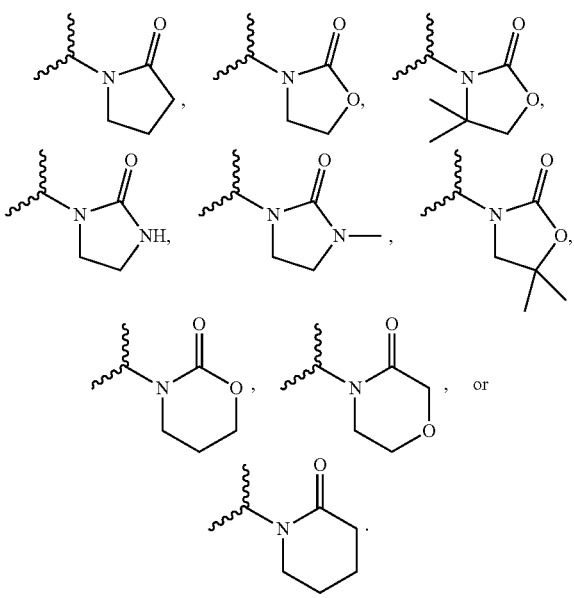

In yet another aspect of the invention, compounds of formula (I) and formula (II) are provided wherein Y is —C(O)—, L is propylene, and $R^6$ is heterocyclyl optionally independently substituted one or more $C_1$-$C_3$ alkyl. In certain embodiments, the heterocyclyl optionally independently substituted one or more $C_1$-$C_3$ alkyl is azetidinyl, pyrrolidinyl, pyrazolidinyl, piperidinyl, piperazinyl, 4-methyl-piperazinyl, 4-acyl-piperazinyl, tetrahydropyranyl, 1,3-dioxolanyl, 1,4-dioxanyl, morpholinyl, dimethylmorpholinyl, thiomorpholinyl, 1,4-dithianyl, or 1,3,5-trithianyl. In other embodiments, the heterocyclyl is:

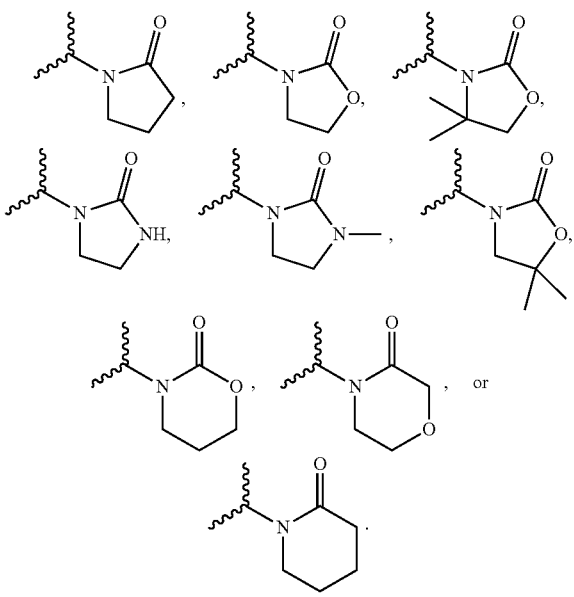

In other embodiments of this aspect, $R^6$ is —$NR^4R^7$. In certain embodiments, $R^7$ is hydroxyl, alkoxy, —$SO_2C_1$-$C_6$alkyl; —$SO_2$cycloalkyl, or —$SO_2$aryl, wherein the cycloalkyl or aryl of each of the —$SO_2$cycloalkyl and —$SO_2$aryl is optionally independently substituted with one or more $R^8$.

In certain embodiments, compounds of formula (I) and formula (II) wherein Y is —C(O)— are:
1-morpholino-2-(4-(((1R,2S)-2-phenylcyclopropyl)amino)piperidin-1-yl)propan-1-one;
N-methoxy-2-(4-(((1R,2S)-2-phenylcyclopropyl)amino)piperidin-1-yl)propanamide;
1-morpholino-3-phenyl-2-(4-(((1R,2S)-2-phenylcyclopropyl)amino)piperidin-1-yl)propan-1-one;
3-(4-(((1R,2S)-2-phenylcyclopropyl)amino)piperidin-1-yl) propanoic acid;
1-morpholino-3-(4-(((1R,2S)-2-phenylcyclopropyl)amino)piperidin-1-yl)propan-1-one;
N-(methylsulfonyl)-3-(4-(((1R,2S)-2-phenylcyclopropyl)amino)piperidin-1-yl)propanamide;
3-(4-(((1R,2S)-2-phenylcyclopropyl)amino)piperidin-1-yl)-1-(piperazin-1-yl)propan-1-one;
3-(4-(((1R,2S)-2-phenylcyclopropyl)amino)piperi din-1-yl)-N-(phenyl sulfonyl)propanamide;
1-(4-methylpiperazin-1-yl)-3-(4-(((1R,2S)-2-phenylcyclopropyl)amino)piperidin-1-yl)propan-1-one;
N-(ethylsulfonyl)-3-(4-(((1R,2S)-2-phenylcyclopropyl)amino)piperidin-1-yl)propanamide;
3-(4-(((1R,2S)-2-phenylcyclopropyl)amino)piperidin-1-yl)-1-thiomorpholinopropan-1-one;
1-(4-methylpiperazin-1-yl)-4-(4-(((1R,2S)-2-phenylcyclopropyl)amino)piperidin-1-yl)butan-1-one;
4-(4-(((1R,2S)-2-phenylcyclopropyl)amino)piperidin-1-yl)-1-(piperazin-1-yl)butan-1-one;
1-morpholino-4-(4-(((1R,2S)-2-phenylcyclopropyl)amino)piperidin-1-yl)butan-1-one;
4-(4-(((1R,2S)-2-phenylcyclopropyl)amino)piperidin-1-yl)-N-(phenyl sulfonyl)butanamide;
4-(4-(((1R,2S)-2-phenylcyclopropyl)amino)piperidin-1-yl) butanoic acid;
N-(cyclopropylsulfonyl)-4-(4-(((1R,2S)-2-phenylcyclopropyl)amino)piperidin-1-yl)butanamide;
N-(ethylsulfonyl)-4-(4-(((1R,2S)-2-phenylcyclopropyl)amino)piperidin-1-yl)butanamide;
N-(methylsulfonyl)-4-(4-(((1R,2S)-2-phenylcyclopropyl)amino)piperidin-1-yl)butanamide;
1-(cis-2,6-dimethylmorpholino)-3-(4-(((1R,2S)-2-phenylcyclopropyl)amino)piperidin-1-yl)propan-1-one;
and pharmaceutically acceptable salts of the foregoing compounds, including, but not limited to, dihydrochloride salts.

In still yet another aspect of the invention, Y is —$NR^4SO_2$— and $R^6$ is $C_1$-$C_6$ alkyl, cycloalkyl or aryl, wherein the cycloalkyl or the aryl is optionally independently substituted with one or more $C_1$-$C_3$ alkyl, halogen, haloalkyl, amino or cyano.

In certain embodiments, compounds of formula (I) and formula (II) wherein Y is —$NR^4SO_2$— are:
N-(2-(4-(((1R,2S)-2-phenylcyclopropyl)amino)piperidin-1-yl)ethyl)methanesulfonamide;
N-(2-(4-(((1R,2S)-2-phenylcyclopropyl)amino)piperidin-1-yl)ethyl)benzenesulfonamide;
N-(2-(4-(((1R,2S)-2-phenylcyclopropyl)amino)piperidin-1-yl)ethyl)propane-2-sulfonamide;
N-(2-(4-(((1R,2S)-2-phenylcyclopropyl)amino)piperidin-1-yl)propyl) methanesulfonamide;
N-methyl-N-(2-(3-((((1R,2S)-2-phenylcyclopropyl)amino)methyl)azetidin-1-yl)ethyl)methanesulfonamide;
N-(2-(3-((((1R,2S)-2-phenylcyclopropyl)amino)methyl) azetidin-1-yl)ethyl)methanesulfonamide;
N-methyl-N-(2-(4-(((1R,2S)-2-phenylcyclopropyl)amino)piperidin-1-yl)ethyl)methanesulfonamide; and N-(2-(4-(((1R,2S)-2-phenylcyclopropyl)amino)piperidin-1-yl)ethyl)cyclopropanesulfonamide;

and pharmaceutically acceptable salts of the foregoing compounds, including, but not limited to, dihydrochloride salts.

In another aspect of the invention, Y is —SO$_2$NR$^4$— and R$^6$ is C$_1$-C$_6$ alkyl or aryl, wherein the aryl is optionally independently substituted with one or more C$_1$-C$_3$ alkyl, halogen, haloalkyl, amino or cyano.

In certain embodiments of this aspect of the invention, compounds of formula (I) and formula (II) wherein Y is —SO$_2$NR$^4$— are N-phenyl-2-(4-(((1R,2S)-2-phenylcyclopropyl)amino)piperidin-1-yl)ethane-1-sulfonamide;

N-methyl-2-(4-(((1R,2S)-2-phenylcyclopropyl)amino)piperidin-1-yl)ethane-1-sulfonamide;

and pharmaceutically acceptable salts of the foregoing compounds, including, but not limited to, dihydrochloride salts.

In still yet another aspect of the invention, Y is —NR$^4$C(O)NR$^4$R$^4$ and each R$^4$ is C$_1$-C$_3$ alkyl. An exemplary compound wherein Y is —NR$^4$C(O)NR$^4$R$^4$ is 1,1-dimethyl-3-(2-(4-(((1R,2S)-2-phenylcyclopropyl)amino)piperidin-1-yl)ethyl)urea.

The compounds of formula (I) and formula (II) may be formulated into pharmaceutical compositions.

Pharmaceutical Compositions

In another aspect, the invention provides pharmaceutical compositions comprising a LSD1 inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In certain other embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods described herein.

Methods of Use

In yet another aspect, the invention provides for methods for inhibiting LSD1 activity in a cell, comprising contacting the cell in which inhibition of LSD1 activity is desired with a therapeutically effective amount of a compound of formula (I), pharmaceutically acceptable salts thereof or pharmaceutical compositions containing the compound or pharmaceutically acceptable salt thereof.

The compositions and methods provided herein are particularly deemed useful for inhibiting LSD1 activity in a cell. In one embodiment, a cell in which inhibition of LSD1 activity is desired is contacted with a therapeutically effective amount of a compound of formula (I) to negatively modulate the activity of LSD1. In other embodiments, a therapeutically effective amount of pharmaceutically acceptable salt or pharmaceutical compositions containing the compound of formula (I) may be used.

By negatively modulating the activity of LSD1, particularly in cases for cells overexpressing the LSD1 enzyme or somatic mutations that activate the LSD1 enzyme, the methods are designed to restore normal cellular transcription expression patterns, e.g., by altering methylation pattern of H3K4, to inhibition undesired cellular proliferation resulting from enhanced LSD1 activity within the cell. The cells may be contacted in a single dose or multiple doses in accordance with a particular treatment regimen to effect the desired negative modulation of LSD1. The degree of mono- and dimethylation of histone H3K4 may be monitored in the cell using well known methods, including those described in Example 83 below, to assess the effectiveness of treatment and dosages may be adjusted accordingly by the attending medical practitioner.

In another aspect, methods of treating cancer comprising administering to a patient having cancer a therapeutically effective amount of a compound of formula (I), pharmaceutically acceptable salts thereof or pharmaceutical compositions comprising the compound or pharmaceutically acceptable salts thereof are provided.

The compositions and methods provided herein may be used for the treatment of a wide variety of cancer including tumors such as prostate, breast, brain, skin, cervical carcinomas, testicular carcinomas, etc More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or postoperatively. The degree of mono- and dimethylation of histone H3K4 may be monitored in the patient using well known methods, including those described in Example 83 below, to access the effectiveness of treatment, along with other prognostic or biological factors, and dosages may be adjusted accordingly by the attending medical practitioner.

REACTION SCHEMES AND EXAMPLES

The compounds of the present invention may be prepared using commercially available reagents using the synthetic methods and reaction schemes described herein, or using other reagents and conventional methods well known to those skilled in the art.

For instance, compounds of the present invention may be prepared according to the general reaction schemes I-V.

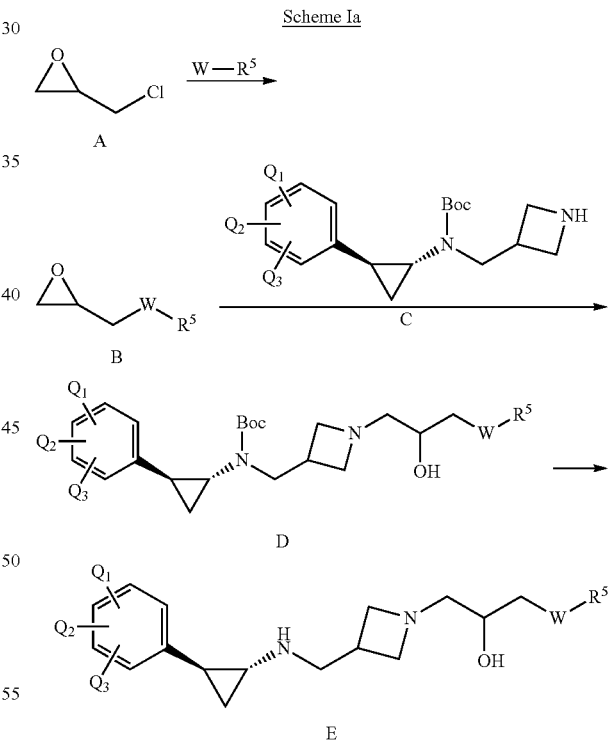

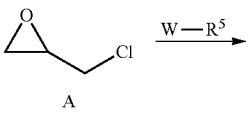

-continued

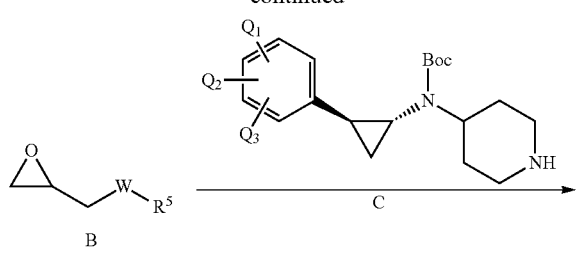

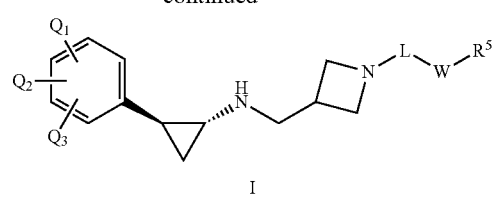

Schemes Ia and Ib illustrate preparation of compounds of formula (I) or formula (II), respectively, wherein W is $NR^4$ or O, (or Y is S, SO, or $SO_2$) and L is an epichlorohydrin derivative. The epichlorihydrin A undergoes substitution with nucleophile $W-R^5$ to afford intermediate B (Step 1). The substitution proceeds in solvents such as MeCN in the presence of a base such as $K_2CO_3$, typically at an elevated temperature. In the case where Y is SO or $SO_2$, the initial substitution with a nucleophile of the form $R^6SH$ will be followed by oxidation to the sulfoxide or sulfone derivative yielding $Y-R^6$. Reaction of B with amines C affords compounds D (Step 2). The epoxide ring opening also typically proceeds under conditions similar to Step 1. Removal of the protecting group in Step 3 to afford compounds E typically proceeds with an acid such as TFA in a solvent such as DCM.

Scheme IIa

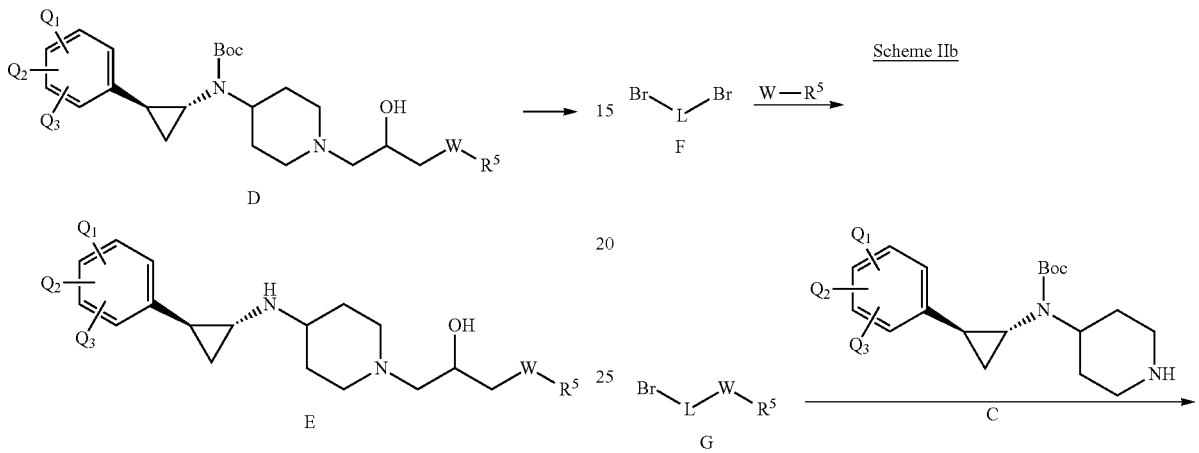

Scheme IIb

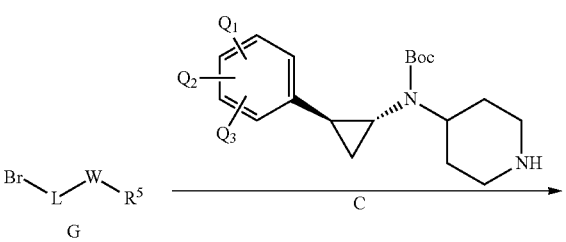

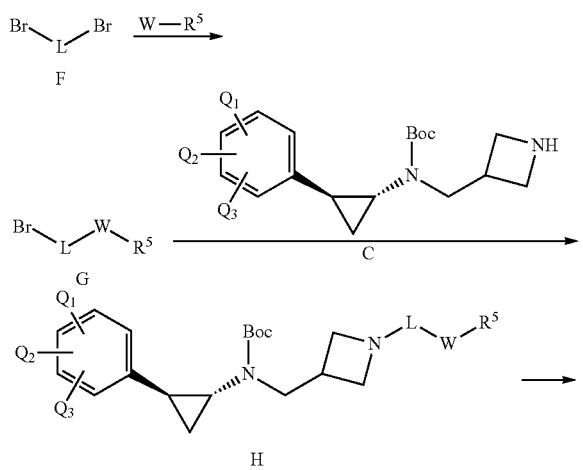

Schemes IIa and IIb illustrate preparation of compounds of formula (I) and formula (II), respectively, wherein W is $NR^4$ or O, (or Y is S, SO or $SO_2$), and L is an alkyl derivative. Reagent F undergoes substitution with nucleophile $W-R^5$ to afford intermediate G (Step 1). The substitution proceeds in solvents such as acetone in the presence of a base such as $K_2CO_3$. In the case where Y is SO or $SO_2$, the initial substitution with a nucleophile of the form $R^6SH$ will be followed by oxidation to the sulfoxide or sulfone derivative yielding $Y-R^6$. Reaction of G with amines C affords compounds H (Step 2). This substitution typically proceeds under conditions similar to Step 1. Alternative bases and solvents such as $Cs_2CO_3$ and MeCN may also be effective. Removal of the protecting group in Step 3 to afford compounds I typically proceeds with an acid such as TFA in a solvent such as DCM.

Scheme IIIa

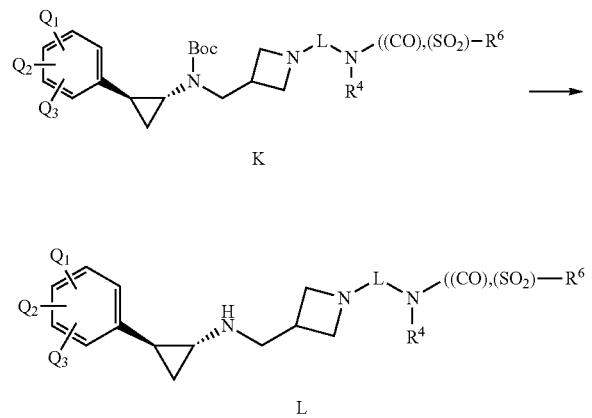

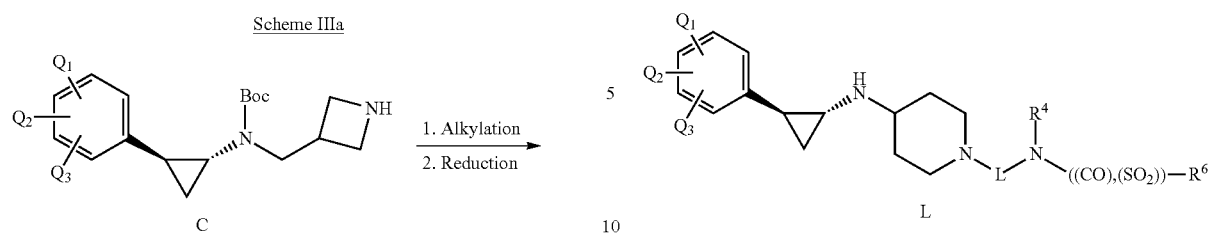

Scheme IIIa and Scheme IIIb illustrate preparation of compounds of formula (I) and formula (II), respectively, wherein Y is NR⁴SO₂ or NR⁴C(O). Intermediate C undergoes alkylation with a nitrile derivative, which is subsequently reduced to afford free amines J. In one case, alkylation with, for example, chloromethyl acetonitrile in a solvent such as acetone with a base such as K₂CO₃ would afford an intermediate that could be reduced to give the amine where L is —CH₂CH₂—. Alternatively, amines J could arise from the alkylation of intermediates C with a protected amine derivative. Functionalization of amines J would give rise to derivatives K, which would give targets L upon deprotection. The functionalization of K would proceed, for example, by reaction with sulfonyl or acyl chlorides. Removal of the Boc protecting group in the final step proceeds with acids such as TFA in solvents such as DCM.

Scheme IVa

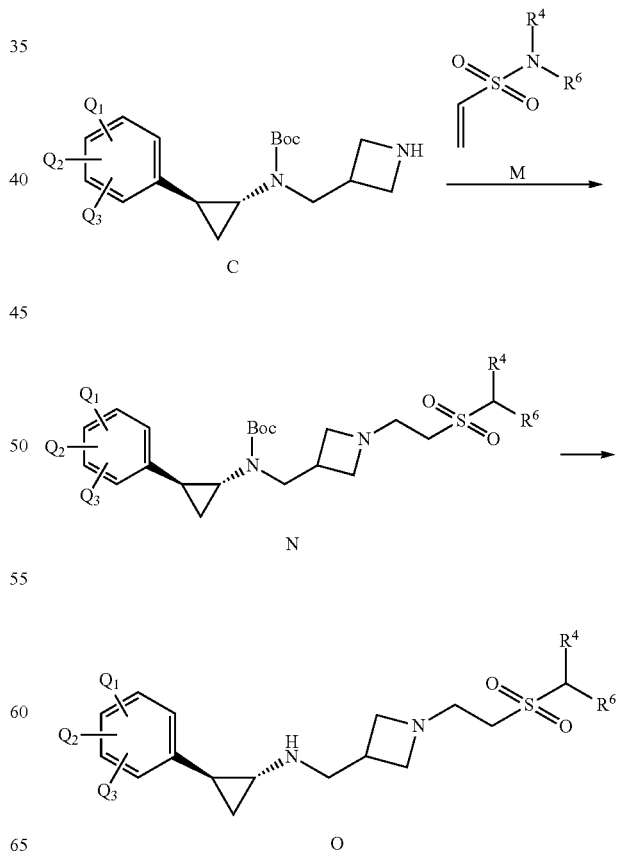

Scheme IIIb

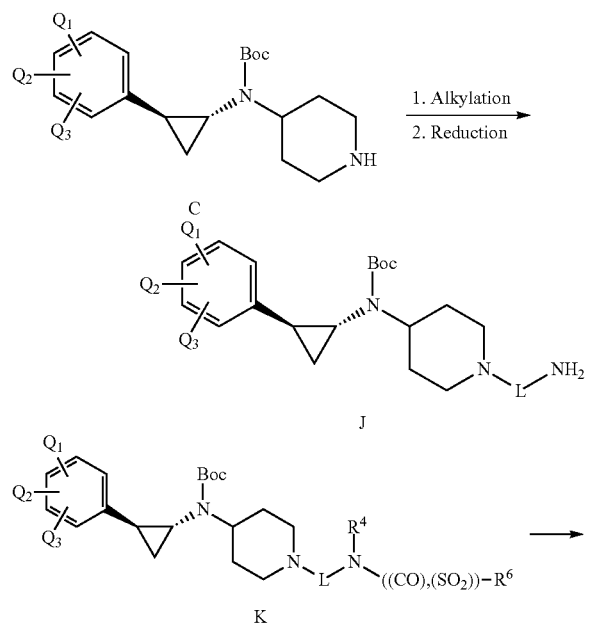

Scheme IVb

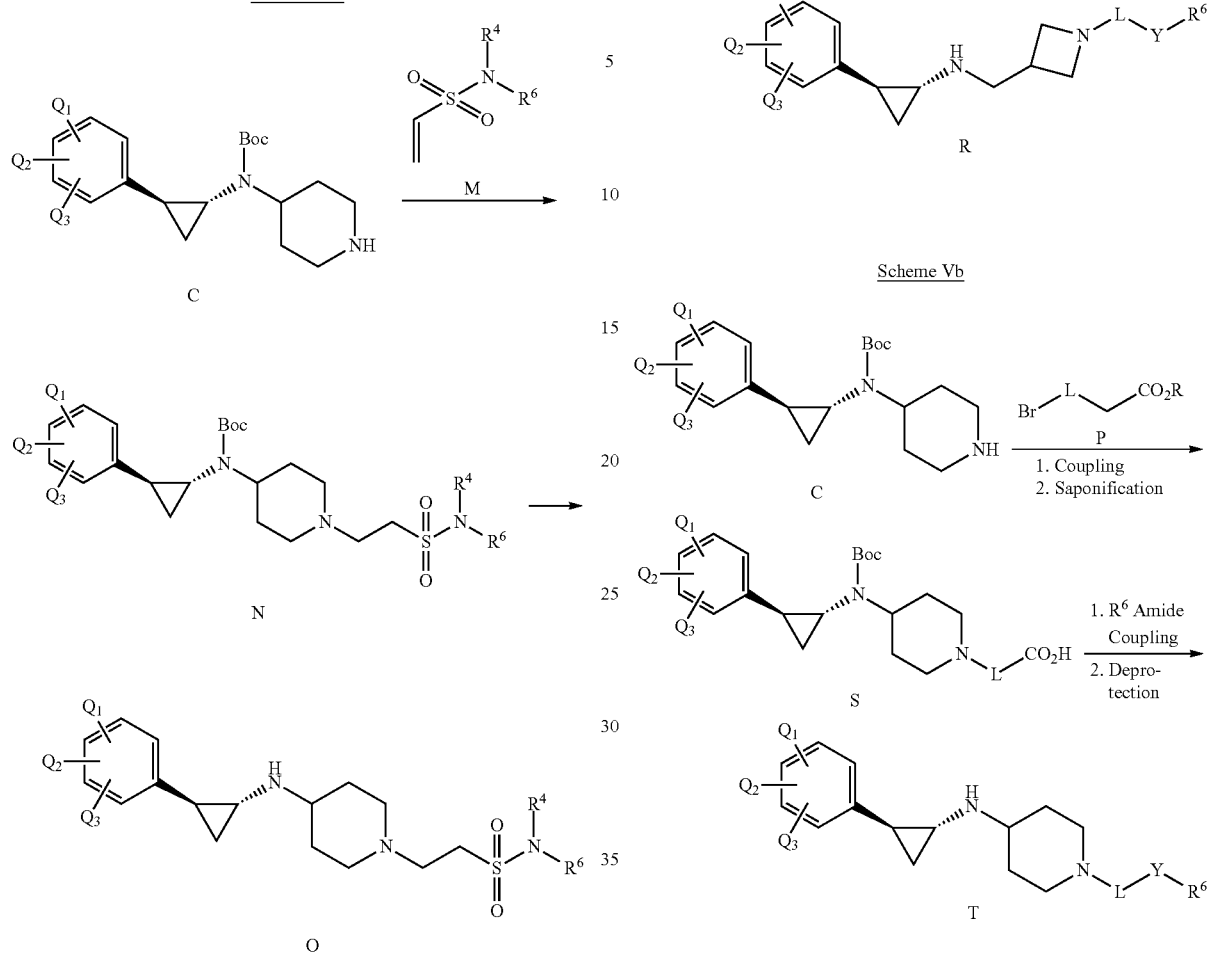

Scheme Vb

Schemes IVa and IVb illustrate preparation of compounds of formula (I) and formula (II), respectively, wherein Y is $SO_2NR^4$. Intermediate C undergoes addition, for example with a vinyl sulfonamide derivative M, to afford compounds N. Removal of the Boc protecting group in the final step proceeds with acids such as TFA in solvents such as DCM to afford derivatives O.

Scheme Va

Schemes Va and Vb illustrate preparation of compounds of formula (I) and formula (II), respectively, wherein Y is —CO—. Intermediate C is alkylated with a halogen derivative P and the ester is cleaved to afford carboxylic acids S. This substitution proceeds in a solvent such as DMF with a base such as TEA and potassium iodide. Removal of the ester group occurs with a base such as NaOH in a solvent such as THF. Amide bond formation with a species $R^6$ followed by removal of the protecting group affords compounds T. The amidation using $R^6$ reaction proceeds, for example, in dichloromethane with EDC/HOBt. Removal of the Boc group proceeds, for example, with a dilute solution of HCl in dioxane.

The following Examples are intended to illustrate further certain embodiments of the invention and are not intended to limit the scope of the invention.

Example 1

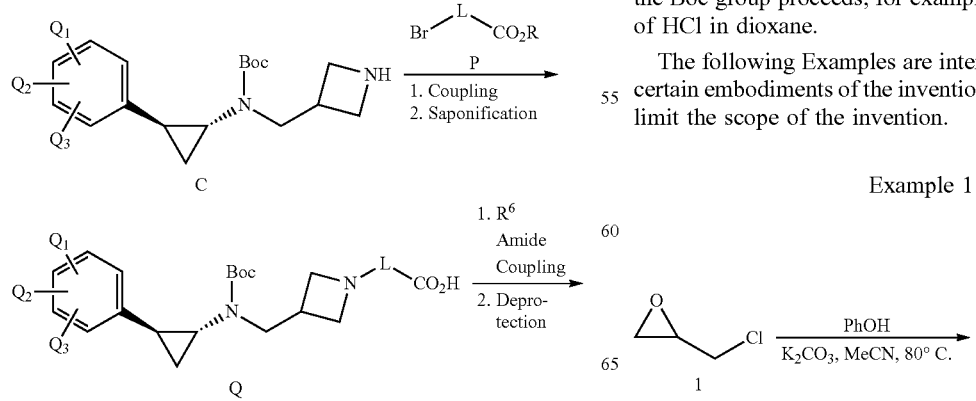

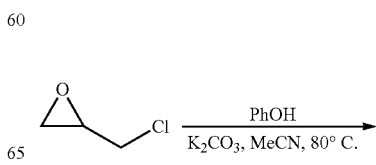

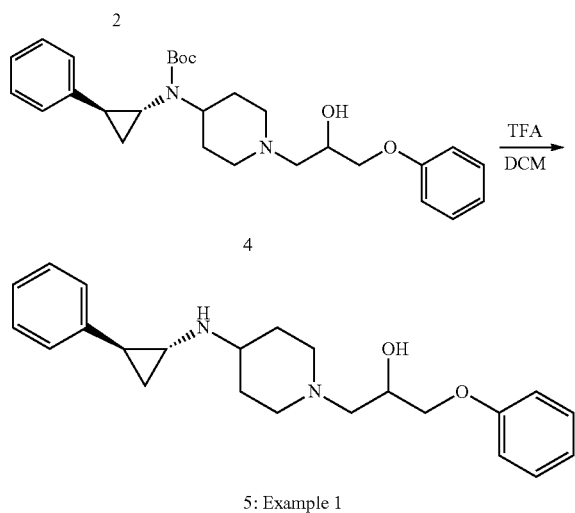

1-phenoxy-3-[4-[[trans-2-phenylcyclopropyl]amino]-1-piperidyl] propan-2-ol (5)

Step 1. 2-(phenoxymethyl)oxirane (2)

A solution of 2-(chloromethyl)oxirane (3.93 g, 42.5 mmol, 3.33 mL, 2.00 eq), phenol (2.00 g, 21.3 mmol, 1.87 mL, 1.00 eq) and K₂CO₃ (8.81 g, 63.8 mmol, 3.00 eq) in MeCN (40.0 mL) was stirred at 80° C. for 12 hours. After completion, the mixture was filtered and the filtrate was concentrated under vacuum. The residue was purified by silica gel chromatography (eluent: PE/EA 25/1) to give 2-(phenoxymethyl)oxirane (2.20 g, 13.9 mmol, 65.5% yield, 95.0% purity) as a colorless oil. LCMS [M+41+1]: 192.

¹H NMR (400 MHz, methanol-d4) δ=7.27-7.23 (m, 2H), 6.94-6.91 (m, 3H), 4.28-4.25 (dd, J=11.2, 2.4 Hz, 1H), 3.86-3.81 (dd, J=11.2, 6.0 Hz, 1H), 3.32-3.30 (m, 1H), 2.86-2.83 (dd, J=5.2, 4.4 Hz, 1H), 2.72-2.71 (dd, J=5.2, 2.8 Hz, 1H).

Step 2. tert-butyl (1-(2-hydroxy-3-phenoxypropyl)piperidin-4-yl)-N-(trans-2-phenylcyclopropyl)carbamate (4)

A suspension of 2-(phenoxymethyl)oxirane (200 mg, 1.33 mmol, 1.00 eq), tert-butyl N-[trans-2-phenylcyclopropyl]-N-(4-piperidyl) carbamate (421 mg, 1.33 mmol, 1.00 eq) and K₂CO₃ (368 mg, 2.66 mmol, 2.00 eq) in MeCN (5.00 mL) was stirred at 80° C. for 14 hours. After completion, the mixture was filtered. The filtrate was concentrated under vacuum. The residue was purified by silica gel chromatography (PE/EA 1/0 to 5/1) to give tert-Butyl N-[1-(2-hydroxy-3-phenoxy-propyl)-4-piperidyl]-N-[trans-2-phenyl-cyclopropyl]carbamate (400 mg, 857 umol, 64.5% yield) as colorless oil. LCMS [M+1]: 467.

¹H NMR (400 MHz, chloroform-d) δ=7.32-7.27 (m, 4H), 7.22-7.18 (m, 1H), 7.11-7.09 (m, 2H), 6.95-6.93 (m, 3H), 4.08-4.06 (m, 1H), 4.00-3.98 (m, 2H), 3.74-3.71 (m, 1H), 3.09-2.92 (m, 2H), 2.59-2.52 (m, 3H), 2.39 (m, 1H), 2.14-2.13 (m, 2H), 2.08-2.06 (m, 2H), 1.82-1.74 (m, 2H), 1.45 (m, 9H), 1.42-1.40 (m, 1H), 1.27-1.16 (s, 1H)

Step 3. 1-phenoxy-3-(4-(((trans)-2-phenylcyclopropyl)amino)piperidin-1-yl)propan-2-ol (5)

A solution of tert-butyl N-[1-(2-hydroxy-3-phenoxy-propyl)-4-piperidyl]-N-[trans-2-phenylcyclopropyl]carbamate (150 mg, 321 umol, 1.00 eq) and TFA (366 mg, 3.21 mmol, 238 uL, 10.0 eq) in DCM (5.00 mL) was stirred at 28° C. for 1 hour. After completion, saturated NaHCO₃ (10 mL) was added into the mixture. The mixture was extracted with DCM (3×20 mL), the combined organic phase was concentrated under vacuum. The residue was purified by Prep-HPLC (Instrument: GX-A; Column: PhenomenexGemini 150*25 mm*10 um; Condition: water (0.05% ammonia hydroxide v/v)-ACN; Begin B: 55; End B: 85; Gradient Time (min): 12; 100% B Hold Time (min): 2; FlowRate (ml/min): 25). 1-phenoxy-3-(4-(((trans)-2-phenylcyclopropyl)amino)piperidin-1-yl)propan-2-ol (5) (51.0 mg, 139 umol, 43.3% yield) was obtained as yellow oil. LCMS [M+1]: 367

¹H NMR (400 MHz, methanol-d4) δ=7.27-7.21 (m, 4H), 7.14-7.12 (m, 1H), 7.05-7.03 (m, 2H), 6.94-6.92 (m, 3H), 4.13 (m, 1H), 4.12-3.91 (m, 2H), 3.07 (m, 2H), 2.65-2.60 (m, 3H), 2.33-2.31 (m, 3H), 1.95-1.90 (m, 3H), 1.55-1.52 (m, 2H), 1.09-1.03 (m, 2H).

Example 2

1-(2-methoxy-3-phenoxy-propyl)-N-[trans-2-phenyl-cyclopropyl]piperidin-4-amine (7)

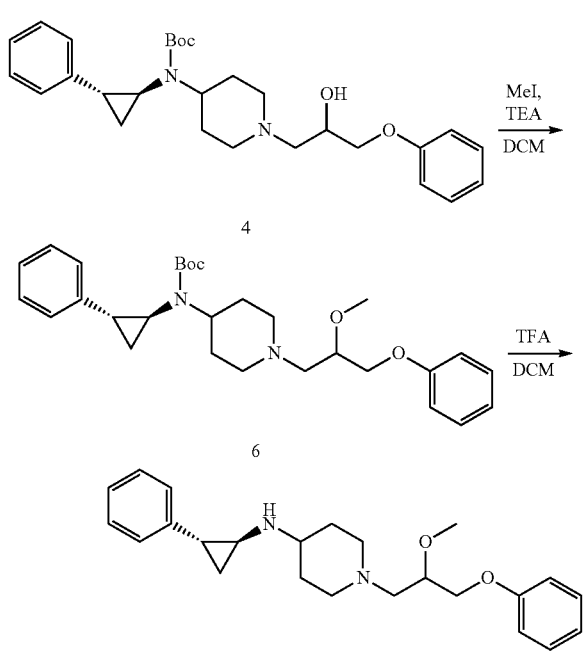

Step 1. tert-butyl N-[1-(2-methoxy-3-phenoxy-propyl)-4-piperidyl]-N-[trans-2-phenylcyclopropyl] carbamate (6)

To a solution of 4 (150 mg, 321 umol, 1.00 eq) in THF (5.00 mL) was added NaH (15.4 mg, 6.4 mmol, 2.00 eq) at 0° C. After stirring for 1 hour, MeI (2.41 g, 17.0 mmol, 1.06 mL, 52.8 eq) was added at 0° C. The mixture was stirred at 28° C. for 2 hours. After completion, the mixture was poured into saturated NH$_4$Cl aq (20 mL), extracted with DCM (3×30 mL), and the combined organic phase was concentrated under vacuum. The residue was purified by Prep-TLC (PE/EA 2/1, Rf=0.8). tert-butyl N-[1-(2-methoxy-3-phenoxy-propyl)-4-piperidyl]-N-[trans-2-phenylcyclopropyl] carbamate (90.0 mg, 180 umol, 56.1% yield, 96.2% purity) was obtained as a yellow oil. LCMS [M+1]: 481

$^1$H NMR (400 MHz, methanol-d4) δ=7.27-7.22 (m, 4H), 7.12-7.10 (m, 3H), 6.95-6.92 (m, 3H), 4.09-4.08 (m, 1H), 4.03-3.99 (m, 1H), 3.75-3.70 (m, 2H), 3.48 (s, 3H), 3.20-3.02 (m, 2H), 2.68-2.60 (m, 3H), 2.28-2.08 (m, 5H), 1.75 (m, 2H), 1.42-1.39 (m, 10H), 1.29-1.24 (m, 1H).

Step 2. 1-(2-methoxy-3-phenoxy-propyl)-N-[trans-2-phenylcyclopropyl] piperidin-4-amine (7)

Treatment of compound 6 with TFA in a manner similar to Example 1 afforded the title compound as a yellow oil (66.0 mg, 160 umol, 85.2% yield, 92% purity). LCMS [M+1]: 381

$^1$H NMR (400 MHz, methanol-d4) δ=7.28-7.22 (m, 4H), 7.15-7.09 (m, 1H), 7.05-7.03 (m, 2H), 6.94-6.91 (m, 3H), 4.11-4.07 (m, 1H), 4.02-3.98 (m, 1H), 3.77 (m, 1H), 3.48-3.47 (m, 3H), 3.05 (m, 2H), 2.68-2.66 (m, 3H), 2.35-2.27 (m, 3H), 1.95-1.91 (m, 3H), 1.63-1.44 (m, 2H), 1.09-1.03 (m, 2H).

Example 3

1-anilino-3-[4-[[trans-2-phenylcyclopropyl]amino]-1-piperidyl] propan-2-ol (10)

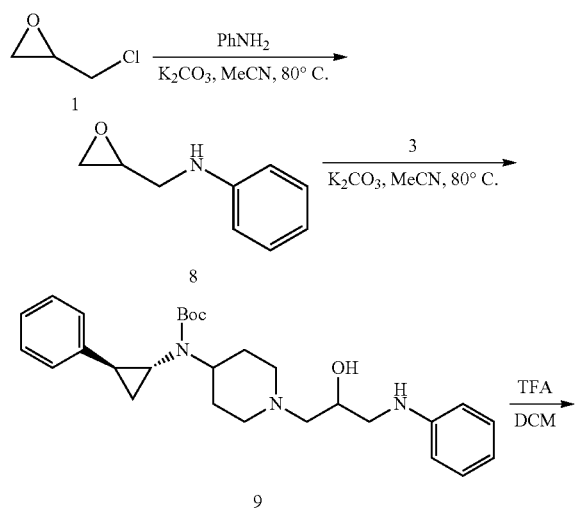

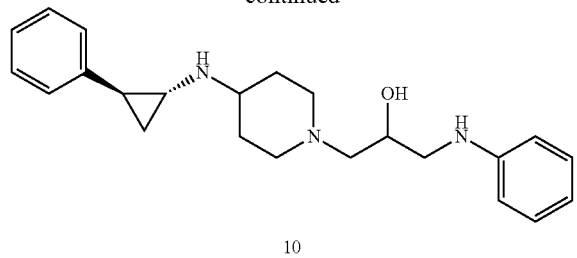

Following the general procedure of Example 1, compound 10 was prepared from compound 1:

Step 1. N-(oxiran-2-ylmethyl)aniline (8)

After completion, the mixture was filtered and the filtrate was concentrated. The residue was purified by Prep-HPLC (Instrument: HPLC-D; Column: Phenomenex Synergi Max-RP 250*80 10 u; Condition: water (0.1% TFA)-ACN; Begin B: 0; End B: 25% ACN; Gradient Time (min): 37 MIN; 52%; FlowRate (ml/min): 80). Compound 8 (800 mg, 3.22 mmol, 15.0% yield, 60.0% purity) was obtained as colorless oil. LCMS [M+1]: 150.

$^1$H NMR (400 MHz, methanol-d4) δ=7.36-7.07 (m, 1H), 6.65-6.60 (m, 1H), 3.42-3.39 (m, 1H), 3.16-3.13 (m, 2H), 2.77-2.75 (m, 1H), 2.63-2.61 (m, 1H)

Step 2. tert-butyl N-[1-(3-anilino-2-hydroxy-propyl)-4-piperidyl]-N-[trans-2-phenylcyclopropyl] carbamate (9)

After completion, the mixture was filtered and the filtrate was concentrated under vacuum. The residue was purified by silica gel chromatography (eluent: PE/EA 1/0 to 5/1). Compound 9 (250 mg, 537 umol, 53.2% yield) was obtained as colorless oil. LCMS [M+1]: 466.

$^1$H NMR (400 MHz, methanol-d4) δ=7.29-7.20 (m, 2H), 7.22-7.09 (m, 5H), 6.66-6.61 (m, 3H), 4.15-4.13 (m, 1H), 3.96-3.71 (m, 2H), 3.18-3.06 (m, 4H), 2.63-2.60 (m, 3H), 2.39-2.18 (m, 2H), 2.13-2.09 (m, 2H), 1.76 (m, 2H), 1.42-1.37 (m, 10H), 1.26-1.23 (m, 1H).

Step 3. 1-anilino-3-[4-[[trans-2-phenylcyclopropyl]amino]-1-piperidyl] propan-2-ol (10)

After completion, saturated NaHCO$_3$ (10 mL) was added into the mixture. The mixture was extracted with DCM (3×20 mL), the combined organic phase was concentrated under vacuum. The residue was purified by Prep-HPLC (Instrument: GX-I; Column: YMC-ActusODS-AQ 150*30 5 u; Condition: water (0.1% TFA)-ACN; Begin B: 8; End B: 38; Gradient Time (min): 11; 100% B Hold Time (min): 2; FlowRate (ml/min): 25). Compound 10 (83.0 mg, 189 umol, 35.3% yield, 2HCl) was obtained as yellow oil. LCMS [M+1]: 366.

$^1$H NMR (400 MHz, methanol-d4) δ=7.31 (m, 2H), 7.25-7.23 (m, 1H), 7.18-7.14 (m, 4H), 6.76-6.71 (m, 3H), 4.25-4.23 (dd, J=10.4, 3.2 Hz, 1H), 3.81-3.77 (m, 2H), 3.67 (m, 1H), 3.35 (m, 1H), 3.25-3.19 (m, 5H), 3.00-2.99 (m, 1H), 2.49-2.39 (m, 3H), 2.11 (m, 2H), 1.55-1.51 (m, 1H), 1.47-1.43 (m, 1H)

Example 4

1-(N-methylanilino)-3-[4-[[trans-2-phenylcyclopropyl]amino]-1-piperidyl]propan-2-ol

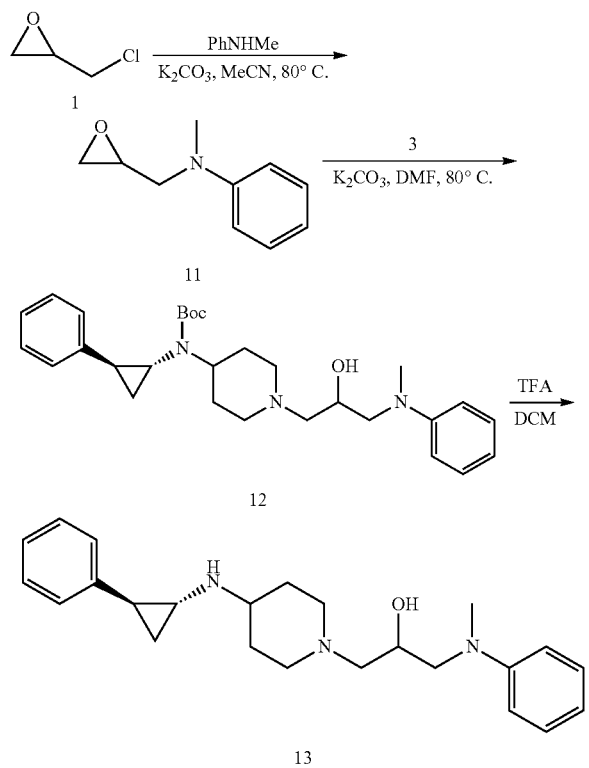

Following the general procedure of Example 1, compound 13 was prepared from compound 1:

Step 1. N-methyl-N-(oxiran-2-ylmethyl)aniline (11)

After completion, the mixture was filtered and the filtrate was concentrated under vacuum. The residue was purified by Prep-HPLC (Instrument: SFC-A; Column: Daiso 250*50 mm, 10 um; Condition: water (0.1% TFA)-ACN; Begin B: 0% ACN; End B: 20% ACN; Gradient Time (min): 34 MIN; 40%; FlowRate (ml/min): 80). Compound 11 (300 mg, 1.58 mmol, 8.47% yield, 86.0% purity) was obtained as a colorless oil.

$^1$H NMR (400 MHz, methanol-d4) δ=7.22-7.17 (m, 2H), 6.81-6.79 (d, J=8.0 Hz, 2H), 6.70-6.67 (m, 1H), 3.70-3.66 (m, 1H), 3.36-3.31 (m, 2H), 2.97 (s, 3H), 2.77-2.75 (m, 1H), 2.56-2.54 (m, 1H).

Step 2. tert-butyl N-[1-[2-hydroxy-3-(N-methylanilino)propyl]-4-piperidyl]-N-[trans-2-phenylcyclopropyl]carbamate (12)

After completion, the mixture was cooled to 28° C., the precipitate was filtered off. The filtrate was concentrated under vacuum. The residue was purified by Prep-TLC (PE/EA 2/1, P1: Rf=0.6) Compound 12 (200 mg, 414 umol, 45.0% yield, 99.2% purity) was obtained as yellow oil. LCMS [M+1]: 480.

$^1$H NMR (400 MHz, methanol-d4) δ=7.26-7.22 (m, 2H), 7.16-7.10 (m, 5H), 6.78-6.76 (m, 2H), 6.65 (m, 1H), 4.13 (br. s., 1H), 3.76-3.75 (m, 1H), 3.39-3.31 (m, 4H), 2.99 (s, 3H), 2.67-2.64 (m, 5H), 2.13-2.11 (m, 3H), 1.90-1.83 (m, 2H), 1.42-1.37 (m, 10H), 1.24-1.22 (m, 1H)

After completion, the mixture was poured into saturated NaHCO$_3$ aq (20.0 mL), then extracted with DCM (2×30.0 mL). The combined organic phase was concentrated under vacuum. The residue was purified by Prep-TLC (eluent: DCM/MeOH 20/1). Compound 13 (60.0 mg, 148 umol, 35.6% yield, 93.8% purity) was obtained as yellow oil. LCMS [M+1]: 380.

$^1$H NMR (400 MHz, methanol-d4) δ=7.22-7.20 (m, 2H), 7.16-7.12 (m, 3H), 7.05-7.03 (m, 2H), 6.77-6.75 (d, J=8.8 Hz, 2H), 6.64-6.63 (m, 1H), 4.08-4.05 (m, 1H), 3.44 (m, 1H), 3.27 (m, 1H), 3.15-3.02 (m, 2H), 2.98 (s, 3H), 2.78-2.67 (m, 1H), 2.57-2.53 (m, 2H), 2.33-2.31 (m, 3H), 2.98-1.90 (m, 3H), 1.54 (m, 2H), 1.09-1.03 (m, 2H).

Example 5

2-methyl-1-phenoxy-3-(4-(((trans)-2-phenylcyclopropyl)amino)piperidin-1-yl)propan-2-ol (16)

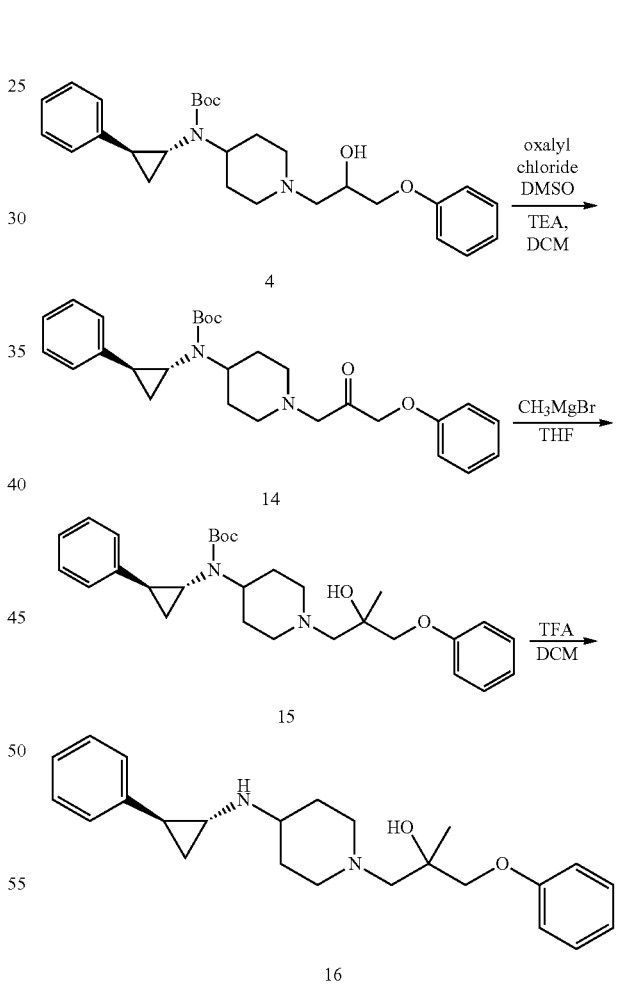

Step 1. tert-butyl N-[1-(2-oxo-3-phenoxy-propyl)-4-piperidyl]-N-[(trans)-2-phenylcyclopropyl]carbamate (14)

To a solution of oxalyl chloride (212 mg, 1.67 mmol, 146 uL, 3.00 eq) in DCM (0.5 mL) was added DMSO (304 mg, 3.90 mmol, 304 uL, 7.00 eq) in DCM (0.5 mL), followed by tert-butyl N-[1-(2-hydroxy-3-phenoxy-propyl)-4-piperidyl]-N-[(trans)-2-phenylcyclopropyl]carbamate (260 mg, 557.21 umol, 1.00 eq) in DCM (1 mL), then the mixture was stirred at −70° C. for 1.5 hours. A solution of TEA (845 mg, 8.36 mmol, 1.16 mL, 15.00 eq) in DCM (0.5 mL) was added to the solution at −70° C., which was stirred at −70~−15° C. for 30 min. After completion, the mixture was quenched with water (10 mL), extracted with DCM (2×10 mL), the combined organic phase were washed with 1 N HCl (10 mL), saturated NaHCO$_3$ aqueous (10 mL), brine (10 mL), dried and concentrated to get the crude product. Compound tert-butyl N-[1-(2-oxo-3-phenoxy-propyl)-4-piperidyl]-N-[(trans)-2-phenylcyclopropyl]carbamate (240 mg, 479 umol, 86.12% yield, 92.9% purity) was obtained as a yellow solid. LCMS [M+1]: 465.4.

Step 2. tert-butyl N-[1-(2-hydroxy-2-methyl-3-phenoxy-propyl)-4-piperidyl]-N-[(1S,2R)-2-phenylcyclopropyl]carbamate (15)

To a solution of tert-butyl N-[1-(2-oxo-3-phenoxy-propyl)-4-piperidyl]-N-[(trans)-2-phenylcyclopropyl]carbamate (240 mg, 516 umol, 1.00 eq) in THF (3.00 mL) was added CH$_3$MgBr (3 M, 344 uL, 2.00 eq) dropwise at 0° C., then the mixture was stirred at 0-20° C. for 3 hours. After completion, the mixture was quenched with water (5 mL), diluted with EA (20 mL), washed with saturated NaHCO$_3$ aq (10 mL), brine (10 mL). The organic phase was dried over Na$_2$SO$_4$, filtered, and concentrated under vacuum. Compound 15 (240 mg, 499 umol, 96% yield) was obtained as a yellow solid which was used for the next step directly without further purification. LCMS [M+1]: 481.2.

Step 3. 2-methyl-1-phenoxy-3-[4-[[(1S,2R)-2-phenylcyclopropyl]amino]-1-piperidyl]propan-2-ol (16)

To a mixture of tert-butyl N-[1-(2-hydroxy-2-methyl-3-phenoxy-propyl)-4-piperidyl]-N-[(trans)-2-phenylcyclopropyl]carbamate (240 mg, 499 umol, 1.00 eq) in DCM (4.00 mL) was added TFA (569 mg, 4.99 mmol, 369 uL, 10.0 eq) in one portion at 20° C., then the mixture was stirred at the same temperature for 1 hour. After completion, saturated NaHCO$_3$ aq (20 mL) was added into the mixture, the mixture was extracted with DCM (3×20 mL). The combined organic phase was washed with brine, dried and concentrated under vacuum. The residue was purified by prep-HPLC (Instrument: GX-D; Column: Boston Green ODS 150*30 5 u; Condition: water (0.225% FA)-ACN; Begin B: 6; End B: 36, Gradient Time (min): 11; 100% B Hold Time (min): 4; FlowRate (ml/min): 25) to give 16 as a colorless solid. LCMS [M+1]: 381.1.

$^1$H NMR (400 MHz, METHANOL-d4) δ=7.28-7.21 (m, 4H), 7.11 (d, J=7.2 Hz, 1H), 7.01 (d, J=7.2 Hz, 2H), 6.93-6.90 (m, 3H), 3.86-3.84 (d, J=7.2 Hz, 1H), 3.80-3.78 (d, J=9.2 Hz, 1H), 2.95-2.88 (m, 2H), 2.58-2.54 (m, 1H), 2.49 (s, 2H), 2.29-2.22 (m, 3H), 1.89-1.79 (m, 3H), 1.46-1.40 (m, 2H), 1.25 (s, 3H), 1.07-0.97 (m, 3H)

Example 6

1-phenoxy-3-[3-[[[(trans)-2-phenylcyclopropyl]amino]methyl]azetidin-1-yl]propan-2-ol (19)

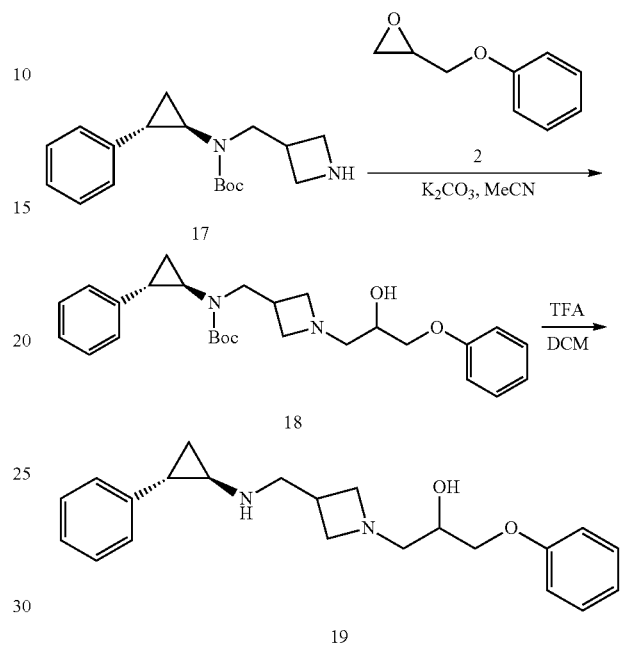

Step 1. tert-butyl N-[[1-(2-hydroxy-3-phenoxy-propyl)azetidin-3-yl]methyl]-N-[(trans)-2-phenylcyclopropyl]carbamate (18)

To a solution of tert-butyl N-(azetidin-3-ylmethyl)-N-[(trans)-2-phenylcyclopropyl]carbamate (100 mg, 331 umol, 1.00 eq) in MeCN (3.00 mL) was added 2-(phenoxymethyl)oxirane 2 (74.5 mg, 496 umol, 67.1 uL, 1.50 eq) and K$_2$CO$_3$ (45.7 mg, 331 umol, 1.00 eq). The mixture was stirred at 80° C. for 12 hours. After completion, the mixture was filtered and the filtrate was concentrated under vacuum. Water (10 mL) and HCl (1M, 1 mL) was added into the mixture. The resulting mixture was extracted with DCM (3×20 mL), the combined organic phase was concentrated under vacuum to give compound 18 (200 mg, crude) was obtained as yellow oil. The crude was used to the next step directly. LCMS [M+1]: 453.

Step 2. 1-phenoxy-3-[3-[[[(trans)-2-phenylcyclopropyl]amino] methyl]azetidin-1-yl]propan-2-ol (19)

A solution of tert-butyl N-[[1-(2-hydroxy-3-phenoxy-propyl)azetidin-3-yl]methyl]-N-[(trans)-2-phenylcyclopropyl]carbamate (200 mg, 442 umol, 1.00 eq) and TFA (50.4 mg, 442 umol, 32.7 uL, 1.00 eq) in DCM (3.00 mL) was stirred at 20° C. for 1 hour. After completion, saturated NaHCO$_3$ aq (10 mL) was added into the mixture, the mixture was extracted with DCM (3×20 mL). The combined organic phase was concentrated under vacuum. The residue was purified by Prep-HPLC (Instrument: GX-D; Column: Boston Green ODS 150*30 5 u; Condition: water (0.225% FA)-ACN; Begin B: 6; End B: 36, Gradient Time (min): 11; 100% B Hold Time (min): 4; FlowRate (ml/min): 25) to give 1-phenoxy-3-[3-[[[(trans)-2-phenylcyclopropyl]amino]methyl]azetidin-1-yl]propan-2-ol (25.0 mg, 71.0 umol, 16.1% yield) as yellow solid. LCMS [M+1]: 353.

$^1$H NMR (400 MHz, methanol-d4) δ=8.33 (br. s, 1H), 7.30-7.22 (m, 4H), 7.13 (m, 1H), 7.08-7.06 (m, 2H), 6.95-6.93 (m, 3H), 4.24 (br. s., 2H), 4.14 (br. s., 1H), 4.01-3.95 (m, 4H), 3.52-3.32 (m, 2H), 3.13-3.07 (m, 3H), 2.42 (br. s., 1H), 1.99 (br. s., 1H), 1.15-1.07 (m, 2H)

Example 7

(R)-1-phenoxy-3-(4-(((1S,2R)-2-phenylcyclopropyl)amino)piperidin-1-yl)propan-2-ol (23)

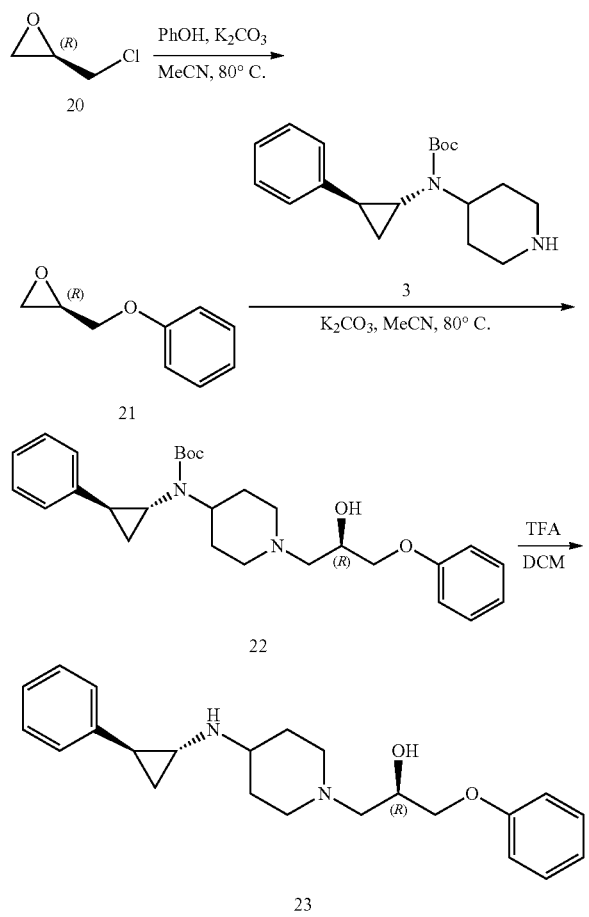

Step 1. (2R)-2-(phenoxymethyl)oxirane (21)

To a solution of phenol (1.00 g, 10.6 mmol, 935 uL, 1.00 eq) in CH$_3$CN (20.0 mL) was added K$_2$CO$_3$ (4.41 g, 31.9 mmol, 3.00 eq) in one portion at 20° C., followed by (2R)-2-(chloromethyl)oxirane (1.97 g, 21.26 mmol, 1.67 mL, 2.00 eq), then the mixture was heated to 70~80° C. and stirred for 8 hours. After completion, the mixture was filtered. The filtrate was concentrated under reduced pressure to give the crude product which was purified over column chromaotograph (PE/EA=50:1~20:1). Compound (2R)-2-(phenoxymethyl)oxirane (1.12 g, 7.35 mmol, 69% yield, 98.5% purity) was obtained as colorless oil.

Step 2. N-[1-[(2R)-2-hydroxy-3-phenoxy-propyl]-4-piperidyl]-N-[(trans)-2-phenylcyclopropyl]carbamate (22)

To a solution of (2R)-2-(phenoxymethyl)oxirane (100 mg, 666 umol, 1.00 eq) and tert-butyl N-[(trans)-2-phenylcyclopropyl]-N-(4-piperidyl)carbamate (211 mg, 666 umol, 1.00 eq) in CH$_3$CN (5.0 mL) was added K$_2$CO$_3$ (184 mg, 1.33 mmol, 2.00 eq) in one portion at 20° C., then the mixture was heated to 80° C. and stirred for 18 hours. After completion, the mixture was filtered, and the filtration was concentrated to give the crude product which was purified over column chromatography (PE/EA=5:1-2:1). Compound 22 (200 mg, 407 umol, 61% yield) was obtained as colorless oil. LCMS [M+1]: 467.2.

Step 3. (2R)-1-phenoxy-3-[4-[[(trans)-2-phenylcyclopropyl] amino]-1-piperidyl]propan-2-ol (23)

To a mixture of 22 (200 mg, 428 umol, 1.00 eq) in DCM (4.00 mL) was added TFA (831 mg, 7.28 mmol, 540 uL, 10.0 eq) in one portion at 20° C., then the mixture was stirred at the same temperature for 1 hour. After completion, saturated NaHCO$_3$ aq (20 mL) was added into the mixture, the mixture was extracted with DCM (3×20 mL). The combined organic phase was washed with brine, dried and concentrated under vacuum. The residue was purified by prep-HPLC (Instrument: GX-D; Column: Boston Green ODS 150*30 5 u; Condition: water (0.225% FA)-ACN; Begin B: 6; End B: 36, Gradient Time (min): 11; 100% B Hold Time (min): 4; FlowRate (ml/min): 25) to give (2R)-1-phenoxy-3-[4-[[(trans)-2-phenylcyclopropyl] amino]-1-piperidyl]propan-2-ol 23 (90.8 mg, 185 umol, 43.2% yield, 98.0% purity) as a yellow solid. LCMS [M+1]: 367.1.

$^1$H NMR (400 MHz, DMSO-d6) δ=7.30-7.22 (m, 4H), 7.20-7.11 (m, 1H), 7.03-7.01 (m, 2H), 6.94-6.92 (d, J=7.8 Hz, 3H), 4.78-4.77 (d, 1H), 3.97-3.94 (m, 1H), 3.93-3.87 (m, 1H), 3.85-3.81 (m, 1H), 2.90-2.72 (m, 2H), 2.45-2.36 (m, 1H), 2.34 (br. s., 2H), 2.24-2.16 (m, 1H), 2.08-1.94 (m, 2H), 1.82-1.67 (m, 3H), 1.41-1.19 (m, 2H), 0.96-0.92 (m, 2H).

Example 8

(S)-1-phenoxy-3-(4-(((1S,2R)-2-phenylcyclopropyl)amino)piperidin-1-yl)propan-2-ol (27)

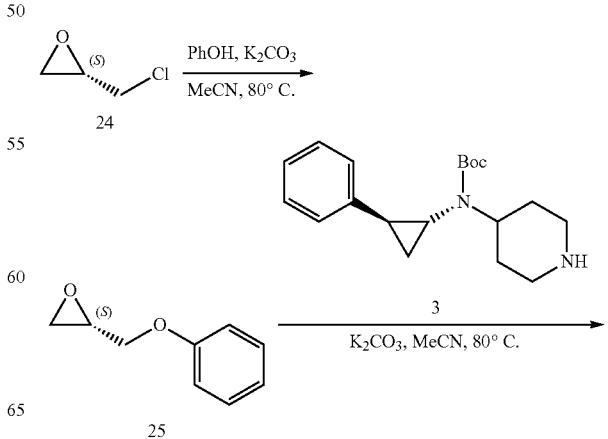

-continued

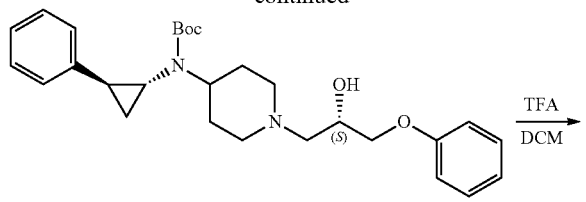

26

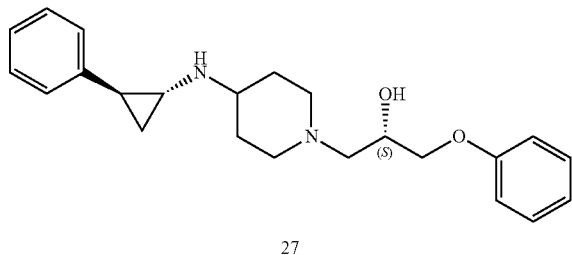

27

Following the general procedure of Example 7, compound 27 was prepared from compound 24.

Step 1. (2S)-2-(phenoxymethyl)oxirane (25)

After completion, the mixture was filtered and the filtrate was concentrated to give the crude product which was purified over column chromaotograph (PE/EA=50:1-20:1). Compound 25 (1.12 g, 7.35 mmol, 69% yield, 98.5% purity) was obtained as colorless oil. LCMS [M+1]: 150.

Step 2. tert-butyl N-[1-[(2S)-2-hydroxy-3-phenoxypropyl]-4-piperidyl]-N-[(trans)-2-phenylcyclopropyl]carbamate (26)

Compound 26 (360 mg, 772 umol, 58% yield) was obtained as colorless oil. LCMS [M+1]: 467.

Step 3. (2S)-1-phenoxy-3-[4-[[(trans)-2-phenylcyclopropl]amino]-1-piperidyl]propan-2-ol (27)

The residue was purified by prep-HPLC (Instrument: GX-D; Column: Boston Green ODS 150*30 5 u; Condition: water (0.225% FA)-ACN; Begin B: 6; End B: 36, Gradient Time (min): 11; 100% B Hold Time (min): 4; FlowRate (ml/min): 25) to give (2S)-1-phenoxy-3-[4-[[(trans)-2-phenylcyclopropyl]amino]-1-piperidyl]propan-2-ol (27) (179 mg, 371 umol, 51% yield, 99.7% purity) as a yellow solid. LCMS [M+1]: 367.

$^1$H NMR (400 MHz, DMSO-d6) δ=7.30-7.20 (m, 4H), 7.12-7.08 (m, 1H), 7.03-7.01 (m, 2H), 6.94-6.92 (d, J=7.6 Hz, 3H), 4.79-4.78 (m, 1H), 3.99-3.93 (m, 1H), 3.93-3.87 (m, 1H), 3.86-3.80 (m, 1H), 2.90-2.72 (m, 2H), 2.45-2.36 (m, 1H), 2.34 (br. s., 2H), 2.24-2.16 (m, 1H), 2.08-1.94 (m, 2H), 1.82-1.67 (m, 3H), 1.33-1.25 (m, 2H), 0.95-0.93 (m, 2H)

Example 9

1-phenoxy-3-[(1R,5S)-6-[[(trans)-2-phenylcyclopropyl]amino]-3-azabicyclo[3.1.1]heptan-3-yl]propan-2-ol (31)

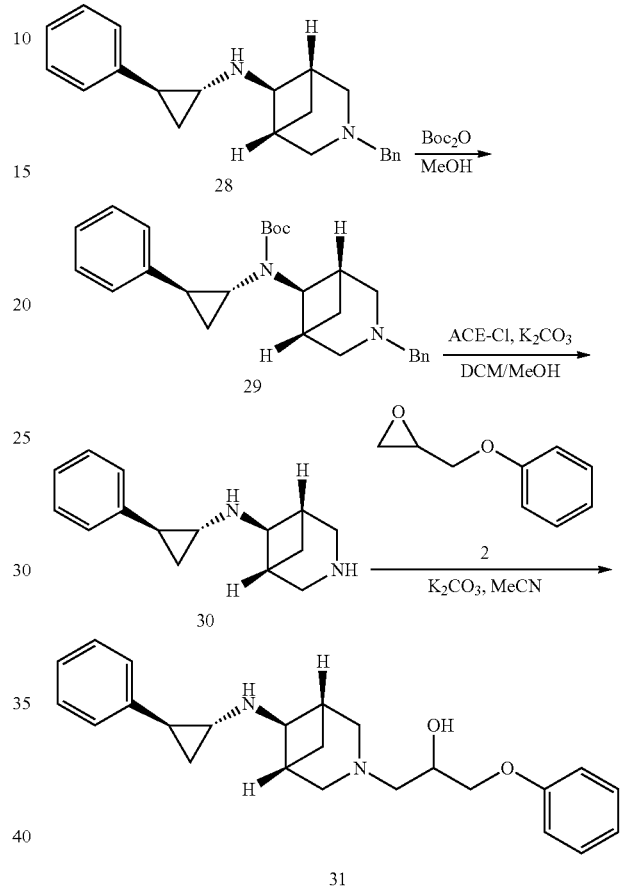

Step 1. tert-butyl N-[(5S)-3-benzyl-3-azabicyclo[3.1.1]heptan-6-yl]-N-[(trans)-2-phenylcyclopropyl]carbamate (29)

To a solution of 3-benzyl-N-(2-phenylcyclopropyl)-3-azabicyclo[3.1.1]heptan-6-amine (50.0 mg, 157 umol, 1.00 eq) in MeOH (2.00 mL) was added (Boc)$_2$O (343 mg, 1.57 mmol, 361 uL, 10.0 eq). The mixture was stirred at 50° C. for 15 hours. After completion, the mixture was concentrated under vacuum. The residue was purified by silica gel chromatography (PE/EA from 100/1 to 5/1) to give tert-butyl N-[(5S)-3-benzyl-3-azabicyclo[3.1.1]heptan-6-yl]-N-[(trans)-2-phenylcyclopropyl]carbamate 29 (50.0 mg, 119 umol, 76.1% yield) as yellow oil. LCMS [M+1]: 419.

Step 2. (5S)—N-[(trans)-2-phenylcyclopropyl]-3-azabicyclo[3.1.1]heptan-6-amine (30)

To a solution of 29 (50.0 mg, 119 umol, 1.00 eq) and K$_2$CO$_3$ (144 mg, 1.43 mmol, 12.0 eq) in DCM (3.00 mL) was added 1-chloroethyl chloroformate (51.2 mg, 358 umol, 3.00 eq). After stirring at 20° C. for 1.5 hours, the reaction mixture was filtered. The filtrate was concentrated under vacuum. The residue was dissolved in MeOH (3.00 mL). The solution was refluxed (65° C.) for 2 hour. After completion, the mixture was filtered and concentrated under vacuum to give (5S)—N-[(trans)-2-phenylcyclopropyl]-3-azabicyclo[3.1.1]heptan-6-amine 30 (27.0 mg, crude) as yellow oil. The crude material was used to the next step directly.

Step 3. 1-phenoxy-3-[(1R,5S)-6-[[(trans)-2-phenyl-cyclopropyl]amino]-3-azabicyclo[3.1.1]heptan-3-yl] propan-2-ol (31)

A mixture of 30 (27.0 mg, 118. umol, 1.00 eq),2-(phenoxymethyl)oxirane (26.6 mg, 177 umol, 24.0 uL, 1.50 eq) and K$_2$CO$_3$ (32.7 mg, 237 umol, 2.00 eq) in MeCN (5.00 mL) was stirred at 80° C. for 2 hours under N$_2$. After completion, the mixture was concentrated under vacuum and purified by Prep-HPLC (Instrument: GX-B; Column: Welch Ultimate AQ-C18 150*30 mm*5 um; Condition: water (0.1% TFA)-ACN; Begin B: 22; End B: 52; Gradient Time (min): 12; 100% B Hold Time (min): 2; FlowRate (ml/min): 25) to give 1-phenoxy-3-[(1R,5S)-6-[[(trans)-2-phenylcyclopropyl] amino]-3-azabicyclo[3.1.1]heptan-3-yl] propan-2-ol 31 (2.80 mg, 7.07 umol, 8.92% yield, 95.6% purity) as yellow oil. LCMS [M+1]: 379.

$^1$H NMR (400 MHz, METHANOL-d4) δ=7.32-7.26 (m, 4H), 7.24-7.22 (m, 1H), 7.18-7.16 (m, 2H), 6.96-6.94 (m, 3H), 4.41 (d, J=6.8 Hz, 1H), 4.06-4.00 (m, 4H), 3.76 (br. s., 3H), 3.53-3.48 (m, 2H), 3.01 (br. s., 1H), 2.85 (br. s., 3H), 2.50 (d, J=3.2 Hz, 1H), 2.15-2.12 (m, 1H), 1.56-1.51 (m, 1H), 1.42-1.36 (m, 1H).

Example 10

(trans)-N-[[1-(2-phenoxyethyl)azetidin-3-yl]methyl]-2-phenyl-cyclopropanamine (35)

Step 1. 2-bromoethoxybenzene (33)

A mixture of phenol (200 mg, 2.13 mmol, 187 uL, 1.00 eq), 1,2-dibromoethane (2.40 g, 12.8 mmol, 962 uL, 6.00 eq) and K$_2$CO$_3$ (1.76 g, 12.8 mmol, 6.00 eq) in acetone (200 mL) was stirred at 80° C. under N$_2$ for 15 hours. After completion, the mixture was filtered and the filtrate was concentrated under vacuum. The residue was purified by Prep-TLC (PE/EA 10/1) to give 2-bromoethoxybenzene (160 mg, 738 umol, 35% yield, 92.8% purity) as colorless oil.

$^1$H NMR (400 MHz, METHANOL-d4) δ=7.29-7.25 (m, 2H), 6.94-6.91 (m, 3H), 4.30-4.27 (m, 2H), 3.69-3.63 (m, 2H).

Step 2. tert-butyl N-[[1-(2-phenoxyethyl)azetidin-3-yl]methyl]-N-[(trans)-2-phenylcyclopropyl]carbamate (34)

A mixture of 33 (66.5 mg, 331 umol, 1.00 eq), 17 (100 mg, 331 umol, 1.00 eq) and Cs$_2$CO$_3$ (215 mg, 661 umol, 2.00 eq) in MeCN (2.00 mL) was stirred at 80° C. under N$_2$ for 2 hours. After completion, the mixture was filtered and the filtrate was concentrated under vacuum to give tert-butyl N-[[1-(2-phenoxyethyl)azetidin-3-yl]methyl]-N-[(trans)-2-phenylcyclopropyl]carbamate 34 (150 mg, crude) as yellow oil. LCMS [M+1]: 423.

Step 3. (trans)-N-[[1-(2-phenoxyethyl)azetidin-3-yl] methyl]-2-phenyl-cyclopropanamine (35)

A mixture of 34 (139 mg, 329 umol, 1.00 eq) and TFA (375 mg, 3.29 mmol, 244 uL, 10.00 eq) in DCM (2.00 mL) was stirred at 10° C. for 1 hour. The mixture was concentrated under vacuum and purified by Prep-HPLC (Instrument: GX-E; Column: Phenomenex Synergi C18 150*30 mm*4 um; Condition: water (0.05% HCl)-ACN; Begin B: 16; End B: 36; Gradient Time (min): 7.8; 100% B Hold Time (min): 2; FlowRate (ml/min): 25) to give (trans)-N-[[1-(2-phenoxyethyl)azetidin-3-yl]methyl]-2-phenyl-cyclopropan-amine 35 (23.0 mg, 67.5 umol, 21% yield, 94.6% purity) as white solid. LCMS [M+1]: 323.

$^1$H NMR (400 MHz, METHANOL-d4) δ=7.35-7.29 (m, 4H), 7.24-7.18 (m, 3H), 7.01-6.97 (m, 3H), 4.43 (br. S., 2H), 4.33-4.25 (m, 4H), 3.70-3.57 (m, 4H), 3.44-3.40 (m, 1H), 3.01-3.00 (d, J=3.2 Hz, 1H), 2.61-2.58 (m, 1H), 1.63-1.59 (m, 1H), 1.43-1.29 (m, 1H).

Example 11

(trans)-N-[[1-(3-phenoxypropyl)azetidin-3-yl] methyl]-2-phenyl-cyclopropanamine (38)

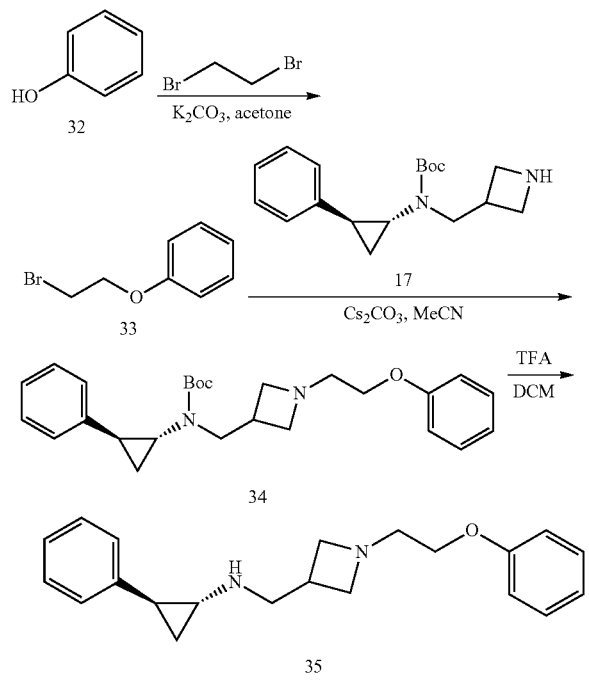

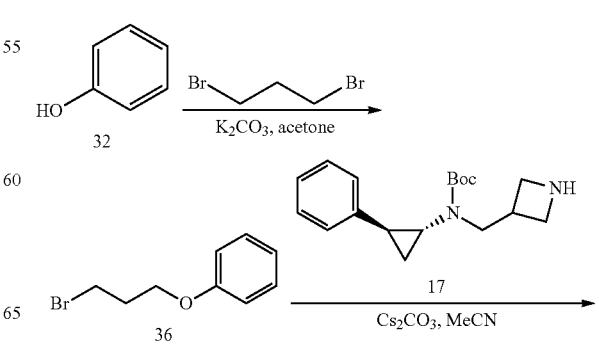

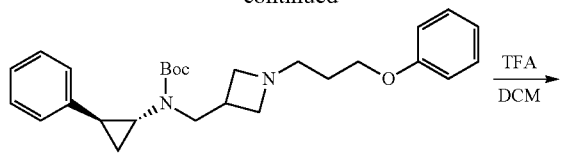
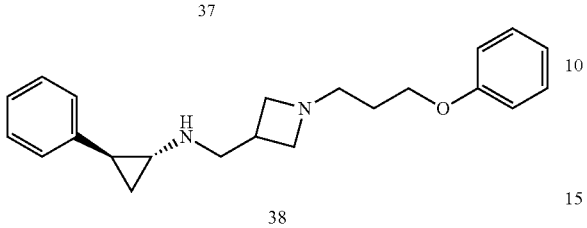

Step 1. 3-bromopropoxybenzene (36)

A mixture of phenol (200 mg, 2.13 mmol, 187 uL, 1.00 eq), 1,3-dibromopropane (2.57 g, 12.8 mmol, 1.30 mL, 6.00 eq) and K$_2$CO$_3$ (1.76 g, 12.8 mmol, 6.00 eq) in acetone (200 mL) was stirred at 80° C. under N$_2$ for 15 hours. After completion, the mixture was filtered and the filtrate was concentrated under vacuum. The residue was purified by Prep-TLC (PE/EA 10/1) to give 3-bromopropoxybenzene (260 mg, 1.21 mmol, 57% yield) as colorless oil.

$^1$H NMR (400 MHz, METHANOL-d4) δ=7.28-7.23 (m, 2H), 6.93-6.90 (m, 3H), 4.10-4.07 (t, J=3.6 Hz, 2H), 3.63-3.60 (t, J=6.4 Hz, 2H), 2.31-2.24 (m, 2H).

Step 2. tert-butyl N-[[1-(3-phenoxypropyl)azetidin-3-yl]methyl]-N-[(trans-2-phenylcyclopropyl]carbamate (37)

A mixture of 36 (71.1 mg, 331 umol, 1.00 eq), 17 (100 mg, 331 umol, 1.00 eq) and Cs$_2$CO$_3$ (215 mg, 661 umol, 2.00 eq) in MeCN (2.00 mL) was stirred at 80° C. under N$_2$ for 2 hours. After completion, the mixture was filtered and the filtrate was concentrated under vacuum to give tert-butyl N-[[1-(3-phenoxypropyl)azetidin-3-yl]methyl]-N-[(trans)-2-phenylcyclopropyl]carbamate 37 (200 mg, crude) as yellow oil. LCMS [M+1]: 437.

Step 3. (trans)-N-[[1-(3-phenoxypropyl)azetidin-3-yl]methyl]-2-phenyl-cyclopropanamine (38)

A mixture of 37 (144 mg, 330 umol, 1.00 eq) and TFA (376 mg, 3.30 mmol, 244 uL, 10.0 eq) in DCM (2.00 mL) was stirred at 10° C. for 1 hour. After completion, the mixture was concentrated under vacuum. The residue was purified by Prep-HPLC (Instrument: GX-E; Column: Phenomenex Synergi C18 150*30 mm*4 um; Condition: water (0.05% HCl)-ACN; Begin B: 20; End B: 40; Gradient Time (min): 7.8; 100% B Hold Time (min): 2; FlowRate (ml/min): 28) to give (trans)-N-[[1-(3-phenoxypropyl)azetidin-3-yl]methyl]-2-phenyl-cyclopropanamine 38 (10.0 mg, 29.0 umol, 9% yield, 97.4% purity) as colorless oil. LCMS [M+1]: 337.

$^1$H NMR (400 MHz, METHANOL-d4) δ=7.32-7.18 (m, 7H), 6.96-6.94 (m, 3H), 4.30-4.29 (m, 3H), 4.10-4.07 (m, 3H), 3.67-3.58 (m, 2H), 3.50-3.48 (m, 2H), 3.39 (m, 1H), 3.00-2.99 (m, 1H), 2.60 (br. s., 1H), 2.09-2.07 (d, J=6 Hz, 2H), 1.64-1.58 (m, 1H), 1.42-1.37 (m, 1H)

Example 12

1-[2-(4-bromophenoxy)ethyl]-N-[(1R,2S)-2-phenylcyclopropyl]piperidin-4-amine

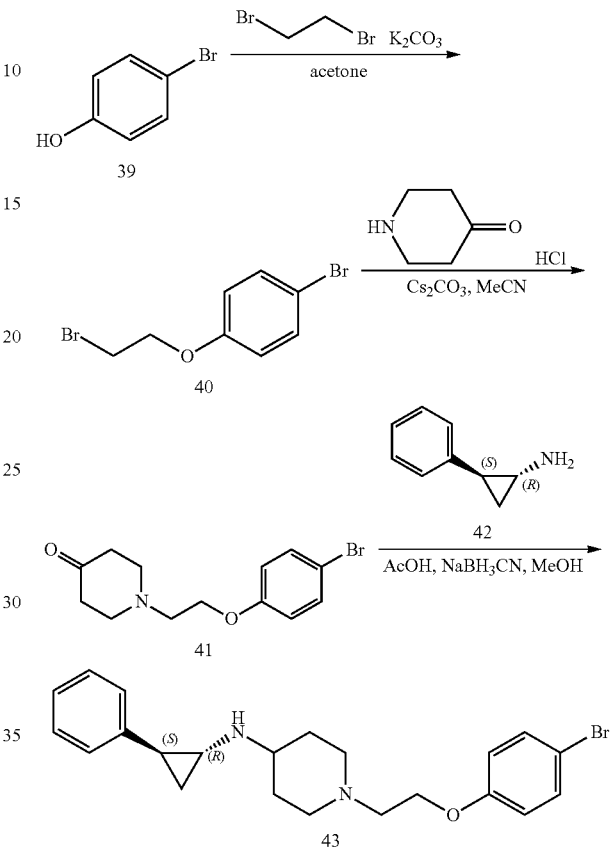

Step 1. 1-bromo-4-(2-bromoethoxy)benzene (40)

To a solution of 4-bromophenol (10.0 g, 57.8 mmol, 1.00 eq) and 1,2-dibromoethane (65.2 g, 347 mmol, 26.2 mL, 6.00 eq) in acetone (200 mL) was added K$_2$CO$_3$ (47.9 g, 347 mmol, 6.00 eq). The mixture was stirred at 80° C. for 15 hours. After completion, the mixture was filtered and concentrated under vacuum. The residue was dissolved in water (50 mL) and extracted with DCM (2×100 mL). The combined organic phase was washed with brine (80 mL), dried with anhydrous Na$_2$SO$_4$, filtered and concentrated under vacuum to give 1-bromo-4-(2-bromoethoxy)benzene (13.0 g, crude) as light brown solid. The crude was used to the next step directly.

Step 2. 1-[2-(4-bromophenoxy)ethyl]piperidin-4-one (41)

To a mixture of 40 (8.00 g, 28.6 mmol, 1.00 eq) and piperidin-4-one (7.75 g, 57.2 mmol, 2.00 eq, HCl) in MeCN (120 mL) was added Cs$_2$CO$_3$ (18.6 g, 57.2 mmol, 2.00 eq). The mixture was stirred at 80° C. for 15 hours under N2. After completion, the mixture was filtered and the filtrated was concentrated under vacuum. The residue was purified by silica gel chromatography (PE/EA from 10/1 to 1/1) to give 1-[2-(4-bromophenoxy)ethyl]piperidin-4-one 41 (6.30 g, 16.5 mmol, 58% yield, 78.0% purity) as yellow oil. LCMS [M+1]: 299.

Step 3. 1-[2-(4-bromophenoxy)ethyl]-N-[(1R,2S)-2-phenylcyclopropyl]piperidin-4-amine (43)

To a solution of 41 (269 mg, 901 umol, 1.20 eq) and (1R,2S)-2-phenylcyclopropanamine 42 (100 mg, 751 umol, 1.00 eq) in MeOH (3.00 mL) was added AcOH (45.1 mg, 751 umol, 42.9 uL, 1.00 eq) at −10° C. After stirring for 1 hour, NaBH$_3$CN (142 mg, 2.25 mmol, 3.00 eq) was added into the mixture. The mixture was stirred at −10° C. for 1 hour. After completion, the mixture was poured into saturated NH$_4$Cl aq (20 mL). The resulting mixture was extracted with DCM (2×30 mL). The combined organic phase was concentrated under vacuum then was purified by Prep-HPLC (Instrument: gx-1; Column: Agela DuraShell 150 mm_25 mm_5 um; Condition: water (0.05% ammonia hydroxide v/v)-ACN; Begin B: 55; End B: 85; Gradient Time (min): 10; 100% B Hold Time (min): 3; FlowRate (ml/min): 25) to give 1-[2-(4-bromophenoxy)ethyl]-N-[(1R,2S)-2-phenylcyclopropyl]piperidin-4-amine 43 (44.0 mg, 96.2 umol, 13% yield, 90.8% purity) as yellow oil. LCMS [M+1]: 417.

$^1$H NMR (400 MHz, METHANOL-d4) δ=7.38-7.36 (d, J=8.4 Hz, 2H), 7.26-7.20 (m, 2H), 7.12-7.11 (m, 1H), 7.04-7.02 (d, J=7.6 Hz, 2H), 6.87-6.84 (d, J=8.8 Hz, 2H), 4.10-4.07 (t, J=5.6 Hz, 2H), 3.03-3.00 (d, J=11.6 Hz, 2H), 2.79-2.76 (t, J=5.6 Hz, 2H), 2.66 (m, 1H), 2.31-2.30 (m, 1H), 2.21-2.15 (t, J=12.7 Hz, 2H), 1.93-1.87 (m, 3H), 1.53-1.48 (m, 2H), 1.07-1.01 (m, 2H).

Example 13

1-(3-Phenoxypropyl)-N-((trans)-2-phenylcyclopropyl)piperidin-4-amine (46)

Scheme 13

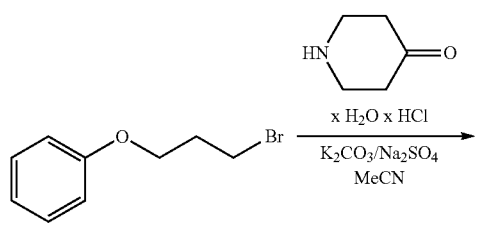

46: Example 13

Step 1. 1-(3-Phenoxypropyl)piperidin-4-one (45)

A suspension of the phenoxypropyl bromide (44) (0.3 mL, 1.90 mmol, d=1.365), piperidone hydrochloride hydrate (0.44 g, 2.86 mmol), K$_2$CO$_3$ (1.05 g, 7.62 mmol), anhydrous Na$_2$SO$_4$ (0.54 g, 3.81 mmol) and KI (47 mg, 0.286 mmol) in MeCN (20 mL) was stirred at reflux conditions for 2.5 hrs. The mixture was cooled to RT, diluted with water and extracted with EA. The extract was dried over Na$_2$SO$_4$, filtered, concentrated and the residue was purified by flash column chromatography, eluent 5% MeOH in EA, to afford title compound 45 (0.45 g, quant. yield) as oil.

$^1$H NMR: 500 MHz, CDCl$_3$, δ (ppm): 7.30-7.26 (m, 2H), 6.96-6.90 (m 3H), 4.06 (t, J=6.3 Hz, 2H), 2.78 (t, J=6.1 Hz, 4H), 2.66 (t, J=7.1 Hz, 2H), 2.46 (t, J=6.8 Hz, 4H), 2.04-1.99 (m, 2H). MS: 233.3 (calcd.), 234.1 (M+H$^+$, found).

Step 2. 1-(3-Phenoxypropyl)-N-((trans)-2-phenylcyclopropyl)piperidin-4-amine (46)

A suspension of ketone 45 (0.49 g, 2.10 mmol) and (trans)-2-phenylcyclopropanamine hydrochloride (0.43 g, 2.52 mmol) in DCE (15 mL) was stirred at RT for 2.0 hrs, cooled to 0° C. then treated with the borohydride (0.80 g, 7.78 mmol). The mixture was allowed to warm to RT and stirred over 4 hrs, diluted with DCM and washed with conc. NaHCO$_3$ solution. The organic phase was further washed with brine, dried over anhydrous Na$_2$SO$_4$, filtered, concentrated and purified by flash chromatography, eluent 5 then 10% MeOH in DCM (MeOH contained 2% ammonia) to form title compound 46 (0.29 g, 39% yield) as honey-like material.

$^1$H NMR: 500 MHz, CD$_3$OD, δ (ppm): 7.29-7.23 (m, 4H), 7.16-7.05 (m, 1H), 7.08-7.05 (m, 2H), 6.94-6.90 (m, 3H), 4.03 (t, J=6.2 Hz, 2H), 3.02 (bd, J=11.7, 2H), 2.73-2.67 (m, 1H), 2.60-2.57 (m, 2H), 2.36-2.33 (m, 1H), 2.16-2.10 (m, 2H), 2.03-1.90 (m, 5H), 1.56-1.48 (m, 2H), 1.11-1.03 (m, 2H). MS: 350.5 (calcd.), 351.1 (M+H$^+$, found).

Example 14

1-(2-Phenoxyethyl)-N-((trans)-2-phenylcyclopropyl)piperidin-4-amine (49)

Scheme 14

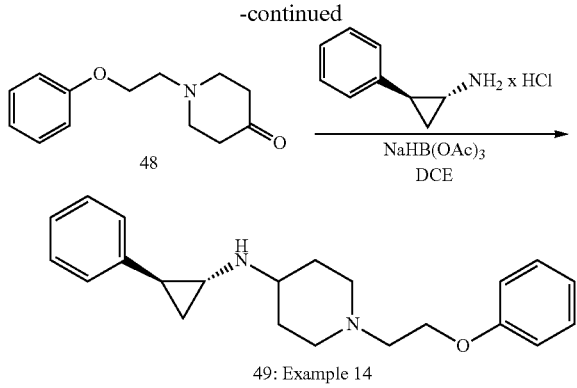

49: Example 14

Step 1. 1-(2-Phenoxyethyl)piperidin-4-one (48)

A suspension of the phenoxyethyl bromide (47) (0.30 g, 1.49 mmol), piperidone hydrochloride hydrate (0.34 g, 2.24 mmol), $K_2CO_3$ (0.83 g, 5.97 mmol), anhydrous $Na_2SO_4$ (0.42 g, 2.98 mmol) and KI (37 mg, 0.224 mmol) in MeCN (15 mL) was stirred at reflux conditions for 2.5 hrs. The mixture was cooled to RT, diluted with water and extracted with EA. The extract was dried over $Na_2SO_4$, filtered, concentrated and the residue was subjected to flash chromatography, eluent 5% MeOH in DCM, to afford title compound 48 (0.20 g, 60% yield) as a liquid.

$^1$H NMR: 500 MHz, $CDCl_3$, δ (ppm): 7.31-7.28 (m, 2H), 6.98-6.91 (m 3H), 4.15 (t, J=5.6 Hz, 2H), 2.95 (t, J=5.6 Hz, 2H), 2.91 (t, J=6.1 Hz, 4H), 2.49 (t, J=6.3 Hz, 4H). MS: 219.3 (calcd.), 219.9 (M+H$^+$, found).

Step 2. 1-(2-Phenoxyethyl)-N-((trans)-2-phenylcyclopropyl)piperidin-4-amine (49)

A suspension of ketone 48 (0.19 g, 0.866 mmol) and (trans)-2-phenylcyclopropanamine hydrochloride (0.18 g, 1.04 mmol) in DCE (10 mL) was stirred at RT for 2.0 hrs, cooled to 0° C. then treated with the borohydride (0.33 g, 1.56 mmol). The mixture was allowed to warm to RT and stirred over 4 hrs. The mixture was then diluted with DCM and washed with conc. $NaHCO_3$ solution. The organic phase was further washed with brine, dried over anhydrous $Na_2SO_4$, filtered, concentrated and purified by flash chromatography, eluent 5 then 10% MeOH in DCM (MeOH contained 2% ammonia) afford title compound 49 (0.19 g, 65% yield) as honey-like material.

$^1$H NMR: 500 MHz, $CD_3OD$, δ (ppm): 7.30-7.23 (m, 4H), 7.16-7.12 (m, 1H), 7.07-7.05 (m, 2H), 6.96-6.92 (m, 3H), 4.14 (t, J=5.7 Hz, 2H), 3.07 (bd, J=12.2, 2H), 2.83 (t, J=5.6 Hz, 2H), 2.73-2.67 (m, 1H), 2.36-2.33 (m, 1H), 2.27-2.19 (m, 2H), 2.01-1.90 (m, 3H), 1.58-1.50 (m, 2H), 1.11-1.03 (m, 2H). MS: 336.5 (calcd.), 337.1 (M+H$^+$, found).

Example 15

2-(4-(2-(4-(((1R,2S)-2-Phenylcyclopropyl)amino)piperidin-1-yl)ethoxy)phenyl)acetic acid di-hydrochloride (56)

Scheme 15

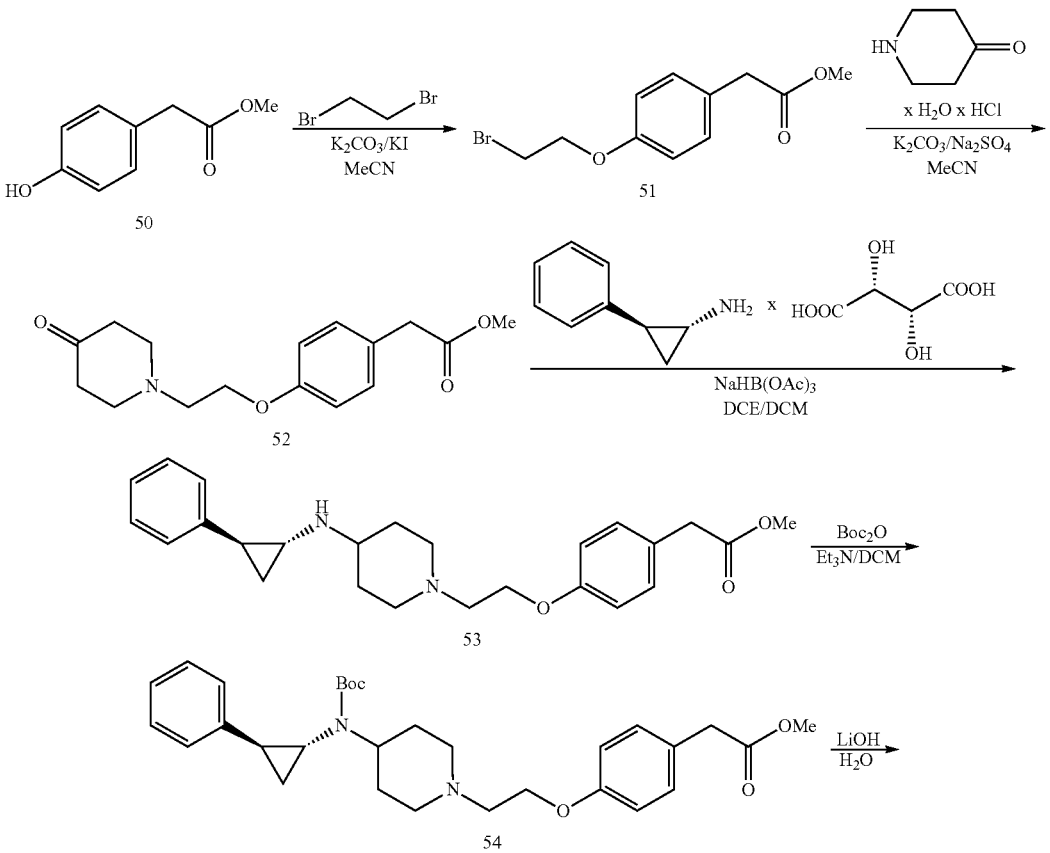

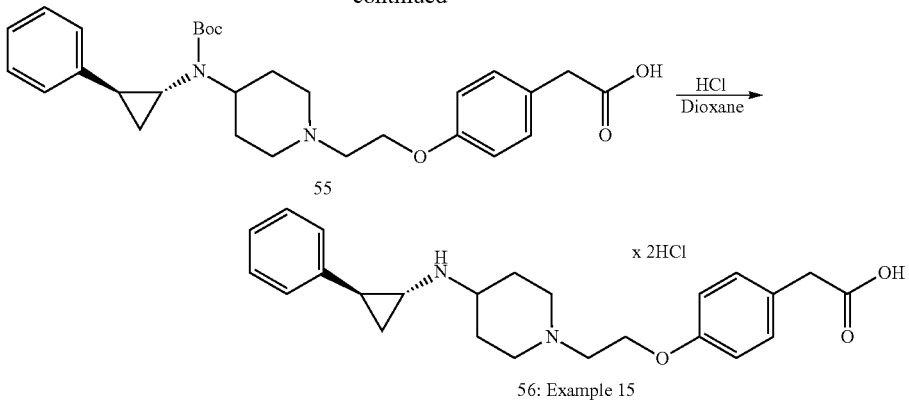

56: Example 15

Step 1. Methyl 2-(4-(2-bromoethoxy)phenyl)acetate (51)

A suspension of methyl 2-(4-hydroxyphenyl)acetate (50) (5.0 g, 30.1 mmol), 1,2-dibromoethane (16 mL, 186 mmol, d=2.18), $K_2CO_3$ (11.50 g, 84.4 mmol) and KI (200 mg, 1.20 mmol) in MeCN (90 mL) was stirred at reflux conditions for 24 hrs. The mixture was diluted with water and extracted with EA. The extract was dried over anhydrous $Na_2SO_4$, filtered and concentrated in vacuum at 40° C. The resultant oil was further kept in a higher vacuum at 60° C. to possibly remove the excess of dibromoethane then purified by flash chromatography, eluent DCM-hexanes (1:1) then EA-hexanes (8:17) to afford title compound 51 (5.05 g, 62% yield).
$^1$H NMR: 500 MHz, $CDCl_3$, δ (ppm): 7.20 (d, J=8.7 Hz, 2H), 6.87 (d, J=8.7 Hz, 2H), 4.28 (t, J=6.3 Hz, 2H), 3.69 (s, 3H), 3.63 (t, J=6.3 Hz, 2H), 3.53 (s, 2H).

Step 2. Methyl 2-(4-(2-(4-oxopiperidin-1-yl)ethoxy)phenyl)acetate (52)

A suspension of the bromide 51 (5.05 g, 18.49 mmol), piperidone hydrochloride hydrate (4.54 g, 29.6 mmol), $K_2CO_3$ (10.22 g, 74.0 mmol), anhydrous $Na_2SO_4$ (5.25 g, 37.0 mmol) and KI (153 mg, 0.924 mmol) in MeCN (100 mL) was stirred at reflux conditions for 18 hrs. The mixture was cooled to RT, diluted with water and extracted with EA. The extract was dried over $Na_2SO_4$, filtered and concentrated. The residue was purified by flash chromatography, eluent 10% MeOH in DCM (MeOH contained 2% ammonia) to afford title compound 52 (5.19 g, 96% yield) as oil.
$^1$H NMR: 500 MHz, $CD_3OD$, δ (ppm): 7.19 (d, J=8.7 Hz, 2H), 6.87 (d, J=8.7 Hz, 2H), 4.13 (t, J=5.6 Hz, 2H), 3.68 (s, 3H), 3.56 (s, 2H), 2.93 (t, J=5.6 Hz, 2H), 2.89 (t, J=6.1 Hz, 4H), 2.48 (t, J=6.2 Hz, 4H). MS: 291.3 (calcd.), 292.0 (M+H$^+$, found).

Step 3. Methyl 2-(4-(2-(4-(((1R,2S)-2-phenylcyclopropyl)amino)piperidin-1-yl)ethoxy)phenyl)acetate (53)

A suspension of ketone 52 (2.5 g, 8.58 mmol), (1R, 2S)-2-phenylcyclopropanamine (2R, 3R)-tartaric acid salt (3.16 g, 11.16 mmol) and a few drops of 6N HCl solution in a solvent mixture DCE (10 mL) and DCM (5 mL) was stirred at RT for 3.0 hrs, cooled to 0° C. then treated with the borohydride (3.27 g, 15.45 mmol). The mixture was allowed to warm to RT and stirred over 14 hrs. The mixture was then diluted with DCM and washed with a $NaHCO_3$ solution. The organic phase was washed with brine, dried over anhydrous $Na_2SO_4$, filtered, concentrated and purified by flash chromatography, eluent 10% MeOH in DCM (MeOH contained 2% ammonia to afford title compound 53 (1.65 g, 47% yield) as honey-like material whose estimated purity was ca 90%. The material was taken to the next step without additional purification. MS: 408.5 (calcd.), 409.0 (M+H$^+$, found).

Step 4. Methyl 2-(4-(2-(4-((tert-butoxycarbonyl)((1R,2S)-2-phenylcyclopropyl)amino)piperidin-1-yl)ethoxy)phenyl)acetate (54)

To a solution of amine 53 (1.65 g, 4.04 mmol) in DCM (20 mL) was added TEA (1.69 mL, 12.12 mmol, d=0.726). The mixture was cooled by an ice-bath then treated with a solution of the Boc-anhydride (1.763 g, 8.08 mmol) in DCM (20 mL). The mixture was stirred at 0-5° C. for 30 min then at ambient temperature for 4 hrs, diluted with DCM, washed with diluted brine, dried over anhydrous $Na_2SO_4$, filtered and concentrated. The residue was purified by flash chromatography, eluent EA-hexanes (1:1) to afford title compound 54 (1.50 g, 73% yield) as honey-like material. The material contained some residual EA.
$^1$H NMR: 500 MHz, $CD_3OD$, δ (ppm): 7.29-7.25 (m, 2H), 7.22-7.14 (m, 5H), 6.91 (d, J=8.7 Hz, 2H), 4.13 (t, J=5.6 Hz, 2H), 3.78-3.71 (m, 1H), 3.69 (s, 3H), 3.60 (s, 2H), 3.17-3.09 (m, 2H), 2.82 (t, J=5.6 Hz, 2H), 2.64-2.61 (m, 1H), 2.28-2.12 (m, 4H), 2.06-2.03 (m, 1H), 1.85-1.82 (m, 1H), 1.78-1.75 (m, 1H), 1.46-1.42 (m, 10H), 1.28-1.24 (m, 1H). MS: 508.7 (calcd.), 509.2 (M+H$^+$, found).

Step 5. 2-(4-(2-(4-((tert-Butoxycarbonyl)((1R,2S)-2-phenylcyclopropyl)amino)piperidin-1-yl)ethoxy)phenyl)acetic acid (55)

To a solution of ester 54 (1.50 g, 2.95 mmol) in 70% aqueous EtOH (35 mL) was added a solution of LiOH×H$_2$O (0.25 g, 5.90 mmol) in water (9 mL). The reaction mixture was stirred at rt for 1 hr, acidified with HCl to pH 5-6 then evaporated to its maximum. The residue was treated with brine and extracted with DCM. The extract was dried over anhydrous $Na_2SO_4$, filtered and the filtrate was evaporated to form foam which was let dry in vacuum overnight to afford title compound 55 (1.42 g, 97% yield). The material was used in the next step with no additional purification. MS: 494.6 (calcd.), 495.2 (M+H$^+$, found).

Step 6. 2-(4-(2-(4-(((1R,2S)-2-Phenylcyclopropyl)amino)piperidin-1-yl)ethoxy)phenyl)acetic acid dihydrochloride (56)

A 4M solution of HCl in dioxane (2 ml, 8.00 mmol) was added to a suspension of the compound 55 (0.200 g, 0.404 mmol) in dioxane (2 mL) at rt and the reaction mixture was stirred at ambient temperature for 3 hrs. The mixture was evaporated to dryness and the resultant white precipitate was triturated with a mixture of MeOH and acetone, collected by filtration and dried to afford title compound 56 (0.17 g, 90% yield) as white solid.

$^1$H NMR: 500 MHz, DMSO-d$_6$, δ (ppm): 12.25 (bs, 1H), 10.74 (bs, 1H), 9.99 (bs, 2H), 7.32-7.29 (m, 2H), 7.24-7.18 (m, 5H), 6.94 (d, J=8.6 Hz, 2H), 4.37 (bt, 2H), 3.66 (bs, 2H), 3.50 (s, 2H), 3.46 (bs, 3H), 3.46 (bs, 2H), 2.96 (bs, 1H), 2.58-2.54 (m, 1H), 2.31 (bs, 2H), 2.10 (bs, 2H), 1.60-1.56 (m, 1H), 1.31-1.27 (m, 1H). MS: 394.5 (calcd.), 395.0 (M+H$^+$, found).

Examples 16 and 17

N-(Methylsulfonyl)-2-(4-(2-(4-(((1R,2S)-2-phenylcyclopropyl)amino)piperidin-1-yl)ethoxy)phenyl)acetamide di-hydrochloride (58) and 2-(4-(2-(4-(((1R,2S)-2-phenylcyclopropyl)amino)piperidin-1-yl)ethoxy)phenyl)-N-(phenyl sulfonyl)acetamide di-hydrochloride (60)

washed with 10% aqueous NaH$_2$PO$_4$ solution then brine. The organic phase was dried over Na$_2$SO$_4$, filtered and evaporated. The residue was purified by flash chromatography, eluent 10, then 15% MeOH in DCM (MeOH contained 2% ammonia) to afford title compound 57 (0.208 mg, 90% yield) as off-white solid.

$^1$H NMR: 500 MHz, DMSO-d$_6$, δ (ppm): 7.27-7.24 (m, 2H), 7.17-7.10 (m, 5H), 6.88 (d, J=8.7 Hz, 2H), 4.06 (t, J=5.7 Hz, 2H), 3.61-3.54 (m, 1H), 3.47 (s, 2H), 3.14 (s, 3H), 3.07-3.03 (m, 2H), 2.77 (bt, 2H), 2.59-2.56 (m, 1H), 2.23-2.16 (m, 2H), 2.08-1.99 (m, 2H), 1.93-1.85 (m, 1H), 1.72-1.64 (m, 2H), 1.35-1.32 (m, 10H), 1.22-1.18 (m, 1H). MS: 571.7 (calcd.), 572.2 (M+H$^+$, found).

Step 2. N-(Methylsulfonyl)-2-(4-(2-(4-(((1R,2S)-2-phenylcyclopropyl)amino)piperidin-1-yl)ethoxy)phenyl)acetamide di-hydrochloride (58)

A 4M solution of HCl in dioxane (3 ml, 12 mmol) was added to a solution of compound 57 (205 mg, 0.359 mmol) in dioxane (2 mL) at rt. The mixture was stirred at ambient temperature for 3 hrs, evaporated to dryness and the resultant white precipitate was triturated with a mixture of acetone and MeOH, collected by filtration and dried to afford title compound 58 (146 mg, 75% yield) as a white solid.

$^1$H NMR: 500 MHz, DMSO-d$_6$, δ (ppm): 11.92 (bs, 1H), 10.65 (bs, 1H), 9.91 (bs, 2H), 7.33-7.30 (m, 2H), 7.24-7.18

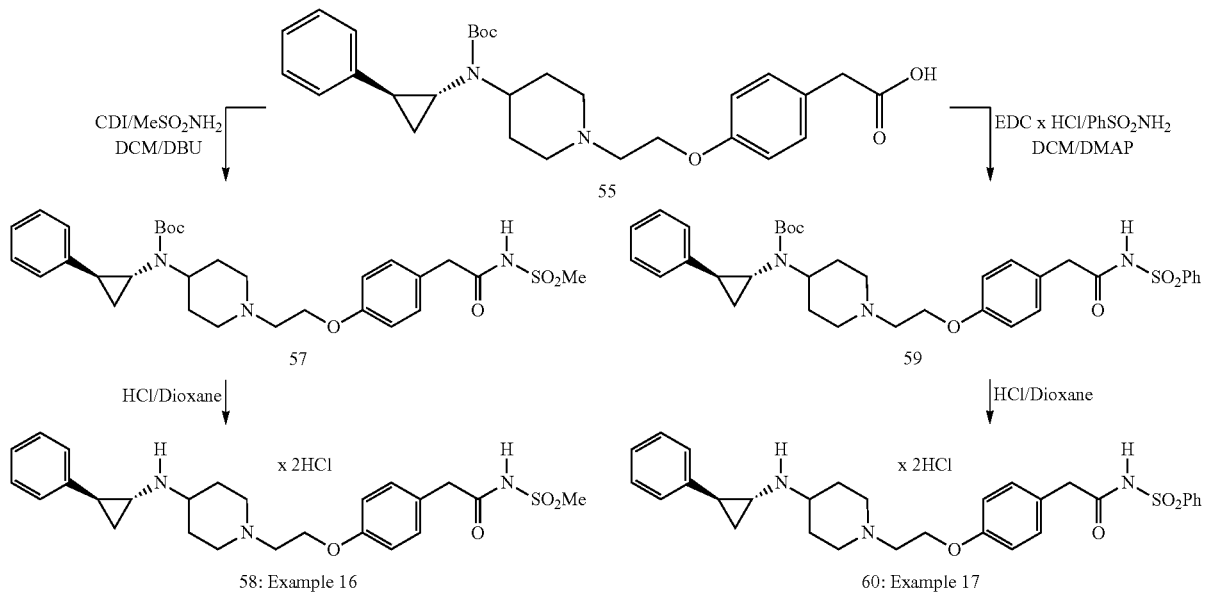

Scheme 16

Step 1. tert-Butyl (1-(2-(4-(2-(methylsulfonamido)-2-oxoethyl)phenoxy)ethyl)piperidin-4-yl)((1R,2S)-2-phenylcyclopropyl)carbamate (57)

To a solution of acid 55 (200 mg, 0.404 mmol) in DCM (5 mL) at 0° C. was added CDI (72 mg, 0.445 mmol). The reaction mixture was stirred for 5 min at 0° C., then for another hour at ambient temperature. To the mixture were added methyl sulfonamide (42 mg, 0.445 mmol) and the DBU (0.121 mL, 0.809 mmol, d=1.018). The combined mixture was stirred overnight, diluted with more DCM and (m, 5H), 6.96 (d, J=8.6 Hz, 2H), 4.37 (bt, 2H), 3.67 (bs, 2H), 3.55 (s, 2H), 3.46 (bs, 3H), 3.22 (s, 3H), 3.12 (bs, 2H), 2.97 (bs, 1H), 2.55 (bs, 1H), 2.30 (bs, 2H), 2.08 (bs, 2H), 1.57 (bs, 1H), 1.32-1.28 (m, 1H). MS: 471.6 (calcd.), 472.1 (M+H$^+$, found).

Step 1. tert-Butyl (1-(2-(4-(2-oxo-2-(phenylsulfonamido)ethyl)phenoxy)ethyl)piperidin-4-yl)((1R,2S)-2-phenylcyclopropyl)carbamate (59)

To a solution of the acid 55 (200 mg, 0.404 mmol) and benzene sulfonamide (95 mg, 0.607 mmol) in DCM (7 mL)

was added EDC×HCl (155 mg, 0.809 mmol) and DMAP (99 mg, 0.809 mmol) at RT. The reaction mixture was stirred at the same conditions overnight, diluted with more DCM then washed with a NaHCO$_3$ solution, water and brine. The organic phase was dried over Na$_2$SO$_4$, filtered and evaporated. The residue was purified by flash chromatography, eluent 10% MeOH in DCM (MeOH contained 2% ammonia). The material required a second purification by flash chromatography, eluent 5% MeOH (with 2% ammonia) in DCM to afford title compound 59 (86 mg, 34% yield) as white solid. MS: 633.8 (calcd.), 634.2 (M+H$^+$, found).

Step 2. 2-(4-(2-(4-(((1R,2S)-2-Phenylcyclopropyl)amino)piperidin-1-yl)ethoxy)phenyl)-N-(phenylsulfonyl)acetamide di-hydrochloride (60)

A 4M solution of HCl in dioxane (1.0 ml, 4 mmol) was added to a solution of compound 59 (86 mg, 0.136 mmol) in dioxane (1.5 mL) at rt. The mixture was stirred at ambient temperature for 3 hrs, evaporated to dryness and the resultant white solid was triturated with acetone, collected by filtration, re-dissolved in water, frozen and freeze-dried to afford title compound 60 (59 mg, 72% yield) as white solid.
$^1$H NMR: 500 MHz, DMSO-d$_6$, δ (ppm): 12.35 (bs, 1H), 10.73 (bs, 1H), 9.97 (bs, 2H), 7.90-7.88 (m, 2H), 7.72-7.69 (m, 1H), 7.62-7.59 (m, 2H), 7.33-7.29 (m, 2H), 7.24-7.18 (m, 3H), 7.11 (d, J=8.7 Hz, 2H), 6.91 (d, J=8.7 Hz, 2H), 4.35 (bt, 2H), 3.64 (bd, 2H), 3.50 (s, 2H), 3.44 (bs, 3H), 3.10 (bs, 2H), 2.96 (bs, 1H), 2.55 (bs, 1H), 2.29 (bs, 2H), 2.09 (bs, 2H), 1.59 (bs, 1H), 1.31-1.27 (m, 1H). MS: 533.7 (calcd.), 534.2 (M+H$^+$, found).

Examples 18 and 19

N,N-Dimethyl-2-(4-(2-(4-(((1R,2S)-2-phenylcyclopropyl)amino)piperidin-1-yl)ethoxy)phenyl)acetamide d-hydrochloride (62) and N-methoxy-2-(4-(2-(4-(((1R,2S)-2-phenylcyclopropyl)amino)piperidin-1-yl)ethoxy)phenyl)acetamide (64)

Step 1. tert-Butyl (1-(2-(4-(2-(dimethylamino)-2-oxoethyl)phenoxy)ethyl)piperidin-4-yl)((1R,2S)-2-phenylcyclopropyl)carbamate (61)

To a solution of acid 55 (200 mg, 0.404 mmol) in DMF (4 mL) were added HOBT×H$_2$O (124 mg, 0.809 mmol) followed by EDC×HCl (233 mg, 1.213 mmol). The reaction mixture was stirred at RT over 2 hrs. Then Me$_2$NH×HCl (165 mg, 2.200 mmol) was added followed by TEA (0.282 mL, 2.022 mmol, d=0.726). The resultant mixture was stirred overnight then diluted with brine. A gummy precipitate was formed which was collected by filtration and re-dissolved in acetone. The solution was dried over Na$_2$SO$_4$, filtered and concentrated. The residue was purified by flash chromatography, eluent 5% MeOH in DCM (MeOH contained 2% ammonia) to afford title compound 61 (144 mg, 68% yield) as glass-like solid. MS: 521.7 (calcd.), 522.3 (M+H$^+$, found).

Step 2. N,N-Dimethyl-2-(4-(2-(4-(((1R,2S)-2-phenylcyclopropyl)amino)piperidin-1-yl)ethoxy)phenyl)acetamide d-hydrochloride (62)

A 4M solution of HCl in dioxane (2 ml, 8 mmol) was added to a solution of compound 61 (144 mg, 0.276 mmol) in dioxane (2 mL) at rt. The mixture was stirred at ambient temperature for 3 hrs, evaporated to dryness and the resultant yellowish gummy precipitate was dissolved in MeOH and filtered. The filtrate was evaporated almost completely and treated with excess acetone. A white precipitate was formed which was collected by filtration, re-dissolved in water, frozen and freeze-dried to afford title compound 62 (113 mg, 83% yield) as off-white solid.
$^1$H NMR: 500 MHz, DMSO-d$_6$, δ (ppm): 10.83 (bs, 1H), 10.03 (bs, 2H), 7.33-7.29 (m, 2H), 7.24-7.15 (m, 5H), 6.93 (d, J=8.6 Hz, 2H), 4.37 (bt, 2H), 3.67 (bd, 2H), 3.61 (s, 2H), 3.46 (bs, 3H), 3.14 (bs, 2H), 2.98 (s, 3H), 2.97 (bs, 1H), 2.81 (s, 3H), 2.59-2.56 (m, 1H), 2.32 (bs, 2H), 2.11 (bs, 2H), 1.61-1.57 (m, 1H), 1.31-1.26 (m, 1H). MS: 421.6 (calcd.), 422.3 (M+H$^+$, found).

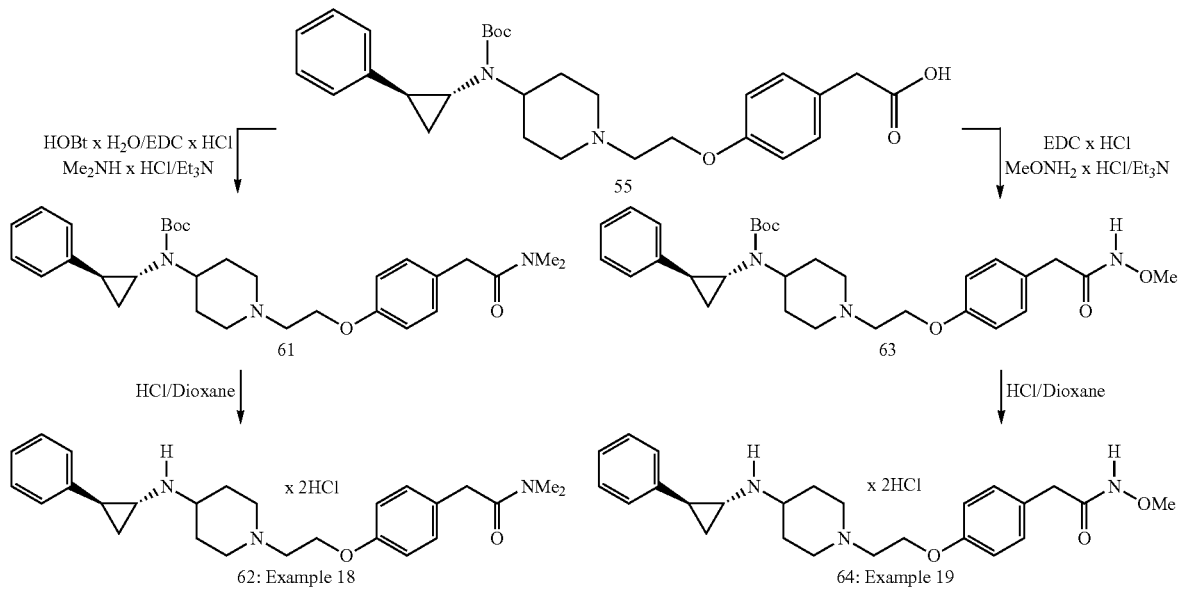

Scheme 17

Step 1. tert-Butyl (1-(2-(4-(2-(methoxyamino)-2-oxoethyl)phenoxy)ethyl)piperidin-4-yl)((1R,2S)-2-phenylcyclopropyl)carbamate (63)

To a solution of acid 55 (185 mg, 0.374 mmol) in DCM (5 mL) were added TEA (0.21 mL, 1.496 mmol, d=0.726), EDC×HCl (143 mg, 0.748 mmol), and the NH₂OMe×HCl (66 mg, 0.785 mmol). The mixture was stirred overnight, diluted with DCM and washed with diluted brine, dried over anhydrous Na₂SO₄, filtered and concentrated under reduced pressure. The residue was purified by flash chromatography, eluent 5% MeOH (containing 2% ammonia) in DCM to afford title compound 63 (73 mg, 37% yield) as white foam. MS: 523.7 (calcd.), 524.2 (M+H⁺, found).

Step 2. N-Methoxy-2-(4-(2-(4-(((1R,2S)-2-phenylcyclopropyl)amino)piperidin-1-yl)ethoxy)phenyl)acetamide (64)

A 4M solution of HCl in dioxane (1.0 ml, 4 mmol) was added to a solution of compound 63 (73 mg, 0.139 mmol) in dioxane (1 mL) at rt. The mixture was stirred at ambient temperature for 3 hrs, evaporated to dryness and the resultant white precipitate was triturated with acetone, collected by filtration, re-dissolved in water, frozen and freeze-dried to afford title compound 64 (67 mg, 93% yield) as white solid.

¹H NMR: 500 MHz, DMSO-d₆, δ (ppm): 11.34 (bs, 1H), 10.89 (bs, 1H), 10.08 (bs, 2H), 7.32-7.29 (m, 2H), 7.24-7.18 (m, 5H), 6.94 (d, J=8.6 Hz, 2H), 4.37 (bt, 2H), 3.66 (bd, 2H), 3.56 (s, 3H), 3.45 (bs, 3H), 3.23 (s, 2H), 3.14 (bs, 2H), 2.95 (bs, 1H), 2.60-2.56 (m, 1H), 2.32 (bs, 2H), 2.12 (bs, 2H), 1.62-1.58 (m, 1H), 1.30-1.26 (m, 1H). MS: 423.6 (calcd.), 424.2 (M+H⁺, found).

Example 20

1-[2-(4-morpholinophenoxy)ethyl]-N—[(R, 2S)-2-phenylcyclopropyl]piperidin-4-amine (66)

Scheme 18

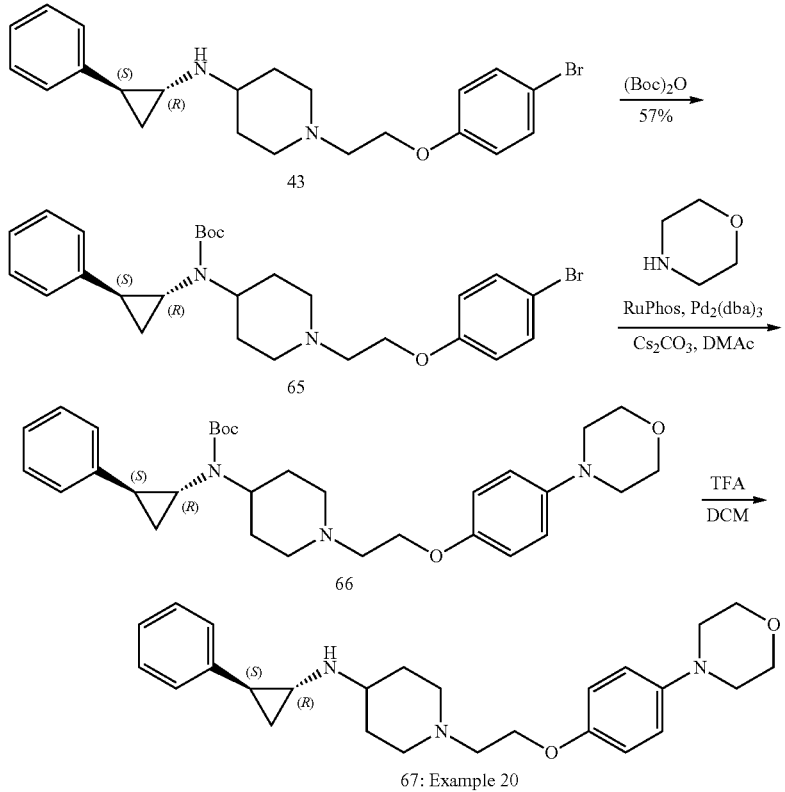

67: Example 20

Step 1. tert-butyl N-[1-[2-(4-bromophenoxy)ethyl]-4-piperidyl]-N-[(1R,2S)-2-phenylcyclopropyl]carbamate (65)

A mixture of 1-[2-(4-bromophenoxy)ethyl]-N-[(1R,2S)-2-phenylcyclopropyl]piperidin-4-amine (43, Example 12), (7.20 g, 17.3 mmol, 1.00 eq) and (Boc)₂O (7.57 g, 34.7 mmol, 7.96 mL, 2.00 eq) in DCM (10.0 mL) was stirred at 50° C. for 5 hours. After completion, the mixture was concentrated under vacuum. The residue was purified by silica gel chromatography (PE/EA from 10/1 to 0/1) to give tert-butyl N-[1-[2-(4-bromophenoxy)ethyl]-4-piperidyl]-N-[(1R,2S)-2-phenylcyclopropyl] carbamate (6.00 g, 9.89 mmol, 57% yield, 85.0% purity) as yellow oil which was re-purified by Prep-HPLC (Instrument: HPLC-A; Column: Phenomenex Gemini C18 250*50 mm*10 um; Condition: water (0.05% ammonia hydroxide v/v)-ACN; Begin B: 70; End B: 95; Gradient Time (min): 31.85%; 100% B Hold Time (min): 5; FlowRate (ml/min): 80) to give tert-butyl N-[1-[2-(4-bromophenoxy)ethyl]-4-piperidyl]-N-[(1R,2S)-2-phenylcyclopropyl]carbamate (1.9 g purity 98.5%) as white solid. LCMS [M+1]: 517

¹H NMR (400 MHz, METHANOL-d4) δ=7.42-7.40 (m, 2H), 7.24-7.22 (m, 2H), 7.15-7.10 (m, 3H), 6.92-6.90 (m, 2H), 4.23-4.21 (m, 2H), 3.82-3.79 (m, 1H), 3.42-3.31 (m, 2H), 3.24-3.22 (m, 2H), 2.67-2.66 (m, 2H), 2.59 (m, 1H), 2.44-2.17 (m, 3H), 2.12-2.11 (m, 1H), 1.98-1.84 (m, 2H), 1.40-1.38 (m, 9H), 1.25-1.22 (m, 1H)

Step 2. 1-[2-(4-morpholinophenoxy)ethyl]-N-[(1R,2S)-2-phenylcyclopropyl]piperidin-4-amine (66)

To a solution of tert-butyl N-[1-[2-(4-bromophenoxy)ethyl]-4-piperidyl]-N-[(1R,2S)-2-phenylcyclopropyl]carbamate (100 mg, 194 umol, 1.00 eq) and morpholine (33.8 mg, 388 umol, 34.1 uL, 2.00 eq) in DMAC (1.00 mL) was added RuPhos (9.05 mg, 19.4 umol, 0.10 eq), Pd₂(dba)₃ (8.88 mg, 9.70 umol, 0.05 eq) and Cs₂CO₃ (190 mg, 582 umol, 3.00 eq). The mixture was stirred at 85° C. under N₂ for 5 hours. After completion, water (10 mL) was added into the mixture. The resulting mixture was extracted with DCM (3×20 mL). The combined organic phase was concentrated under vacuum. The residue was purified by prep-TLC (DCM/MeOH 20/1) to give 1-[2-(4-morpholinophenoxy)ethyl]-N-[(1R,2S)-2-phenylcyclopropyl]piperidin-4-amine (100 mg, 83.3% purity, 82.4% yield) as yellow oil. LCMS [M+1]: 522

Step 3. 1-[2-(4-morpholinophenoxy)ethyl]-N-[(1R,2S)-2-phenylcyclopropyl]piperidin-4-amine (67, Example 20)

A mixture of tert-butyl N-[1-[2-(4-morpholinophenoxy)ethyl]-4-piperidyl]-N-[(1R,2S)-2-phenylcyclopropyl]carbamate (100 mg, 192 umol, 1.00 eq) and TFA (219 mg, 1.92 mmol, 142 uL, 10.0 eq) in DCM (1.00 mL) was stirred at 15° C. for 1 hour. After completion, the reaction mixture was concentrated under vacuum. The rediue was purified by prep-HPLC (Instrument: LC-E; Column: Phenomenex Synergi C18 150*30 mm*4 um; Condition: water (0.05% ammonia hydroxide v/v)-ACN; Begin B: 1; End B: 21; Gradient Time (min): 10.5; 100% B Hold Time (min): 2; FlowRate (ml/min): 25). The desired fractions were collected and lyophilized to give 1-[2-(4-morpholinophenoxy)ethyl]-N-[(1R,2S)-2-phenylcyclopropyl]piperidin-4-amine (40 mg, 75.34 umol, 39.30% yield, 3 HCl) as a white solid. LCMS [M+1]: 422

1H NMR (400 MHz, methanol-d4) δ=7.77 (d, J=8.8 Hz, 2H), 7.33-7.19 (m, 7H), 4.52-4.49 (m, 2H), 4.16-4.12 (m, 4H), 3.87-3.67 (m, 9H), 3.34 (m, 2H), 3.05-3.04 (m, 1H), 2.60-2.59 (m, 1H), 2.48-2.45 (m, 2H), 2.25-2.22 (m, 2H), 1.62-1.60 (m, 1H), 1.45-1.29 (m, 1H).

Following the teachings of the Reaction Schemes and synthetic routes set forth herein, the following compounds were prepared:

TABLE 1

Exemplary Compounds of Formula (I) and Formula (II)

| Ex. # | Structure | Method | LCMS [M + 1] Observed | ¹H NMR |
|---|---|---|---|---|
| 21 | 1-(2-(4-(4-methylpiperazin-1-yl)phenoxy)ethyl)-N-((1R,2S)-2-phenylcyclopropyl)piperidin-4-amine | Example 20 | 435.2 | (400 MHz, METHANOL-d4) δ = 7.42-7.40 (m, 2H), 7.24-7.22 (m, 2H), 7.15-7.10 (m, 3H), 6.92-6.90 (m, 2H), 4.23-4.21 (m, 2H), 3.82-3.79 (m, 1H), 3.42-3.31 (m, 2H), 3.24-3.22 (m, 2H), 2.67-2.66 (m, 2H), 2.59 (m, 1H), 2.44-2.17 (m, 3H), 2.12-2.11 (m, 1H), 1.98-1.84 (m, 2H), 1.40-1.38 (m, 9H) 1.25-1.22 (m, 1H) |
| 22 | 3-(4-(2-(4-(((1R,2S)-2-phenylcyclopropyl)amino)piperidin-1-yl)ethoxy)phenyl)oxazolidin-2-one | Example 20 | 422.1 | (400 MHz, deuterium oxide) δ = 7.40-7.33 (m, 4H), 7.30-7.26 (m, 1H), 7.17 (d, J = 7.2 Hz, 2H), 7.03 (d, J = 9.2 Hz, 2H), 4.59 (t, J = 8.0 Hz, 2H), 4.38-4.37 (m, 2H), 4.08-4.04 (m, 2H), 3.85-3.69 (m, 3H), 3.65-3.55 (m, 2H), 3.30-3.15 (m, 2H), 2.99-2.96 (m, 1H), 2.52-2.40 (m, 3H), 2.11-1.95 (m, 2H), 1.54-1.43 (m, 2H). |
| 23 | 1-methyl-3-(4-(2-(4-(((1R,2S)-2-phenylcyclopropyl)amino)piperidin-1-yl)ethoxy)phenyl)imidazolidin-2-one | Example 20 | 435.3 | (400 MHz, deuterium oxide) δ = 7.36-7.28 (m, 5H), 7.17 (d, J = 7.6 Hz, 2H), 6.99 (d, J = 9.6 Hz, 2H), 4.36-4.33 (m, 2H), 3.80-3.71 (m, 5H), 3.63-3.55 (m, 2H), 3.50-3.46 (m, 2H), 3.26-3.15 (m, 2H), 2.99-2.97 (m, 2H), 2.78 (s, 3H), 2.50-2.43 (m, 3H), 2.07-1.93 (m, 2H), 1.52-1.44 (m, 2H). |

TABLE 1-continued

Exemplary Compounds of Formula (I) and Formula (II)

| Ex. # | Structure | Method | LCMS [M + 1] Observed | ¹H NMR |
|---|---|---|---|---|
| 24 | 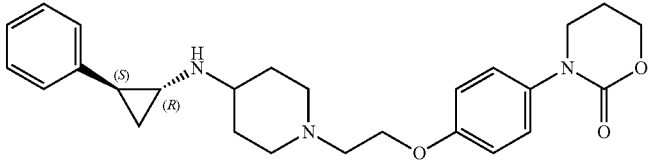<br>3-(4-(2-(4-(((1R,2S)-2-phenylcyclopropyl)amino)piperidin-1-yl)ethoxy)phenyl)-1,3-oxazinan-2-one | Example 20 | 436.3 | (400 MHz, deuterium oxide) δ = 7.31-7.27 (m, 2H), 7.24-7.20 (m, 3H), 7.11 (d, J = 7.2 Hz, 2H), 6.97 (d, J = 8.8 Hz, 2H), 4.37 (t, J = 5.2 Hz, 2H), 4.33-4.31 (m, 2H), 3.78-3.75 (d, J = 11.6 Hz, 2H), 3.70-3.60 (m, 1H), 3.59-3.54 (m, 4H), 3.30-3.20 (m, 2H), 2.95-2.91 (m, 1H), 2.45-2.35 (m, 3H), 2.12-2.06 (m, 2H), 2.04-1.90 (m, 2H), 1.48-1.32 (m, 2H). |
| 25 | 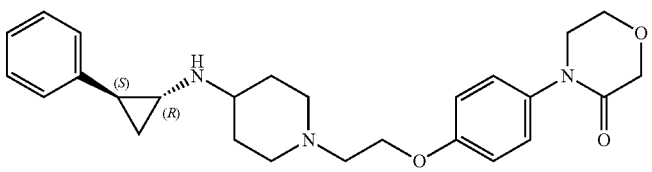<br>4-(4-(2-(4-(((1R,2S)-2-phenylcyclopropyl)amino)piperidin-1-yl)ethoxy)phenyl)morpholin-3-one | Example 20 | 436.2 | (400 MHz, deuterium oxide) δ = 7.32-7.27 (m, 2H), 7.25-7.23 (m, 3H), 7.15 (d, J = 7.2 Hz, 2H), 7.03 (d, J = 8.8 Hz, 2H), 4.37-4.35 (m, 2H), 4.29 (s, 2H), 4.02 (t, J = 4.8 Hz, 2H), 3.85-3.77 (m, 2H), 3.75-3.65 (m, 3H), 3.60-3.55 (m, 2H), 3.23-3.15 (m, 2H), 2.97-2.93 (m, 1H), 2.48-2.41 (m, 3H), 2.05-1.95 (m, 2H), 1.50-1.42 (m, 2H). |
| 26 | 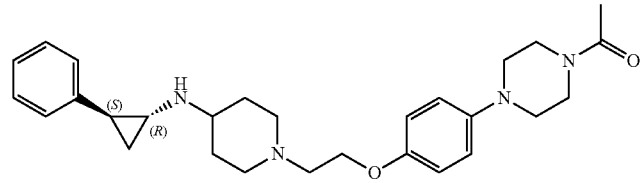<br>1-(4-(4-(2-(4-(((1R,2S)-2-phenylcyclopropyl)amino)piperidin-1-yl)ethoxy)phenyl)piperazin-1-yl)ethan-1-one | Example 20 | 463.4 | (400 MHz, deuterium oxide) δ = 7.56-7.36 (d, J = 8.8 Hz, 2H), 7.36-7.33 (m, 2H), 7.29-7.25 (m, 1H), 7.18-7.14 (m, 4H), 4.45-4.38 (m, 2H), 4.05-3.95 (m, 4H), 3.83-3.62 (m, 9H), 3.23-3.15 (m, 2H), 3.01-2.95 (m, 1H), 2.55-2.44 (m, 3H), 2.17 (s, 3H), 2.10-1.95 (m, 2H) |
| 27 | 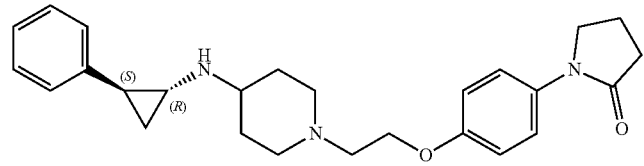<br>1-(4-(2-(4-(((1R,2S)-2-phenylcyclopropyl)amino)piperidin-1-yl)ethoxy)phenyl)pyrrolidin-2-one | Example 20 | 420.4 | (400 MHz, deuterium oxide) δ = 7.37-7.33 (m, 4H), 7.32-7.28 (m, 1H), 7.18-7.16 (d, H = 7.6 Hz, 2H), 7.04-7.02 (d, J = 8.4 Hz, 2H), 4.38-4.36 (m, 2H), 3.84-3.82 (m, 4H), 3.77-3.68 (m, 1H), 3.63-3.55 (m, 2H), 3.25-3.13 (m, 2H), 3.00-2.97 (m, 1H), 2.57 (t, J = 8.0 Hz, 2H), 2.50-2.40 (m, 3H), 2.17-2.11 (m, 2H), 2.08-1.95 (br. s., 2H), 1.52-1.44 (m, 2H) |
| 28 | 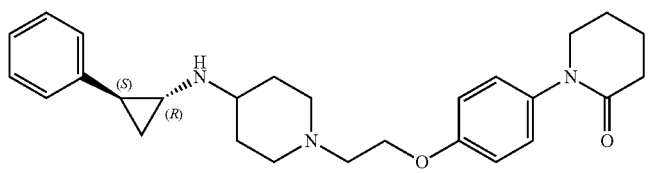<br>1-(4-(2-(4-(((1R,2S)-2-phenylcyclopropyl)amino)piperidin-1-yl)ethoxy)phenyl)piperidin-2-one | Example 20 | 434.2 | (400 MHz, D₂O) δ = 7.36-7.33 (m, 2H), 7.29-7.27 (m, 1H), 7.19-7.15 (m, 4H), 7.03 (d, J = 8.8 Hz, 2H), 4.37 (br. s., 2H), 3.83 (d, J = 12.4 Hz, 2H), 3.90-3.80 (m, 1H), 3.65-3.55 (d, J = 4.0 Hz, 4H), 3.25-3.10 (m, 2H), 3.03-2.95 (m, 1H), 2.55-2.40 (m, 5H), 2.10-1.95 (br. s., 2H), 1.95-1.80 (m, 4H), 1.55-1.42 (m, 2H). |

TABLE 1-continued

Exemplary Compounds of Formula (I) and Formula (II)

| Ex. # | Structure | Method | LCMS [M + 1] Observed | $^1$H NMR |
|---|---|---|---|---|
| 29 | 1-(2-(phenylamino)ethyl)-N-((1R,2S)-2-phenylcyclopropyl)piperidin-4-amine | Example 12 | 336.0 | (400 MHz, methanol-d$_4$) δ 7.48-7.38 (m, 2H), 7.37-7.31 (m, 2H), 7.30-7.24 (m, 3H), 7.24-7.18 (m, 3H), 3.92-3.81 (m, 4H), 3.81-3.71 (m, 1H), 3.60-3.48 (m, 2H), 3.32-3.24 (m, 2H), 3.06 (td, J = 3.6, 7.2 Hz, 1H), 2.60-255 (m, 1H), 2.52-2.41 (m, 2H), 2.31-2.14 (m, 2H), 1.65-1.55 (m, 1H), 1.52-1.41 (m, 1H). |
| 30 | N-((1R,2S)-2-phenylcyclopropyl)-1-(2-(4-(piperidin-1-yl)phenoxy)ethyl)piperidin-4-amibe | Example 20 | 420.0 | (400 MHz, chloroform-d) δ = 7.27-7.23 (m, 2H), 7.20-7.15 (m, 1H), 7.02 (d, J = 7.6 Hz, 2H), 6.90 (d, J = 8.8 Hz, 2H), 6.82 (d, J = 9.2 Hz, 2H), 4.06 (t, J = 6.0 Hz, 2H), 3.72 (q, J = 6.8 Hz, 1H), 305-2.95 (m, 5H), 2.80 (t, J = 5.6 Hz, 2H), 2.73-2.60 (m, 1H), 2.41-2.30 (m, 1H), 2.25-2.10 (m, 2H), 1.93-1.74 (m, 3H), 1.73-1.69 (m, 2H), 1.56-1.53 (m, 3H), 1.50-1.40 (m, 2H), 1.27-1.23 (m, 2H), 1.07 (m, 1H), 1.00-0.98 (m, 1H). |
| 31 | 2-(4-(2-hydroxy-3-(4-(((1R,2S)-2-phenylcyclopropyl)amino)piperidin-1-yl)propoxy)phenyl)acetic acid | Example 7 | 425.2 | (400 MHz, methanol-d4) δ = 7.35-7.31 (m, 2H), 7.27-7.18 (m, 5H), 6.94-6.91 (d, J = 8.8 Hz, 2H), 4.42-4.40 (m, 1H), 4.05-3.99 (m, 2H), 3.92-3.80 (m, 2H), 3.75-3.65 (m, 1H), 3.55 (s, 2H), 3.46-3.35 (m, 2H), 3.30-3.15 (m, 2H), 3.03-3.01 (m, 1H), 2.54-2.52 (m, 1H), 2.48-2.39 (m, 2H), 2.20-2.05 (m, 2H), 1.58-1.56 (m, 1H), 1.48-1.45 (m, 1H). |
| 32 | 1-(2-(methyl(phenyl)amino)ethyl)-N-((1R,2S)-2-phenylcyclopropyl)piperidin-4-amine | Example 12 | 350.2 | (400 MHz, methanol-d$_4$) δ = 7.54-7.46 (m, 2H), 7.44-7.40 (m, 2H), 7.38-7.28 (m, 2H), 7.25-7.23 (m, 1H), 7.23-7.17 (m., 3H), 4.05 (t, J = 6.8 Hz, 2H), 3.90-3.70 (m, 3H), 3.45-3.40 (m, 2H), 3.30-3.25 (m, 2H), 3.28 (s, 3H), 3.10-3.04 (m, 1H), 2.60-2.55 (m, 1H), 2.54-2.45 (m, 2H), 2.25-2.17 (m, 2H), 1.65-1.58 (m, 1H), 1.47-1.43 (m, 1H) |
| 33 | 1-(2-((4-bromophenyl)amino)ethyl)-N-((1R,2S)-2-phenylcyclopropyl)piperidin-4-amine | Example 12 | 416.1 | (400 MHz, methanol-d$_4$) δ 7.50 (d, J = 8.8 Hz, 2H), 7.38-7.18 (m, 5H), 7.11 (d, J = 8.8 Hz, 2H), 3.93-3.67 (m, 5H), 3.55-3.52 (m, 2H), 3.26-3.22 (, 2H), 3.11-3.02 (m, 1H), 2.63-2.59 (m, 1H), 2.53-2.47 (m, 2H), 2.29-2.16 (m, 2H), 1.70-1.57 (m, 1H), 1.49-1.45 (m, 1H) |

TABLE 1-continued
Exemplary Compounds of Formula (I) and Formula (II)
| Ex. # | Structure | Method | LCMS [M + 1] Observed | $^1$H NMR |
|---|---|---|---|---|
| 34 | ![structure] 4-(2-hydroxy-3-(4-(((1R,2S)-2-phenylcyclopropyl)amino)piperidin-1-yl)propoxy)benzoic acid | Example 7 | 411.4 | (400 MHz, D2O) δ = 7.94-7.93 (d, J = 8.8 Hz, 2H), 3.37-7.34 (m, 2H), 7.30-7.26 (m, 1H), 7.18 (d, J = 7.2 Hz, 2H), 7.01 (d, J = 8.8 Hz, 2H), 4.48-4.46 (m, 1H), 4.17-4.09 (m, 2H), 3.85-3.38 (m, 3H), 3.48-3.35 (m, 2H), 3.32-3.05 (m, 2H), 3.02-2.95 (m, 1H), 2.52-2.40 (m, 3H), 2.13-2.95 (m, 2H), 1.54-1.45 (m, 2H). |
Example 35
(E)-3-(4-(2-hydroxy-3-(4-(((1R,2S)-2-phenylcyclopropyl)amino)piperidin-1-yl)propoxy)phenyl)acrylic acid (73)
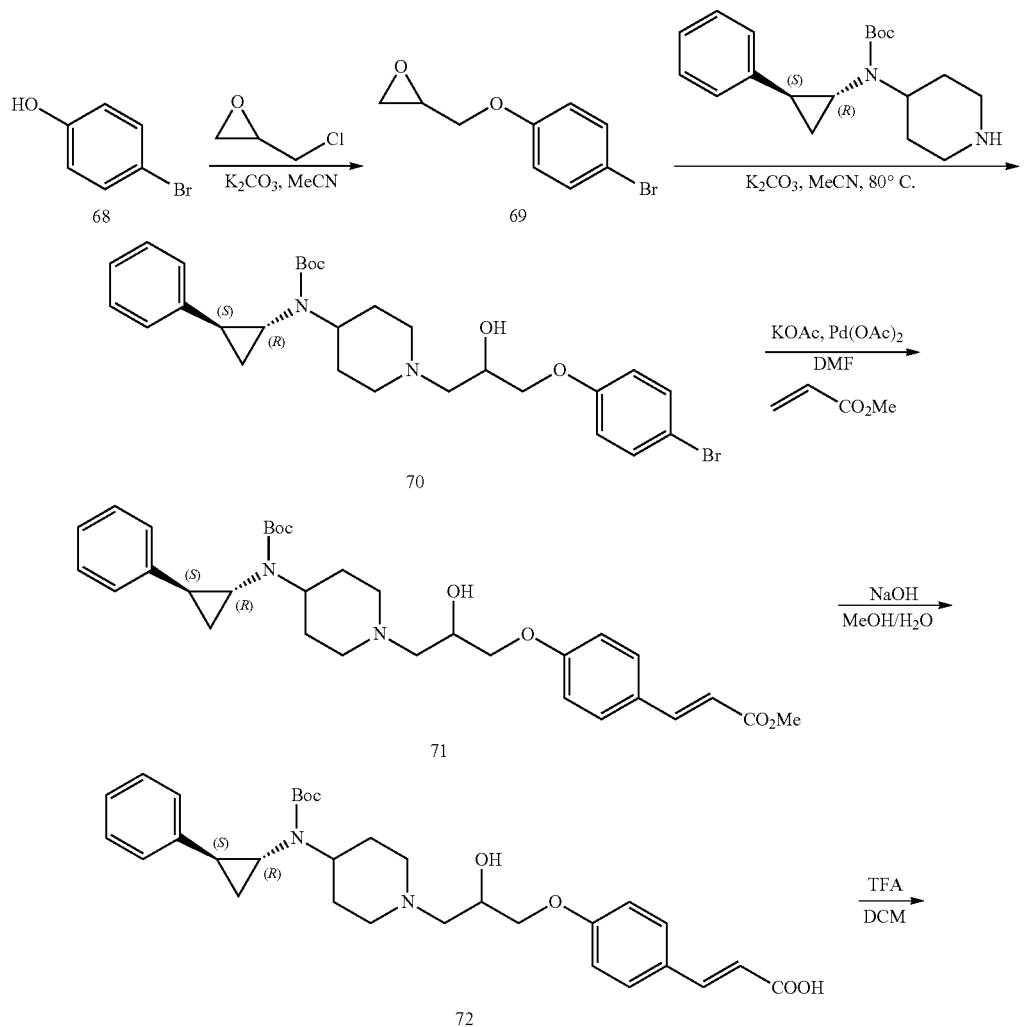

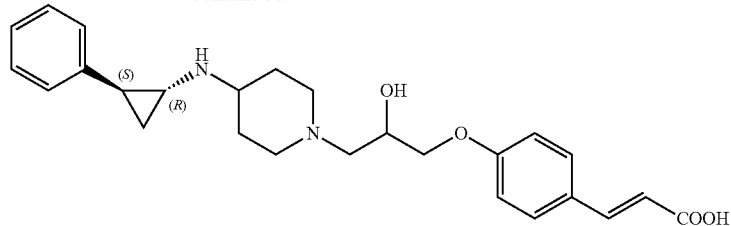

73: Example 34

Step 1. 2-[(4-bromophenoxy)methyl]oxirane

To a mixture of 4-bromophenol (10.0 g, 57.8 mmol, 2.00 eq) and 2-(chloromethyl)oxirane (12.9 g, 140 mmol, 11.0 mL, 4.85 eq) in MeCN (200 mL) was added $K_2CO_3$ (11.9 g, 86.7 mmol, 3.00 eq) in one portion. The mixture was stirred at 90° C. for 12 hours. After completion, the mixture was concentrated, diluted with DCM (150 mL), then washed with $H_2O$ (150 mL). The organic phase was washed with brine (150 mL×2), dried over $Na_2SO_4$, filtered and concentrated. The residue was purified by silica gel chromatography (Petroleum ether/Ethyl acetate=100/1~50/1) to give 2-[(4-bromophenoxy)methyl]oxirane (9.10 g, crude) as white solid 1H NMR (400 MHz, chloroform-d) δ 7.46-7.36 (m, 1H), 6.88-6.79 (m, 1H), 4.25-4.22 (m, 1H), 3.95-3.91 (m, 1H), 3.41-3.31 (m, 1H), 3.00-2.87 (m, 1H), 2.82-2.72 (m, 1H).

Step 2. tert-butyl N-[1-[3-(4-bromophenoxy)-2-hydroxy-propyl]-4-piperidyl]-N-[(1R, 2S)-2-phenyl-cyclopropyl]carbamate To a mixture of 2-[(4-bromophenoxy)methyl]oxirane (3.00 g, 13.10 mmol, 1.00 eq) and tert-butyl N-[(1R,2S)-2-phenylcyclopropyl]-N-(4-piperidyl)carbamate (4.56 g, 14.4 mmol, 1.10 eq) in MeCN (50.0 mL) was added $K_2CO_3$ (3.62 g, 26.2 mmol, 2.00 eq), and the reaction was stirred at 85° C. for 12 hours. After completion, the reaction was added water (80 mL), then extracted with EA (60 mL×2), the combined organic layers were dried over $Na_2SO_4$, filtered and concentrated. The residue was purified by column chromatography (SiO$_2$, Petroleum ether/Ethyl acetate=10/1-3/1) to give the product tert-butyl N-[1-[3-(4-bromophenoxy)-2-hydroxy-propyl]-4-piperidyl]-N-[(1R, 2S)-2-phenylcyclopropyl]carbamate (5.50 g, 9.79 mmol, 74.7% yield, 97.1% purity) as yellow solid. LCMS [M+1]: 545,547

$^1$H NMR (400 MHz, chloroform-d) δ 7.29 (d, J=8.8 Hz, 2H), 7.24-7.17 (m, 2H), 7.15-7.07 (m, 1H), 7.01 (d, J=7.2 Hz, 2H), 6.73 (d, J=8.8 Hz, 2H), 4.02-3.91 (m, 1H), 3.88-3.85 (m, 2H), 3.70-3.39 (m, 2H), 3.07-2.92 (m, 1H), 2.85-2.78 (m, 1H), 2.57-2.36 (m, 3H), 2.35-2.21 (m, 1H), 2.14-1.83 (m, 4H), 1.77-1.61 (m, 2H), 1.47-1.24 (m, 10H), 1.21-1.14 (m, 1H).

Step 3. (E)-3-[4-[3-[4-[tert-butoxycarbonyl-[(1R, 2S)-2-phenylcyclopropyl]amino]-1-piperidyl]-2-hydroxy-propoxy]phenyl]prop-2-enoate Compound 71: To a mixture of tert-butyl N-[1-[3-(4-bromophenoxy)-2-hydroxy-propyl]-4-piperidyl]-N-[(1R, 2S)-2-phenylcyclopropyl]carbamate (800 mg, 1.47 mmol, 1.00 eq) and methyl prop-2-enoate (470 mg, 5.46 mmol, 489 uL, 3.71 eq) in DMF (15.0 mL) was added KOAc (158 mg, 1.61 mmol, 1.10 eq), Pd(OAc)$_2$ (32.9 mg, 147 umol, 0.10 eq) and tris-o-tolylphosphane (44.6 mg, 147 umol, 0.10 eq), the reaction was stirred at 120° C. for 12 hours. After completion, the reaction was added water (30 mL), extracted with EA (25 mL×2), the combined organic layers were dried over $Na_2SO_4$, filtered and concentrated. The residue was purified by column chromatography (SiO$_2$, Petroleum ether/ Ethyl acetate=10/1-1/1) to give the product (E)-3-[4-[3-[4-[tert-butoxycarbonyl-[(1R,2S)-2-phenylcyclopropyl] amino]-1-piperidyl]-2-hydroxy-propoxy]phenyl]prop-2-enoate (400 mg, 719 umol, 48.9% yield, 99% purity) as yellow oil. LCMS [M+1]: 551

Step 4. (E)-3-[4-[3-[4-[tert-butoxycarbonyl-[(1R, 2S)-2-phenylcyclopropyl]amino]-1-piperidyl]-2-hydroxy-propoxy]phenyl]prop-2-enoic acid To a mixture of methyl (E)-3-[4-[3-[4-[tert-butoxycarbonyl-[(1R,2S)-2-phenylcyclopropyl] amino]-1-piperidyl]-2-hydroxy-propoxy]phenyl]prop-2-enoate (200 mg, 363 umol, 1.00 eq) in MeOH (3.00 mL) and H$_2$O (1.00 mL) was added NaOH (58.1 mg, 1.45 mmol, 4.00 eq), and the reaction was stirred at 15° C. for 12 hours. After completion, the reaction was added water (10 mL), then extracted with DCM (15 mL×2), the combined organic layers were dried over Na$_2$SO$_4$, filtered and concentrated to give (E)-3-[4-[3-[4-[tert-butoxycarbonyl-[(1R,2S)-2-phenylcyclopropyl] amino]-1-piperidyl]-2-hydroxy-propoxy]phenyl]prop-2-enoic acid (150 mg, 254 umol, 69.9% yield, 90.8% purity) as yellow solid which was used for the next step without further purification. LCMS [M+1]: 537

Step 5. E)-3-[4-[2-hydroxy-3-[4-[[(1R,2S)-2-phenyl-cyclopropyl]amino]-1-piperidyl]propoxy]phenyl] prop-2-enoic acid To a mixture of (E)-3-[4-[3-[4-[tert-butoxycarbonyl-[(1R, 2S)-2-phenylcyclopropyl]amino]-1-piperidyl]-2-hydroxy-propoxy]phenyl]prop-2-enoic acid (150 mg, 279 umol, 1.00 eq) in DCM (1.00 mL) was added TFA (1.54 g, 13.5 mmol, 1.00 mL, 48.3 eq), the reaction was stirred at 15° C. for 1 hour. After completion, the reaction was concentrated, diluted with CH$_3$CN (3 mL), then the mixture was adjusted with Na$_2$CO$_3$ solid to pH 6-7, the solid was filtered. The filtrate was purified by Prep-HPLC (Instrument: GX-B; Column: Welch Ultimate AQ-C18 150*30 mm*5 um; Condition: water (0.1% TFA)-ACN; Begin B: 20; End B: 43; Gradient Time (min): 10; 100% B Hold Time (min): 3; FlowRate (ml/min): 25) to give (E)-3-[4-[2-hydroxy-3-[4-[[(1R,2S)-2-phenylcyclopropyl]amino]-1-piperidyl] propoxy]phenyl]prop-2-enoic acid (64.0 mg, 96.1 umol, 34.4% yield, 99.8% purity, 2 TFA) as white solid. LCMS [M+1]: 437

$^1$H NMR (400 MHz, methanol-$d_4$) δ 7.64 (d, J=16.0 Hz, 1H), 7.60-7.57 (m, 2H), 7.39-7.31 (m, 2H), 7.30-7.17 (m, 3H), 7.02 (d, J=8.8 Hz, 2H), 6.37 (d, J=16.0 Hz, 1H), 4.46-4.42 (m, 1H), 4.16-4.03 (m, 2H), 3.88-3.84 (m, 2H), 3.75-3.69 (m, 1H), 3.41-3.48 (m, 2H), 3.32-3.15 (m, 2H), 3.03-3.01 (m, 1H), 2.58-2.35 (m, 3H), 2.25-2.01 (m, 2H), 1.61-1.43 (m, 2H).

Example 36

Synthesis of Intermediate 79: tert-butyl ((1R, 2S)-2-phenylcyclopropyl)(piperidin-4-yl)carbamate

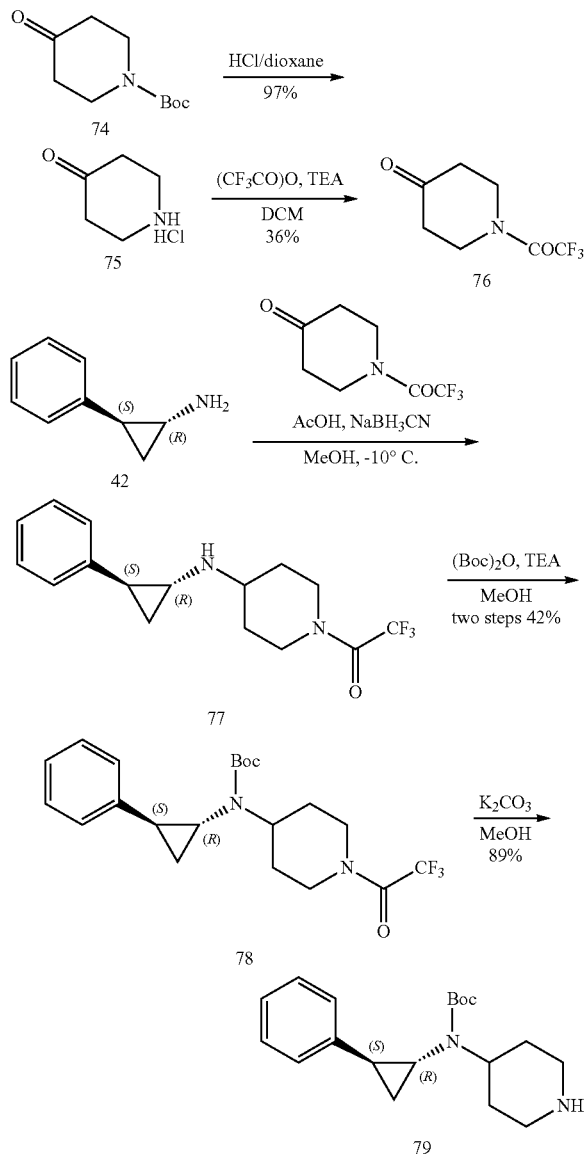

Compound 79 was prepared from compound 74 and 42.

Compound 75: To a mixture of tert-butyl 4-oxopiperidine-1-carboxylate (100 g, 502 mmol, 1.00 eq) in dioxane (750 mL) was added HCl/dioxane (750 mL), and the reaction was stirred at 15° C. for 12 hours. After completion, the precipitated solid was filtered, washed with dioxane (400 mL), then the solid was dried under vacuum. The product piperidin-4-one (66.0 g, 487 mmol, 97.0% yield, HCl) was obtained as white solid.

$^1$H NMR (400 MHz, Deuterium oxide) δ 3.20 (t, J=5.8 Hz, 4H), 1.92 (t, J=5.8 Hz, 4H)

Compound 76: To a mixture of 75 (66.0 g, 487 mmol, 1.00 eq, HCl) in DCM (600 mL) was added TEA (197 g, 1.95 mol, 270 mL, 4.00 eq) and $(CF_3CO)_2O$ (307 g, 1.46 mol, 203 mL, 3.00 eq) dropwise at 0° C., the mixture was stirred at 0-15° C. for 12 hours under $N_2$. After completion, the reaction mixture was washed with water (2×800 mL), diluted with HCl aqueous (0.5 N, 2×800 mL), sat. aqueous $NaHCO_3$ (2×800 mL) successively, the organic layer was dried over $Na_2SO_4$, filtered and concentrated. The residue was triturated with petroleum ether (200 mL), the precipitated solid was filtered and dried under vacuum to give 1-(2,2,2-trifluoroacetyl)piperidin-4-one (34.5 g, 177 mmol, 36.3% yield) as yellow solid.

$^1$H NMR (400 MHz, Chloroform-d) δ 4.01-3.89 (m, 4H), 2.62-2.56 (m, 4H) Compound 77: To a mixture of (1R, 2S)-2-phenylcyclopropanamine (23.0 g, 173 mmol, 1.00 eq) and 1-(2,2,2-trifluoroacetyl)piperidin-4-one (35.4 g, 181 mmol, 1.05 eq) in MeOH (500 mL) was added AcOH (31.1 g, 518 mmol, 29.6 mL, 3.00 eq), the reaction was stirred at 15° C. for 0.5 hour, then the mixture was cooled to −10° C. and $NaBH_3CN$ (32.6 g, 518 mmol, 3.00 eq) was added to the mixture, the mixture was stirred at −10~15° C. for 11.5 hours. After completion, the reaction mixture was added to $H_2O$ (500 mL) and concentrated. The residue was extracted with DCM (2×400 mL), the combined organic layers were dried over $Na_2SO_4$, filtered and concentrated. The product 2,2,2-trifluoro-1-[4-[[(1R, 2S)-2-phenylcyclopropyl]amino]-1-piperidyl] ethanone (59.2 g, crude) was obtained as yellow solid which was used for the next step without further purification. LCMS [M+1]: 313 Compound 78: To a mixture of 2,2,2-trifluoro-1-[4-[[(1R, 2S)-2-phenylcyclopropyl]amino]-1-piperidyl]ethanone (59.2 g, 189 mmol, 1.00 eq) in MeOH (200 mL) was added $(Boc)_2O$ (82.7 g, 379 mmol, 87.1 mL, 2.00 eq) and TEA (57.5 g, 568 mmol, 78.8 mL, 3.00 eq), the mixture was stirred at 50° C. for 12 hours. After completion, the reaction mixture was concentrated. The residue was purified by column chromatography ($SiO_2$, Petroleum ether/Ethyl acetate=100/1 to 5/1) to give tert-butyl N-[(1R, 2S)-2-phenylcyclopropyl]-N-[1-(2,2,2-trifluoroacetyl)-4-piperidyl] carbamate (42.3 g, 79.8 mmol, 42.1% yield, 77.8% purity) as colorless oil. LCMS [M-99]: 313

Compound 79: To a mixture of tert-butyl N-[(1R, 2S)-2-phenylcyclopropyl]-N-[1-(2,2,2-trifluoroacetyl)-4-piperidyl]carbamate (40.0 g, 96.9 mmol, 1.00 eq) in MeOH (200 mL) and $H_2O$ (50.0 mL) was added $K_2CO_3$ (53.6 g, 388 mmol, 4.00 eq), the mixture was stirred at 15° C. for 12 hours. After completion, the reaction mixture was added water (500 mL), then extracted with DCM (3×400 mL), the combined organic layers were dried over $Na_2SO_4$, filtered and concentrated to give tert-butyl N-[(1R, 2S)-2-phenylcyclopropyl]-N-(4-piperidyl)carbamate (27.3 g, 65.4 mmol, 88.9% yield, 75.8% purity) as yellow solid. LCMS [M+1]: 317.

$^1$H NMR (400 MHz, Methanol-$d_4$) δ 7.32-7.22 (m, 2H), 7.19-7.11 (m, 3H), 3.82-3.73 (m, 1H), 3.16-3.03 (m, 2H), 2.67-2.57 (m, 3H), 2.16-2.11 (m, 1H), 2.08-1.71 (m, 4H), 1.46-1.39 (m, 10H), 1.34-1.20 (m, 1H).

1-[2-[(2-methyl-4-pyridyl)oxy]ethyl]-N-[(1R, 2S)-2-phenylcyclopropyl]piperidin-4-amine

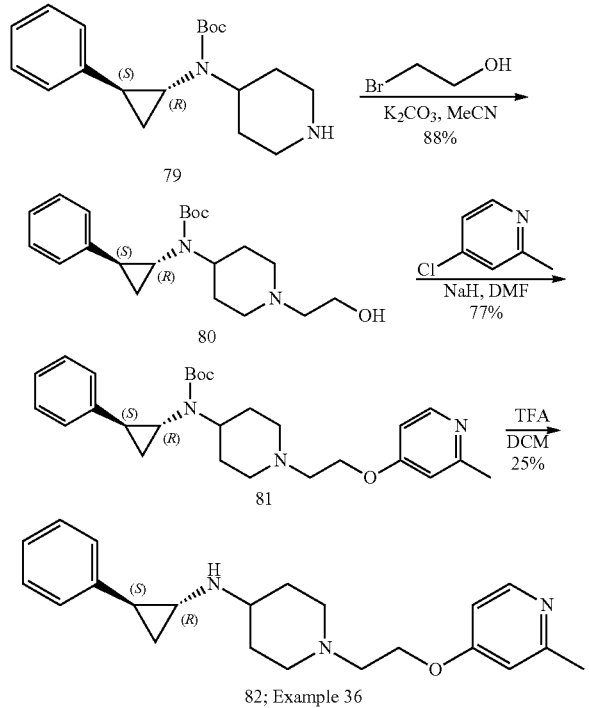

Example 36 was prepared from compound 79:

Compound 80: To a solution of tert-butyl N-[(1R,2S)-2-phenylcyclopropyl]-N-(4-piperidyl)carbamate (300 mg, 948 umol, 1.00 eq) and 2-bromoethanol (237 mg, 1.90 mmol, 135 uL, 2.00 eq) in MeCN (6.00 mL) was added K$_2$CO$_3$ (262 mg, 1.90 mmol, 2.00 eq). The mixture was stirred at 85° C. for 5 hours. After completion, the precipitate was filtered off and the filtrate was concentrated under vacuum. The residue was purified by silica gel (DCM/MeOH from 100/1 to 10/1), and the combined fractions were concentrated. tert-butyl N-[1-(2-hydroxyethyl)-4-piperidyl]-N-[(1R,2S)-2-phenylcyclopropyl]carbamate 80 (300 mg, 798 umol, 84.1% yield, 95.8% purity) was obtained as yellow oil. LCMS [M-55]: 305

Compound 81: To a solution of tert-butyl N-[1-(2-hydroxyethyl)-4-piperidyl]-N-[(1R,2S)-2-phenylcyclopropyl]carbamate (100 mg, 277 umol, 1.00 eq) in DMF (2.00 mL) was added NaH (22.2 mg, 555 umol, 60% purity, 2.00 eq). After stirring at 15° C. for 1 hour, 2-methyl-4-chloropyridine (76.6 mg, 555 umol, 2.00 eq) was added. The mixture was stirred at 85° C. for 15 hours. The precipitate was filtered off and the filtrate was concentrated under vacuum and purified by Prep-TLC (DCM/MeOH 10/1, Rf: 0.3).

tert-butyl N-[1-[2-[(2-methyl-4-pyridyl)oxy]ethyl]-4-piperidyl]-N-[(1R,2S)-2-phenylcyclopropyl]carbamate (200 mg, 213 umol, 76.6% yield, 48.0% purity) was obtained as a yellow oil. LCMS [M+1]: 452

Compound 82, Example 36: A mixture of tert-butyl N-[1-[2-[(2-methyl-4-pyridyl)oxy]ethyl]-4-piperidyl]-N-[(1R, 2S)-2-phenylcyclopropyl]carbamate (200 mg, 443 umol, 1.00 eq) and TFA (1.51 g, 13.3 mmol, 984 uL, 30.00 eq) in DCM (2.00 mL) was stirred at 15° C. for 1 hour. After completion, the reaction mixture was concentrated under vacuum. The residue was purified by prep-HPLC (column: Phenomenex Gemini 150*25 mm*10 um; mobile phase: [water (0.05% ammonia hydroxide v/v)-ACN]; B %: 35%-65%, 10 min). The desired fractions were collected and lyophilized to give 1-[2-[(2-methyl-4-pyridyl)oxy]ethyl]-N-[(1R,2S)-2-phenylcyclopropyl]piperidin-4-amine (39.0 mg, 111 umol, 25.1% yield) as colorless oil. LCMS [M+1]: 352.

$^1$H NMR (400 MHz, METHANOL-d$_4$) δ=8.19-8.18 (d, J=6 Hz, 1H), 7.23-7.20 (m, 2H), 7.11 (m, 1H), 7.04-7.02 (m, 2H), 6.86 (, 1H), 6.86-6.80 (m, 1H), 4.20-4.18 (t, J=5.2 Hz, 2H), 3.02-2.99 (br d, J=11.6 Hz, 2H), 2.81-2.79 (br t, J=5.6 Hz, 2H), 2.66 (m, 1H), 2.46 (s, 3H), 2.30-2.29 (m, 1H), 2.19-2.18 (m, 2H), 1.94-1.88 (m, 3H), 1.50 (m, 2H), 1.07-1.01 (m, 2H)

Example 37

1-morpholino-2-(4-(((1R, 2S)-2-phenylcyclopropyl)amino)piperidin-1-yl)propan-1-one

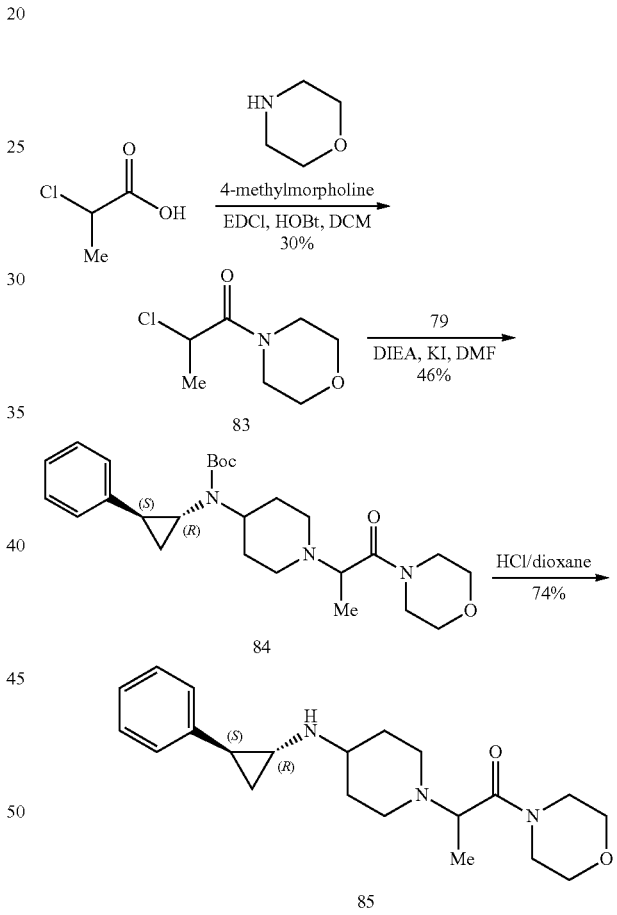

Compound 85, Example 37, was prepared from 2-chloropropionic acid: Compound 83: N-Methylmorpholine (1.50 ml, 13.8 mmol), followed by 1-hydroxybenzotriazole (1.48 g, 11.0 mmol) and 1-(3-dimethylaminopropyl)-3-ethyl carbodiimide hydrochloride (2.31 g, 12.0 mmol) were added to a stirred, ice-cooled solution of 2-chloropropionic acid (1.00 g, 9.20 mmol) in dichloromethane (30.0 ml). The resulting solution was stirred at about 0° C. for 45 minutes. Morpholine (2.40 ml, 27.6 mmol) was then added, the cooling bath removed and the reaction mixture stirred at 20° C. for 12 hrs. The residue was partitioned between ethyl acetate (50.0 mL) and water (30.0 mL), then the separated organic phase and washed with brine (30.0 mL), dried over sodium sulfate, and evaporated under reduced pressure to give a residue. The residue was purified by prep-TLC (dichloromethane/Methanol 10/1) to give 2-chloro-1-morpholinopropan-1-one (500 mg, 2.81 mmol, 30.5% yield) as colorless oil.

$^1$H NMR (400 MHz, methanol-d$_4$) δ=4.91 (q, J=6.4 Hz, 1H), 3.75-3.50 (m, 8H), 1.62 (d, J=6.4 Hz, 3H).

Compound 84: To a solution of 2-chloro-1-morpholinopropan-1-one (100 mg, 562 umol, 1.00 eq.) in DMF (5.00 mL) was added DIEA (291 mg, 2.25 mmol, 393 uL, 4.00 eq.), tert-butyl N-[(1R, 2S)-2-phenylcyclopropyl]-N-(4-piperidyl)carbamate (356 mg, 1.13 mmol, 2.00 eq.) and potassium iodide (18.6 mg, 112 umol, 0.20 eq.). The reaction mixture was stirred at 50° C. for 12 hrs. Then the reaction mixture was partitioned between water (30.0 mL) and ethyl acetate (50.0 mL). The organic phase was separated, washed with brine (30.0 mL), dried over anhydrous sodium sulfate, filtered and concentrated under reduced pressure to give a residue. The residue was purified by prep-TLC (SiO$_2$, Petroleum ether/Ethyl acetate 1/1) to give tert-butyl N-[1-[(1R)-1-methyl-2-morpholino-2-oxo-ethyl]-4-piperidyl]-N-[(1R, 2S)-2-phenylcyclopropyl]carbamate (120 mg, 262 umol, 46.5% yield) as a white solid. LCMS [M+1]: 458.

Compound 85: A solution of tert-butyl N-[1-[(1R)-1-methyl-2-morpholino-2-oxo-ethyl]-4-piperidyl]-N-[(1R, 2S)-2-phenylcyclopropyl]carbamate (120 mg, 262 umol, 1.00 eq.) in HCl/dioxane (4 M, 2 mL) was stirred at 0° C. for 2 hrs. A white solid was formed. The reaction mixture was filtered and the filter cake was concentrated to give (2R)-1-morpholino-2-[4-[[(1R, 2S)-2-phenylcyclopropyl]amino]-1-piperidyl]propan-1-one (70.0 mg, 195 umol, 74.7% yield) as a white solid. LCMS [M+1]: 358.

$^1$H NMR (400 MHz, methanol-d$_4$) δ=7.37-7.30 (m, 2H), 7.29-7.17 (m, 3H), 4.61 (br d, J=6.4 Hz, 1H), 3.93 (br d, J=10.8 Hz, 1H), 3.81-3.50 (m, 10H), 3.31-3.17 (m, 2H), 3.09-3.01 (m, 1H), 2.66-2.37 (m, 3H), 2.31-1.99 (m, 2H), 1.67-1.59 (m, 1H), 1.57 (d, J=6.4 Hz, 3H), 1.52-1.37 (m, 1H).

Example 38

1-methyl-3-(2-(4-(((1R,2S)-2-phenylcyclopropyl)amino)piperidin-1-yl)ethyl)urea

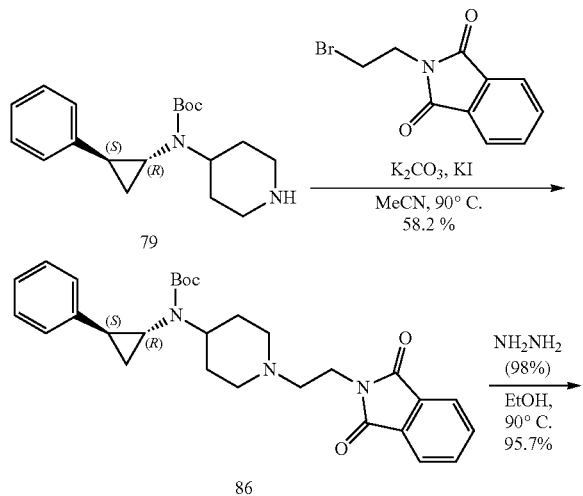

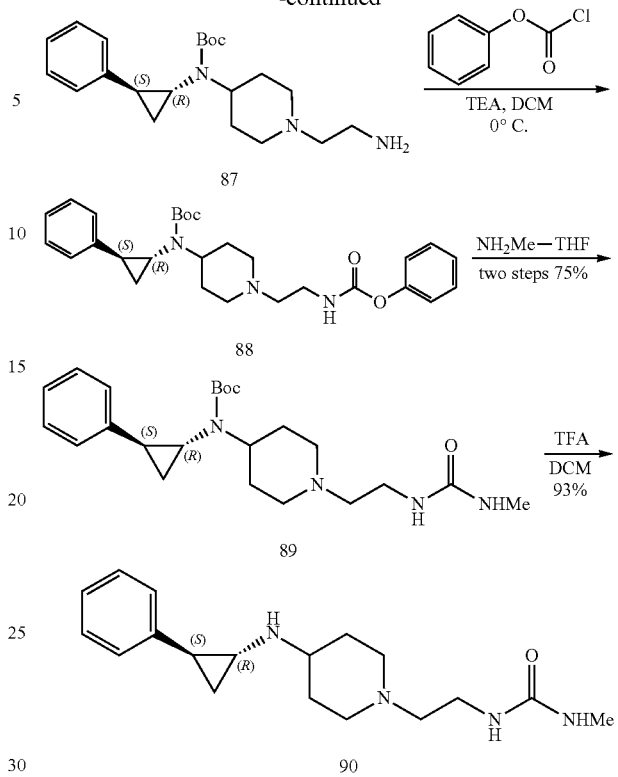

Compound 90, Example 38, was prepared from compound 79.

Compound 86: To a mixture of tert-butyl N-[(1R, 2S)-2-phenylcyclopropyl]-N-(4-piperidyl)carbamate (5.00 g, 15.8 mmol, 1.00 eq.) and 2-(2-bromoethyl)isoindoline-1,3-dione (6.02 g, 23.7 mmol, 1.50 eq.) in acetonitrile (50.0 mL) was added potassium carbonate (8.74 g, 63.2 mmol, 4.00 eq.) and potassium iodide (263 mg, 1.58 mmol, 0.1 eq.), and then warmed to reflux at 90° C. for 18 hrs. Once complete, the reaction mixture was concentrated in vacuo to remove the solvent, water (40 mL) was added, and the aqueous layer extracted with DCM (50.0 mL×3). The combined organic fractions were dried over anhydrous sodium sulfate, and concentrated in vacuo to give a residue. The residue was purified by column chromatography (Petroleum ether: Ethyl acetate 10:1 to 2:1) to give tert-butyl (1-(2-(1, 3-dioxoisoindolin-2-yl)ethyl)piperidin-4-yl)((1R, 2S)-2-phenylcyclopropyl)carbamate (4.50 g, 9.19 mmol, 58.2% yield) as a yellow oil.

$^1$H NMR (400 MHz, CD$_3$C$_1$) δ=7.88-7.81 (m, 2H), 7.76-7.69 (m, 2H), 7.24-7.12 (m, 3H), 7.06-7.01 (m, 2H), 3.85-3.75 (m, 2H), 3.74-3.62 (m, 1H), 3.12-2.94 (m, 2H), 2.67-2.55 (m, 2H), 2.54-2.47 (m, 1H), 2.12-2.06 (m, 2H), 1.95 (dq, J=3.6, 12.0 Hz, 1H), 1.83 (dq, J=4.0, 12.0 Hz, 1H), 1.77-1.70 (m, 1H), 1.66 (br s, 2H), 1.40 (s, 9H), 1.37-1.30 (m, 1H), 1.20 (q, J=6.4 Hz, 1H).

Compound 87: To a solution of tert-butyl N-[1-[2-(1, 3-dioxoisoindolin-2-yl)ethyl]-4-piperidyl]-N-[(1R, 2S)-2-phenylcyclopropyl]carbamate (4.40 g, 8.99 mmol, 1.00 eq.) in ethanol (50.0 mL) was added hydrazine monohydrate (4.59 g, 89.9 mmol, 4.46 mL, 98.0% purity, 10.0 eq.). The mixture was stirred at 90° C. for 1 hr. Once complete, the reaction mixture was concentrated in vacuo to remove the solvent; water (50 mL) was added and the aqueous phase extracted with ethyl acetate (40.0 mL×2). The combined organic layers were dried over anhydrous sodium sulfate and concentrated in vacuo to give tert-butyl (1-(2-aminoethyl)piperidin-4-yl)((1R, 2S)-2-phenylcyclopropyl)carbamate (3.40 g, 8.61 mmol, 95.7% yield, 91% purity) as a light-yellow oil. LCMS [M+1]: 360

Compound 88: To a mixture of tert-butyl N-[1-(2-aminoethyl)-4-piperidyl]-N-[(1R,2S)-2-phenylcyclopropyl]carbamate (200 mg, 556 umol, 1.00 eq) in DCM (10 mL) was added TEA (169 mg, 1.67 mmol, 231 uL, 3.00 eq) and a solution of phenyl carbonchloridate (104 mg, 668 umol, 83.6 uL, 1.20 eq) in DCM (5 mL). The reaction was stirred at −10-0° C. for 3 hours under N₂. After completion, the reaction was diluted with DCM (10 mL), then washed with H₂O (3×25 mL), the organic layer was dried over Na₂SO₄, filtered and concentrated to give the product tert-butyl N-[1-[2-(phenoxycarbonylamino)ethyl]-4-piperidyl]-N-[(1R,2S)-2-phenylcyclopropyl]carbamate (200 mg, crude) as yellow solid which was used for the next step without further purification.

Compound 89: A mixture of tert-butyl N-[1-[2-(phenoxycarbonylamino)ethyl]-4-piperidyl]-N-[(1R,2S)-2-phenylcyclopropyl]carbamate (200 mg, 417 umol, 1.00 eq) in methylamine (2 M, 4.62 mL, 22.1 eq) (in THF) was stirred at 15° C. for another 3 hours under N₂. After completion, the reaction was diluted with DCM (15 mL), then washed with H₂O (3×20 mL), the organic layer was dried over Na₂SO₄, filtered and concentrated. The residue was purified by prep-TLC (Dichloromethane:Methanol=10:1). The product tert-butyl N-[1-[2-(methylcarbamoylamino)ethyl]-4-piperidyl]-N-[(1R,2S)-2-phenylcyclopropyl]carbamate (130 mg, 312 umol, 74.8% yield, 100% purity) was obtained as white solid. LCMS [M+1]: 417

Compound 90: To a mixture of tert-butyl N-[1-[2-(methylcarbamoylamino)ethyl]-4-piperidyl]-N-[(1R,2S)-2-phenylcyclopropyl]carbamate (130 mg, 312 umol, 1.00 eq) in DCM (1.00 mL) was added TFA (1.54 g, 13.5 mmol, 1.00 mL, 43.3 eq), and the reaction was stirred at 15° C. for 1 hour. After completion, the reaction was concentrated, diluted with CH₃CN (3 mL), then the mixture was adjusted with Na₂CO₃ solid to pH 7-8, and the remaining solid was removed by filtration. The filtrate was purified by prep-HPLC (Instrument: GX-A; Column: Phenomenex Gemini 150*25 mm*10 um; Condition: water (0.05% ammonia hydroxide v/v)-ACN; Begin B: 28; End B: 50; Gradient Time (min): 10; 100% B Hold Time (min): 2; FlowRate (ml/min): 25), the obtained product was concentrated and then lyophilized to give 1-methyl-3-[2-[4-[[(1R,2S)-2-phenylcyclopropyl]amino]-1-piperidyl]ethyl]urea (92.7 mg, 291 umol, 93.2% yield, 99.2% purity) as colorless oil. LCMS [M+1]: 317

¹H NMR (400 MHz, Methanol-d4) δ 7.27-7.17 (m, 2H), 7.13-7.08 (m, 1H), 7.07-6.99 (m, 2H), 3.24 (t, J=6.6 Hz, 2H), 2.94-2.91 (m, 2H), 2.72-2.59 (m, 4H), 2.44 (t, J=6.8 Hz, 2H), 2.34-2.24 (m, 1H), 2.13-2.00 (m, 2H), 1.98-1.84 (m, 3H), 1.53-1.39 (m, 2H), 1.09-0.99 (m, 2H).

Example 39

N-[2-[4-[[(1R, 2S)-2-phenylcyclopropyl] amino]-1-piperidyl]ethyl]propane-2-sulfonamide

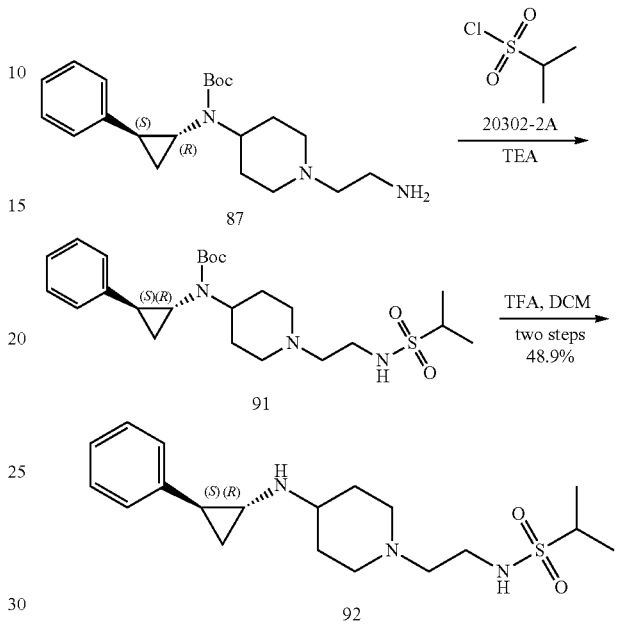

Compound 92, Example 39, was prepared from compound 87:

Compound 91: To a mixture of tert-butyl N-[1-(2-aminoethyl)-4-piperidyl]-N-[(1R, 2S)-2-phenylcyclopropyl]carbamate (500 mg, 1.39 mmol, 1.00 eq.) in DCM (20.0 mL) was added TEA (422 mg, 4.17 mmol, 578 uL, 3.00 eq.) and propane-2-sulfonyl chloride (396 mg, 2.78 mmol, 310 uL, 2.00 eq.) at 0° C. The mixture was warmed to 25° C. slowly and stirred for 15 hrs at 25° C. Once complete, the reaction mixture was poured into sat. sodium bicarbonate (30.0 mL), and extracted with DCM (40.0 mL×2). The combined organic layers were dried over anhydrous sodium sulfate and concentrated under reduced pressure to remove solvent to give tert-butyl (1-(2-(1-methylethyl sulfonamido)ethyl)piperidin-4-yl)((1R, 2S)-2-phenylcyclopropyl)carbamate (700 mg, crude) as an orange oil which used for the next step without further purification. LCMS [M+1]: 466

Compound 92: To a solution of tert-butyl N-[1-[2-(isopropylsulfonylamino)ethyl]-4-piperidyl]-N-[(1R, 2S)-2-phenylcyclopropyl]carbamate (700 mg, 1.50 mmol, 1.00 eq.) in DCM (10.0 mL) was added TFA (10.0 mL) at 0° C., and the resulting mixture was stirred for 1 hr at 0-25° C. Once complete, the reaction mixture was concentrated in vacuo to remove solvent, diluted with acetonitrile (3.00 mL), and the pH was adjusted with sodium hydroxide (1 M) to pH=7-8. Solids were removed by filtration, and the residue was purified by prep-HPLC (base condition) to give compound N-(2-(4-(((1R, 2S)-2-phenylcyclopropyl)amino)piperidin-1-yl)ethyl)propane-2-sulfonamide (260 mg, 680 umol, two steps 48.9% yield, 95.6% purity) as a yellow oil. LCMS [M+1]: 366.

¹H NMR (400 MHz, CD₃OD) δ=7.25-7.18 (m, 2H), 7.14-7.08 (m, 1H), 7.05-7.00 (m, 2H), 3.29-3.22 (m, 1H), 3.18 (t, J=6.8 Hz, 2H), 2.93 (d, J=11.6 Hz, 2H), 2.64 (m, J=4.0, 10.8 Hz, 1H), 2.50 (t, J=6.8 Hz, 2H), 2.34-2.26 (m,

1H), 2.15-2.01 (m, 2H), 1.98-1.84 (m, 3H), 1.52-1.39 (m, 2H), 1.32 (d, J=6.8 Hz, 6H), 1.10-0.97 (m, 2H).

Example 40

(E)-3-(4-(2-(4-(((1R,2S)-2-Phenylcyclopropyl)amino)piperidin-1-yl)ethoxy)phenyl)acrylic (94)

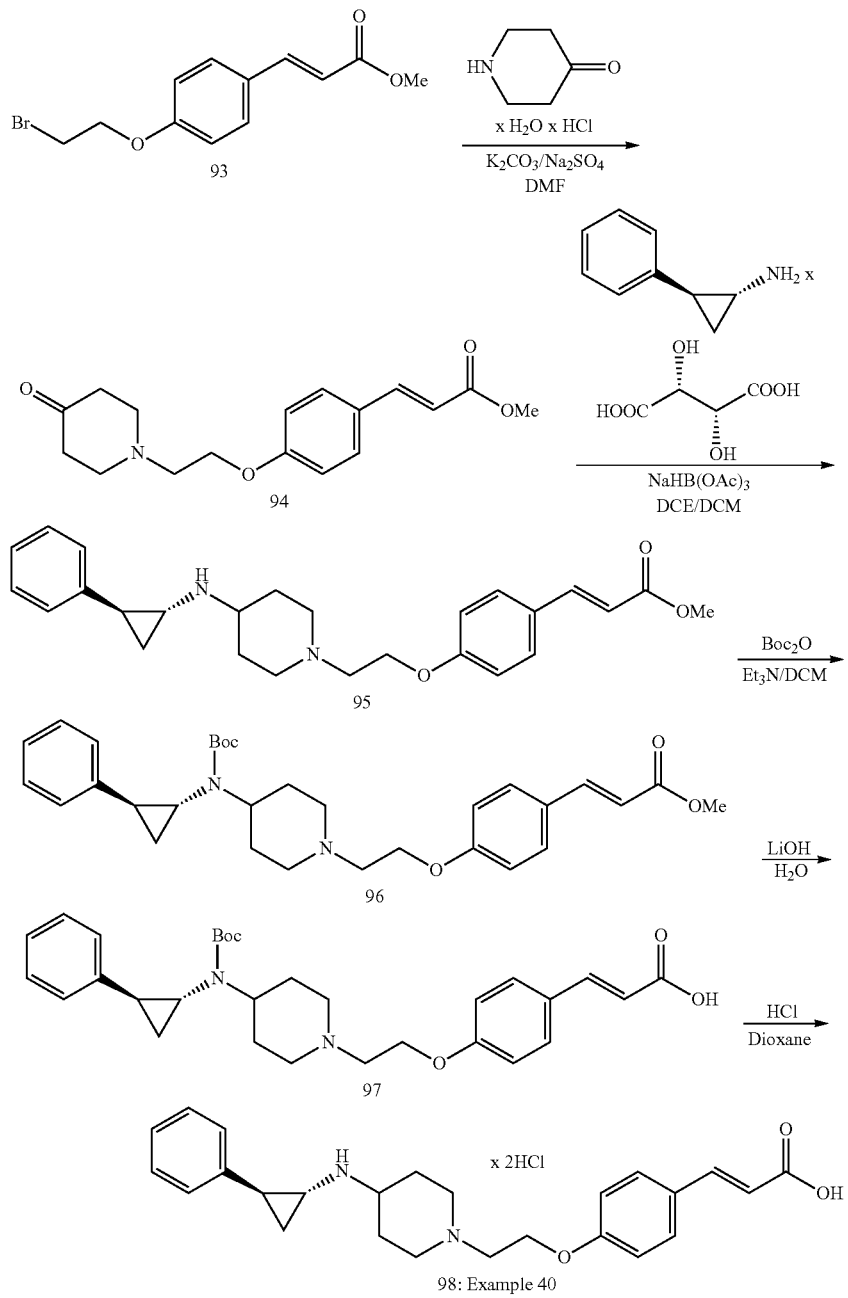

in DMF (25 mL) was stirred at 90° C. overnight, cooled to RT, diluted with brine and extracted with EA. The extract was washed with brine and dried over anhydrous $Na_2SO_4$, filtered and evaporated. The remaining oil was purified by flash column chromatography, eluent 10% hexanes in EA then pure EA to afford title compound 94 (1.65 g, 52% yield) as a white solid.

Step 1. (E)-Methyl 3-(4-(2-(4-oxopiperidin-1-yl)ethoxy)phenyl)acrylate (94)

A suspension of (E)-methyl 3-(4-(2-bromoethoxy)phenyl)acrylate (93) (3.00 g, 10.52 mmol, described in WO 2008/033747), 4-piperidone hydrochloride hydrate (1.697 g, 11.05 mmol), $K_2CO_3$ (4.36 g, 31.6 mmol), KI (105 mg, 0.631 mmol) and anhydrous $Na_2SO_4$ (2.99 g, 21.04 mmol)

$^1$H NMR: 500 MHz, $CDCl_3$, δ (ppm): 7.65 (d, J=16.0 Hz, 1H), 7.48 (d, J=8.6 Hz, 2H), 6.92 (d, J=8.8 Hz, 2H), 6.32 (d, J=16.0 Hz, 1H), 4.17 (t, J=5.6 Hz, 2H), 3.79 (s, 3H), 2.95 (t, J=5.6 Hz, 2H), 2.90 (t, J=6.1 Hz, 4H), 2.49 (t, J=6.2 Hz, 4H). MS: 303.4 (calcd.), 304.2 (M+H$^+$) and 322.1 (M+H$_2$O+H$^+$) (found).

Step 2. (E)-Methyl 3-(4-(2-(4-(((1R,2S)-2-phenylcyclopropyl)amino)piperidin-1-yl)ethoxy)phenyl)acrylate (95)

To the suspension of the (1R, 2S)-2-phenylcyclopropanamine (2R, 3R)-tartaric acid salt (2.03 g, 7.07 mmol) and ketone 94 (1.65 g, 5.44 mmol) in a mixture of DCM (10 mL) and DCE (10 mL) were added 4 A molecular sieves (2 g) and glacial AcOH (0.5 mL). The resultant mixture was stirred at RT for 6 hrs, cooled to 0° C. and treated with the borohydride (2.075 g, 9.79 mmol). The mixture was stirred at 0° C. for 30 min then allowed to warm to RT and stirred altogether for 18 hrs. The mixture was then diluted with DCM and filtered through a pad of celite. The filtrate was sequentially washed with a NaHCO$_3$ solution and brine, dried over anhydrous Na$_2$SO$_4$, filtered, concentrated and the residue was purified by flash column chromatography, eluent 10% MeOH in DCM (MeOH contained 2% ammonia), to afford title compound 95 (1.27 g, 56% yield) as an oil which has solidified in vacuum. MS: 420.5 (calcd.), 421.2 (M+H$^+$, found).

Step 3. (E)-Methyl 3-(4-(2-(4-((tert-butoxycarbonyl)((1R,2S)-2-phenylcyclopropyl)amino)piperidin-1-yl)ethoxy)phenyl)acrylate (96)

To a solution of amine 95 (1.27 g, 3.02 mmol) in DCM (10 mL) was added TEA (2.53 mL, 18.12 mmol). The mixture was cooled by an ice-bath then treated with a solution of the Boc-anhydride (2.64 g, 12.08 mmol) in DCM (15 mL). The mixture was stirred at 0-5° C. for 30 min then at ambient temperature for 8 hrs, diluted with DCM, washed with water, dried over anhydrous Na$_2$SO$_4$, filtered and concentrated. The residue was purified by flash column chromatography, eluent EA-hexanes (4:1) to afford title compound 96 (1.189 g, 76% yield) as a honey-like material that contains ca 0.7 M of EA (NMR). The product was taken to the next step as is.

$^1$H NMR: 500 MHz, MeOD, δ (ppm): 7.64 (d, J=16.0 Hz, 1H), 7.55 (d, J=8.8 Hz, 2H), 7.26-7.23 (m, 2H), 7.16-7.11 (m, 3H), 6.97 (d, J=8.8 Hz, 2H), 6.39 (d, J=16.0 Hz, 1H), 4.16 (t, J=5.6 Hz, 2H), 3.77 (s, 3H), 3.75-3.68 (m, 1H), 3.15-3.11 (m, 1H), 3.10-3.06 (m, 1H), 2.81 (t, J=5.5 Hz, 2H), 2.62-2.59 (m, 1H), 2.25-2.09 (m, 4H), 2.06-1.98 (m, 1H), 1.82-1.79 (m, 1H), 1.76-1.72 (m, 1H), 1.43-1.39 (m, 10H), 1.25-1.21 (m, 1H). MS: 520.7 (calcd.), 521.3 (M+H$^+$, found).

Step 4. (E)-3-(4-(2-(4-((tert-butoxycarbonyl)((1R,2S)-2-phenylcyclopropyl)amino)piperidin-1-yl)ethoxy)phenyl)acrylic acid (97)

To a solution of ester 96 (1.189 g, 2.284 mmol) in THF (15 mL) was added a solution of LiOH×H$_2$O (422 mg, 10.05 mmol) in water (15 mL). The reaction mixture was stirred at rt for 48 hrs, acidified to pH 4 with HCl then evaporated to its maximum to remove the THF. The residual aqueous solution was diluted with brine and extracted with DCM. The extract was dried over anhydrous Na$_2$SO$_4$, filtered and the filtrate was evaporated in vacuum to afford title compound 97 (1.014 g, 88% yield) as a white fluffy material. MS: 506.6 (calcd.), 507.3 (M+H$^+$, found).

Step 5. (E)-3-(4-(2-(4-(((1R,2S)-2-Phenylcyclopropyl)amino)piperidin-1-yl)ethoxy)phenyl)acrylic acid di-hydrochloride (98)

To a solution of compound 97 (200 mg, 0.395 mmol) in dioxane (3.0 mL) at rt was added a 4M solution of HCl in dioxane (3.0 ml, 11.84 mmol)). The mixture was stirred at ambient temperature for 3 hrs, evaporated to dryness in vacuum; and the resultant white precipitate was triturated with acetone, collected by filtration and dried to afford title compound 98 (169 mg 89% yield) as a white solid.

$^1$H NMR: 500 MHz, DMSO-d$_6$, δ (ppm): 12.25 (bs, 1H), 10.85 (bs, 1H), 10.01 (bs, 2H), 7.67 (d, J=8.8 Hz, 2H), 7.55 (d, J=15.9 Hz, 1H), 7.32-7.29 (m, 2H), 7.24-7.18 (m, 3H), 7.04 (d, J=8.8 Hz, 2H), 6.41 (d, J=16.0 Hz, 1H), 4.45 (bt, 2H), 3.68 (bs, 2H), 3.66 (bs, 1H), 3.48 (bs, 3H), 3.14 (bs, 2H), 2.97 (bs, 1H), 2.57 (m, 1H), 2.32 (bs, 2H), 2.12 (bs, 1H), 1.61-1.57 (m, 1H), 1.31-1.27 (m, 1H). MS: 406.5 (calcd.), 407.3 (M+H$^+$, found).

Example 41

N-[2-[4-[[(1R,2S)-2-phenylcyclopropyl]amino]-1-piperidyl]propyl]methanesulfonamide

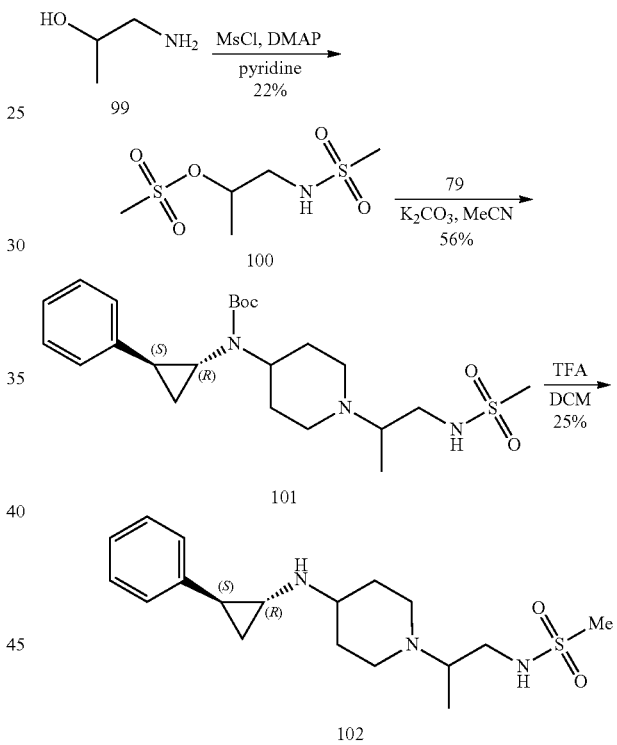

Compound 102, Example 41, was prepared from compound 99:

Compound 100: To a solution of 1-aminopropan-2-ol (1.00 g, 13.3 mmol, 1.04 mL, 1.00 eq) in pyridine (1.70 mL) was added DMAP (48.8 mg, 399 umol, 0.03 eq) at 0° C. MsCl (3.05 g, 26.6 mmol, 2.06 mL, 2.00 eq) was added into the mixture drop-wise. The reaction mixture was stirred at 0-10° C. for 1 hour. After completion, water (10 mL) and HCl (1M, 10 mL) was added into the mixture. The resulting mixture was extracted with DCM (3×30 mL). The combined organic phase was dried with anhydrous Na$_2$SO$_4$, filtered and the filtrate was concentrated under vacuum to give [2-(methanesulfonamido)-1-methyl-ethyl] methanesulfonate (700 mg, 3.03 mmol, 22.7% yield) as yellow oil.

$^1$H NMR (400 MHz, CHLOROFORM-d) δ=5.13-5.11 (m, 1H), 4.92-4.87 (m, 1H), 3.48-3.40 (s, 1H), 3.30-3.32 (s, 1H), 3.09 (s, 3H), 3.02 (m, 3H), 1.46 (s, 3H).

Compound 101: To a solution of tert-butyl N-[(1R,2S)-2-phenylcyclopropyl]-N-(4-piperidyl)carbamate (100 mg, 316 umol, 1.00 eq) and [2-(methanesulfonamido)-1-methyl-ethyl]methanesulfonate (73.1 mg, 316 umol, 1.00 eq) in MeCN (3.00 mL) was added K$_2$CO$_3$ (87.4 mg, 632 umol, 2.00 eq). The reaction mixture was stirred at 85° C. for 3 hours. After completion, the precipitate was filtrated off and the filtrate was concentrated under vacuum. The residue was purified by prep-TLC (DCM/MeOH=10/1). tert-Butyl N-[1-[2-(methanesulfonamido)-1-methyl-ethyl]-4-piperidyl]-N-[(1R,2S)-2-phenylcyclopropyl]carbamate (80.0 mg, 177 umol, 56.1% yield) was obtained as yellow oil. LCMS [M+1]: 452.

Compound 102: To a solution of tert-butyl N-[1-[2-(methanesulfonamido)-1-methyl-ethyl]-4-piperidyl]-N-[(1R,2S)-2-phenylcyclopropyl]carbamate (50.0 mg, 111 umol, 1.00 eq) in DCM (1.00 mL) was added TFA (379 mg, 3.32 mmol, 246 uL, 30.0 eq). The reaction mixture was stirred at 25° C. for 1 hour. After completion, the reaction mixture was concentrated under vacuum. The residue was purified by prep-HPLC (column: Phenomenex Synergi C18 150*25*10 um; mobile phase: [water (0.05% HCl)-ACN]; B %: 5%-25%, 7.8 min). The desired fractions were collected and lyophilized to give N-[2-[4-[[(1R,2S)-2-phenylcyclopropyl]amino]-1-piperidyl]propyl]methanesulfonamide (12.0 mg, 28.3 umol, 25.5% yield, 2HCl) as white solid. LCMS [M+1]: 352.

$^1$H NMR (400 MHz, DEUTERIUM OXIDE) δ=7.33-7.22 (m, 3H), 7.14-7.12 (m, 2H), 3.97 (br s, 2H), 3.67-3.63 (m, 2H), 3.15 (m, 3H), 3.09 (s, 3H), 2.94 (m, 1H), 2.92 (m, 1H), 2.46-2.39 (m, 3H), 2.08 (m, 1H), 1.93 (m, 1H), 1.48-1.30 (m, 2H), 1.23 (m, 3H).

Example 42

1-[2-(4-bromophenoxy)ethyl]-4-[[(1R,2S)-2-phenyl-cyclopropyl]amino]piperidin-2-one

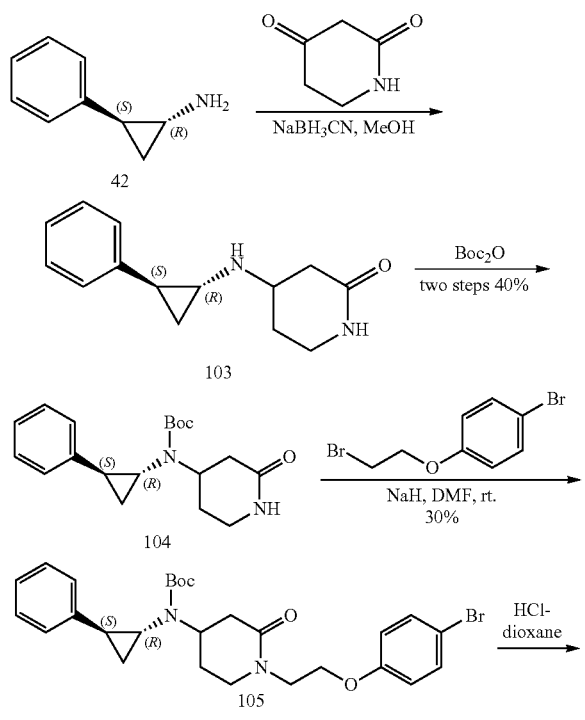

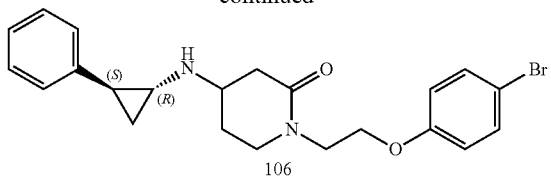

Compound 106, Example 42, was prepared from compound 42:

Compound 103: To a mixture of piperidine-2,4-dione (84.9 mg, 751 umol, 1.00 eq) in MeOH (4.00 mL) was added (1R,2S)-2-phenylcyclopropanamine (100 mg, 751 umol, 1.00 eq) at 25° C. After stirring at 25° C. for 1 hour, AcOH (90.2 mg, 1.50 mmol, 85.9 uL, 2.00 eq) was added. The resulting mixture was stirred at 25° C. for 2 hours. After completion, water (20 mL) was added into the combined mixture. The resulting mixture was extracted with DCM (3×30 mL). The combined organic phase was dried with anhydrous Na$_2$SO$_4$, filtered and concentrated under vacuum. 4-[[(1R, 2S)-2-phenylcyclopropyl]amino]piperidin-2-one (200 mg, crude) was obtained as yellow oil. The crude was used to the next step directly.

Compound 104: To a solution of 4-[[(1R,2S)-2-phenyl-cyclopropyl]amino]piperidin-2-one (340 mg, 1.48 mmol, 1.00 eq) in MeOH (2.00 mL) was added Boc$_2$O (644 mg, 2.95 mmol, 678 uL, 2.00 eq) and Et$_3$N (299 mg, 2.95 mmol, 409 uL, 2.00 eq). The reaction mixture was stirred at 60° C. for 2 hours. After completion, the reaction mixture was concentrated under vacuum. The residue was purified by silica gel chromatography (DCM/MeOH from 50/1 to 20/1). tert-butyl N-(2-oxo-4-piperidyl)-N-[(1R,2S)-2-phenylcyclopropyl]carbamate (200 mg, 551 umol, 37.2% yield, 91.0% purity) was obtained as yellow oil. LCMS [M-55]: 275.

Compound 105: To a solution of tert-butyl N-(2-oxo-4-piperidyl)-N-[(1R,2S)-2-phenylcyclopropyl]carbamate (150 mg, 454 umol, 1.00 eq) in DMF (2.00 mL) was added NaH (36.3 mg, 908 umol, 60% purity, 2.00 eq) at 0° C. After stirring at 0° C. for 1 hour, 1-bromo-4-(2-bromoethoxy)benzene (254 mg, 908 umol, 2.00 eq) was added. The reaction mixture was stirred at 0-10° C. for 1 hour. After completion, water (10 mL) was added into the mixture. The resulting mixture was extracted with DCM (3×30 mL). The combined organic phase was dried with anhydrous Na$_2$SO$_4$, filtrated and concentrated under vacuum. The residue was purified by prep-TLC (DCM/MeOH=10/1). tert-butyl N-[1-[2-(4-bromophenoxy)ethyl]-2-oxo-4-piperidyl]-N-[(1R, 2S)-2-phenylcyclopropyl]carbamate (40.0 mg, 75.6 umol, 16.6% yield) as yellow oil. LCMS [M+1, M+3]: 529, 531.

Compound 106: To a solution of tert-butyl N-[1-[2-(4-bromophenoxy)ethyl]-2-oxo-4-piperidyl]-N-[(1R,2S)-2-phenylcyclopropyl]carbamate (40.0 mg, 75.6 umol, 1.00 eq) in dioxane (2.00 mL) was added HCl/dioxane (4 M, 2.00 mL, 105.9 eq). The reaction mixture was stirred at 28° C. for 1 hour. After completion, the reaction mixture was concentrated under vacuum to give 1-[2-(4-bromophenoxy)ethyl]-4-[[(R, 2S)-2-phenylcyclopropyl]amino]piperidin-2-one (27.0 mg, 52.5 umol, 69.5% yield, 97.6% purity, 2HCl) as yellow solid. LCMS [M+1, M+23]: 429, 451.

$^1$H NMR (400 MHz, METHANOL-d4) δ=7.38-7.23 (m, 5H), 7.13-7.11 (m, 2H), 6.83-6.81 (m, 2H), 4.16 (br s, 2H), 3.70-3.44 (m, 5H), 2.85-2.83 (m, 2H), 2.45-2.40 (m, 2H), 2.26 (br s, 1H), 1.92-1.74 (m, 1H), 1.45-1.39 (m, 2H).

Example 43

2-(2-Fluoro-4-(2-(4-(((1R,2S)-2-phenylcyclopropyl)amino)piperidin-1-yl)ethoxy)phenyl)acetic acid dihydrochloride (113)

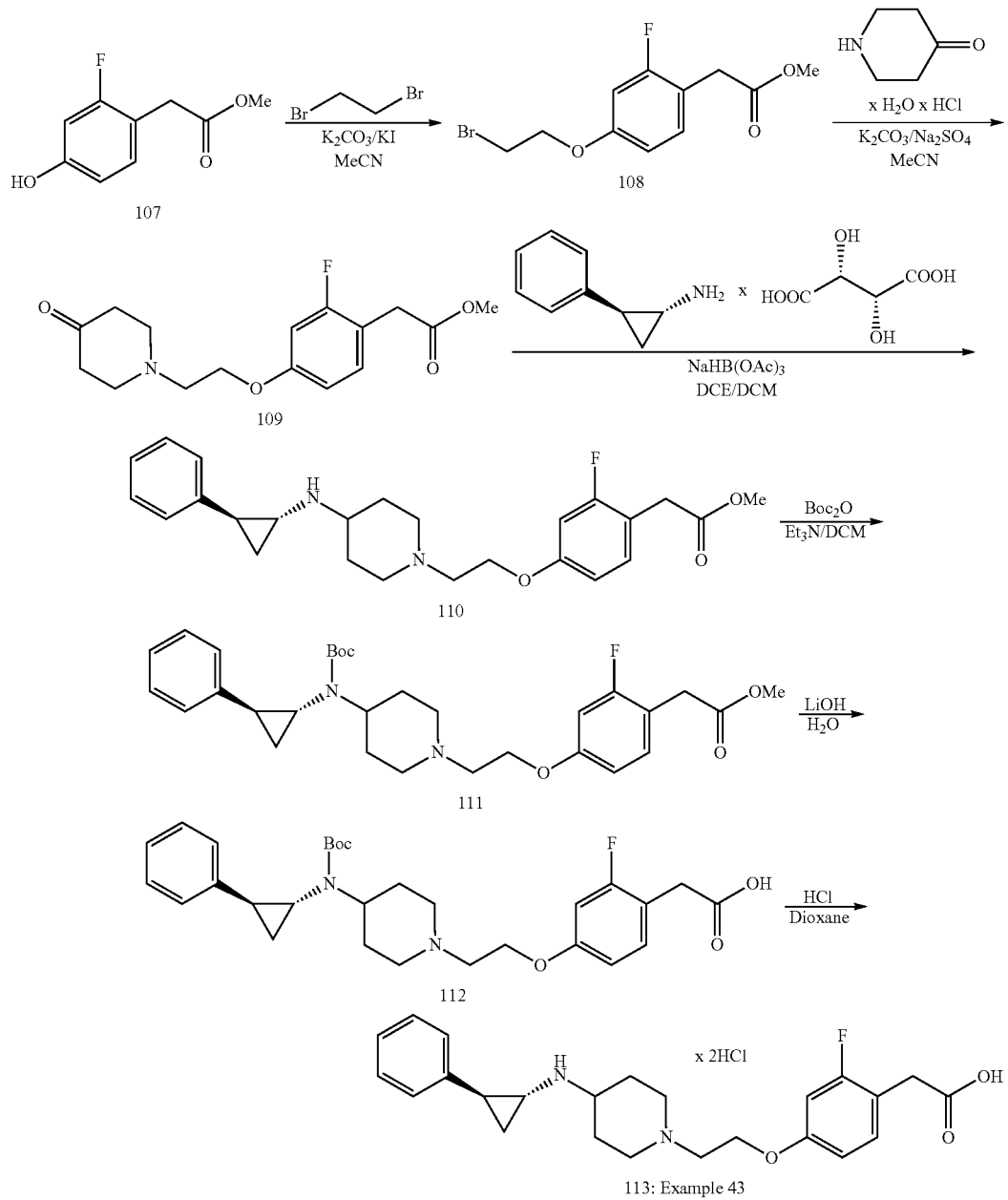

113: Example 43

Step 1. Methyl 2-(4-(2-bromoethoxy)-2-fluorophenyl)acetate (108)

A suspension of methyl 2-(2-fluoro-4-hydroxyphenyl)acetate (107) (4.0 g, 21.72 mmol, WO 2012/138845), 1,2-dibromoethane (12.0 mL, 139 mmol), $K_2CO_3$ (8.41 g, 60.8 mmol) and KI (100 mg, 0.602 mmol) in MeCN (70 mL) was stirred for 24 hr at reflux conditions. The mixture was then cooled to RT, diluted with water and extracted with EA. The extract was dried over anhydrous $Na_2SO_4$, filtered and concentrated in vacuum. The resultant oil was subjected to flash column chromatography, eluent EA-hexanes (1:4) to afford title compound 108 (4.65 g, 74% yield) as yellowish oil.

$^1$H NMR: 500 MHz, CDCl$_3$, δ (ppm): 7.16 (t, J=8.5 Hz, 1H), 6.69-6.63 (m, 2H), 4.26 (t, J=6.3 Hz, 2H), 3.70 (s, 3H), 3.62, (t, J=6.2 Hz, 2H), 3.61 (s, 2H).

Step 2. Methyl 2-(2-fluoro-4-(2-(4-oxopiperidin-1-yl)ethoxy)phenyl)acetate (109)

A suspension of the bromide 108 (4.65 g, 15.97 mmol), piperidone hydrochloride hydrate (3.68 g, 23.96 mmol), $K_2CO_3$ (8.83 g, 63.9 mmol), anhydrous $Na_2SO_4$ (4.54 g, 31.9 mmol) and KI (265 mg, 1.597 mmol) in MeCN (90 mL)

was stirred at reflux conditions for 18 hrs. The mixture was cooled to RT, diluted with water and extracted with EA. The extract was dried over anhydrous $Na_2SO_4$, filtered and concentrated. The residue was purified by flash column chromatography, eluent 10% MeOH in DCM (MeOH contained 2% ammonia) to afford title compound 109 (4.60 g, 93% yield) as an oil.

$^1$H NMR: 500 MHz, $CDCl_3$, δ (ppm): 7.15 (t, J=8.6 Hz, 1H), 6.69-6.63 (m, 2H), 4.11 (t, J=5.6 Hz, 2H), 3.70 (s, 3H), 3.60 (s, 2H), 2.92 (t, J=5.6 Hz, 2H), 2.89 (t, J=6.1 Hz, 4H), 2.48 (t, J=6.2 Hz, 4H). MS: 309.3 (calcd.), 310.2 (M+H$^+$, found).

Step 3 Methyl 2-(2-fluoro-4-(2-(4-(((1R,2S)-2-phenylcyclopropyl)amino)piperidin-1-yl)ethoxy)phenyl)acetate (110)

To the suspension of (1R, 2S)-2-phenylcyclopropanamine (2R, 3R)-tartaric acid salt (3.36 g, 11.85 mmol) and ketone 109 (2.82 g, 9.12 mmol) in a mixture of DCE (20 mL) and DCM (20 mL) were added 4 A molecular sieves (3 g) and glacial acetic acid (0.5 mL). The resultant mixture was stirred at RT for 16 hrs, cooled to 0° C. then treated with the borohydride (3.48 g, 16.41 mmol). The mixture was stirred at 0° C. for 30 min then allowed to warm to RT, stirred altogether for 3 hrs, diluted with DCM and filtered through a celite pad. The filtrate was sequentially washed with a 10% $NaHCO_3$ solution and brine, dried over anhydrous $Na_2SO_4$, filtered and concentrated. The residue was purified by flash column chromatography, eluent 10% MeOH in DCM (MeOH contained 2% ammonia) to afford title compound 110 (4.07 g, 105% yield) as an oil. The material was taken to the next step with no extra purification. MS: 426.5 (calcd.), 427.2 (M+H$^+$, found).

Step 4. Methyl 2-(4-(2-(4-((tert-butoxycarbonyl)((1R,2S)-2-phenylcyclopropyl)amino)piperidin-1-yl)ethoxy)-2-fluorophenyl)acetate (111)

To a solution of the amine 110 (4.07 g, 9.54 mmol) in DCM (40 mL) was added TEA (4.0 ml, 28.7 mmol). The mixture was cooled by an ice-bath then treated with a solution of Boc-anhydride (4.17 g, 19.08 mmol) in DCM (40 mL). The mixture was stirred at 0-5° C. for 30 min then at ambient temperature overnight, diluted with DCM, washed with dilute brine, dried over anhydrous $Na_2SO_4$, filtered and concentrated. The residue was purified by flash column chromatography, eluent EA-hexanes (1:1, then 4:1) to afford title compound 111 (3.72 g, 74% yield) as a honey-like material. The product contained ca 0.5 M of EA and was taken to the next step as is.

$^1$H NMR: 500 MHz, $CDCl_3$, δ (ppm): 7.28-7.25 (m, 2H, overlaps with the residual solvent signal), 7.18-7.11 (m, 2H), 7.09-7.07 (m, 2H), 6.67-6.61 (m, 2H), 4.04 (t, J=5.9 Hz, 2H), 3.79-3.73 (m, 1H), 3.70 (s, 3H), 3.60 (s, 2H), 3.05-2.97 (m, 2H), 2.76 (t, J=5.9 Hz, 2H), 2.56-2.53 (m, 1H), 2.20-2.05 (m, 4H), 1.97-1.89 (m, 1H), 1.80-1.71 (m, 2H), 1.42 (s, 9H), 1.40-1.37 (m, 1H), 1.23-1.19 (m, 1H). MS: 526.6 (calcd.), 527.4 (M+H$^+$, found).

Step 5. 2-(4-(2-(4-((tert-Butoxycarbonyl)((1R,2S)-2-phenylcyclopropyl)amino)piperidin-1-yl)ethoxy)-2-fluorophenyl)acetic acid (112)

To a solution of ester 111 (3.72 g, 7.06 mmol) in THF (35 mL) was added a solution of LiOH hydrate (741 mg, 17.66 mmol) in 35 mL water. The reaction mixture was stirred at rt for 2 hrs, acidified to pH 6-7 then evaporated to its maximum. The residue was treated with brine and extracted with DCM. The extract was dried over anhydrous $Na_2SO_4$, filtered and the filtrate was evaporated to afford title compound 112 (3.57 g, 99% yield) as a white fluffy solid. MS: 512.6 (calcd.), 513.3 (M+H$^+$, found).

Step 6. 2-(2-Fluoro-4-(2-(4-(((1R,2S)-2-phenylcyclopropyl)amino)piperidin-1-yl)ethoxy)phenyl)acetic acid di-hydrochloride (113)

To a solution of the compound 112 (3.57 g, 6.96 mmol) in dioxane (20 mL) was added a 4M solution of HCl in dioxane (40 ml, 160 mmol) at rt. The mixture was stirred for 3 hrs, diluted with acetone and evaporated almost to completion. The resultant white precipitate was triturated with acetone, collected by filtration and dried in vacuum to afford title compound 113 (2.908 g, 86% yield) as a white solid.

$^1$H NMR: 500 MHz, $DMSO_6$, δ (ppm): 12.39 (bs, 1H), 11.05 and 10.86 (two bs, 1H), 10.05 (bs, 2H), 7.33-7.19 (m, 6H), 6.90 (dd, J=2.4 and 11.7 Hz, 1H), 6.81 (dd, J=2.2 and 8.4 Hz, 1H), 4.42 (bt, 2H), 3.68 (bs, 1H), 3.66 (bs, 1H), 3.55 (s, 2H), 3.46 (bs, 3H), 3.13 (bs, 2H), 2.97 (bs, 1H), 2.58 (m, 1H), 2.33 (bs, 2H), 2.11 (bs, 2H), 1.62-1.58 (m, 1H), 1.31-1.28 (m, 1H). MS: 412.5 (calcd.), 413.2 (M+H$^+$, found).

Example 44

N,2-dimethyl-N-[2-[4-[[(R, 2S)-2-phenylcyclopropyl]amino]-1-piperidyl]ethyl]pyridin-4-amine

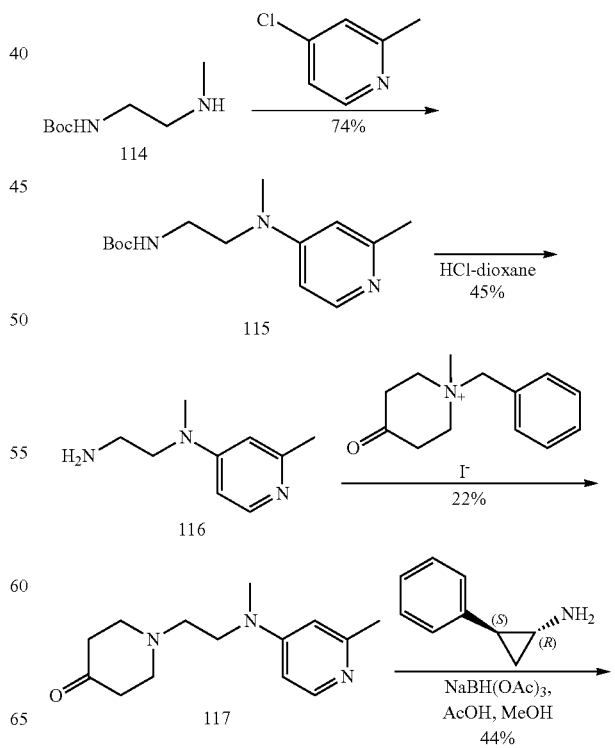

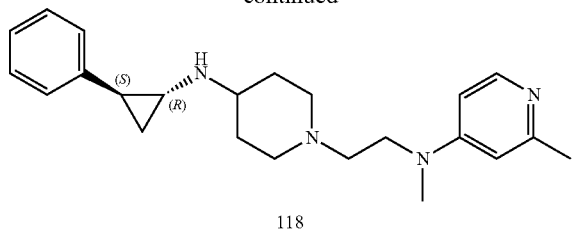

118

Compound 118, Example 44, was prepared from compound 114:

Compound 115: To a solution of 4-chloro-2-methyl-pyridine (1.00 g, 7.84 mmol, 1.00 eq) and tert-butyl N-[2-(methylamino)ethyl]carbamate (1.37 g, 7.84 mmol, 1.00 eq) in DMAC (20.0 mL) was added $K_2CO_3$ (2.17 g, 15.7 mmol, 2.00 eq), RuPhos (366 mg, 784 umol, 0.10 eq) and $Pd_2(dba)_3$ (359 mg, 392 umol, 0.05 eq). The reaction mixture was stirred at 90° C. under $N_2$ for 12 hours. After completion, water (15 mL) was added into the mixture. The resulting mixture was extracted with EA (3×20 mL). The combined organic phase was concentrated under vacuum. The residue was purified by silica gel chromatography (DCM/MeOH from 30/1 to 5/1) to give tert-butyl N-[2-[methyl-(2-methyl-4-pyridyl)amino]ethyl]carbamate (1.80 g, 5.83 mmol, 74.3% yield, 85.9% purity) as yellow oil. LCMS [M+1]: 266.

$^1$H NMR (400 MHz, METHANOL-$d_4$) δ=7.94-7.93 (d, J=6.0 Hz, 1H), 6.56-6.54 (m, 2H), 3.52-3.48 (t, J=6.4 Hz, 2H), 3.26-3.24 (m, 2H), 3.02 (s, 3H), 2.38 (s, 3H), 1.39 (s, 9H).

Compound 116: To a mixture of tert-butyl N-[2-[methyl-(2-methyl-4-pyridyl)amino]ethyl]carbamate (1.30 g, 4.90 mmol, 1.00 eq) in MeOH (10.0 mL) was added HCl/dioxane (4.90 mmol, 10.0 mL, 1.00 eq). The reaction mixture was stirred at 25° C. for 2 hours. After completion, the reaction mixture was concentrated under vacuum. The residue was dissolve in MeOH (20 mL) and a basic ion-exchange resin was added into the mixture. The resulting mixture was stirred at 25° C. for 5 hours. The solids were removed by filtration and the filtrate was concentrated under vacuum to give N'-methyl-N'-(2-methyl-4-pyridyl)ethane-1,2-diamine (500 mg, 2.23 mmol, 45.5% yield, 90.0% purity, HCl) as yellow oil.

Compound 117: To a mixture of N'-methyl-N'-(2-methyl-4-pyridyl)ethane-1,2-diamine (1.00 g, 6.05 mmol, 1.00 eq) and $K_2CO_3$ (125 mg, 908 umol, 0.150 eq) in EtOH (14.0 mL) was added the mixture of 1-benzyl-1-methyl-1-azinan-4-one (3.01 g, 9.08 mmol, 1.50 eq) in $H_2O$ (4.00 mL) at 90° C. for 0.5 hour. The reaction mixture was stirred at 90° C. for another 1 hour. After completion, the reaction mixture was concentrated under vacuum. The residue was purified by silica gel chromatography (DCM/MeOH from 30/1 to 10/1). Then purified by prep-HPLC (column: Phenomenex Synergi Max-RP 250*50 mm*10 um; mobile phase: [water (0.05% ammonia hydroxide v/v)-ACN]; B %: 15%-40%, 25 MIN; 69% min) to give 1-[2-[methyl-(2-methyl-4-pyridyl)amino]ethyl]piperidin-4-one (350 mg, 1.35 mmol, 22.4% yield, 95.6% purity) as a colorless oil. LCMS [M+1]: 248.

$^1$H NMR (400 MHz, METHANOL-$d_4$) δ=7.97-7.95 (m, 1H), 6.56-6.51 (m, 2H), 3.65-3.55 (m, 2H), 3.07-3.03 (d, J=16.4 Hz, 3H), 2.86-2.85 (m, 2H), 2.72-2.71 (m, 1H), 2.57 (m, 3H), 2.46-2.44 (m, 2H), 2.39 (s, 3H), 1.79 (m, 2H).

Compound 118: To a solution of (1R,2S)-2-phenylcyclopropanamine (20.0 mg, 150 umol, 1.00 eq) in MeOH (3.00 mL) was added 1-[2-[methyl-(2-methyl-4-pyridyl)amino]ethyl]piperidin-4-one (44.6 mg, 180 umol, 1.20 eq) at −10° C., then AcOH (18.0 mg, 300 umol, 17.2 uL, 2.00 eq) was added. 1 hour later, $NaBH(OAc)_3$ (95.5 mg, 451 umol, 3.00 eq) was added. The reaction mixture was stirred at −10-25° C. for 2 hours. After completion, water (10 mL) was added into the mixture. The resulting mixture was extracted with DCM (3×20 mL). The combined organic phase was concentrated under vacuum. The residue was purified by prep-HPLC (column: Phenomenex Synergi C18 150*25*10 um; mobile phase: [water (0.05% HCl)-ACN]; B %: 0%-20%, 7.8 min).

The desired fraction were collected and lyophilized to give N,2-dimethyl-N-[2-[4-[[(1R,2S)-2-phenylcyclopropyl]amino]-1-piperidyl]ethyl]pyridin-4-amine (32.0 mg, 67.2 umol, 44.7% yield, 99.5% purity, 3HCl) as a yellow oil. LCMS [M+1]: 365.

$^1$H NMR (400 MHz, $D_2O$) δ=7.98-7.96 (d, J=7.6 Hz, 1H), 7.39-7.35 (m, 2H), 7.32-7.30 (m, 1H), 7.20-7.18 (m, 2H), 6.85 (d, J=6.8 Hz, 1H), 6.80-6.79 (m, 1H), 4.01-3.97 (m, 2H), 3.77-3.74 (m, 3H), 3.46-3.42 (m, 2H), 3.23 (m, 2H), 3.17 (s, 3H), 3.01-2.99 (m, 1H), 2.52-2.49 (m, 6H), 2.07-1.94 (m, 2H), 1.55-1.47 (m, 2H).

Example 45

N-phenyl-2-(4-(((1R,2S)-2-phenylcyclopropyl)amino)piperidin-1-yl)ethanesulfonamide

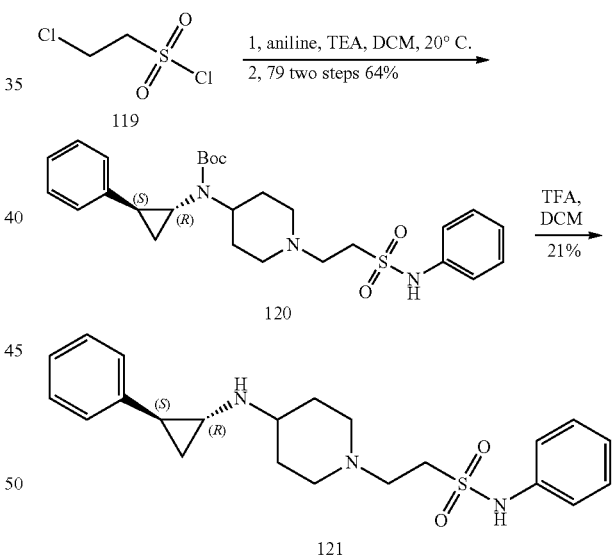

Compound 121, Example 45, was prepared from 119:

Compound 120: To a solution of 2-chloroethanesulfonyl chloride (70.0 mg, 429 umol, 44.8 uL, 1.00 eq) in DCM (5.00 mL) was added TEA (108 mg, 1.07 mmol, 148 uL, 2.50 eq) and aniline (31.9 mg, 343 umol, 31.3 uL, 0.80 eq) at 20° C. After stirring for 2 hrs, tert-butyl ((1R, 2S)-2-phenylcyclopropyl)(piperidin-4-yl)carbamate (163 mg, 515 umol, 1.20 eq) was added and stirred for 0.5 hrs more. The reaction mixture was concentrated. The residue was purified by prep-TLC to give tert-butyl ((1R,2S)-2-phenylcyclopropyl)(1-(2-(N-phenylsulfamoyl)ethyl)piperidin-4-yl)carbamate (60.0 mg, 273 umol, 63.6% yield) as a yellow solid. LCMS [M+1]: 500.

Compound 121: To a solution of tert-butyl ((1R, 2S)-2-phenylcyclopropyl) (1-(2-(N-phenylsulfamoyl)ethyl)piperidin-4-yl)carbamate (60.0 mg, 120 umol, 1.00 eq.) in DCM (3.00 mL) was added TFA (1.85 g, 16.2 mmol, 1.20 mL, 134 eq.) at 0° C. Then the reaction mixture was stirred at 20° C. for 12 hr. The reaction mixture was neutralized to 7-8 with saturated sodium bicarbonate and then concentrated. The solid was removed by filtration and the filtrate was concentrated to give a residue which purified by prep-HPLC (formic acid) to give N-phenyl-2-(4-(((1R, 2S)-2-phenylcyclopropyl)amino)piperidin-1-yl)ethanesulfonamide (10.0 mg, 25.0 umol, 20.8% yield) as a white solid. LCMS [M+1]: 400.

$^1$H NMR (400 MHz, methanol-d4) δ=8.23 (br s, 2H), 7.36-7.29 (m, 2H), 7.27-7.20 (m, 4H), 7.11 (td, J=7.2, 11.2 Hz, 2H), 7.03 (d, J=7.6 Hz, 2H), 3.27-3.19 (m, 2H), 2.73-2.63 (m, 4H), 2.62-2.55 (m, 1H), 2.35-2.26 (m, 1H), 1.97-1.82 (m, 3H), 1.73 (br d, J=11.2 Hz, 2H), 1.34-1.21 (m, 2H), 1.07-0.94 (m, 2H).

Example 46

1-morpholino-3-phenyl-2-(4-(((1R,2S)-2-phenylcyclopropyl)amino)piperidin-1-yl)propan-1-one

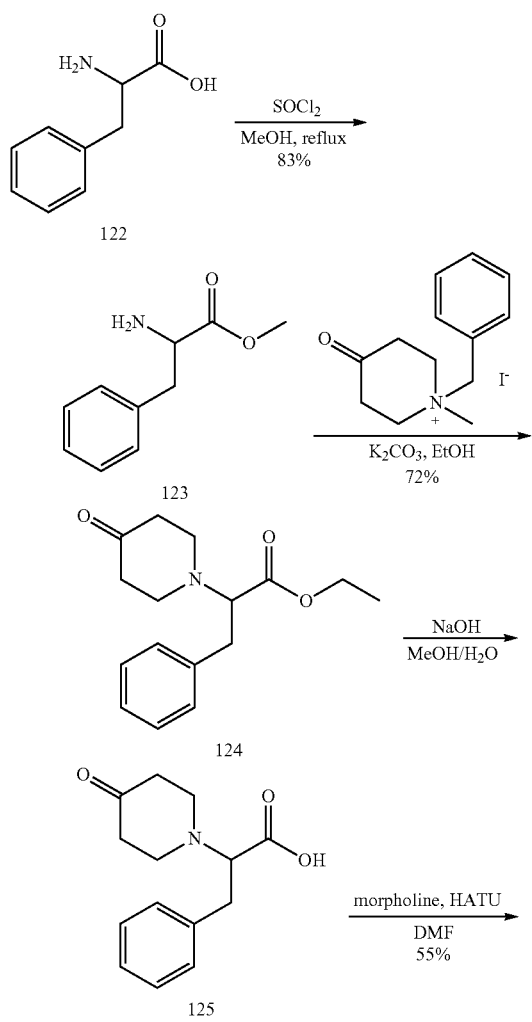

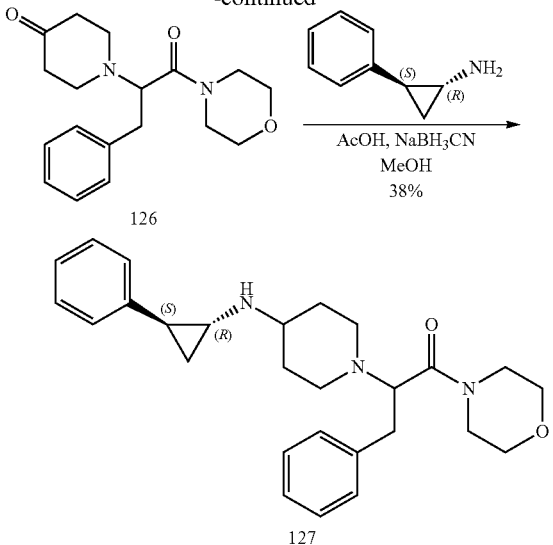

Compound 127, Example 46, was prepared from compound 122.

Compound 123: To a mixture of 2-amino-3-phenyl-propanoic acid (2.00 g, 12.1 mmol, 1.00 eq) in MeOH (30.0 mL) was added SOCl$_2$ (4.32 g, 36.3 mmol, 2.63 mL, 3.00 eq) in portions at 0° C. The reaction mixture was stirred at 0° C. for 0.5 hour, then the mixture was heated to 70° C. and stirred at 70° C. for 2.5 hours. After completion, the reaction mixture was concentrated. The residue was diluted with EA (30 mL), washed with sat. aq. NaHCO$_3$ (2×30 mL), the organic layer was washed with brine (2×30 mL), dried over Na$_2$SO$_4$, filtered and concentrated. The product methyl 2-amino-3-phenyl-propanoate (1.80 g, 10.0 mmol, 82.9% yield) was obtained as a yellow oil.

$^1$H NMR (400 MHz, Chloroform-d) δ 7.36-7.20 (m, 5H), 3.79-3.73 (m, 4H), 3.12 (dd, J=5.2, 13.6 Hz, 1H), 2.88 (dd, J=8.0, 13.6 Hz, 1H)

Compound 124: To a mixture of methyl 2-amino-3-phenyl-propanoate (1.80 g, 10.0 mmol, 1.00 eq) and K$_2$CO$_3$ (208 mg, 1.51 mmol, 0.15 eq) in EtOH (20.0 mL) was added a mixture of 1-benzyl-1-iodo-1-methyl-2,3,5,6-tetrahydropyridin-4-one (4.99 g, 15.1 mmol, 1.50 eq) in H$_2$O (10.0 mL) in portions at 78° C., then the mixture was heated to 90° C. and stirred at 90° C. for 3 hours. After completion, the reaction mixture was diluted with water (30 mL) and extracted with EA (3×30 mL). The combined organic layers were dried over Na$_2$SO$_4$, filtered and concentrated. The residue was purified by column chromatography (Petroleum ether/Ethyl acetate=10/1-5/1) to give ethyl 2-(4-oxo-1-piperidyl)-3-phenyl-propanoate (2.00 g, 6.73 mmol, 67.1% yield, 92.7% purity) as yellow oil.

$^1$H NMR (400 MHz, Chloroform-d) δ 7.33-7.21 (m, 5H), 4.15-4.07 (m, 2H), 3.63 (dd, J=6.8, 8.8 Hz, 1H), 3.17-2.97 (m, 4H), 2.95-2.84 (m, 2H), 2.51-2.37 (m, 4H), 1.19 (t, J=7.2 Hz, 3H)

Compound 125: To a mixture of ethyl 2-(4-oxo-1-piperidyl)-3-phenyl-propanoate (500 mg, 1.82 mmol, 1.00 eq) in MeOH (10.0 mL) and H$_2$O (2.00 mL) was added NaOH (291 mg, 7.28 mmol, 4.00 eq), the reaction mixture was stirred at 20° C. for 3 hours. After completion, the reaction mixture was adjusted to pH ~6, then concentrated. The solid was dissolved with MeOH (10 mL), concentrated, the residue was triturated with DCM (15 mL), the solid was filtered and dried. The product 2-(4-oxo-1-piperidyl)-3-phenyl-propanoic acid (380 mg, 1.34 mmol, 73.6% yield, HCl) was obtained as gray solid.

$^1$H NMR (400 MHz, DMSO-$d_6$) δ 7.34-7.16 (m, 5H), 3.55 (dd, J=6.8, 8.0 Hz, 1H), 3.04-2.76 (m, 6H), 2.46-2.21 (m, 4H)

Compound 126: To a mixture of 2-(4-oxo-1-piperidyl)-3-phenyl-propanoic acid (200 mg, 809 umol, 1.00 eq) in DMF (8.00 mL) wasd added HATU (615 mg, 1.62 mmol, 2.00 eq) and DIPEA (209 mg, 1.62 mmol, 282 uL, 2.00 eq) at 0° C. The resulting mixture was stirred at 0° C. for 0.5 hour, morpholine (141 mg, 1.62 mmol, 142 uL, 2.00 eq) was added, and the mixture was stirred at 0-15° C. for 11.5 hours. After completion, the reaction mixture was diluted with water (30 mL), then extracted with DCM (2×15 mL), the combined organic layer was washed with brine (2×40 mL), dried over Na$_2$SO$_4$, filtered and concentrated. The residue was purified by prep-TLC (Petroleum ether: Ethyl acetate=1:1) to give 1-(1-benzyl-2-morpholino-2-oxo-ethyl)piperidin-4-one (140 mg, 442 umol, 54.7% yield, 100% purity) as yellow solid. LCMS [M+1]: 317.

$^1$H NMR (400 MHz, Chloroform-d) δ 7.32-7.20 (m, 5H), 3.85 (dd, J=4.0, 10.0 Hz, 1H), 3.62-3.41 (m, 6H), 3.29-3.02 (m, 5H), 2.99-2.92 (m, 3H), 2.46 (t, J=6.0 Hz, 4H)

Compound 127: To a mixture of 1-(1-benzyl-2-morpholino-2-oxo-ethyl)piperidin-4-one (140 mg, 442 umol, 1.00 eq) in MeOH (10.0 mL) was added (1R,2S)-2-phenyl-cyclopropanamine (58.9 mg, 442 umol, 1.00 eq) and AcOH (53.1 mg, 885 umol, 50.6 uL, 2.00 eq) at −10° C. The resulting mixture was stirred at −10° C. for 0.5 hour, NaBH$_3$CN (83.4 mg, 1.33 mmol, 3.00 eq) was added in portions, and the mixture was stirred at 0-15° C. for 11.5 hours. After completion, the reaction mixture was diluted with water (15 mL), then extracted with DCM (2×15 mL), the organic layer was dried over Na$_2$SO$_4$, filtered and concentrated. The residue was purified by prep-HPLC (Instrument: GX-F; Column: Phenomenex Gemini 150*25 mm*10 um; Condition: water (0.05% HCl)-ACN; Begin B: 5; End B: 29; Gradient Time (min): 8; 100% B Hold Time (min): 2; FlowRate (ml/min): 25), the obtained product was concentrated and then lyophilized. The product 1-morpholino-3-phenyl-2-[4-[[(1R,2S)-2-phenylcyclopropyl]amino]-1-piperidyl]propan-1-one (85.0 mg, 168 umol, 37.9% yield, 100% purity, 2HCl) was obtained as a white solid. LCMS [M+1]: 434.

$^1$H NMR (400 MHz, Deuterium oxide) δ 7.41-7.29 (m, 5H), 7.28-7.18 (m, 3H), 7.15 (d, J=8.0 Hz, 2H), 4.16-3.92 (m, 1H), 3.75-3.71 (m, 1H), 3.62-3.45 (m, 4H), 3.41-3.06 (m, 7H), 3.04-2.90 (m, 2H), 2.85-2.62 (m, 1H), 2.56-2.33 (m, 3H), 2.33-2.20 (m, 1H), 2.16-1.91 (m, 2H), 1.53-1.39 (m, 2H)

Example 47

1-(2-(4-bromophenoxy)ethyl)-4-(((1R,2S)-2-phenyl-cyclopropyl)amino)piperidine-2,6-dione

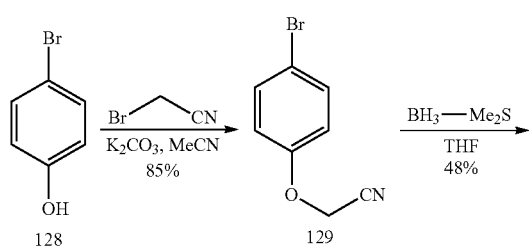

-continued

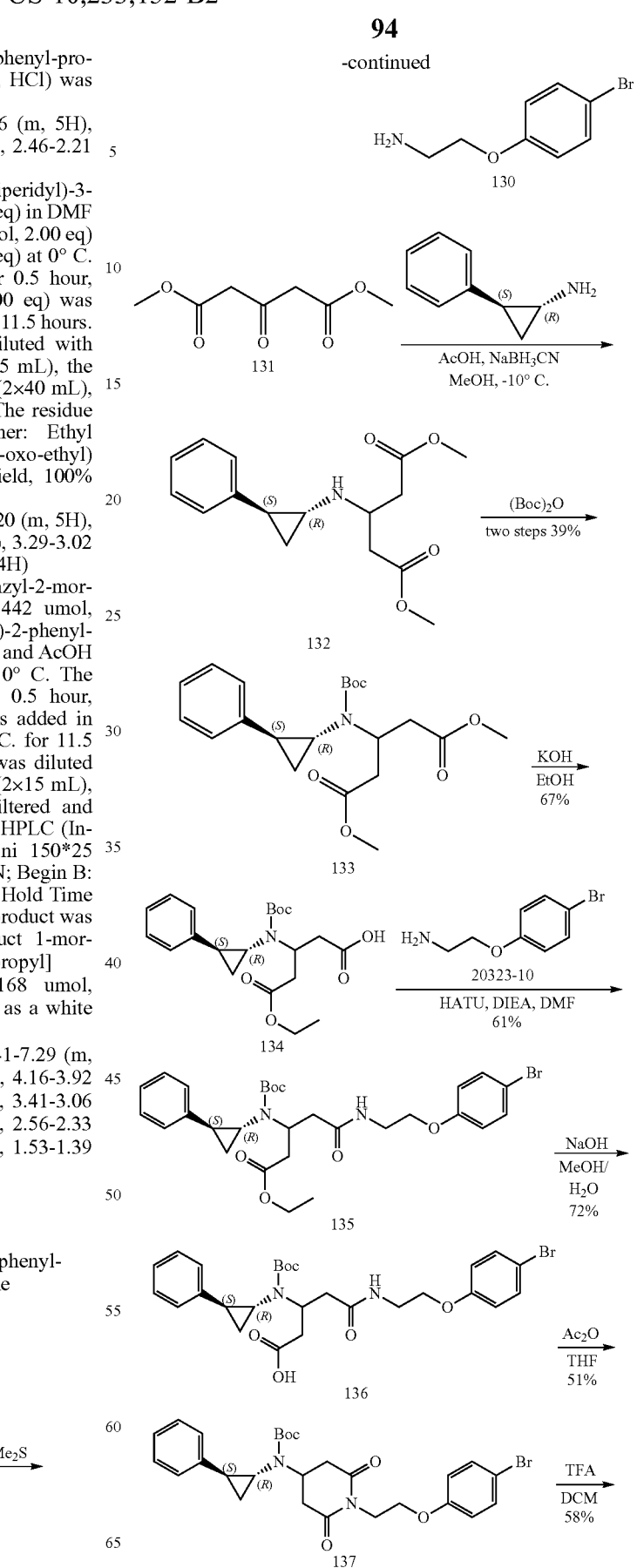

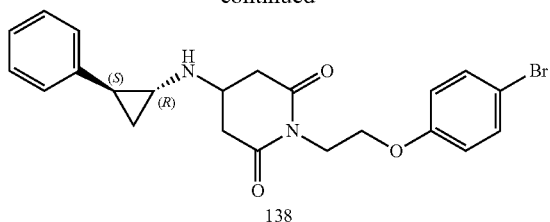

138

Compound 138, Example 47, was prepared from compound 128.

Compound 129: To a mixture of 4-bromophenol (2.00 g, 11.6 mmol, 1.00 eq) and 2-bromoacetonitrile (1.66 g, 13.9 mmol, 924 uL, 1.20 eq) in MeCN (30.0 mL) was added $K_2CO_3$ (3.99 g, 28.9 mmol, 2.50 eq), and the mixture was stirred at 80° C. for 3 hours. After completion, solids were removed by filtration and the filtrate concentrated. The residue was purified by column chromatography ($SiO_2$, Petroleum ether/Ethyl acetate=I/O to 10:1) to give 2-(4-bromophenoxy)acetonitrile (2.10 g, 9.83 mmol, 85.1% yield, 99.3% purity) as white solid.

$^1$H NMR (400 MHz, Chloroform-d) δ 7.49 (d, J=9.2 Hz, 2H), 6.90 (d, J=9.2 Hz, 2H), 4.77 (s, 2H).

Compound 130: To a mixture of 2-(4-bromophenoxy) acetonitrile (1.90 g, 8.96 mmol, 1.00 eq) in THF (20.0 mL) was added $BH_3$.THF (1 M, 26.9 mL, 3.00 eq) in portions at 0° C., the reaction was stirred at 0° C. for 2 hours, then the reaction mixture was heated to 80° C. and stirred at 80° C. for 12 hours. After completion, the reaction mixture was quenched with MeOH (30 mL) until no gas was formed, then concentrated. The residue was purified by column chromatography ($SiO_2$, Petroleum ether:Ethyl acetate=5:1 to Dichloromethane:Methanol=10:1) to give 2-(4-bromophenoxy)ethanamine (1.60 g, 7.26 mmol, 80.9% yield, 97.9% purity) as yellow oil. LCMS [M+1, M+3]: 216, 218.

Compound 132: To a mixture of dimethyl 3-oxopentanedioate (686 mg, 3.94 mmol, 567 uL, 1.05 eq) and (1R,2S)-2-phenylcyclopropanamine (500 mg, 3.75 mmol, 1.00 eq) in MeOH (15.0 mL) was added AcOH (450 mg, 7.50 mmol, 429 uL, 2.00 eq) at −10° C. The mixture was stirred at −10° C. for 1 hour, then $NaBH_3CN$ (707 mg, 11.3 mmol, 3.00 eq) was added to the mixture in portions at −10° C., and the reaction was stirred at −10~0° C. for 2 hours. After completion, the reaction mixture was added to water (20 mL), then extracted with DCM (2×20 mL). The combined organic layers were dried over $Na_2SO_4$, filtered and concentrated to give dimethyl 3-[[(1R,2S)-2-phenylcyclopropyl]amino]pentanedioate (1.00 g, crude) as yellow oil. LCMS [M+1]: 292.

Compound 133: A mixture of dimethyl 3-[[(1R,2S)-2-phenylcyclopropyl]amino]pentanedioate (900 mg, 3.09 mmol, 1.00 eq) in $(Boc)_2O$ (9.50 g, 43.5 mmol, 10.0 mL, 14.1 eq) was stirred at 15° C. for 12 hours. After completion, the mixture was purified by column chromatography ($SiO_2$, Petroleum ether/Ethyl acetate=100/1 to 5/1) to give dimethyl 3-[tert-butoxycarbonyl-[(1R,2S)-2-phenylcyclopropyl] amino]pentanedioate (500 mg, 1.20 mmol, 38.7% yield, 93.7% purity) as a colorless oil. LCMS [M-99]: 292

$^1$H NMR (400 MHz, Chloroform-d) δ 7.31-7.25 (m, 2H), 7.22-7.08 (m, 3H), 4.38-4.29 (m, 1H), 3.71 (s, 3H), 3.64 (s, 3H), 3.10-2.93 (m, 2H), 2.77-2.63 (m, 3H), 2.18-2.14 (m, 1H), 1.48-1.35 (m, 10H), 1.31-1.14 (m, 1H).

Compound 134: To a mixture of dimethyl 3-[tert-butoxycarbonyl-[(1R,2S)-2-phenylcyclopropyl]amino]pentanedioate (400 mg, 1.02 mmol, 1.00 eq) in EtOH (15.0 mL) was added KOH (80.8 mg, 1.22 mmol, 85% purity, 1.20 eq), and the reaction was stirred at 15° C. for 4 hours. After completion, the reaction mixture was adjusted with 1 M HCl to pH ~6, then extracted with DCM (2×15 mL). The combined organic layers were dried over $Na_2SO_4$, filtered and concentrated to give 3-[tert-butoxycarbonyl-[(1R,2S)-2-phenylcyclopropyl]amino]-5-ethoxy-5-oxo-pentanoic acid (270 mg, 684 umol, 67.1% yield, 99.2% purity) as yellow oil. LCMS [M-99]: 292.

Compound 135: To a mixture of 3-[tert-butoxycarbonyl-[(1R,2S)-2-phenylcyclopropyl]amino]-5-ethoxy-5-oxo-pentanoic acid (330 mg, 843 umol, 1.00 eq) in DMF (10.0 mL) was added HATU (641 mg, 1.69 mmol, 2.00 eq) and DIPEA (218 mg, 1.69 mmol, 294 uL, 2.00 eq) at 0° C. After the reaction was stirred at 0° C. for 0.5 hour, 2-(4-bromophenoxy)ethanamine (237 mg, 1.10 mmol, 1.30 eq) was added, and the mixture was stirred at 0-15° C. for 11.5 hours. After completion, the reaction mixture was added to water (15 mL), then extracted with DCM (2×15 mL), the combined organic layer was dried over $Na_2SO_4$, filtered and concentrated. The residue was purified by column chromatography (Petroleum ether:Ethyl acetate=50:1-3:1) to give ethyl 5-[2-(4-bromophenoxy)ethylamino]-3-[tert-butoxycarbonyl-[(1R,2S)-2-phenylcyclopropyl]amino]-5-oxo-pentanoate (330 mg, 515 umol, 61.1% yield, 92% purity) as a yellow oil. LCMS [M-99]: 489,491.

Compound 136: To a mixture of ethyl 5-[2-(4-bromophenoxy)ethylamino]-3-[tert-butoxycarbonyl-[(1R,2S)-2-phenylcyclopropyl]amino]-5-oxo-pentanoate (250 mg, 424 umol, 1.00 eq) in MeOH (2.00 mL) and $H_2O$ (500 uL) was added NaOH (67.9 mg, 1.70 mmol, 4.00 eq), and the mixture was stirred at 15° C. for 3 hours. After completion, the reaction mixture was diluted with 0.5 M HCl aqueous solution to pH-7, then the mixture was added to water (10 mL), and extracted with DCM (2×10 mL). The combined organic layers were dried over $Na_2SO_4$, filtered and concentrated to give 5-[2-(4-bromophenoxy)ethylamino]-3-[tert-butoxycarbonyl-[(1R,2S)-2-phenylcyclopropyl] amino]-5-oxo-pentanoic acid (180 mg, 306 umol, 72.1% yield, 95.4% purity) as yellow solid. LCMS [M-99, M+23]: 463, 585.

Compound 137: To a mixture of 5-[2-(4-bromophenoxy) ethylamino]-3-[tert-butoxycarbonyl-[(1R,2S)-2-phenylcyclopropyl]amino]-5-oxo-pentanoic acid (120 mg, 214 umol, 1.00 eq) in THF (4.00 mL) was added $Ac_2O$ (43.6 mg, 427 umol, 40.0 uL, 2.00 eq), and the reaction was stirred at 70° C. for 12 hours under $N_2$. After completion, the reaction mixture was concentrated. The residue was purified by prep-TLC (Petroleum ether: Ethyl acetate=3:1) to give tert-butyl N-[1-[2-(4-bromophenoxy)ethyl]-2,6-dioxo-4-piperidyl]-N-[(1R,2S)-2-phenylcyclopropyl]carbamate (60.0 mg, 109 umol, 51.4% yield, 99.5% purity) as a white solid. LCMS [M-55, M+23]: 487, 567.

$^1$H NMR (400 MHz, Chloroform-d) δ 7.40-7.19 (m, 5H), 7.11-7.04 (m, 2H), 6.81-6.74 (m, 2H), 4.18 (t, J=6.2 Hz, 2H), 4.13-4.03 (m, 3H), 3.45-3.30 (m, 2H), 2.93-2.82 (m, 2H), 2.74-2.67 (m, 1H), 2.19-2.06 (m, 1H), 1.42 (s, 9H), 1.33-1.25 (m, 2H).

Compound 138: To a mixture of tert-butyl N-[1-[2-(4-bromophenoxy)ethyl]-2,6-dioxo-4-piperidyl]-N-[(1R,2S)-2-phenylcyclopropyl]carbamate (60.0 mg, 110 umol, 1.00 eq) in DCM (500 uL) was added TFA (770 mg, 6.75 mmol, 500 uL, 61.2 eq), and the reaction was stirred at 15° C. for 1 hour. After completion, the reaction mixture was concentrated. The residue was purified by prep-HPLC ((Instrument: GX-E; Column: Phenomenex Synergi C18 150*25*10 um; Condition: water (0.05% HCl)-ACN; Begin B: 35; End B:

55; Gradient Time (min): 7.8; 100% B Hold Time (min): 2; FlowRate (ml/min): 28). The obtained product was concentrated and then lyophilized. The product 1-[2-(4-bromophenoxy)ethyl]-4-[[(1R,2S)-2-phenylcyclopropyl]amino]piperidine-2,6-dione (30.8 mg, 63.9 umol, 57.9% yield, 99.8% purity, HCl) was obtained as a yellow oil. LCMS [M+1]: 443, 445.

¹H NMR (400 MHz, Methanol-d₄) δ 7.41-7.31 (m, 4H), 7.29-7.17 (m, 3H), 6.85 (d, J=8.4 Hz, 2H), 4.20-4.06 (m, 5H), 3.32-3.22 (m, 2H), 3.18-3.01 (m, 3H), 2.65-2.54 (m, 1H), 1.68-1.56 (m, 1H), 1.53-1.43 (m, 1H).

Example 48

1-Morpholino-3-(4-(((1R,2S)-2-phenylcyclopropyl)amino)piperidin-1-yl)propan-1-one di-hydrochloride (142)

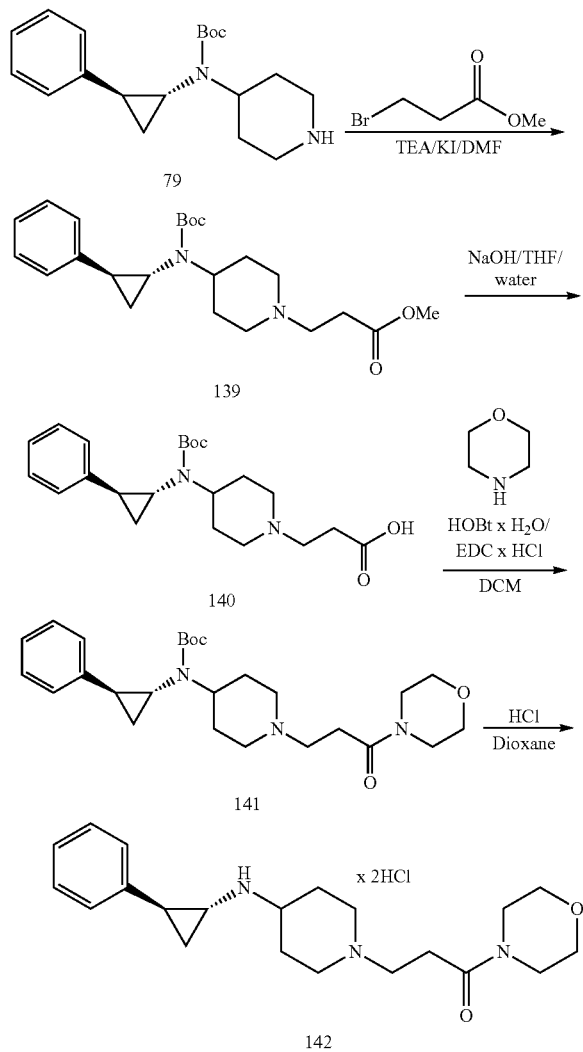

Step 1. Methyl 3-(4-((tert-butoxycarbonyl)((1R,2S)-2-phenylcyclopropyl)amino)piperidin-1-yl)propanoate (139)

To a solution of the intermediate 79 (1.00 g, 3.16 mmol) in DMF (8 mL) were added TEA (1.189 mL, 8.53 mmol), KI (131 mg, 0.790 mmol) and methyl-3-bromopropionate (0.345 mL, 3.16 mmol). The reaction mixture was stirred at RT for 4 hrs, diluted with brine and extracted with EA. The extract was washed with brine, dried over anhydrous Na₂SO₄, filtered and concentrated. The residue was subjected to flash column chromatography, eluent EA-hexanes (4:1) to afford title compound 65 (1.027 g, 81% yield) as a gum. The product contains 0.18 M of EA per 1M of the desired compound.

¹H NMR: 500 MHz, acetone-d₆, δ (ppm): 7.32-7.28 (m, 2H), 7.21-7.18 (m, 3H), 3.68-3.62 (m, 1H), 3.65 (s, 3H), 3.00-2.93 (m, 2H), 2.65-2.61 (m, 3H), 2.48 (t, J=7.2 Hz, 2H), 2.19-2.10 (m, 3H), 2.06-2.00 (m, 2H), 1.76-1.67 (m, 2H), 1.43 (s, 9H), 1.42-1.38 (m, 1H), 1.29-1.25 (m, 1H). MS: 402.5 (calcd.), 403.3 (M+H⁺, found).

Step 2. 3-(4-((tert-Butoxycarbonyl)((1R,2S)-2-phenylcyclopropyl)amino)piperidin-1-yl)propanoic acid (140)

To a solution of ester 139 (1.027 g, 2.55 mmol) in THF (20 mL) was added a solution of NaOH (153 mg, 3.83 mmol) in water (10 mL). The reaction mixture was stirred at rt for 2 hrs. acidified to pH 5 with HCl. The acidic solution was evaporated in vacuum to form a glassy solid. The material was then suspended in DCM, treated with hexanes and evaporated to afford the title compound 140 (1.13 g, 99% yield) as white fluffy solid which contained 1.5 eq of NaCl. The material was taken to the next step as is. MS: 388.5 (calcd.), 389.7 (M+H⁺, found).

Step 3. tert-Butyl (1-(3-morpholino-3-oxopropyl)piperidin-4-yl)((1R,2S)-2-phenylcyclopropyl)carbamate (141)

To a suspension of acid 140 (800 mg, 1.79 mmol) in DCM (30 mL) was added HOBt hydrate (548 mg, 3.58 mmol), EDC hydrochloride (1.029 g, 5.37 mmol) and morpholine (0.627 mL, 7.16 mmol). The reaction mixture was stirred overnight at rt, diluted with more DCM and washed with brine. The organic phase was dried over Na₂SO₄, filtered and concentrated. The residue was purified by flash column chromatography, eluent 5 then 10% MeOH (with 2% ammonia) in DCM to afford title compound 141 (748 mg, 91% yield) as a honey-like material that contains ca 0.6 M of DCM per 1M of the product. The material was taken to the next step as is.

¹H NMR: 500 MHz, CD₃OD, δ (ppm): 7.26-7.23 (m, 2H), 7.16-7.10 (m, 3H), 3.72-3.68 (m, 1H), 3.67-3.62 (m, 4H), 3.57-3.53 (m, 4H), 3.05-2.98 (m, 2H), 2.69-2.66 (m, 2H), 2.62-2.56 (m, 3H), 2.13-2.09 (m, 4H), 2.02-1.94 (m, 1H), 1.82-1.79 (m, 1H), 1.75-1.72 (m, 1H), 1.41 (s, 9H), 1.40-1.38 (m, 1H), 1.25-1.21 (m, 1H). MS: 457.6 (calcd.), 458.4 (M+H⁺, found).

Step 4. 1-Morpholino-3-(4-(((1R,2S)-2-phenylcyclopropyl)amino)piperidin-1-yl)propan-1-one di-hydrochloride (142)

To a solution of compound 141 (748 mg, 1.635 mmol) in dioxane (7.0 mL) at rt was added a 4M HCl solution of in dioxane (12.0 ml, 48 mmol). The mixture was stirred at ambient temperature for 3 hrs, evaporated to dryness in vacuum. The resultant white precipitate was triturated with acetone to afford title compound 142 (637 mg, 91% yield) as a white solid (Example 48).

¹H NMR: 500 MHz, DMSO-d₆, δ (ppm): 10.71 and 10.52 (two bs, 1H, mixture of rotamers), 10.18 and 10.02 (2 bs, 2H, mixture of rotamers), 7.32-7.29 (m, 2H), 7.24-7.17 (m, 3H), 3.61-3.59 (m, 4H), 3.56-3.54 (m, 2H), 3.45-3.44 (m, 5H), 3.24 (bt, 2H), 3.03-2.94 (m, 3H), 2.89 (t, J=7.6 Hz, 2H), 2.68-2.65 and 2.59-2.55 (two m, 1H, mixture of rotamers), 2.32-2.21 (bs, 2H), 2.11-2.01 (m, 2H), 1.66 and 1.60-1.56 (bs and m, 1H, mixture of rotamers), 1.31-1.27 (m, 1H). MS: 357.5 (calcd.), 358.7 (M+H⁺, found).

Following the general teachings of the Reaction Schemes and specific synthetic routes set forth herein, the additional following compounds were prepared:

TABLE 2

Further Exemplary Compounds of Formula (I) and Formula (II)

| Ex. # | Structure | Method | LCMS [M + 1] Observed | ¹H NMR |
|---|---|---|---|---|
| 49 | 2-(4-(3-(4-(((1R,2S)-2-phenylcyclopropyl)amino)piperidin-1-yl)propoxy)phenyl)acetic acid | Scheme 2b | 409.4 | (400 MHz, methanol-d₄) δ 7.38-7.30 (m, 2H), 7.29-7.18 (m, 5H), 6.91 (d, J = 8.8 Hz, 2H), 4.13 (t, J = 5.4 Hz, 2H), 3.89-3.68 (m, 3H), 3.60-3.52 (m, 2H), 3.40-3.31 (m, 2H), 3.26-3.12 (m, 2H), 3.07-3.04 (m, 1H), 2.67-2.42 (m, 3H), 2.34-2.09 (m, 4H), 1.65-1.56 (m, 1H), 1.52-1.46 (m, 1H). |
| 50 | 1-(4-((2-(4-(((1R,2S)-2-phenylcyclopropyl)amino)piperidin-1-yl)ethyl)amino)phenyl)piperidin-2-one | Example 20 | 433.3 | (400 MHz, deuterium oxide) δ 7.28-7.21 (m, 2H), 7.20-7.14 (m, 3H), 7.13-7.03 (m, 4H), 3.70-3.57 (m, 5H), 3.50-3.47 (m, 2H), 3.40-3.36 (m, 2H), 3.19-3.02 (m, 2H), 2.89-2.85 (m, 1H), 2.45-2.28 (m, 5H), 2.00-1.72 (m, 6H), 1.45-1.29 (m, 2H) |
| 51 | 3-(4-((2-(4-(((1R,2S)-2-phenylcyclopropyl)amino)piperidin-1-yl)ethyl)amino)phenyl)-1,3-oxazinan-2-one | Example 20 | 435.4 | (400 MHz, deuterium oxide) δ 7.32-7.17 (m, 5H), 7.10 (d, J = 7.6 Hz, 2H), 7.03 (d, J = 8.8 Hz, 2H), 4.35 (t, J = 5.2 Hz, 2H), 3.74-3.54 (m, 7H), 3.44-3.34 (m, 2H), 3.13-3.04 (m, 2H), 2.93-2.86 (m, 1H), 2.48-2.31 (m, 3H), 2.15-1.85 (m, 4H), 1.50-1.32 (m, 2H) |
| 52 | 4-(4-((2-(4-(((1R,2S)-2-phenylcyclopropyl)amino)piperidin-1-yl)ethyl)amino)phenyl)morpholin-3-one | Example 20 | 435.2 | (400 MHz, deuterium oxide) δ 7.38-7.04 (m, 7H), 7.00-6.76 (m, 2H), 4.24 (s, 2H), 4.05-3.91 (m, 2H), 3.74-3.51 (m, 7H), 3.42-3.28 (m, 2H), 3.20-3.09 (m, 2H), 2.94-2.86 (m, 1H), 2.51-2.25 (m, 3H), 2.02-1.84 (m, 2H), 1.51-1.30 (m, 2H) |
| 53 | 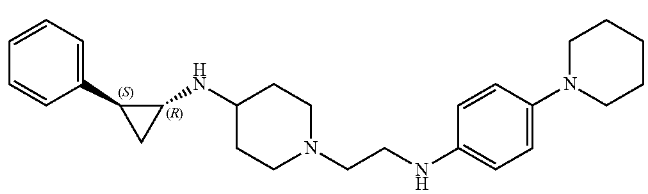 | Example 20 | 419.3 | (400 MHz, deuterium oxide) δ 7.36-7.26 (m, 4H), 7.25-7.17 (m, 1H), 7.12-7.10 (m, 2H), 6.78-6.75 (m, 2H), 3.79-3.58 (m, 3H), 3.57-3.39 (m, 6H), 3.35-3.26 (m, 2H), 3.20-2.99 (m, 2H), 2.93-2.91 (m, 1H), 2.54-2.29 (m, 3H), 2.06-1.70 (m, 7H), 1.60-1.32 (m, 3H) |

TABLE 2-continued

Further Exemplary Compounds of Formula (I) and Formula (II)

| Ex. # | Structure | Method | LCMS [M + 1] Observed | ¹H NMR |
|---|---|---|---|---|
| | N-((1R,2S)-2-phenylcyclopropyl)-1-(2-((4-(piperidin-1-yl)phenyl)amino)ethyl)piperidin-4-amine | | | |
| 54 | 1-(2-((4-morpholinophenyl)amino)ethyl)-N-((1R,2S)-2-phenylcyclopropyl)piperidin-4-amine | Example 20 | 421.2 | (400 MHz, deuterium oxide) δ 7.33 (d, J = 8.8 Hz, 2H), 7.28-7.12 (m, 3H), 7.08-7.02 (m, 2H), 6.77 (d, J = 8.0 Hz, 2H), 4.02-3.92 (m, 4H), 3.72-3.45 (m, 9H), 3.29-3.24 (m., 2H), 3.12-3.06 (m, 2H), 2.94-2.82 (m, 1H), 2.48-2.23 (m, 3H), 2.04-1.85 (m, 2H), 1.49-1.28 (m, 2H) |
| 55 | 1-(2-((4-(4-methylpiperazin-1-yl)phenyl)amino)ethyl)-N-((1R,2S)-2-phenylcyclopropyl)piperidin-4-amine | Example 20 | 434.3 | (400 MHz, deuterium oxide) δ 7.40-6.99 (m, 9H), 3.95-3.54 (m, 9H), 3.51-3.05 (m, 8H), 3.00-2.86 (m, 4H), 2.51-2.29 (m, 3H), 2.05-1.88 (m, 2H), 1.52-1.33 (m, 2H) |
| 56 | 1-(4-((2-(4-(((1R,2S)-2-phenylcyclopropyl)amino)piperidin-1-yl)ethyl)amino)phenyl)pyrrolidin-2-one | Example 20 | 419.3 | (400 MHz, deuterium oxide) δ 7.42 (d, J = 8.4 Hz, 2H), 7.29-7.10 (m, 5H), 7.09-6.99 (m, 2H), 3.83-3.54 (m, 7H), 3.42-3.38 (m, 2H), 3.14-3.08 (m, 2H), 2.89-2.72 (m, 1H), 2.53-2.27 (m, 5H), 2.08-1.82 (m, 4H), 1.45-1.26 (m, 2H) |
| 57 | 3-(4-((2-(4-(((1R,2S)-2-phenylcyclopropyl)amino)piperidin-1-yl)ethyl)amino)phenyl)oxazolidin-2-one | Example 20 | 421.2 | (400 MHz, deuterium oxide) δ 7.36 (d, J = 8.8 Hz, 2H), 7.29-7.23 (m, 2H), 7.22-7.16 (m, 1H), 7.08-7.03 (m, 4H), 4.40 (t, J = 8.2 Hz, 2H), 3.98 (t, J = 8.2 Hz, 2H), 3.71-3.57 (m, 5H), 3.42-3.33 (m, 2H), 3.16-3.04 (m, 2H), 2.90-2.88 (m, 1H), 2.47-2.29 (m, 3H), 2.02-1.85 (m, 2H), 1.50-1.31 (m, 2H). |
| 58 | 1-methyl-3-(4-((2-(4-(((1R,2S)-2-phenylcyclopropyl)amino)piperidin-1-l)ethyl)amino)phenyl)imidazolidin-2-one | Example 20 | 434.2 | (400 MHz, deuterium oxide) δ 7.57-7.33 (m, 2H), 7.33-7.04 (m, 7H), 3.91-3.55 (m, 7H), 3.52-3.34 (m, 4H), 3.21-3.06 (m, 2H), 2.92-2.90 (m, 4H), 2.48-2.32 (m, 3H), 2.05-1.85 (m, 2H), 1.50-1.33 (m, 2H). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 59 | N-(2-(4-(((1R,2S)-2-phenylcyclopropyl)amino)piperidin-1-yl)ethyl)methanesulfonamide | Scheme 3b | 338.1 | (400 MHz, methanol-$d_4$) δ, 7.37-7.31 (m, 2H), 7.29-7.24 (m, 1H), 7.22 (d, J = 7.6 Hz, 2H), 3.86 (d, J = 12.0 Hz, 2H), 3.79-3.64 (m, 1H), 3.61-3.47 (m, 2H), 3.39-3.34 (m, 2H), 3.28-3.15 (m, 2H), 3.10-3.00 (m, 4H), 2.60-2.54 (m, 1H), 2.48 (t, J = 12.4 Hz, 2H), 2.20-2.05 (m, 2H), 1.65-1.56 (m, 1H), 1.50-1.43 (m, 1H) |
| 60 | N-(2-(4-(((1R,2S)-2-phenylcyclopropyl)amino)piperidin-1-yl)ethyl)benzenesulfonamide | Scheme 3b | 400.2 | (400 MHz, methanol-$d_4$) δ, 7.93 (d, J = 7.2 Hz, 2H), 7.73-7.67 (m, 1H), 7.67-7.60 (m, 2H), 7.39-7.30 (m, 2H), 7.30-7.24 (m, 1H), 7.22 (d, J = 7.6 Hz, 2H), 3.84 (d, J = 12.8 Hz, 2H), 3.77-3.67 (m, 1H), 3.50 (br. s., 1H), 3.30-3.18 (m, 4H), 3.09-3.04 (m, 1H), 2.62-2.55 (m, 1H), 2.49 (t, J = 12.8 Hz, 2H), 2.35 (br. s., 1H), 2.23-2.13 (m, 2H), 1.73-1.58 (m, 1H), 1.50-1.42 (q, J = 7.1 Hz, 1H). |
| 61 | 4-(3-(4-(((1R,2S)-2-phenylcyclopropyl)amino)piperidin-1-yl)propoxy)benzoic acid | Scheme 2b | 395.2 | (400 MHz, DMSO-$d_6$) δ 10.55 (s, 1H), 10.24-9.59 (m, 3H), 7.91 (d, J = 8.4 Hz, 2H), 7.37-7.28 (m, 2H), 7.27-7.16 (m, 3H), 7.03 (d, J = 8.8 Hz, 2H), 4.14 (t, J = 5.8 Hz, 2H), 3.65-3.53 (m, 2H), 3.54-3.46 (m, 1H), 3.21-3.09 (m, 2H), 3.07-2.92 (m, 3H), 2.39-1.95 (m, 7H), 1.63-1.52 (m, 1H), 1.33-1.29 (m, 1H). |
| 62 | (E)-3-(4-(3-(4-(((1R,2S)-2-phenylcyclopropyl)amino)piperidin-1-yl)propoxy)phenyl)acrylic acid | Example 34 | 421.2 | (400 MHz, DMSO-$d_6$) δ 12.27 (br. s., 1H), 10.59 (br. s., 1H), 9.98 (br. s., 2H), 7.65 (d, J = 8.4 Hz, 2H), 7.55 (d, J = 16.0 Hz, 1H), 7.40-7.28 (m, 2H), 7.27-7.15 (m, 3H), 6.98 (d, J = 8.0 Hz, 2H), 6.39 (d, J = 16.0 Hz, 1H), 4.11 (t, J = 5.6 Hz, 2H), 3.66-3.55 (m, 2H), 3.20-3.08 (m, 3H), 3.02-2.96 (m, 3H), 2.41-1.95 (m, 7H), 1.64-1.53 (m, 1H), 1.36-1.25 (m, 1H) |
| 63 | 1-(4-(4-((2-(4-(((1R,2S)-2-phenylcyclopropyl)amino)piperidin-1-yl)ethyl)amino)phenyl)piperazin-1-yl)ethan-1-one | Example 20 | 462.2 | (400 MHz, deuterium oxide) δ 7.28 (d, J = 8.8 Hz, 2H), 7.19-7.10 (m, 3H), 7.05-6.96 (m, 2H), 6.78-6.75 (m, 2H), 3.88-3.73 (m, 4H), 3.68-3.51 (m, 5H), 3.39-3.36 (m, 4H), 3.27-3.22 (m, 2H), 3.04-2.98 (m., 2H), 2.84-2.80 (m., 1H), 2.42-2.22 (m, 3H), 2.01 (s, 3H), 1.98-1.82 (m, 2H), 1.43-1.22 (m, 2H) |

TABLE 2-continued

Further Exemplary Compounds of Formula (I) and Formula (II)

| Ex. # | Structure | Method | LCMS [M + 1] Observed | ¹H NMR |
|---|---|---|---|---|
| 64 | 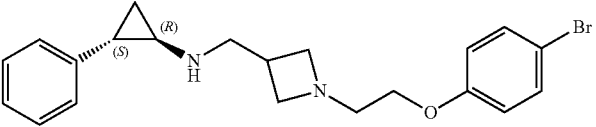<br>(1R,2S)-N-((1-(2-(4-bromophenoxy)ethyl)azetidin-3-yl)methyl)-2-phenylcyclopropan-1-amine | Example 12 | 403.1 | (400 MHz, Methanol-$d_4$) δ7.46 (d, J = 9.2 Hz, 2H), 7.38-7.29 (m, 2H), 7.29-7.18 (m, 3H), 6.96 (d, J = 9.2 Hz, 2H), 4.50-4.41 (m, 2H), 4.36-4.20 (m, 4H), 3.82-3.57 (m, 4H), 3.48-3.37 (m, 1H), 3.07-2.96 (m, 1H), 2.64-2.58 (m, 1H), 1.64-1.59 (m, 1H), 1.46-1.41 (m, 1H) |
| 65 | 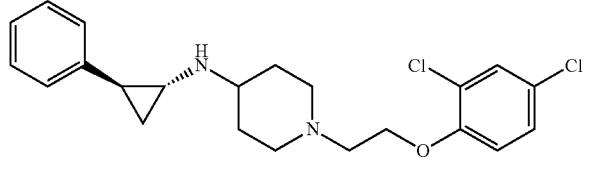<br>1-(2-(2,4-dichlorophenoxy)ethyl)-N-((1R,2S)-2-phenylcyclopropyl)piperidin-4-amine | Scheme 2b | 405.1 | (400 MHz, Methanol-$d_4$) δ7.50 (d, J = 2.8 Hz, 1H), 7.39-7.31 (m, 3H), 7.30-7.16 (m, 4H), 4.61-4.50 (m, 2H), 4.01-3.95 (m, 2H), 3.84-3.66 (m, 3H), 3.42-3.36 (m, 2H), 3.08-3.04 (m, 1H), 2.63-2.40 (m, 3H), 2.24-2.18 (m, 2H), 1.71-1.57 (m, 1H), 1.52-1.46 (m, 1H) |
| 66 | 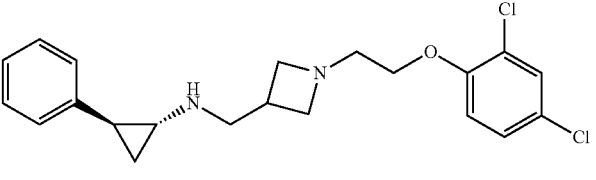<br>(1R,2S)-N-((1-(2-(2,4-dichlorophenoxy)ethyl)azetidin-3-yl)methyl)-2-phenylcyclopropan-1-amine | Example 11 | 391.0 | (400 MHz, deuterium oxide) δ7.49 (d, J = 2.8 Hz, 1H), 7.39-7.29 (m, 3H), 7.29-7.18 (m, 3H), 7.15 (d, J = 8.8 Hz, 1H), 4.61-4.48 (m, 2H), 4.42-4.26 (m., 4H), 3.83-3.76 (m, 2H), 3.73-3.60 (m, 2H), 3.43-3.34 (m, 1H), 3.06-2.98 (m, 1H), 2.62-2.55 (m, 1H), 1.64-1.56 (m, 1H), 1.47-1.41 (m, 1H). |
| 67 | 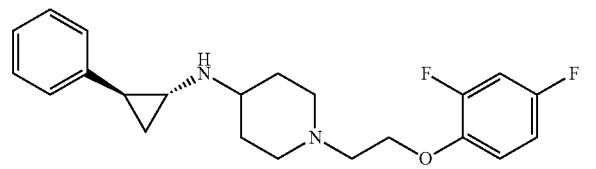<br>1-(2-(2,4-difluorophenoxy)ethyl)-N-((1R,2S)-2-phenylcyclopropyl)piperidin-4-amine | Scheme 2b | 373.2 | (400 MHz, deuterium oxide) δ7.31-7.23 (m, 2H), 7.22-7.16 (m, 1H), 7.09 (d, J = 7.2 Hz, 2H), 7.04-7.00 (m, 1H), 6.95-6.91 (m, 1H), 6.86-6.77 (m, 1H), 4.37-4.26 (m, 2H), 3.83-3.59 (m, 3H), 3.57-3.48 (m., 2H), 3.21-3.13 (m, 2H), 2.94-2.87 (m, 1H), 2.49-2.30 (m, 3H), 2.06-1.88 (m, 2H), 1.50-1.33 (m, 2H) |
| 68 | 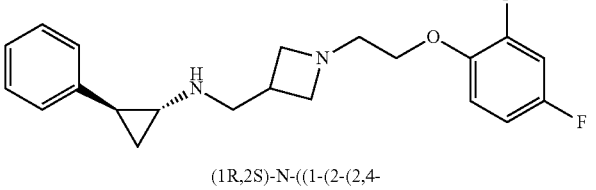<br>(1R,2S)-N-((1-(2-(2,4-difluorophenoxy)ethyl)azetidin-3-yl)methyl)-2-phenylcyclopropan-1-amine | Example 11 | 359.2 | (400 MHz, deuterium oxide) δ7.26-7.19 (m, 2H), 7.17-7.11 (m, 1H), 7.07 (d, J = 7.2 Hz, 2H), 7.02-6.88 (m, 2H), 6.85-6.77 (m, 1H), 4.42-4.28 (m, 2H), 4.21-3.98 (m, 4H), 3.68-3.42 (m, 4H), 3.39-3.25 (m, 1H), 2.94-2.83 (m, 1H), 2.44-2.38 (m, 1H), 1.47-1.38 (m, 1H), 1.36-1.28 (m, 1H). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 69 | (E)-3-(4-(2-hydroxy-3-(4-(((1R,2S)-2-phenylcyclopropyl)amino)piperidin-1-yl)propoxy)phenyl)-N-(methylsulfonyl)acrylamide | Example 35 | 514.3 | (400 MHz, deuterium oxide) δ 7.57 (d, J = 15.6 Hz, 1H), 7.51 (d, J = 8.8 Hz, 2H), 7.34-7.19 (m, 3H), 7.12 (d, J = 7.6 Hz, 2H), 6.98-6.88 (m, 2H), 6.29 (d, J = 16 Hz, 1H), 4.49-4.42 (m, 1H), 4.12-3.98 (m, 2H), 3.84-3.61 (m, 3H), 3.43-3.25 (m, 5H), 3.24-3.00 (m, 2H), 2.94-2.92 (m, 1H), 2.51-2.31 (m, 3H), 2.12-1.92 (m, 2H), 1.53-1.36 (m, 2H). |
| 70 | (1R,2S)-2-phenyl-N-((1-(2-(p-tolyloxy)ethyl)azetidin-3-yl)methyl)cyclopropan-1-amine | Example 10 | 337.2 | (400 MHz, METHANOL-d₄) δ = 7.31-7.29 (d, J = 7.6 Hz, 2H), 7.25-7.18 (m, 3H), 7.12-7.10 (d, J = 8.4 Hz, 2H), 6.88-6.85 (d, J = 8.4 Hz, 2H), 4.50-4.38 (m, 2H), 4.20 (m, 4H), 3.69 (m, 4H), 3.40 (br s, 1H), 3.01 (br s, 1H), 2.61-2.56 (m, 1H), 2.27 (s, 3H), 1.60-1.57 (m, 1H), 1.43-1.39 (q, J = 6.8 Hz, 1H) |
| 71 | (1R,2S)-2-phenyl-N-((1-(2-(pyridin-2-yloxy)ethyl)azetidin-3-yl)methyl)cyclopropan-1-amine | Example 10 | 324.2 | (400 MHz, METHANOL-d₄) δ = 8.36-8.35 (br d, J = 5.2 Hz, 1H), 8.25 (br s, 1H), 7.40-7.38 (br d, J = 6.4 Hz, 2H), 7.31-7.29 (m, 2H), 7.24-7.19 (m, 3H), 4.70 (br s, 2H), 4.50-4.47 (m, 2H), 4.32-4.30 (m, 2H), 3.84 (br s, 2H), 3.73 (br s, 1H), 3.61-3.59 (br d, J = 5.2 Hz, 1H), 3.41 (br s, 1H), 3.02 (br s, 1H), 2.64-2.59 (m, 1H), 1.65-1.59 (m, 1H), 1.41-1.39 (m, 1H) |
| 72 | 4-(2-(4-(((1R,2S)-2-phenylcyclopropyl)amino)piperidin-1-yl)ethoxy)benzoic acid | Example 15 | 381.1 | (400 MHz, Deuterium oxide) δ 7.89-7.81 (m, 2H), 7.32-7.18 (m, 3H), 7.10 (d, J = 7.2 Hz, 2H), 6.99-6.91 (m, 2H), 4.43-4.29 (m, 2H), 3.82-3.60 (m, 3H), 3.58-3.52 (m, 2H), 3.34-3.08 (m, 2H), 2.94-2.89 (m, 1H), 2.50-2.31 (m, 3H), 2.06-1.89 (m, 2H), 1.50-1.34 (m, 2H) |
| 73 | N-(cyclopropylsulfonyl)-4-(2-(4-(((1R,2S)-2-phenylcyclopropyl)amino)piperidin-1-yl)ethoxy)benzamide | Example 16 | 484.2 | ¹H NMR: 500 MHz, DMSO-d₆, δ (ppm): 11.93 (bs, 1H), 10.93 (bs, 1H), 10.01 (bs, 2H), 7.96 (d, J = 9.0 Hz, 2H), 7.32-7.29 (m, 2H), 7.24-7.18 (m, 3H), 7.12 (d, J = 9.0 Hz, 2H), 4.50 (bt, 2H), 3.69-3.67 (m, 2H), 3.50-3.49 (m, 4H), 3.18-3.10 (m, 3H), 2.97 (bs, 1H), 2.57 (bs, 1H), 2.31 (bs, 2H), 2.12 (bs, 1H), 1.59 (bs, 1H), 1.31-1.29 (m, 1H), 1.17-1.08 (m, 4H). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 74 | 4-(2-(4-((((1R,2S)-2-phenylcyclopropyl)amino)piperidin-1-yl)ethoxy)-N-(phenylsulfonyl)benzamide | Example 16 | 520.2 | ¹H NMR: 500 MHz, DMSO-d₆, δ (ppm): 12.40 (bs, 1H), 10.88 (bs, 1H), 9.99 (bs, 2H), 8.00-7.99 (m, 2H), 7.89 (d, J = 9.0 Hz, 2H), 7.73-7.70 (m, 1H), 7.66-7.62 (m, 2H), 7.32-7.29 (m, 2H), 7.24-7.17 (m, 3H), 7.08 (d, J = 9.0 Hz, 2H), 4.48 (bt, 2H), 3.68-3.65 (m, 2H), 3.48 (bs, 4H), 3.13 (bs, 2H), 2.97 (bs, 1H), 2.57 (bs, 1H), 2.30 (bs, 2H), 2.10 (bs, 1H), 1.59 (bs, 1H), 1.31-1.28 (m, 1H). |
| 75 | (E)-N-(methylsulfonyl)-3-(4-(3-(4-((((1R,2S)-2-phenylcyclopropyl)amino)piperidin-1-yl)propoxy)phenyl)acrylamide | Example 16 | 498.3 | (400 MHz, deuterium oxide) □ 7.53-7.45 (m, 3H), 7.32-7.24 (m, 2H), 7.24-7.18 (m, 1H), 7.10 (d, J = 7.2 Hz, 2H), 6.87 (d, J = 8.8 Hz, 2H), 6.20 (d, J = 16.0 Hz, 1H), 4.07 (t, J = 5.4 Hz, 2H), 3.77-3.58 (m, 3H), 3.33-3.21 (m, 5H), 3.11-2.96 (m, 2H), 2.93-2.85 (m, 1H), 2.50-2.32 (m, 3H), 2.20-2.10 (m, 2H), 1.96-1.82 (m, 2H), 1.51-1.34 (m, 2H) |
| 76 | 3-(4-(2-(3-((((1R,2S)-2-phenylcyclopropyl)amino)methyl)azetidin-1-yl)ethoxy)phenyl)-1,3-oxazinan-2-one | Examples 10 and 20 | 422.2 | (400 MHz, deuterium oxide) □ 7.28-7.21 (m, 2H), 7.20-7.13 (m, 3H), 7.08 (d, J = 7.6 Hz, 2H), 6.93-6.85 (m, 2H), 4.38-4.25 (m, 4H), 4.20-3.99 (m, 4H), 3.66-3.50 (m, 5H), 3.48-3.44 (m, 1H), 3.39-3.26 (m, 1H), 2.92-2.81 (m, 1H), 2.47-2.38 (m, 1H), 2.10-2.05 (m, 2H), 1.49-1.38 (m, 1H), 1.36-1.25 (m, 1H). |
| 77 | 4-(4-(2-(3-((((1R,2S)-2-phenylcyclopropyl)amino)methyl)azetidin-1-yl)ethoxy)phenyl)morpholin-3-one | Examples 10 and 20 | 422.2 | (400 MHz, deuterium oxide) □ 7.26-7.19 (m, 2H), 7.19-7.12 (m, 3H), 7.07 (d, J = 7.6 Hz, 2H), 6.95-6.87 (m, 2H), 4.36-4.25 (m, 2H), 4.23-4.20 (m, 2H), 4.19-4.07 (m, 3H), 4.06-3.99 (m, 1H), 3.95 (t, J = 5.0 Hz, 2H), 3.64-3.60 (m, 3H), 3.55-3.52 (m, 2H), 3.48-3.44 (m, 1H), 3.42-3.30 (m, 1H), 2.91-2.79 (m, 1H), 2.49-2.36 (m, 1H), 1.49-1.37 (m, 1H), 1.35-1.25 (m, 1H) |
| 78 | 1-(4-(2-(3-((((1R,2S)-2-phenylcyclopropyl)amino)methyl)azetidin-1-yl)ethoxy)phenyl)piperidin-2-one | Examples 10 and 20 | 420.2 | (400 MHz, deuterium oxide) □ 7.29-7.20 (m, 2H), 7.19-7.13 (m, 1H), 7.12-7.04 (m, 4H), 6.94-6.86 (m, 2H), 4.37-4.24 (m, 2H), 4.20-3.99 (m, 4H), 3.65-3.43 (m, 6H), 3.38-3.26 (m, 1H), 2.92-2.81 (m, 1H), 2.47-2.33 (m, 3H), 1.86-1.73 (m, 4H), 1.48-1.38 (m, 1H), 1.37-1.27 (m, 1H) |

TABLE 2-continued

Further Exemplary Compounds of Formula (I) and Formula (II)

| Ex. # | Structure | Method | LCMS [M + 1] Observed | ¹H NMR |
|---|---|---|---|---|
| 79 | 3-(4-((2-(3-((((1R,2S)-2-phenylcyclopropyl)amino)methyl)azetidin-1-yl)ethyl)amino)phenyl)-1,3-oxazinan-2-one | Examples 10 and 20 | 421.2 | (400 MHz, deuterium oxide) δ 7.31-7.23 (m, 2H), 7.22-7.05 (m, 5H), 6.81 (d, J = 7.6 Hz, 2H), 4.42-4.08 (m, 5H), 4.02-3.89 (m, 1H), 3.61-3.24 (m, 9H), 2.85-2.78 (m, 1H), 2.44-2.40 (m, 1H), 2.11-2.06 (m, 2H), 1.46-1.37 (m, 1H), 1.32-1.29 (m, 1H) |
| 80 | (1R,2S)-2-phenyl-N-((1-(2-(4-(piperazin-1-yl)phenoxy)ethyl)azetidin-3-yl)methyl)cyclopropan-1-amine | Examples 10 and 20 | 407.2 | (400 MHz, deuterium oxide) □ 7.36 (d, J = 9.2 Hz, 2H), 7.28-7.20 (m, 2H), 7.19-7.12 (m, 1H), 7.09 (d, J = 7.2 Hz, 2H), 7.02-6.94 (m, 2H), 4.40-4.25 (m, 2H), 4.23-4.00 (m, 4H), 3.74-3.67 (m, 4H), 3.66-3.61 (m, 1H), 3.61-3.54 (m, 6H), 3.51-3.46 (m, 1H), 3.42-3.31 (m, 1H), 2.92-2.82 (m, 1H), 2.49-2.38 (m, 1H), 1.49-1.39 (m, 1H), 1.34-1.30 (m, 1H) |
| 81 | (1R,2S)-N-((1-(2-(4-(4-methylpiperazin-1-yl)phenoxy)ethyl)azetidin-3-yl)methyl)-2-phenylcyclopropan-1-amine | Examples 10 and 20 | 421.2 | (400 MHz, deuterium oxide) □ 7.33-7.20 (m, 4H), 7.18-7.11 (m, 1H), 7.08 (d, J = 7.2 Hz, 2H), 7.02-6.92 (m, 2H), 4.41-4.24 (m, 2H), 4.23-4.00 (m, 4H), 3.86-3.66 (m, 4H), 3.65-3.27 (m, 9H), 2.93 (s, 3H), 2.91-2.81 (m, 1H), 2.45-2.41 (m, 1H), 1.48-1.39 (m, 1H), 1.36-1.26 (m, 1H) |
| 82 | 1-(4-(4-(2-(3-((((1R,2S)-2-phenylcyclopropyl)amino)methyl)azetidin-1-yl)ethoxy)phenyl)piperazin-1-yl)ethan-1-one | Examples 10 and 20 | 449.3 | (400 MHz, deuterium oxide) □ 7.48 (d, J = 9.2 Hz, 2H), 7.26-7.18 (m, 2H), 7.16-7.10 (m, 1H), 7.08 (d, J = 7.2 Hz, 2H), 7.05-6.98 (m, 2H), 4.37-4.26 (m, 2H), 4.21-4.01 (m, 4H), 3.98-3.82 (m, 4H), 3.71-3.52 (m, 7H), 3.49-3.47 (m, 1H), 3.39-3.28 (m, 1H), 2.91-2.81 (m, 1H), 2.44-2.41 (m, 1H), 2.09 (s, 3H), 1.49-1.39 (m, 1H), 1.33-1.30 (m, 1H) |
| 83 | N,6-dimethyl-N-(2-(4-(((1R,2S)-2-phenylcyclopropyl)amino)piperidin-1-yl)ethyl)pyridin-3-amine | Example 11 | 365.2 | (400 MHz, METHANOL-$d_4$) δ = 7.96-7.95 (d, J = 3.2 Hz, 1H), 7.28-7.25 (m, 3H), 7.17-7.15 (m, 2H), 7.11-7.09 (m, 2H), 3.61-3.59 (m, 2H), 3.26 (m, 2H), 3.12 (m, 1H), 2.97 (s, 3H), 2.86 (m, 2H), 2.63-2.61 (m, 3H), 2.42 (s, 3H), 2.17-2.11 (m, 3H), 1.70-1.67 (m, 2H), 1.30-1.22 (m, 2H). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 84 | 1-(2-((5-methylpyridin-2-yl)oxy)ethyl)-N-((1R,2S)-2-phenylcyclopropyl)piperidin-4-amine | Scheme 2b | 352.3 | (400 MHz, METHANOL + D$_2$O-d$_4$) δ = 8.10 (s, 1H), 8.05-8.03 (br d, J = 8.4 Hz, 1H), 7.35-7.29 (m, 2H), 7.25-7.19 (m, 4H), 4.76-4.74 (m, 2H), 3.88-3.85 (br d, J = 12.4 Hz, 2H), 3.76-3.72 (m, 3H), 3.42-3.34 (m, 2H), 3.01-2.99 (m, 1H), 2.57-2.47 (m, 3H), 2.36 (s, 3H), 2.20-2.17 (m, 2H), 1.61-1.58 (m, 1H), 1.47-1.45 (m, 1H) |
| 85 | 1-(2-((6-methylpyridin-3-yl)oxy)ethyl)-N-((1R,2S)-2-phenylcyclopropyl)piperidin-4-amine | Scheme 2b | 352.1 | (400 MHz, D$_2$O) δ = 8.31 (d, J = 2.0 Hz, 1H), 8.04 (d, J = 2.0, 1H), 7.76-7.74 (d, J = 8.8 Hz, 1H), 7.36-7.34 (m, 2H), 7.32-7.26 (m, 1H), 7.17-7.15 (br d, J = 7.6 Hz, 2H), 4.55-4.53 (m, 2H), 3.82-3.69 (m, 5H), 3.28-3.25 (m, 2H), 2.99-2.97 (m, 1H), 2.65 (s, 3H), 2.50-2.43 (m, 3H), 2.05 (br s, 2H), 1.52-1.44 (m, 2H) |
| 86 | 1-(2-((4-bromophenyl)(methyl)amino)ethyl)-N-((1R,2S)-2-phenylcyclopropyl)piperidin-4-amine | Scheme 2b | 428.0; 430.0 | (400 MHz, Methanol-d$_4$) δ 7.46 (d, J = 8.8 Hz, 2H), 7.37-7.30 (m, 2H), 7.29-7.19 (m, 3H), 7.06 (d, J = 8.8 Hz, 2H), 3.96-3.91 (m, 2H), 3.85-3.67 (m, 3H), 3.43-3.37 (m, 2H), 3.34-3.26 (m, 2H), 3.12-3.04 (m, 4H), 2.62-2.58 (m, 1H), 2.49-2.43 (m, 2H), 2.31-2.12 (m, 2H), 1.67-1.58 (m, 1H), 1.48-1.45 (m, 1H) |
| 87 | N-(methylsulfonyl)-4-(2-(4-(((1R,2S)-2-phenylcyclopropyl)amino)piperidin-1-yl)ethoxy)benzamide | Scheme 3b | 458.1 | ¹H NMR: 500 MHz, DMSO-d$_6$, δ (ppm): 11.98 (bs, 1H), 10.82 (bs, 1H), 9.93 (bs, 2H), 7.97 (d, J = 9.0 Hz, 2H), 7.33-7.29 (m, 2H), 7.25-7.18 (m, 3H), 7.12 (d, J = 9.0 Hz, 2H), 4.49 (bt, 2H), 3.68-3.66 (m, 2H), 3.50 (bs, 4H), 3.36 (s, 3H), 3.14 (bs, 2H), 2.98 (bs, 1H), 2.56 (bs, 1H), 2.30 (bs, 2H), 2.11 (bs, 1H), 1.58 (bs, 1H), 1.32-1.28 (m, 1H). |
| 88 | N-(ethylsulfonyl)-4-(2-(4-(((1R,2S)-2-phenylcyclopropyl)amino)piperidin-1-yl)ethoxy)benzamide | Scheme 3b | 472.2 | ¹H NMR: 500 MHz, DMSO-d$_6$, δ (ppm): 11.87 (bs, 1H), 10.94 (bs, 1H), 10.01 (bs, 2H), 7.97 (d, J = 8.9 Hz, 2H), 7.32-7.29 (m, 2H), 7.24-7.18 (m, 3H), 7.12 (d, J = 9.0 Hz, 2H), 4.50 (bt, 2H), 3.68-3.66 (m, 2H), 3.53-3.48 (m, 6H), 3.14 (bs, 2H), 2.97 (bs, 1H), 2.58 (bs, 1H), 2.31 (bs, 2H), 2.12 (bs, 1H), 1.59 (bs, 1H), 1.31-1.27 (m, 1H), 1.25 (t, J = 7.4 Hz, 3H). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 89 | (1S,2R)-N-((1-(2-((5-(4-methylpiperazin-1-yl)pyridin-2-yl)oxy)ethyl)azetidin-3-yl)methyl)-2-phenylcyclopropan-1-amine | Example 20 | 422.3 | (400 MHz, METHANOL-$d_4$ δ = 7.79-7.77 (m, 1H), 7.74 (br d, J = 8.4 Hz, 1H), 7.33-7.29 (m, 2H), 7.25-7.21 (m, 3H), 7.09-7.06 (br d, J = 9.2 Hz, 1H), 4.56 (br s, 2H), 4.44-4.24 (m, 4H), 3.80-3.77 (m, 5H), 3.64-3.61 (m, 3H), 3.39 (m, 1H), 3.33 (m, 1H), 3.28 (m, 1H), 3.17-3.14 (m, 2H), 3.03 (m, 1H), 2.97 (s, 3H), 2.61-2.57 (m, 1H), 1.63-1.58 (m, 1H), 1.42-1.39 (q, J = 6.8 Hz, 1H). |
| 90 | 2-(4-(2-(3-((((1S,2R)-2-phenylcyclopropyl)amino)methyl)azetidin-1-yl)ethoxy)phenyl)acetic acid | Scheme 2a | 381.2 | (400 MHz, deuterium oxide) δ 7.31-7.18 (m, 5H), 7.12 (d, J = 7.6 Hz, 2H), 6.87 (d, J = 8.8 Hz, 2H), 4.42-4.30 (m, 2H), 4.22-4.02 (m, 4H), 3.68-3.53 (m, 5H), 3.52-3.49 (m, 1H), 3.42-3.31 (m, 1H), 2.93-2.85 (m, 1H), 2.47-2.44 (m, 1H), 1.50-1.43 (m, 1H), 1.40-1.33 (m, 1H). |
| 91 | 3-(4-(methyl(2-(4-((((1R,2S)-2-phenylcyclopropyl)amino)piperidin-1-yl)ethyl)amino)phenyl)-1,3-oxazinan-2-one | Example 20 | 449.3 | (400 MHz, Deuterium oxide) δ 7.34-7.28 (m, 4H), 7.27-7.20 (m, 1H), 7.19-7.10 (m, 4H), 4.39 (t, J = 5.4 Hz, 2H), 3.83 (t, J = 7.4 Hz, 2H)), 3.72-3.53 (m, 5H), 3.39-3.28 (m, 2H), 3.20-3.00 (m, 5H), 2.96-2.90 (m, 1H), 2.49-2.32 (m, 3H), 2.17-2.09 (m, 2H), 2.04-1.88 (m, 2H), 1.50-1.37 (m, 2H) |
| 92 | 4-(2-(3-((((1R,2S)-2-phenylcyclopropyl)amino)methyl)azetidin-1-yl)ethoxy)benzoic acid | Scheme 2a | 367.0 | (400 MHz, Deuterium Oxide) δ = 7.99-7.97 (m, 2H), 7.32-7.24 (m, 3H), 7.17-7.15 (m, 2H), 7.01-6.98 (d, J = 8.8 Hz, 2H), 4.42-4.37 (m, 2H), 4.27-4.11 (m, 4H), 3.77-3.70 (m, 1H), 3.69-3.60 (m, 2H), 3.56-3.54 (d, J = 6.8 Hz, 1H), 3.43-3.41 (m, 1H), 2.94-2.92 (m, 1H), 2.53-2.48 (m, 1H), 1.52-1.43 (m, 1H), 1.41-1.40 (m, 1H) |
| 93 | 2-(4'-(2-(3-((((1S,2R)-2-phenylcyclopropyl)amino)methyl)azetidin-1-yl)ethoxy)-[1,1'-biphenyl]-4-yl)-N-(phenylsulfonyl)acetamide | Scheme 3a | 520.3 | (400 MHz, deuterium oxide) δ 7.83 (d, J = 7.6 Hz, 2H), 7.63 (t, J = 7.6 Hz, 1H), 7.51-7.47 (m, 2H), 7.26-7.20 (m, 2H), 7.16-7.06 (m, 3H), 7.00 (d, J = 8.4 Hz, 2H), 6.76 (d, J = 8.4 Hz, 2H), 4.35-4.25 (m, 2H), 4.17-3.98 (m, 4H), 3.62-3.45 (m, 6H), 3.37-3.28 (m, 1H), 2.90-2.82 (m, 1H), 2.44-2.41 (m, 1H), 1.48-1.41 (m, 1H), 1.37-1.31 (m, 1H) |

TABLE 2-continued

Further Exemplary Compounds of Formula (I) and Formula (II)

| Ex. # | Structure | Method | LCMS [M + 1] Observed | ¹H NMR |
|---|---|---|---|---|
| 94 | 3-(6-(2-(4-(((1R,2S)-2-phenylcyclopropyl)amino)piperidin-1-yl)ethoxy)pyridin-3-yl)-1,3-oxazinan-2-one | Example 20 | 437.2 | (400 MHz, D$_2$O) δ = 8.11 (d, J = 2.8 Hz, 1H), 7.80-7.78 (m, 1H), 7.36-7.32 (m, 2H), 7.28-7.27 (m, 1H), 7.17-7.15 (d, J = 7.6 Hz, 2H), 7.00-6.98 (d, J = 8.8 Hz, 1H), 4.62-4.60 (m, 2H), 4.46-4.43 (t, J = 5.2 Hz, 2H), 3.85-3.82 (br d, J = 12.0 Hz, 2H), 3.68-3.62 (m, 5H), 3.26-3.15 (m, 2H), 2.98-2.96 (m, 1H), 2.49-2.43 (m, 3H), 2.19-2.16 (m, 2H), , 2.01 (m, 2H), 1.50-1.43 (m, 2H) |
| 95 | N-((1R,2S)-2-phenylcyclopropyl)-1-(2-(p-tolyloxy)ethyl)piperidin-4-amine | Example 11 | 351.3 | (400 MHz, deuterium oxide) δ 7.36-7.26 (m, 2H), 7.26-7.18 (m, 1H), 7.17-7.09 (m, 4H), 6.89-6.81 (m, 2H), 4.27 (t, J = 4.8 Hz, 2H), 3.80-3.57 (m, 3H), 3.56-3.48 (m, 2H), 3.23-3.08 (m, 2H), 3.02-2.89 (m, 1H), 2.49-2.31 (m, 3H), 2.23-2.14 (m, 3H), 2.07-1.86 (m, 2H), 1.50-1.36 (m, 2H) |
| 96 | 3-(4-(2-(4-(methyl((1R,2S)-2-phenylcyclopropyl)amino)piperidin-1-yl)ethoxy)phenyl)-1,3-oxazinan-2-one | Example 20 | 450.3 | (400 MHz, D$_2$O) δ = 7.34-7.29 (m, 2H), 7.27-7.23 (m, 3H), 7.16 (br s, 2H), 7.02-7.00 (m, 2H), 4.41-4.35 (m, 4H), 3.81 (m, 2H), 3.63-3.55 (m, 5H), 3.20-3.15 (m, 3H), 3.02 (s, 3H), 2.60 (m, 3H), 2.16-2.11 (m, 4H), 1.55-1.54 (m, 2H). |
| 97 | 3-(5-(2-(4-(((1R,2S)-2-phenylcyclopropyl)amino)piperidin-1-yl)ethoxy)pyridin-2-yl)-1,3-oxazinan-2-one | Example 20 | 437.2 | (400 MHz, D$_2$O) δ = 8.20-8.19 (d, J = 3.2 Hz, 1H), 7.81-7.78 (m, 1H), 7.58-7.56 (d, J = 9.2 Hz, 1H), 7.32-7.25 (m, 3H), 7.16-7.14 (d, J = 7.2 Hz, 2H), 4.51-4.45 (br s, 4H), 3.83-3.63 (m, 7H), 3.22-3.20 (m, 2H), 2.98-2.97 (m, 1H), 2.48-2.46 (m, 3H), 2.22-2.19 (m, 2H), 2.03 (m, 2H), 1.51-1.42 (m, 2H). |
| 98 | 2-(4-(2-(1-methyl-3-((((1R,2S)-2-phenylcyclopropyl)amino)methyl)-λ4-azetidin-1-yl)ethoxy)phenyl)-N-(methylsulfonyl)acetamide | Scheme 3a | 472.2 | (400 MHz, deuterium oxide) δ 7.38-7.31 (m, 2H), 7.30-7.19 (m, 5H), 7.00 (d, J = 8.8 Hz, 2H), 4.71-4.63 (m, 2H), 4.50-4.40 (m, 4H), 4.00-3.93 (m, 2H), 3.77-3.68 (m, 1H), 3.67-3.60 (m, 2H), 3.41-3.37 (m, 2H), 3.35 (s, 3H), 3.23 (s, 3H), 3.05-3.00 (m, 1H), 2.65-2.59 (m, 1H), 1.66-1.60 (m, 1H), 1.45-1.41 (m, 1H) |

TABLE 2-continued

Further Exemplary Compounds of Formula (I) and Formula (II)

| Ex. # | Structure | Method | LCMS [M + 1] Observed | ¹H NMR |
|---|---|---|---|---|
| 99 | N-methyl-1-(2-((6-methylpyridin-3-yl)oxy)ethyl)-N-((1R,2S)-2-phenylcyclopropyl)piperidin-4-amine | Example 11 | 366.2 | (400 MHz, D$_2$O) δ = 8.31 (d, J = 2.8 Hz, 1H), 8.06-8.03 (m, 1H), 7.77-7.75 (d, J = 8.8 Hz, 1H), 7.35-7.34 (m, 2H), 7.30-7.28 (m, 1H), 7.18-7.16 (m, 2H), 4.55-4.53 (m, 2H), 3.84-3.81 (m, 3H), 3.69-3.67 (m, 2H), 3.26 (m, 2H), 3.16-3.15 (m, 1H), 3.04 (s, 3H), 2.65 (s, 3H), 2.62-2.39 (m, 3H), 2.20-2.16 (m, 2H), 1.62-1.55 (m, 2H). |
| 100 | N-methyl-N-(2-(4-(((1R,2S)-2-phenylcyclopropyl)amino)piperidin-1-yl)ethyl)acetamide | Example 39 | 316.1 | (400 MHz, CD$_3$OD) δ = 7.25-7.18 (m, 2H), 7.15-7.08 (m, 1H), 7.03 (m, J = 7.6 Hz, 2H), 3.53-3.44 (m, 2H), 3.05 (s, 2H), 3.00-2.90 (m, 3H), 2.70-2.59 (m, 1H), 2.56-2.46 (m, 2H), 2.33-2.27 (m, 1H), 2.22-2.00 (d, 6H), 1.98-1.81 (m, 3H), 1.50-1.38 (m, 2H), 1.09-0.97 (m, 2H). |
| 101 | (1R,2S)-N-((1-(2-((6-methylpyridin-3-yl)oxy)ethyl)azetidin-3-yl)methyl)-2-phenylcyclopropan-1-amine | Example 11 | 338.1 | (400 MHz, METHANOL-d$_4$ δ = 8.08 (d, J = 2.8 Hz, 1H), 7.31-7.30 (m, 1H), 7.24-7.20 (m, 3H), 7.17-7.13 (m, 1H), 7.06-7.04 (m, 2H), 4.09-4.07 (t, J = 5.2 Hz, 2H), 3.77-3.73 (t, J = 8.4 Hz, 2H), 3.34-3.31 (s, 2H), 3.08-3.05 (t, J = 5.2 Hz, 2H), 2.96-2.94 (d, J = 7.2 Hz, 2H), 2.82-2.81 (m, 1H), 2.45 (s, 3H), 2.33-2.32 (m, 1H), 1.91-1.90 (m, 1H), 1.09-1.01 (m, 2H). |
| 102 | 4-(2-(1-methyl-3-((((1R,2S)-2-phenylcyclopropyl)amino)methyl)-λ4-azetidin-1-yl)ethoxy)-N-(methylsulfonyl)benzamide | Scheme 3a | 458.1 | (400 MHz, deuterium oxide) □ 7.29-7.20 (m, 2H), 7.19-7.13 (m, 1H), 7.12-7.04 (m, 4H), 6.94-6.86 (m, 2H), 4.37-4.24 (m, 2H), 4.20-3.99 (m, 4H), 3.65-3.43 (m, 6H), 3.38-3.26 (m, 1H), 2.92-2.81 (m, 1H), 2.47-2.33 (m, 3H), 1.86-1.73 (m, 4H), 1.48-1.38 (m, 1H), 1.37-1.27 (m, 1H) |
| 103 | 3-(5-(2-(3-(((((1R,2S)-2-phenylcyclopropyl)amino)methyl)azetidin-1-yl)ethoxy)pyridin-2-yl)-1,3-oxazinan-2-one | Example 20 | 423.1 | (400 MHz, D$_2$O) δ = 8.05-8.03 (m, 1H), 7.51 (m, 1H), 7.43-7.41 (d, J = 8.8 Hz, 1H), 7.26-7.24 (m, 2H), 7.18-7.16 (m, 1H), 7.10-7.08 (m, 2H), 4.43-4.40 (m, 2H), 4.33-4.42 (m, 6H), 3.72-3.69 (m, 3H), 3.60-3.55 (m, 2H), 3.49-3.47 (m, 1H), 3.34 (m, 1H), 2.86-2.85 (m, 1H), 2.43 (m, 1H), 2.18-2.14 (m, 2H), 1.44-1.43 (m, 1H), 1.35-1.33 (q, J = 7.2 Hz, 1H) |

TABLE 2-continued

Further Exemplary Compounds of Formula (I) and Formula (II)

| Ex. # | Structure | Method | LCMS [M + 1] Observed | ¹H NMR |
|---|---|---|---|---|
| 104 | 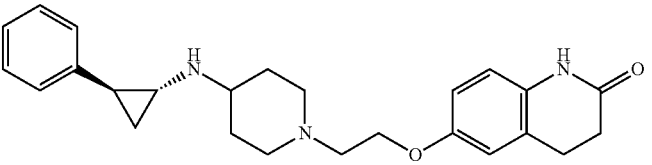 [SMILES: CN(C1CCN(CCOc2ccc(N3CCCOC3=O)cc2)CC1)[C@@H]1C[C@H]1c1ccccc1]<br>6-(2-(4-(((1R,2S)-2-phenylcyclopropyl)amino)piperidin-1-yl)ethoxy)-3,4-dihydroquinolin-2-(1H)-one | Example 11 | 406.0 | (400 MHz, Deuterium oxide) δ 7.34-7.28 (m, 2H), 7.27-7.21 (m, 1H), 7.13 (d, J = 7.2 Hz, 2H), 6.86-6.77 (m, 3H), 4.29-4.24 (m, 2H), 3.50-3.48 (m, 1H), 3.85-3.48 (m, 4H), 3.26-3.07 (m, 2H), 2.97-2.93 (m, 1H), 2.89-2.81 (m, 2H), 2.53-2.33 (m, 5H), 2.09-1.90 (m, 2H), 1.52-1.37 (m, 2H) |
| 105 | 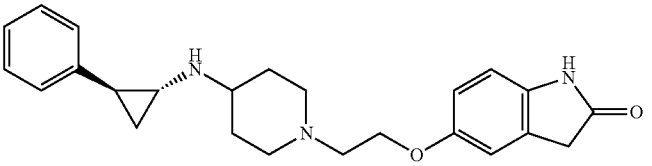<br>5-(2-(4-(((1R,2S)-2-phenylcyclopropyl)amino)piperidin-1-yl)ethoxy)indolin-2-one | Example 11 | 392.2 | (400 MHz, methanol-d₄) δ, 7.39-7.29 (m, 2H), 7.28-7.17 (m, 3H), 7.04 (d, J = 2.0 Hz, 1H), 6.97-6.88 (m, 1H), 6.87-6.81 (m, 1H), 4.42-4.35 (m, 2H), 3.88 (br d, J = 12.4 Hz, 2H), 3.82-3.73 (m, 1H), 3.67-3.59 (m, 2H), 3.34 (br s, 2H), 3.31 (br s, 2H), 3.09-3.01 (m, 1H), 2.60 (br s, 1H), 2.50 (br t, J = 11.6 Hz, 2H), 2.37-2.15 (m, 2H), 1.67-1.58 (m, 1H), 1.49-1.43 (m, 1H) |
| 106 | 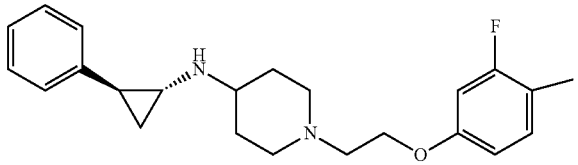<br>1-(2-(3-fluoro-4-methylphenoxy)ethyl)-N-((1R,2S)-2-phenylcyclopropyl)piperidin-4-amine | Example 11 | 369.1 | (400 MHz, methanol-d₄) δ, 7.38-7.29 (m, 2H), 7.30-7.27 (m, 1H), 7.24-7.19 (m, 2H), 7.18-7.16 (m, 1H), 6.81-6.71 (m, 2H), 4.43-4.34 (m, 2H), 3.85 (br d, J = 11.6 Hz, 2H), 3.73 (br s, 1H), 3.62 (br s, 2H), 3.30-3.22 (m, 2H), 3.03 (td, J = 4.0, 7.6 Hz, 1H), 2.56 (br s, 1H), 2.47 (br s, 2H), 2.25-2.16(m, 5H), 1.60 (br s, 1H), 1.47-1.42 (m, 1H) |
| 107 | 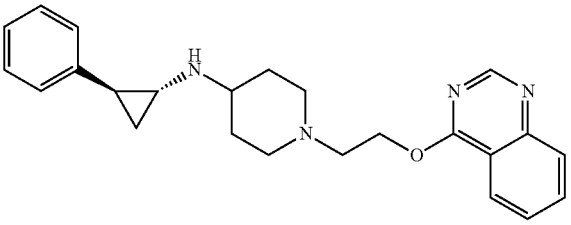<br>N-((1R,2S)-2-phenylcyclopropyl)-1-(2-(quinazolin-4-yloxy)ethyl)piperidin-4-amine | Example 36 | 389.5 | (400 MHz, METHANOL-d₄) δ = 8.74 (s, 1H), 8.27-8.25 (d, J = 8.0 Hz, 1H), 7.94-7.90 (m, 2H), 7.69-7.67 (m, 1H), 7.23-7.19 (m, 2H), 7.12-7.10 (m, 1H), 7.03-7.02 (d, J = 7.2 Hz, 2H), 4.79-4.76 (t, J = 5.2 Hz, 2H), 3.10-2.96 (m, 2H), 2.94-2.93 (m, 2H), 2.74-2.59 (m, 1H), 2.30-2.28 (m, 3H), 1.94-1.88 (m, 3H), 1.51-1.48 (m, 2H), 1.06-1.00 (m, 2H). |
| 108 | 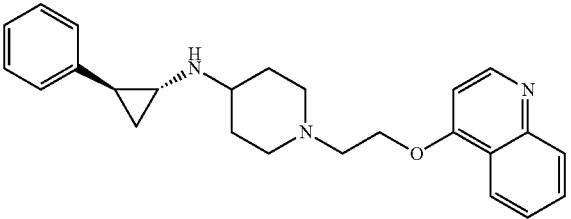<br>N-((1R,2S)-2-phenylcyclopropyl)-1-(2-(quinolin-4-yloxy)ethyl)piperidin-4-amine | Example 36 | 388.2 | (400 MHz, Methanol-d₄) δ 8.69 (d, J = 5.2 Hz, 1H), 8.28 (d, J = 8.4 Hz, 1H), 7.96 (d, J = 8.4 Hz, 1H), 7.77 (t, J = 7.6 Hz, 1H), 7.62-7.55 (m, 1H), 7.26-7.21 (m, 2H), 7.15-7.10 (m, 1H), 7.09-7.00 (m, 3H), 4.44 (t, J = 5.2 Hz, 2H), 3.16-3.08 (m, 2H), 3.01 (t, J = 5.4 Hz, 2H), 2.78-2.64 (m, 1H), 2.42-2.26 (m, 3H), 2.07-1.78 (m, 3H), 1.62-1.47 (m, 2H), 1.14-1.00 (m, 2H) |

TABLE 2-continued

Further Exemplary Compounds of Formula (I) and Formula (II)

| Ex. # | Structure | Method | LCMS [M + 1] Observed | ¹H NMR |
|---|---|---|---|---|
| 109 | N-((1R,2S)-2-phenylcyclopropyl)-1-(2-(pyrimidin-5-yloxy)ethyl)piperidin-4-amine | Example 11 | 339.1 | (400 MHz, CHLOROFORM-d) δ = 8.87 (s, 1H), 8.44 (s, 2H), 7.37-7.13 (m, 4H), 7.04 (d, J = 7.0 Hz, 2H), 4.21 (t, J = 5.7 Hz, 2H), 2.96 (br d, J = 11.4 Hz, 2H), 2.89-2.78 (m, 2H), 2.73-2.61 (m, 1H), 2.41-2.33 (m, 1H), 2.21 (br t, J = 11.4 Hz, 2H), 2.01-1.84 (m, 3H), 1.54-1.38 (m, 2H), 1.14-0.96 (m, 2H) |
| 110 | 1-(2-(3,5-difluorophenoxy)ethyl)-N-((1R,2S)-2-phenylcyclopropyl)piperidin-4-amine | Example 11 | 372.9 | (400 MHz, deuterium oxide) δ 7.34-7.27 (m, 2H), 7.26-7.20 (m, 1H), 7.13 (d, J = 7.6 Hz, 2H), 6.60-6.52 (m, 3H), 4.31 (t, J = 4.6 Hz, 2H)), 3.80-3.60 (m, 3H), 3.57-3.53 (m, 2H), 3.26-3.07 (m, 2H), 2.94-2.92 (m, 1H), 2.50-2.32 (m, 3H), 2.02-1.87 (m, 2H), 1.52-1.36 (m, 2H) |
| 111 | 1-(2-(3,5-dichlorophenoxy)ethyl)-N-((1R,2S)-2-phenylcyclopropyl)piperidin-4-amine | Example 11 | 406.9 | (400 MHz, deuterium oxide) δ 7.35-7.28 (m, 2H), 7.27-7.20 (m, 1H), 7.17-7.07 (m, 3H), 6.94 (d, J = 1.6 Hz, 2H), 4.31 (t, J = 4.6 Hz, 2H), 3.79-3.62 (m, 3H), 3.62-3.54 (m, 2H), 3.24-3.10 (m, 2H), 2.95-2.92 (m, 1H), 2.50-2.33 (m, 3H), 2.06-1.89 (m, 2H), 1.50-1.37 (m, 2H) |
| 112 | 1-(2-((6-methylpyridazin-3-yl)oxy)ethyl)-N-((1R,2S)-2-phenylcyclopropyl)piperidin-4-amine | Example 36 | 353.2 | (400 MHz, CD₃OD) δ = 7.51-7.47 (m, 1H), 7.24-7.20 (m, 2H), 7.13-7.09 (m, 2H), 7.04-7.02 (m, 2H), 4.58-4.55 (t, J = 5.6 Hz, 2H), 3.04-3.01 (m, 2H), 2.84-2.01 (t, J = 5.6 Hz, 2H),2.69-2.60 (m, 1H), 2.56 (s, 3H), 2.32-2.28 (m, 1H), 2.21-2.15 (m, 2H), 1.94-1.87 (m,3H), 1.53-1.41 (m, 2H), 1.08-0.99 (m, 2H). |
| 113 | 1-(2-(3-fluorophenoxy)ethyl)-N-((1R,2S)-2-phenyl-cyclopropyl)piperidin-4-amine | Example 11 | 355.1 | (400 MHz, CHLOROFORM-d) δ = 7.36-7.22 (m, 6H), 6.88-6.78 (s, 3H), 4.45-4.42 (t, J = 4.8 Hz, 2H), 3.88-3.65 (m, 5H), 3.36-3.27 (m, 2H), 3.06-3.03 (m, 1H), 2.57-2.48 (m, 3H), 2.20-2.17 (m, 2H), 1.61-1.47 (m, 2H). |
| 114 | 1-(2-((6-methylpyridin-2-yl)oxy)ethyl)-N-((1R,2S)-2-phenylcyclopropyl)piperidin-4-amine | Example 36 | 352.2 | (400 MHz, CD₃OD) δ = 7.64-7.60 (t, J = 7.6 Hz, 1H), 7.33-7.17 (m, 5H), 6.89 (d, J = 7.2 Hz, 1H), 6.69 (d, J = 8.0 Hz, 1H), 4.69-4.67 (m, 2H), 3.88-3.85 (m, 2H), 3.73-3.61 (m, 3H), 2.29-3.23 (m, 2H), 3.03-2.99 (m, 1H), 2.53-2.43 (m, 6H), 2.16-2.07 (m, 2H), 1.57-1.52 (m, 1H), 1.47-1.42 (m, 1H). |

TABLE 2-continued

Further Exemplary Compounds of Formula (I) and Formula (II)

| Ex. # | Structure | Method | LCMS [M + 1] Observed | $^1$H NMR |
|---|---|---|---|---|
| 115 | 1-(2-((2-methylpyrimidin-5-yl)oxy)ethyl)-N-((1R,2S)-2-phenylcyclopropyl)piperidin-4-amine | Example 11 | 353.1 | (400 MHz, D$_2$O) δ = 8.69-8.68 (d, J = 2.8 Hz, 2H), 7.35-7.24 (m, 3H), 7.16-7.14 (d, J = 7.6 Hz, 2H), 4.57-4.55 (t, J = 4.4 Hz, 2H), 3.83-3.68 (m, 5H), 3.23 (m, 2H), 2.98-2.96 (m, 1H), 2.70 (s, 3H), 2.50-2.43 (m, 3H), 2.04 (br s, 2H), 1.51-1.41 (m, 2H). |
| 116 | N-methyl-N-(2-(3-((((1R,2S)-2-phenylcyclopropyl)amino)methyl)azetidin-1-yl)ethyl)methanesulfonamide | Example 41 | 338.1 | (400 MHz, CD$_3$OD) δ = 7.25-7.03 (m, 5H), 3.51-3.45 (m, 2H), 3.11-3.06 (m, 2H), 2.97-2.94 (m, 2H), 2.89-2.87 (m, 2H), 2.85-2.82 (m, 6H), 2.69-2.62 (m, 3H), 2.29-2.26 (m, 1H), 1.90-1.85 (m, 1H), 1.97-0.97 (m, 2H). |
| 117 | 2-(4-(((1R,2S)-2-phenylcyclopropyl)amino)piperidin-1-yl)ethan-1-ol | Example 36 | 261.3 | (400 MHz, METHANOL-d$_4$) δ = 7.25-7.22 (m, 2H), 7.14-7.06 (m, 1H), 7.06-7.04 (m, 2H), 3.69-3.66 (t, J = 6.4 Hz, 2H), 2.99-2.96 (m, 2H), 2.66 (m, 1H), 2.54-2.51 (t, J = 6.4 Hz, 2H), 2.32 (m, 1H), 2.13-2.12 (m, 2H), 1.92-1.90 (m, 3H), 1.57-1.40 (m, 2H), 1.08-1.02 (m, 2H). |
| 118 | N-(1-(2-(4-(2-oxo-1,3-oxazinan-3-yl)phenoxy)ethyl)piperidin-4-yl)-N-((1R,2S)-2-phenylcyclopropyl)acetamide | Example 20 | 478.1 | (400 MHz, METHANOL-d$_4$) δ = 7.33-7.29 (m, 4H), 7.20-7.18 (m, 3H), 7.09-7.06 (d, J = 8.8 Hz, 2H), 4.46-4.41 (m, 4H), 4.14 (m, 1H), 3.75-3.69 (m, 4H), 3.61-3.59 (m, 2H), 3.25 (m, 2H), 3.02 (br s, 1H), 2.78-2.61 (m, 1H), 2.58-2.44 (m, 1H), 2.37 (m, 1H), 2.24-2.18 (m, 5H), 2.07-2.03 (m, 2H), 1.62-1.61 (m, 1H), 1.46-1.45 (m, 1H). |
| 119 | 1-(2-methoxyethyl)-N-((1R,2S)-2-phenylcyclopropyl)piperidin-4-amine | Example 36 | 275.2 | (400 MHz, Methanol-d$_4$) δ 7.28-7.21 (m, 2H), 7.17-7.10 (m, 1H), 7.09-6.99 (m, 2H), 3.57-3.49 (m, 2H), 3.34-3.32 (m, 3H), 3.07-2.92 (m, 2H), 2.69-2.52 (m, 3H), 2.34-2.30 (m, 1H), 2.20-2.03 (m, 2H), 1.98-1.85 (m, 3H), 1.56-1.43 (m, 2H), 1.13-1.00 (m, 2H). |

TABLE 2-continued

Further Exemplary Compounds of Formula (I) and Formula (II)

| Ex. # | Structure | Method | LCMS [M + 1] Observed | $^1$H NMR |
|---|---|---|---|---|
| 120 | 1-(2-((1,3-dimethyl-1H-pyrazol-5-yl)oxy)ethyl)-N-((1R,2S)-2-phenylcyclopropyl)piperidin-4-amine | Example 11 | 355.2 | (400 MHz, Methanol-d$_4$) δ 7.29-7.18 (m, 2H), 7.16-7.09 (m, 1H), 7.08-7.01 (m, 2H), 5.48 (s, 1H), 4.18 (t, J = 5.4 Hz, 2H), 3.53 (s, 3H), 3.02-2.96 (m, 2H), 2.78 (t, J = 5.6 Hz, 2H), 2.73-2.55 (m, 1H), 2.34-2.29 (m, 1H), 2.21-2.13 (m, 5H), 2.00-1.85 (m, 3H), 1.65-1.42 (m, 2H), 1.11-1.00 (m, 2H) |
| 121 | 1-(2-((1-methyl-1H-pyrazol-3-yl)oxy)ethyl)-N-((1R,2S)-2-phenylcyclopropyl)piperidin-4-amine | Example 11 | 341.2 | (400 MHz, Methanol-d$_4$) δ 7.34 (d, J = 2.0 Hz, 1H), 7.28-7.19 (m, 2H), 7.17-7.09 (m, 1H), 7.09-7.01 (m, 2H), 5.66 (d, J = 2.4 Hz, 1H), 4.21 (t, J = 5.6 Hz, 2H), 3.72 (s, 3H), 3.03-3.00 (m, 2H), 2.76 (t, J = 5.4 Hz, 2H), 2.71-2.53 (m, 1H), 2.34-2.29 (m, 1H), 2.21-2.15 (m, 2H), 1.99-1.74 (m, 3H), 1.65-1.43 (m, 2H), 1.11-1.00 (m, 2H) |
| 122 | N-(2-(3-((((1R,2S)-2-phenylcyclopropyl)amino)methyl)azetidin-1-yl)ethyl)methanesulfonamide | Example 41 | 324.1 | (400 MHz, methanol-d$_4$) δ = 7.27-7.21 (m, 2H), 7.16-7.11 (m, 1H), 7.08-7.04 (m, 2H), 3.51 (t, J = 8.0 Hz, 2H), 3.04 (t, J = 6.8 Hz, 2H), 2.99 (br t, J = 6.4 Hz, 2H), 2.95 (s, 3H), 2.91 (d, J = 7.6 Hz, 2H), 2.70 (td, J = 7.2, 14.4 Hz, 1H), 2.62 (t, J = 6.8 Hz, 2H), 2.30 (td, J = 3.6, 7.2 Hz, 1H), 1.90 (ddd, J = 3.2, 6.0, 9.2 Hz, 1H), 1.10-0.98 (m, 2H). |
| 123 | 3-(4-(2-(3-((((1R,2S)-2-phenylcyclopropyl)amino)methyl)azetidin-1-yl)ethoxy)phenyl)-1,3-oxazinan-2-one | Example 20 | 423.0 | (400 MHz, METHANOL-d$_4$) δ = 8.18 (d, J = 2.4 Hz, 1H), 7.76-7.74 (dd, J = 2.8, 8.8 Hz, 1H), 7.34-7.18 (m, 5H), 6.91-6.88 (d, J = 9.2 Hz, 1H), 4.59-4.56 (m, 2H), 4.49-4.46 (m, 4H), 4.21 (br s, 2H), 3.74-3.69 (m, 4H), 3.60-3.58 (br d, J = 6.8 Hz, 2H), 3.44-3.35 (m, 1H), 2.99-2.97(m, 1H), 2.53 (m, 1H), 2.25-2.2 (m, 2H), 1.56-1.52 (m, 1H), 1.43-1.40 (q, J = 6.8 Hz, 1H). |
| 124 | 1-(2-isopropoxyethyl)-N-((1R,2S)-2-phenylcyclopropyl)piperidin-4-amine | Example 36 | 303.1 | (400 MHz, CD$_3$OD) □ = 7.27-7.20 (m, 2H), 7.16-7.10 (m, 1H), 7.08-7.02 (m, 2H), 3.63-3.56 (m, 3H), 2.98 (d, J = 12.4 Hz, 2H), 2.70-2.61 (m, 1H), 2.56 (t, J = 6.0 Hz, 2H), 2.32 (m, 1H), 2.13 (tt, J = 2.8, 12.0 Hz, 2H), 1.98-1.86 (m, 3H), 1.57-1.42 (m, 2H), 1.16 (d, J = 6.0 Hz, 6H), 1.10-1.00 (m, 2H). |
| 125 | 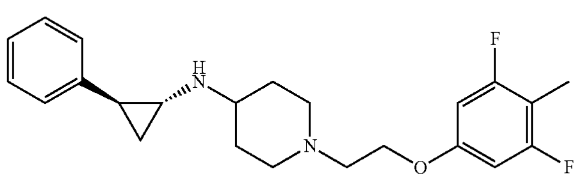 [SMILES: Cc1c(F)cc(OCCN2CCC(N[C@@H]3C[C@H]3c3ccccc3)CC2)cc1F] | Example 11 | 387.1 | (400 MHz, METHANOL-d$_4$) δ = 7.40-7.18 (m, 5H), 6.74-6.63 (m, 2H), 4.48-4.32 (m, 2H), 3.92-3.58 (m, 5H), 3.31-3.08 (m, 2H), 2.94-2.91 (t, J = 7.6 Hz, 1H), 2.45-2.35 (m, 3H), 2.04-1.91 (m, 5H), 1.53-1.42 (m, 2H) |

TABLE 2-continued

Further Exemplary Compounds of Formula (I) and Formula (II)

| Ex. # | Structure | Method | LCMS [M + 1] Observed | $^1$H NMR |
|---|---|---|---|---|
| | 1-(2-(3,5-difluoro-4-methylphenoxy)ethyl)-N-((1R,2S)-2-phenylcyclopropyl)piperidin-4-amine | | | |
| 126 | 1-(2-((5-methyl-1,3,4-thiadiazol-2-yl)oxy)ethyl)-N-((1R,2S)-2-phenylcyclopropyl)piperidin-4-amine | Example 11 | 359.1 | (400 MHz, CD3OD) δ = 7.14-7.10 (m, 2H), 7.03-6.99 (m, 1H), 6.94-6.92 (d, J = 7.6 Hz, 2H), 4.49-4.46 (t, J = 5.4 Hz, 2H), 2.90-2.87 (br d, J = 11.2 Hz, 2H), 2.73-2.62 (t, J = 5.4 Hz, 2H), 2.59-2.51 (m, 1H), 2.49 (s, 3H), 2.30 (td, J = 3.6, 7.6 Hz, 1H), 2.22-2.08 (m, 2H), 1.98-1.83 (m, 3H), 1.54-1.40 (m, 2H), 1.12-0.97 (m, 2H). |
| 127 | 2-(2-(4-(((1R,2S)-2-phenylcyclopropyl)amino)piperidin-1-yl)ethoxy)isonicotinic acid | Example 11 | 382.1 | (400 MHz, METHANOL-d$_4$) δ = 8.14-8.13 (m, 1H), 7.40-7.39 (d, J = 5.2 Hz, 1H), 7.28-7.24 (m, 3H), 7.17-7.07 (m, 3H), 4.61-4.58 (m, 2H), 3.48-3.45 (m, 2H), 3.30-3.28 (m, 2H), 3.04 (m, 1H), 2.84 (m, 2H), 2.47-2.46 (m, 1H), 2.17-2.15 (m, 2H), 2.03-2.02-(m, 1H), 1.76-1.72 (m, 2H), 1.19-1.13 (m, 2H). |
| 128 | N-methyl-2-(4-(((1R,2S)-2-phenylcyclopropyl)amino)piperidin-1-yl)ethane-1-sulfonamide | Example 39 | 338.1 | (400 MHz, methanol-d$_4$) δ = 7.26-7.22 (m, 2H), 7.16-7.11 (m, 1H), 7.08-7.02 (m, 2H), 3.29-3.20 (m, 2H), 2.95 (br d, J = 12.0 Hz, 2H), 2.84-2.77 (m, 2H), 2.75-2.71 (m, 3H), 2.70-2.63 (m, 1H), 2.32 (ddd, J = 3.2, 4.4, 7.2 Hz, 1H), 2.20-2.09 (m, 2H), 2.02-1.87 (m, 3H), 1.55-1.40 (m, 2H), 1.13-0.99 (m, 2H). |
| 129 | N-methyl-N-(2-(4-(((1R,2S)-2-phenylcyclopropyl)amino)piperidin-1-yl)ethyl)methanesulfonamide | Example 39 | 352.1 | (400 MHz, methanol-d$_4$) δ = 7.28-7.20 (m, 2H), 7.16-7.10 (m, 1H), 7.05 (d, J = 8.0 Hz, 2H), 3.30 (t, J = 6.8 Hz, 2H), 3.02-2.94 (m, 2H), 2.89 (d, J = 7.2 Hz, 6H), 2.71-2.62 (m, 1H), 2.57 (t, J = 6.8 Hz, 2H), 2.31 (td, J = 3.6, 7.2 Hz, 1H), 2.10 (br t, J = 11.6 Hz, 2H), 1.99-1.84 (m, 3H), 1.54-1.40 (m, 2H), 1.12-0.99 (m, 2H). |
| 130 | N-(2-(4-(((1R,2S)-2-phenylcyclopropyl)amino)piperidin-1-yl)ethyl)cyclopropanesulfonamide | Example 38 | 364.1 | (400 MHz, methanol-d$_4$) δ = 7.26-7.21 (m, 2H), 7.16-7.10 (m, 1H), 7.07-7.03 (m, 2H), 2.96 (br d, J = 12 Hz, 2H), 2.72-2.62 (m, 1H), 2.60-2.50 (m, 3H), 2.32 (ddd, J = 3.6, 4.4, 7.6 Hz, 1H), 2.16-2.06 (m, 2H), 1.99-1.86 (m, 3H), 1.55-1.42 (m, 2H), 1.11-0.96 (m, 6H). |

TABLE 2-continued

Further Exemplary Compounds of Formula (I) and Formula (II)

| Ex. # | Structure | Method | LCMS [M + 1] Observed | $^1$H NMR |
|---|---|---|---|---|
| 131 | 1,1-dimethyl-3-(2-(4-(((1R,2S)-2-phenylcyclopropyl)amino)piperidin-1-yl)ethyl)urea | Example 37 | 331.2 | (400 MHz, Methanol-d$_4$) δ 7.24 (t, J = 7.4 Hz, 2H), 7.16-7.10 (m, 1H), 7.05 (d, J = 7.2 Hz, 2H), 3.32-3.28 (m, 2H), 2.30-2.96 (m, 2H), 2.89 (s, 6H), 2.70-2.62 (m, 1H), 2.49 (t, J = 6.8 Hz, 2H), 2.37-2.28 (m, 1H), 2.15-2.06 (m, 2H), 2.01-1.86 (m, 3H), 1.56-1.41 (m, 2H), 1.11-1.01 (m, 2H) |
| 132 | N-methoxy-2-(4-(((1R,2S)-2-phenylcyclopropyl)amino)piperidin-1-yl)propanamide | Example 45 | 318.1 | (400 MHz, methanol-d$_4$) δ = 7.29-7.21 (m, 2H), 7.16-7.09 (m, 1H), 7.08-7.00 (m, 2H), 3.75-3.66 (m, 3H), 3.00 (q, J = 6.8 Hz, 1H), 2.94-2.85 (m, 2H), 2.68-2.59 (m, 1H), 2.36-2.25 (m, 2H), 2.24-2.14 (m, 1H), 2.01-1.84 (m, 3H), 1.55-1.40 (m, 2H), 1.29-1.22 (m, 3H), 1.12-0.97 (m, 2H). |
| 133 | 3-(4-(2-(4-(methyl((1R,2S)-2-phenylcyclopropyl)amino)piperidin-1-yl)ethoxy)phenyl)oxazolidin-2-one | Example 20 | 436.2 | (400 MHz, CHLOROFORM-d) δ = 7.44-7.42 (m, 2H), 7.28-7.24 (m, 2H), 7.17 (m, 1H), 7.05-7.03 (d, J = 7.6 Hz, 2H), 6.93-6.90 (m, 2H), 4.49-4.45 (m, 2H), 4.17 (br t, J = 5.2 Hz, 2H), 4.05-4.01 (m, 2H), 3.17-3.15(br d, J = 10.8 Hz, 2H), 2.90 (br s, 2H), 2.55 (br s, 1H), 2.43 (s, 3H), 2.28-2.26 (m, 2H), 2.08-1.99 (m, 2H), 1.98-1.87 (m, 2H), 1.86-1.73 (m, 2H), 1.19-1.18 (m, 1H), 1.07-1.02 (q, J = 6.0 Hz, 1H). |
| 134 | 1-(2-(4-bromo-2-fluorophenoxy)ethyl)-N-((1R,2S)-2-phenylcyclopropyl)piperidin-4-amine | Example 11 | 435.0 | (400 MHz, CD$_3$Cl) δ = 7.21-7.04 (m, 5H), 6.95 (d, J = 7.6 Hz, 2H), 6.78 (t, J = 8.8 Hz, 1H), 4.05 (t, J = 6.0 Hz, 2H), 2.86 (d, J = 11.2 Hz, 2H), 2.73 (t, J = 6.0 Hz, 2H), 2.64-2.49 (m, 1H), 2.27 (m, J = 3.6, 7.2 Hz, 1H), 2.11 (t, J = 11.6 Hz, 2H), 1.91-1.74 (m, 3H), 1.45-1.29 (m, 2H), 0.99 (m, J = 4.8, 9.2 Hz, 1H), 0.92 (q, J = 6.0 Hz, 1H). |
| 135 | N-((1R,2S)-2-phenylcyclopropyl)-1-(2-(pyridin-3-yloxy)ethyl)piperidin-4-amine | Example 11 | 338.1 | (400 MHz, D$_2$O) δ = 8.48-8.47 (d, J = 2.8 Hz, 1H), 8.38-8.36 (d, J = 5.6 Hz, 1H), 8.14-8.13 (m, 1H), 7.94-7.93 (m, 1H), 7.29-7.27 (m, 2H), 7.23-7.21 (d, J = 7.6 Hz, 1H), 7.13-7.10 (m, 2H), 4.57-4.55 (m, 2H), 3.97-3.66 (m, 5H), 3.23-3.21(br d, J = 8.0 Hz, 2H), 2.97-2.90 (m, 1H), 2.46-2.39 (m, 3H), 2.02 (br s, 2H), 1.48-1.39 (m, 2H). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 136 | 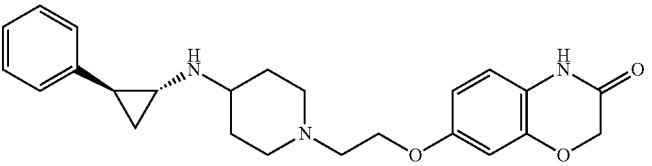<br>7-(2-(4-(((1R,2S)-2-phenylcyclopropyl)amino)piperidin-1-yl)ethoxy)-2H-benzo[b][1,4]oxazin-3(4H)-one | Example 11 | 408.1 | (400 MHz, Deuterium oxide) δ 7.34-7.26 (m, 2H), 7.25-7.18 (m, 1H), 7.11 (d, J = 7.6 Hz, 2H), 6.80 (d, J = 8.4 Hz, 1H), 6.62-6.54 (m, 2H), 4.51 (d, J = 1.6 Hz, 2H), 4.25 (t, J = 4.4 Hz, 2H), 3.79-3.58 (m, 3H), 3.56-3.45 (m, 2H), 3.24-3.06 (m 2H), 2.94-2.90 (m, 1H), 2.48-2.33 (m, 3H), 2.06-1.90 (m, 2H), 1.49-1.36 (m, 2H) |
| 137 | 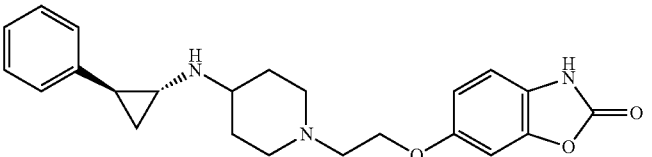<br>6-(2-(4-(((1R,2S)-2-phenylcyclopropyl)amino)piperidin-1-yl)ethoxy)benzo[d]oxazol-2-(3H)-one | Example 11 | 394.1 | (400 MHz, Deuterium oxide) δ 7.37-7.18 (m, 3H), 7.12 (d, J = 7.6 Hz, 2H), 6.96 (d, J = 8.4 Hz, 1H), 6.87 (s, 1H), 6.76 (d, J = 8.4 Hz, 1H), 4.32-4.24 (m, 2H), 3.92-3.63 (m, 3H), 3.58-3.49 (m, 2H), 3.23-3.12 (m, 2H), 3.03-2.86 (m, 1H), 2.55-2.32 (m, 3H), 2.06-1.92 (m, 2H), 1.56-1.34 (m, 2H) |
| 138 | 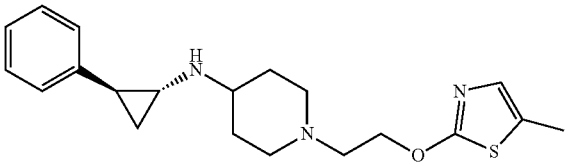 [SMILES: Cc1cnc(OCCN2CCC(N[C@@H]3C[C@H]3c3ccccc3)CC2)s1]<br>1-(2-((5-methylthiazol-2-yl)oxy)ethyl)-N-((1R,2S)-2-phenylcyclopropyl)piperidin-4-amine | Example 36 | 358.2 | (400 MHz, D₂O) δ = 7.32-7.29 (m, 2H), 7.25-7.21 (m, 1H), 7.14-7.12 (m, 2H), 6.94 (s, 1H), 4.75 (m, 2H), 3.78-3.66 (m, 5H), 3.19 (br s, 2H), 2.95-2.93 (m, 1H), 2.47-2.40 (m, 3H), 2.28 (s, 3H), 2.06 (br s, 2H), 1.49-1.40 (m, 2H) |
| 139 | 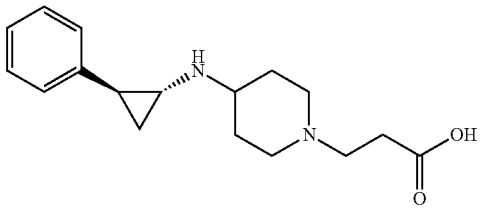 [SMILES: O=C(O)CCN1CCC(N[C@@H]2C[C@H]2c2ccccc2)CC1]<br>3-(4-(((1R,2S)-2-phenylcyclopropyl)amino)piperidin-1-yl)propanoic acid | Example 48 | 289.1 | (400 MHz, DEUTERIUM OXIDE) δ = 7.40-7.18 (m, 3H), 7.16-7.11 (m, 2H), 3.74-3.57 (m, 3H), 3.38 (br t, J = 6.4 Hz, 2H), 3.19-3.01 (m, 2H), 2.93 (td, J = 4.4, 7.7 Hz, 1H), 2.87-2.74 (m, 2H), 2.50-2.25 (m, 3H), 1.94 (br s, 2H), 1.51-1.35 (m, 2H) |
| 140 | 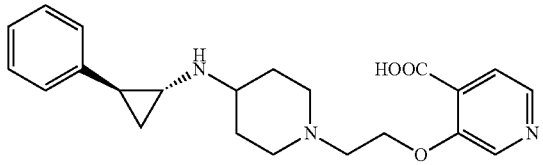<br>3-(2-(4-(((1R,2S)-2-phenylcyclopropyl)amino)piperidin-1-yl)ethoxy)isonicotinic acid | Example 36 | 382.1 | (400 MHz, D₂O) δ = 8.60 (s, 1H), 8.52-8.50 (d, J = 5.8 Hz, 1H), 7.90-7.88 (d, J = 5.6 Hz, 1H), 7.38-7.35 (m, 2H), 7.31-7.29 (m, 1H), 7.20-7.18 (d, J = 7.2 Hz, 2H), 4.66-4.64 (m, 2H), 3.85-3.83 (m, 2H), 3.72 (m, 3H), 3.29-3.26 (m, 2H), 3.02-3.00 (m, 1H), 2.53-2.47 (m, 3H), 2.06 (m, 2H), 1.55-1.46 (m, 2H). |

TABLE 2-continued

Further Exemplary Compounds of Formula (I) and Formula (II)

| Ex. # | Structure | Method | LCMS [M + 1] Observed | $^1$H NMR |
|---|---|---|---|---|
| 141 | 2-((2-(4-(((1R,2S)-2-phenylcyclopropyl)amino)piperidin-1-yl)ethyl)amino)isonicotinic acid | Example 36 | 381.1 | (400 MHz, Deuterium oxide) δ 7.90 (d, J = 6.4 Hz, 1H), 7.42 (s, 1H), 7.37-7.20 (m, 4H), 7.14 (d, J = 7.2 Hz, 2H), 3.86 (t, J = 6.2 Hz, 2H), 3.80-3.64 (m, 3H), 3.47 (t, J = 6.2 Hz, 2H), 3.26-3.10 (m, 2H), 3.00-2.92 (m, 1H), 2.51-2.37 (m, 3H), 2.10-1.92 (m, 2H), 1.55-1.39 (m, 2H) |
| 142 | 3-((2-(4-(((1R,2S)-2-phenylcyclopropyl)amino)piperidin-1-yl)ethyl)amino)isonicotinic acid | Example 36 | 381.1 | (400 MHz, Deuterium oxide) δ 8.17 (s, 1H), 8.11 (d, J = 5.6 Hz, 1H), 7.90 (d, J = 5.6 Hz, 1H), 7.26-7.19 (m, 2H), 7.18-7.11 (m, 1H), 7.08-7.02 (m, 2H), 3.79-3.56 (m, 5H), 3.40-3.32 (m 2H), 3.22-3.00 (m, 2H), 2.92-2.82 (m, 1H), 2.44-2.22 (m, 3H), 2.02-1.82 (m, 2H), 1.49-1.30 (m, 2H) |
| 143 | N-(methylsulfonyl)-3-(4-(((1R,2S)-2-phenylcyclopropyl)amino)piperidin-1-yl)propanamide | Example 48 | 366.1 | $^1$H NMR 500 MHz, DMSO-d$_6$, δ (ppm): 12.03 (bs, 1H), 10.72 (bs, 1H), 9.97 (bs, 2H), 7.32-7.29 (m, 2H), 7.24-7.18 (m, 3H), 3.57-3.51 (m, 3H), 3.27 (m, 2H), 3.26 (s, 3H), 3.02 (bs, 2H), 2.07 (m, 1H), 2.89 (t, J = 7.3 Hz, 2H), 2.57 (m, 1H), 2.29 (bs, 2H), 2.07 (m, 2H), 1.59 (m, 1H), 1.31-1.27 (m, 1H). |
| 144 | 3-(4-(((1R,2S)-2-phenylcyclopropyl)amino)piperidin-1-yl)-1-(piperazin-1-yl)propan-1-one | Example 48 | 357.3 | $^1$H NMR 500 MHz, DMSO-d$_6$, δ (ppm): 10.98 and 10.71 (two bs, 1H, mixture of rotamers), 10.25 and 10.06 (2 bs, 2H, mixture of rotamers), 9.52 and 9.44 (2 bs, 2H, mixture of rotamers), 7.32-7.29 (m, 2H), 7.24-7.18 (m, 3H), 3.70 (bs, 4H), 3.60 (bs, 2H), 3.45 (bs, 1H), 3.24 (bt, 2H), 3.15 (bs, 2H), 3.05-3.01 (m, 4H), 2.95-2.93 (m, 3H), 2.67 and 2.58 (two m, 1H, mixture of rotamers), 2.32-2.24 (m, 2H), 2.08 (bs, 2H), 1.67 and 1.60-1.57 (bs and m, 1H, mixture of rotamers), 1.31-1.27 (m, 1H). |
| 145 | (structure) | Example 48 | 428.2 | $^1$H NMR 500 MHz, DMSO-d$_6$, δ (ppm): 12.51 (bs, 1H), 10.59 (bs, 1H), 9.96 (bs, 2H), 7.94-7.92 (m, 2H), 7.72-7.69 (m, 1H), 7.64-7.61 (m, 2H), 7.32-7.29 (m, 2H), 7.24-7.18 (m, 3H), 3.42-3.40 (m, 3H), 3.16 (bt, 2H), 2.96-2.93 (m, 3H), 2.85 (t, J = 7.1 Hz, 2H), 2.56 (m, 1H), 2.23 (bs, 2H), 2.02 (m, 2H), 1.59-1.55 (m, 1H), 1.30-1.26 (m, 1H). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 146 | 3-(4-(((1R,2S)-2-phenylcyclopropyl)amino)piperidin-1-yl)-N-(phenylsulfonyl)propanamide 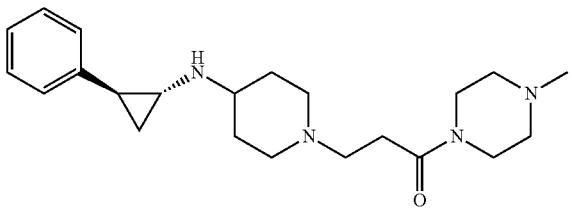 1-(4-methylpiperazin-1-yl)-3-(4-(((1R,2S)-2-phenylcyclopropyl)amino)piperidin-1-yl)propan-1-one | Example 48 | 371.3 | ¹H NMR 500 MHz, DMSO-d₆, δ (ppm): 11.42 (bs, 1H,), 11.03 and 10.76 (2 bs, 1H, mixture of rotamers), 10.05 (2 bs, 2H), 7.32-7.29 (m, 2H), 7.24-7.18 (m, 3H), 4.40 (bs, 1H), 4.03 (bs, 1H), 3.60-3.53 (m, 3H), 3.45 (bs, 1H), 3.43 (bs, 1H), 3.24 (bt, 2H), 3.04 (bs, 4H), 2.96 (bs, 4H), 2.75 (s, 3H), 2.67 and 2.59 (two m, 1H, mixture of rotamers), 2.33 (bs, 1H), 2.30 (bs, 1H), 2.23 (bs, 1H), 2.08 (m, 2H), 1.66 and 1.61-1.57 (bs and m, 1H, mixture of rotamers), 1.31-1.27 (m, 1H). |
| 147 | 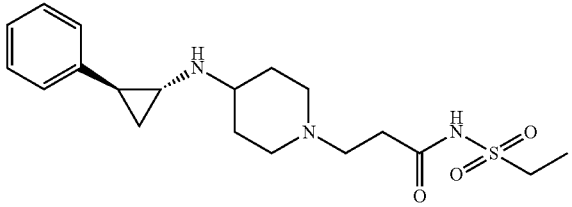 [SMILES: CCS(=O)(=O)NC(=O)CCN1CCC(N[C@@H]2C[C@H]2c2ccccc2)CC1] N-(ethylsulfonyl)-3-(4-(((1R,2S)-2-phenylcyclopropyl)amino)piperidin-1-yl)propanamide | Example 48 | 380.2 | ¹H NMR 500 MHz, DMSO-d₆, δ (ppm): 11.93 (bs, 1H), 10.76 (bs, 1H), 10.02 (bs, 2H), 7.32-7.29 (m, 2H), 7.24-7.18 (m, 3H), 3.54-3.50 (m, 3H), 3.36 (q, J = 7.4 Hz, 2H), 3.27 (bt, 2H), 3.01-2.90 (m, 5H), 2.67 and 2.57 (two m, 1H, rotamers), 2.29 (bs, 2H), 2.08 (m, 2H), 1.60 (m, 1H), 1.31-1.27 (m, 1H), 1.23 (t, J = 7.4 Hz, 3H). |
| 148 | 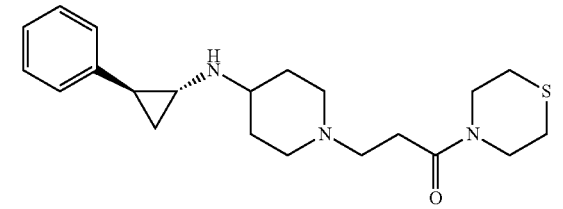 3-(4-(((1R,2S)-2-phenylcyclopropyl)amino)piperidin-1-yl)-1-thiomorpholinopropan-1-one | Example 48 | 374.7 | ¹H NMR 500 MHz, DMSO-d₆, δ (ppm): 10.63 and 10.47 (two bs, 1H, mixture of rotamers), 10.15 and 10.00 (two bs, 2H, mixture of rotamers), 7.33-7.30 (m, 2H), 7.24-7.18 (m, 3H), 3.73-3.68 (m, 4H), 3.61 (bt, 2H), 3.45 (bs, 1H), 3.24 (bt, 2H), 3.06-2.93 (m, 3H), 2.89 (t, J = 7.7 Hz, 2H), 2.66-2.64 (m, 2H), 2.59-2.53 (m, 3H), 2.30 and 2.21 (two bs, 2H), 2.11-2.01 (m, 2H), 1.66 and 1.60-1.56 (bs and m, 1H, mixture of rotamers), 1.31-1.27 (m, 1H). |
| 149 | 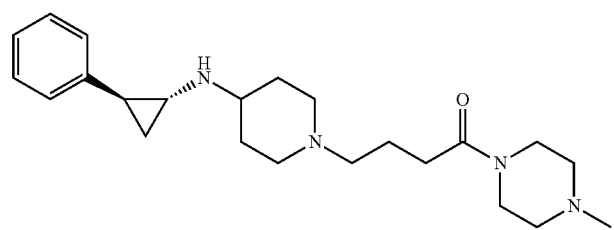 1-(4-methylpiperazin-1-yl)-4-(4-(((1R,2S)-2-phenylcyclopropyl)amino)piperidin-1-yl)butan-1-one | Example 48 | 385.3 | ¹H NMR 500 MHz, DMSO-d₆, δ (ppm): 11.33 and 11.19 (two bs, 1H, mixture of rotamers), 11.00 and 10.70 (two bs, 1H, mixture of rotamers), 10.22 and 10.03 (two bs, 2H, mixture of rotamers), 7.32-7.29 (m, 2H), 7.24-7.18 (m, 3H), 4.42 (bd, 1H), 4.02 (bd, 1H), 3.57-3.38 (m, 6H), 3.08-2.91 (m, 8H), 2.74 (s, 3H), 2.66 and 2.59-2.55 (two m, 1H, mixture of rotamers), 2.32 (bs, 1H), 2.29 (bs, 1H), 2.30 (bs, 1H), 2.24-2.23 (m, 1H), 2.15-2.05 (m, 2H), 1.96-1.89 (m, 2H), 1.67 and 1.61-1.57 (two m, 1H, mixture of rotamers), 1.30-1.26 (m, 1H). MS: 384.6 (calcd.), 385.3 (M + H⁺, found). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 150 | 4-(4-(((1R,2S)-2-phenylcyclopropyl)amino)piperidin-1-yl)-1-(piperazin-1-yl)butan-1-one | Example 48 | 371.3 | ¹H NMR 500 MHz, DMSO-d₆, δ (ppm): 11.00 and 10.69 (two bs, 1H, mixture of rotamers), 10.04 (bs, 2H), 9.48 and 9.41 (two bs, 2H, mixture of rotamers), 7.32-7.29 (m, 2H), 7.24-7.18 (m, 3H), 3.69-3.67 (m, 4H), 3.57 (bs, 2H), 3.46 (bs, 1H), 3.12 (bs, 2H), 3.02-2.97 (7H), 2.69-2.64 and 2.60-2.56 (two m, 1H, mixture of rotamers), 2.32 (bs, 1H), 2.30 (bs, 1H), 2.23 (bs, 1H), 2.14-2.05 (m, 1H), 2.14-2.05 (m, 2H), 1.96-1.88 (m, 2H), 1.67 and 1.61-1.57 (two m, 1H, mixture of rotamers), 1.30-1.26 (m, 1H). |
| 151 | 1-morpholino-4-(4-(((1R,2S)-2-phenylcyclopropyl)amino)piperidin-1-yl)butan-1-one | Example 48 | 372.3 | ¹H NMR 500 MHz, DMSO-d₆, δ (ppm): 10.78 and 10.52 (two bs, 1H, mixture of rotamers), 10.14 and 10.00 (two bs, 2H, mixture of rotamers), 7.32-7.29 (m, 2H), 7.24-7.18 (m, 3H), 3.58-3.53 (m, 6H), 3.44-3.41 (m, 4H), 3.11-3.07 and 3.02-2.94 (two m, 5H, mixture of rotamers), 2.67-2.63 and 2.59-2.55 (two m, 1H, mixture of rotamers), 2.43 (t, J = 7.1 Hz, 2H), 2.32 (bs, 1H), 2.29 (bs, 1H), 2.23-2.20 (m, 1H), 2.13-2.03 (m, 2H), 1.94-1.88 (m, 2H), 1.68-1.64 and 1.61-1.57 (two m, 1H, mixture of rotamers), 1.33-1.27 (m, 1H). |
| 152 | 4-(4-(((1R,2S)-2-phenylcyclopropyl)amino)piperidin-1-yl)-N-(phenylsulfonyl)butanamide | Example 48 | 442.2 | ¹H NMR 500 MHz, DMSO-d₆, δ (ppm): 12.26 (bs, 1H), 10.50 (bs, 1H), 9.97 (bs, 2H), 7.93-7.91 (m, 2H), 7.74-7.70 (m, 1H), 7.65-7.61 (m, 2H), 7.32-7.29 (m, 2H), 7.24-7.19 (m, 3H), 3.50 (bs, 2H), 3.44 (bs, 1H), 2.96-2.91 (m, 4H), 2.56 (bs, 1H), 2.35 (t, J = 7.2 Hz, 2H), 2.25 (bs, 2H), 2.05 (m, 3H), 1.85-1.79 (m, 2H), 1.58 (bs, 1H), 1.30-1.26 (m, 1H). |
| 153 | 4-(4-(((1R,2S)-2-phenylcyclopropyl)amino)piperidin-1-yl)butanoic acid | Example 48 | 303.2 | ¹H NMR 500 MHz, DMSO-d₆, δ (ppm): 12.29 (bs, 1H), 10.88 and 10.56 (two bs, 1H), 10.05 (bs, 2H), 7.32-7.29 (m, 2H), 7.24-7.18 (m, 3H), 3.56 (bs, 2H), 3.46 (m, 1H), 3.00-2.96 (m, 5H), 2.58 (m, 1H), 2.34-2.22 (m, 4H), 2.08 (m, 2H), 1.94-1.66 (m, 2H), 1.61-1.57 (m, 1H), 1.31-1.27 (m, 1H). |
| 154 | N-(cyclopropylsulfonyl)-4-(4-(((1R,2S)-2-phenylcyclopropyl)amino)piperidin-1-yl)butanamide | Example 48 | 406.6 | ¹H NMR 500 MHz, DMSO-d₆, δ (ppm): 11.77 (bs, 1H), 10.62 (bs, 1H), 10.01 (bs, 2H), 7.32-7.29 (m, 2H), 7.24-7.18 (m, 3H), 3.56 (bs, 2H), 3.46 (bs, 1H), 2.99-2.91 (m, 6H), 2.57 (bs, 1H), 2.40 (t, J = 7.2 Hz, 2H), 2.31 (bs, 1H), 2.29 (bs, 1H), 2.08 (m, 2H), 1.97-1.91 (m, 2H), 1.59 (bs, 1H), 1.31-1.27 (m, 1H), 1.10-1.07 (m, 4H). MS: 405.6 (calcd.), 406.6 (M + H⁺, found). |

TABLE 2-continued

Further Exemplary Compounds of Formula (I) and Formula (II)

| Ex. # | Structure | Method | LCMS [M + 1] Observed | ¹H NMR |
|---|---|---|---|---|
| 155 | N-(ethylsulfonyl)-4-(4-(((1R,2S)-2-phenylcyclopropyl)amino)piperidin-1-yl)butanamide | Example 48 | 394.7 | ¹H NMR 500 MHz, DMSO-$d_6$, δ (ppm): 11.70 (bs, 1H), 10.58 (bs, 1H), 9.99 (bs, 2H), 7.32-7.29 (m, 2H), 7.24-7.18 (m, 3H), 3.57 (bs, 2H), 3.46 (bs, 1H), 3.35 (q, J = 7.4 Hz, 2H), 2.97 (bs, 4H), 2.57 (m, 1H), 2.41 (t, J = 7.1 Hz, 2H), 2.31 (bs, 1H), 2.28 (bs, 1H), 2.21 (bs, 1H), 2.07 (m, 2H), 1.96-1.90 (m, 2H), 1.60-1.56 (m, 1H), 1.31-1.27 (m, 1H), 1.21 (t, J = 7.3 Hz, 3H). |
| 156 | N-(methylsulfonyl)-4-(4-(((1R,2S)-2-phenylcyclopropyl)amino)piperidin-1-yl)butanamide | Example 48 | 380.2 | ¹H NMR 500 MHz, DMSO-$d_6$, δ (ppm): 11.83 (bs, 1H), 10.62 (bs, 1H), 10.02 (bs, 2H), 7.33-7.30 (m, 2H), 7.25-7.19 (m, 3H), 3.57 (bs, 2H), 3.51-3.47 (m, 1H), 3.25 (s, 3H), 2.98 (bs, 4H), 2.68 and 2.58 (m and bs, 1H, mixture of rotamers), 2.43 (t, J = 7.1 Hz, 2H), 2.33 (bs, 1H), 2.30 (bs, 1H), 2.23 (bs, 1H), 2.09 (bs, 2H), 1.97-1.91 (m, 2H), 1.62-1.58 (m, 1H), 1.32-1.28 (m, 1H). |
| 157 | 2-(3-chloro-4-(2-(4-(((1R,2S)-2-phenylcyclopropyl)amino)piperidin-1-yl)ethoxy)phenyl)acetic acid | Example 43 | 429.7 | ¹H NMR 500 MHz, DMSO$_6$, δ (ppm): 12.36 (bs, 1H), 10.95 (bs, 1H), 10.00 (bs, 2H), 7.37 (d, J = 2.4 Hz, 1H), 7.32-7.29 (m, 2H), 7.24-7.14 (m, 5H), 4.48 (bt, 2H), 3.72 (bs, 2H), 3.55 (s, 2H), 3.51 (bs, 2H), 3.47 (bs, 1H), 3.19 (bs, 2H), 2.97 (bs, 1H), 2.57 (m, 1H), 2.33 (bs, 2H), 2.11 (bs, 2H), 1.61-1.57 (m, 1H), 1.31-1.27 (m, 1H). MS: 429.0 (calcd.). |
| 158 | 2-(3-fluoro-4-(2-(4-(((1R,2S)-2-phenylcyclopropyl)amino)piperidin-1-yl)ethoxy)phenyl)acetic acid | Example 43 | 413.7 | ¹H NMR 500 MHz, DMSO$_6$, δ (ppm): 12.36 (bs, 1H), 11.18 and 10.93 (two bs, 1H), 10.04 (bs, 2H), 7.32-7.29 (m, 2H), 7.21-7.15 (m, 5H), 7.05 (m, 1H), 4.47 (bt, 2H), 3.68 (bs, 1H), 3.67 (bs, 1H), 3.54 (s, 2H), 3.59 (bs, 3H), 3.15 (bs, 2H), 2.96 (bs, 1H), 2.58 (m, 1H), 2.33 (bs, 2H), 2.10 (bs, 2H), 1.61-1.57 (m, 1H), 1.31-1.26 (m, 1H). MS: 412.5 (calcd.). |
| 159 | 2-(3-methyl-4-(2-(4-(((1R,2S)-2-phenylcyclopropyl)amino)piperidin-1-yl)ethoxy)phenyl)acetic acid | Example 43 | 409.7 | ¹H NMR 500 MHz, DMSO$_6$, δ (ppm): 12.20 (bs, 1H), 11.12 and 10.90 (two bs, 1H), 9.98 (bs, 2H), 7.32-7.29 (m, 2H), 7.24-7.18 (m, 3H), 7.06-7.05 (m, 2H), 6.90-6.89 (m, 1H), 4.37 (bt, 2H), 3.67 (bs, 1H), 3.66 (bs, 1H), 3.48 (bs, 2H), 3.46 (s, 2H), 3.17 (bs, 2H), 2.96 (bs, 1H), 2.64 and 2.56 (two m, 1H, rotamers), 2.33 (bs, 2H), 2.16 (s, 3H), 2.11 (bs, 2H), 1.60-1.56 (m, 1H), 1.31-1.27 (m, 1H). |

TABLE 2-continued

Further Exemplary Compounds of Formula (I) and Formula (II)

| Ex. # | Structure | Method | LCMS [M + 1] Observed | $^1$H NMR |
|---|---|---|---|---|
| 160 | 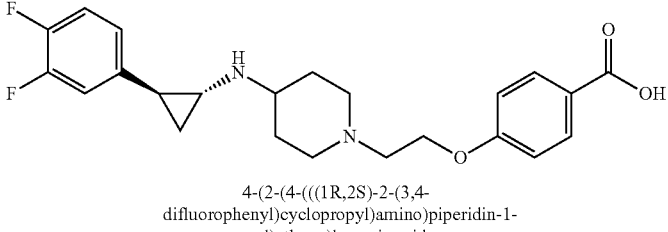<br>4-(2-(4-(((1R,2S)-2-(3,4-difluorophenyl)cyclopropyl)amino)piperidin-1-yl)ethoxy)benzoic acid | Example 43 | 417.6 | $^1$H NMR 500 MHz, DMSO$_6$, δ (ppm): 12.69 (bs, 1H), 11.21 and 10.96 (two bs, 1H), 10.12 (bs, 2H), 7.93 (d, J = 8.9 Hz, 2H), 7.40-7.29 (m, 2H), 7.12-7.08 (m, 3H), 4.49 (bt, 2H), 3.69 (bs, 1H), 3.67 (bs, 1H), 3.50-3.43 (m, 3H), 3.15 (bs, 2H), 3.01 (bs, 1H), 2.61 (m, 1H), 2.34 (bs, 1H), 2.32 (bs, 1H), 2.11 (bs, 2H), 1.64-1.60 (m, 1H), 1.35-1.31 (m, 1H). |
| 161 | 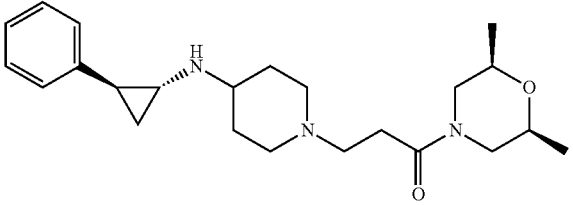 [SMILES: C[C@@H]1CN(C(=O)CCN2CCC(N[C@@H]3C[C@H]3c3ccccc3)CC2)C[C@H](C)O1]<br>1-(cis-2,6-dimethylmorpholino)-3-(4-(((1R,2S)-2-phenylcyclopropyl)amino)piperidin-1-yl)propan-1-one | Example 43 | 386.7 | $^1$H NMR: 500 MHz, D$_2$O, δ (ppm): 7.44-7.40 (m, 2H), 7.37-7.33 (m, 1H), 7.25-7.23 (m, 2H), 4.32-4.29 (m, 1H), 3.82-3.66 (m, 7H), 3.49 (bt, 2H), 3.18 (bs, 2H), 3.07-3.01 (m, 2H), 2.99-2.91 (m, 2H), 2.58-2.49 (m, 4H), 2.06 (bs, 2H), 1.60-1.50 (m, 2H), 1.27-1.21 (m, 6H, mixture of rotamers). |

The compounds of the present invention have two or more chiral centers and are synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or entantiomers as described, for example, in Examples 7 & 8. Unless otherwise indicated, all chiral (enantiomeric and diastereomeric) and racemic forms are within the scope of the invention.

Example A

This Example illustrates that exemplary compounds of the present invention inhibit LSD1 enzymatic activity.

Ten-point dose-response curves for compounds shown in Table 3 were determined using a fluorescence coupling enzymatic assay using purified N-terminal truncated human LSD1 enzyme (aa 151-852; Genbank Accession No NM015013) containing an N-terminal His-Tag (Reaction Biology Corp). In this assay, hydrogen peroxide is produced by the LSD1 FAD-dependent demethylase activity using a horseradish peroxidase/Amplex Red coupling reaction resulting in the production of highly fluorescent compound, Resorufin, which is detected at 590 nM.

Briefly, compounds of the present invention were solubilized in DMSO and a series of 10, three-fold serial dilutions were made for each compound in 15% DMSO. The initial starting concentration for the serial dilutions of each compound was 10 μM. Control samples lacking compound, LSD1 enzyme or various reaction components also were prepared and processed in parallel with compound test samples.

An aliquot of each serial dilution of test compound was added to a 96 well plate containing 50 nM purified N-truncated LSD1 enzyme (RBC Cat# PDM-11-350), 50 mM Tris-HCl, pH 7.5, 0.05% CHAPS and 1% DMSO in a 10 microliter reaction volume. The plate was pre-incubated at room temperature for 30 min to which 10 M of histone 3.3 peptide (aa 1-21) was added to initiate the enzymatic reaction. The reaction mixture was incubated at room temperature for one hour. After one hour, 10 μl of a detection mixture of horseradish peroxidase (Sigma Cat #P8375) and Amplex Red (InVitrogen A36006) was added and kinetic measurements were read at 5 minute intervals for a period of 30 minutes using an Envision Multiplate Reader (PerkinElmer; excitation at 535 nM and emmission read at 590 nM). The IC$_{50}$ value for each compound was determined from each 10-point dose-response curve using GraphPad Prism 4 software with a sigmodial dose response. The results for exemplary compounds of Formula (I) and Formula (II) are shown in Table 3.

TABLE 3

Inhibition of LSD1 Activity by Exemplary Compounds of Formula (I)

| Example Number | IC$_{50}$ (nM) |
|---|---|
| 1 | 36 |
| 2 | 110 |
| 3 | 33 |
| 4 | 47 |

TABLE 3-continued

Inhibition of LSD1 Activity by Exemplary Compounds of Formula (I)

| Example Number | $IC_{50}$ (nM) |
|---|---|
| 5 | 17 |
| 6 | 28 |
| 7 | 15 |
| 8 | 13 |
| 9 | 110 |
| 10 | 8 |
| 11 | 10 |
| 12 | 5 |
| 13 | 25 |
| 14 | 16 |
| 15 | 11 |
| 16 | 7 |
| 17 | 4 |
| 18 | 7 |
| 19 | 3 |
| 20 | 5 |
| 21 | 5 |
| 22 | 5 |
| 23 | 4 |
| 24 | 3 |
| 25 | 46 |
| 26 | 50 |
| 27 | 116 |
| 28 | 8 |
| 29 | 4 |
| 30 | 14 |
| 31 | 87 |
| 32 | 22 |
| 33 | <1 |
| 34 | 3 |
| 35 | 21 |
| 36 | 33 |
| 37 | 108 |
| 38 | 23 |
| 39 | 25 |
| 40 | 11 |
| 41 | 15 |
| 42 | 10 |
| 43 | 17 |
| 44 | 9 |
| 45 | 225 |
| 46 | 58 |
| 47 | 74 |
| 48 | 10 |
| 49 | 21 |
| 50 | 3 |
| 51 | 6 |
| 52 | 6 |
| 53 | 12 |
| 54 | 7 |
| 55 | 4 |
| 56 | 5 |
| 57 | 2 |
| 58 | 3 |
| 59 | 8 |
| 60 | 1 |
| 61 | 12 |
| 62 | 8 |
| 63 | 14 |
| 64 | 0.9 |
| 65 | 8 |
| 66 | 4 |
| 67 | 8 |
| 68 | 6 |
| 69 | 33 |
| 70 | 8 |
| 71 | 31 |
| 72 | 17 |
| 73 | 5 |
| 74 | 4 |
| 75 | 20 |
| 76 | 11 |
| 77 | 10 |
| 78 | 7 |
| 79 | 31 |
| 80 | 22 |
| 81 | 23 |
| 82 | 39 |
| 83 | 76 |
| 84 | 19 |
| 85 | 6 |
| 86 | 7 |
| 87 | 22 |
| 88 | 25 |
| 89 | 4 |
| 90 | 20 |
| 91 | 4 |
| 92 | 123 |
| 93 | 46 |
| 94 | 17 |
| 95 | 5 |
| 96 | 624 |
| 97 | 57 |
| 98 | 13 |
| 99 | 349 |
| 100 | 39 |
| 101 | 319 |
| 102 | 14 |
| 103 | 19 |
| 104 | 5 |
| 105 | 6 |
| 106 | 14 |
| 107 | 27 |
| 108 | 11 |
| 109 | 24 |
| 110 | 9 |
| 111 | 7 |
| 112 | 35 |
| 113 | 9 |
| 114 | 12 |
| 115 | 14 |
| 116 | 38 |
| 117 | 17 |
| 118 | 709 |
| 119 | 38 |
| 120 | 18 |
| 121 | 24 |
| 122 | 31 |
| 123 | 8 |
| 124 | 71 |
| 125 | 19 |
| 126 | 19 |
| 127 | 286 |
| 128 | 2 |
| 129 | 10 |
| 130 | 14 |
| 131 | 19 |
| 132 | 232 |
| 133 | 15 |
| 134 | 26 |
| 135 | 25 |
| 136 | 11 |
| 137 | 7 |
| 138 | 18 |
| 139 | 277 |
| 140 | 154 |
| 141 | 11 |
| 142 | 127 |
| 143 | 221 |
| 144 | 9 |
| 145 | 21 |
| 146 | 8 |
| 147 | 148 |
| 148 | 15 |
| 149 | 14 |
| 150 | 5 |
| 151 | 9 |
| 152 | 20 |
| 153 | 192 |
| 154 | 440 |

TABLE 3-continued

Inhibition of LSD1 Activity by Exemplary Compounds of Formula (I)

| Example Number | IC$_{50}$ (nM) |
|---|---|
| 155 | 134 |
| 156 | 231 |
| 157 | 3 |
| 158 | 8 |
| 159 | 20 |
| 160 | 15 |
| 161 | 17 |

Example B

This Example illustrates that exemplary compounds of the present invention inhibit the growth of tumor cell lines that express LSD1.

The MV4-11 cell line cell line was established from the blast cells of a 10-year-old male with biphenotypic B-myelomonocytic leukemia. This cell line expresses a leukemic fusion protein (MLL-AF9+), LSD1 and has been shown to be sensitive to inhibitors of LSD1.

Inhibition of LSD1-mediated cellular proliferation by compounds of Formula (I) or Formula (II) was measured in a CellTiter Glo luminescence assay (Promega Corp), which determines the number of viable cells by quantitating the amount of ATP, using a BMG LabTech CLARIOStar instrument in accordance with the manufacturer's instructions. Briefly, MV4-11 cells were plated at a density of 1000 cells/90 μl/well in 96 well culture plates and cultured in IMDM medium (Gibco) supplemented with 10% fetal bovine serum (FBS) and 1% penicillin and 1% streptomycin at 37° C. A series of 3-fold serial dilutions of each test compound of Formula (I) was prepared in IMDM medium lacking FBS and added to the cells at final concentrations ranging from 1 μM to 0.01 nM. Control samples lacking test compound or cells were processed in parallel. The plates were incubated at 37° C. for four days and thereafter 50 μl fresh medium containing the same concentration of test compound was added. The plates were incubated for an additional three days (Day 7). A baseline measurement, as described below, was taken for a time zero point at Day 0.

At Day 7, the supernatant was removed by aspiration and the plate was allowed to equilibrate to room temperature (~15 min). The cells were lysed using 45 μl (30 μl for Day 0) of Cell Titer Glo reagent (Promega Corp). The plates were shaken for two minutes and incubated at room temperature for 30 minutes. The degree of inhibition of cell viability was determined using a spectrophotometric readout by measuring the luminescence at 340 nm and the EC$_{50}$ concentration for each compound was calculated using Graph Pad Prism 4 software. The results are shown in Table 4. Key: N/D=not determined.

TABLE 4

Inhibition of LSD1-mediated Cell Proliferation by Exemplary Compounds of Formula (I) and Formula (II)

| Example Number | IC$_{50}$ (nM) |
|---|---|
| 1 | 13 |
| 2 | 34 |
| 3 | 2 |
| 4 | 14 |
| 5 | <1 |
| 6 | 14 |
| 7 | 2 |
| 8 | 2 |
| 9 | 3 |
| 10 | <1 |
| 11 | <1 |
| 12 | <1 |
| 13 | 2 |
| 14 | 2 |
| 15 | <1 |
| 16 | 33 |
| 17 | 8 |
| 18 | <1 |
| 19 | 1 |
| 20 | <1 |
| 21 | <1 |
| 22 | <1 |
| 23 | <1 |
| 24 | <1 |
| 25 | <1 |
| 26 | <1 |
| 27 | <1 |
| 28 | <1 |
| 29 | <1 |
| 30 | <1 |
| 31 | 10 |
| 32 | 33 |
| 33 | <1 |
| 34 | <1 |
| 35 | 3 |
| 36 | 28 |
| 37 | 2 |
| 38 | <1 |
| 39 | 5 |
| 40 | <1 |
| 41 | <1 |
| 42 | 28 |
| 43 | 10 |
| 44 | 1 |
| 45 | 56 |
| 46 | 10 |
| 47 | 885 |
| 48 | 3 |
| 49 | 14 |
| 50 | <1 |
| 51 | <1 |
| 52 | <1 |
| 53 | <1 |
| 54 | <1 |
| 55 | <1 |
| 56 | <1 |
| 57 | <1 |
| 58 | <1 |
| 59 | <1 |
| 60 | <1 |
| 61 | 7 |
| 62 | 4 |
| 63 | <1 |
| 64 | 11 |
| 65 | 7 |
| 66 | 9 |
| 67 | 4 |
| 68 | 10 |
| 69 | 28 |
| 70 | 4 |
| 71 | 2 |
| 72 | 10 |
| 73 | 3 |
| 74 | 3 |
| 75 | 10 |
| 76 | <1 |
| 77 | <1 |
| 78 | 117 |

TABLE 4-continued

Inhibition of LSD1-mediated Cell Proliferation by Exemplary Compounds of Formula (I) and Formula (II)

| Example Number | IC$_{50}$ (nM) |
|---|---|
| 79 | <1 |
| 80 | <1 |
| 81 | <1 |
| 82 | <1 |
| 83 | 5 |
| 84 | 1 |
| 85 | <1 |
| 86 | 5 |
| 87 | 22 |
| 88 | 5 |
| 89 | <1 |
| 90 | 34 |
| 91 | <1 |
| 92 | 9 |
| 93 | 24 |
| 94 | <1 |
| 95 | <1 |
| 96 | 67 |
| 97 | <1 |
| 98 | >1000 |
| 99 | 28 |
| 100 | <1 |
| 101 | 3 |
| 102 | N/D |
| 103 | <1 |
| 104 | <1 |
| 105 | <1 |
| 106 | 10 |
| 107 | <1 |
| 108 | <1 |
| 109 | <1 |
| 110 | 5 |
| 111 | 13 |
| 112 | <1 |
| 113 | 3 |
| 114 | 3 |
| 115 | 1 |
| 116 | 6 |
| 117 | 2 |
| 118 | 23 |
| 119 | 5 |
| 120 | 3 |
| 121 | 6 |
| 122 | 5 |
| 123 | <1 |
| 124 | 7 |
| 125 | 29 |
| 126 | 4 |
| 127 | 530 |
| 128 | <1 |
| 129 | <1 |
| 130 | <1 |
| 131 | 2 |
| 132 | 7 |
| 133 | 61 |
| 134 | 3 |
| 135 | 1 |
| 136 | <1 |
| 137 | <1 |
| 138 | 3 |
| 139 | 37 |
| 140 | 30 |
| 141 | 60 |
| 142 | 38 |
| 143 | 10 |
| 144 | <1 |
| 145 | 3 |
| 146 | <1 |
| 147 | 9 |
| 148 | 3 |
| 149 | <1 |
| 150 | <1 |
| 151 | 2 |
| 152 | 6 |
| 153 | 13 |
| 154 | 1 |
| 155 | 1 |
| 156 | 8 |
| 157 | 28 |
| 158 | 29 |
| 159 | 10 |
| 160 | 10 |
| 161 | 1 |

As evidenced in Examples A & B, many of the compounds of formula (I) and formula (II) of the present invention demonstrate at least 10-fold, at least 20-fold, at least 30-fold, at least 40-fold or as much as at least 50-fold greater potency than the LSD1 inhibitor GSK2879552

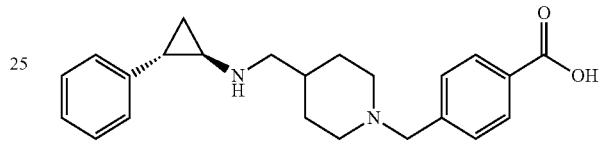

presently in Phase I clinical trials (ClinicalTrials.gov Identifier: NCT02177812).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method of treating cancer in a subject in need thereof, the method comprising administering to the subject a therapeutically effective amount of a compound of formula (I) or formula (II):

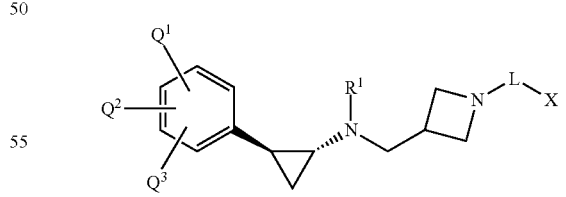

Formula (I)

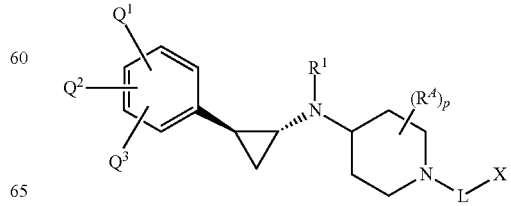

Formula (II)

or a pharmaceutically acceptable salt thereof:
wherein:
$R^1$ is hydrogen, $C_1$-$C_4$ alkyl or $C_1$-$C_4$ acyl;
L is —$(CH_2)_s$—$CR^2R^3$—$(CH_2)_n$—;
$R^2$ and $R^3$ are each independently hydrogen, $C_1$-$C_4$ alkyl, —$OR^4$ or aralkyl;
each $R^4$ is independently hydrogen or $C_1$-$C_4$ alkyl;
X is —W—$R^5$ or Y—$R^6$;
W is —$NR^4$— or —O—;
Y is —C(O)—, —S—, —SO—, —$SO_2$—, —$NR^4SO_2$—, —$SO_2NR^4$— or —$NR^4C(O)$—;
$R^5$ is acyl, $C_1$-$C_4$ alkyl, cycloalkyl, heterocyclyl, aryl or heteroaryl, wherein each of said cycloalkyl, heterocyclyl, aryl or heteroaryl is optionally independently substituted with one or more $R^8$;
$R^6$ is $C_1$-$C_6$ alkyl, aryl, —$NR^4R^7$ or heterocyclyl optionally independently substituted on one or more carbon atoms with $C_1$-$C_6$ alkyl, halogen, cyano, haloalkyl or optionally independently substituted on one or more nitrogen atom with —$C(O)C_1$-$C_6$alkyl; —$C(O)OC_1$-$C_6$ alkyl; —$C(O)NR^4C_1$-$C_6$alkyl, or —$S(O)_2NR^4C_1$-$C_6$ alkyl;
$R^7$ is hydroxyl, alkoxy, —$SO_2C_1$-$C_6$alkyl; —$SO_2$cycloalkyl, or —$SO_2$aryl, wherein the cycloalkyl or aryl of each of the —$SO_2$cycloalkyl and —$SO_2$aryl is optionally independently substituted with one or more $R^8$;
each $R^8$ is halogen, hydroxyl, amino, cyano, $C_1$-$C_6$ alkyl, $C_2$-$C_6$ alkenyl, $C_2$-$C_6$ alkynyl, haloalkyl, alkoxy, alkylamino, dialkylamino, cycloalkyl, aryl, heteroaryl, heterocyclyl, aralkyl, heteroarylalkyl, —$(CH_2)_n COOR^4$, —$(CH_2)_n C(O)NR^4OC_1$-$C_6$alkyl; —$(CH_2)_n C(O)NR^4SO_2C_1$-$C_6$alkyl, —$(CH_2)_n C(O)NR^4SO_2$cycloalkyl, —$(CH_2)_n C(O)NR^4SO_2$aryl, —$C_2$-$C_6$ alkenylC(O)$OR^4$, —$C_2$-$C_6$ alkenylC(O)$NR^4SO_2C_1$-$C_4$ alkyl, or —$C_2$-$C_6$ alkenylC(O) $NR^4SO_2$aryl, wherein each of the cycloalkyl, aryl, heteroaryl, heterocyclyl is optionally independently substituted with one or more $C_1$-$C_3$ alkyl or —$CH_2NR^4SO_2$aryl;
m is 0 or 1;
s is 0 or 1;
each n is 0, 1, or 2;
each p is 0, 1 or 2;
each $R^A$ group is independently oxo or $C_1$-$C_3$ alkyl, or two $R^A$ groups on different ring atoms together form a $C_1$-$C_3$ bridge in which one of the bridge carbons is optionally replaced with —NH—; and
each $Q^1$, $Q^2$ and $Q^3$ is independently hydrogen, halogen, haloalkyl, $C_1$-$C_4$-alkyl, or $C_1$-$C_4$-alkoxy,
wherein the cancer is Lung, or Hematologic cancer.

2. The method of claim 1, wherein the cancer is Ewing's sarcoma, myelodysplastic syndrome, or leukemia.

3. The method of claim 1, wherein W is —O— and s is 1 and m is 0.

4. The method of claim 3, wherein the aryl is phenyl optionally independently substituted with one or more $R^8$.

5. The method of claim 4, wherein the heterocyclyl is azetidinyl, pyrrolidinyl, pyrazolidinyl, piperidinyl, piperazinyl, 4-methyl-piperazinyl, 4-acyl-piperazinyl, tetrahydropyranyl, 1,3-dioxolanyl, 1,4-dioxanyl, morpholinyl, dimethyl-morpholinyl, thiomorpholinyl, 1,4-dithianyl, or 1,3,5-trithianyl.

6. The method of claim 5, wherein the heteroaryl is pyridyl, 6-methyl-pyridyl, 4-carboxy-pyridyl, dihydroquinolinone, indolinone, quinazolinyl, quinolinyl, pyrimidinyl, 2-methyl-pyrimidinyl, pyridazinyl, 6-methyl-pyridiazinyl, pyrazolyl, 1-methyl-pyrazolyl, 5-methyl-pyrazolyl, 1,3-dimethyl-pyrazolyl, thiazolyl, 5-methyl-thiazolyl, benzo[d]oxazol-2(3H)-one, 2H-benzo[b][1,4]oxazin-3(4H)-one, thiadiazolyl or 5-methyl-thiadiazolyl.

7. The method of claim 1, wherein W is —$NR^4$— and s is 1 and m is 0.

8. The method of claim 7, wherein the aryl is phenyl optionally independently substituted with one or more $R^8$.

9. The method of claim 8, wherein the heterocyclyl is azetidinyl, pyrrolidinyl, pyrazolidinyl, piperidinyl, piperazinyl, 4-methyl-piperazinyl, 4-acyl-piperazinyl, tetrahydropyranyl, 1,3-dioxolanyl, 1,4-dioxanyl, morpholinyl, dimethyl-morpholinyl, thiomorpholinyl, 1,4-dithianyl, or 1,3,5-trithianyl.

10. The method of claim 9, wherein the heteroaryl is pyridyl, 6-methyl-pyridyl, 4-carboxy-pyridyl, dihydroquinolinone, indolinone, quinazolinyl, quinolinyl, pyrimidinyl, 2-methyl-pyrimidinyl, pyridazinyl, 6-methyl-pyridiazinyl, pyrazolyl, 1-methyl-pyrazolyl, 5-methyl-pyrazolyl, 1,3-dimethyl-pyrazolyl, thiazolyl, 5-methyl-thiazolyl, benzo[d]oxazol-2(3H)-one, 2H-benzo[b][1,4]oxazin-3(4H)-one, thiadiazolyl or 5-methyl-thiadiazolyl.

11. The method of claim 1, wherein Y is —C(O)—, s is 0, m is 0, $R^2$ is $C_1$-$C_4$ alkyl or aralkyl, $R^3$ is hydrogen and $R^6$ is heterocyclyl.

12. The method of claim 11, wherein the heterocyclyl is piperazinyl, 4-methyl-piperazinyl, 4-acyl-piperazinyl, morpholinyl, dimethyl-morpholinyl, or thiomorpholinyl.

13. The method of claim 1, wherein Y is —C(O)—, s is 1, m is 0, $R^2$ and $R^3$ are each independently hydrogen, and $R^6$ is heterocyclyl.

14. The method of claim 13, wherein the heterocyclyl is piperazinyl, 4-methyl-piperazinyl, 4-acyl-piperazinyl, morpholinyl, dimethyl-morpholinyl, or thiomorpholinyl.

15. The method of claim 1, wherein Y is —C(O)—, s is 1, m is 1, $R^2$ and $R^3$ are each hydrogen, and $R^6$ is heterocyclyl.

16. The method of claim 15, wherein the heterocyclyl is piperazinyl, 4-methyl-piperazinyl, 4-acyl-piperazinyl, morpholinyl, dimethyl-morpholinyl, or thiomorpholinyl.

17. The method of claim 1, wherein Y is —C(O)—, s is 1, m is 1, $R^2$ and $R^3$ are each hydrogen, and $R^6$ is —$NR^4R^7$.

18. The method of claim 1, wherein Y is —$NR^4SO_2$—, m is 1, $R^2$ and $R^3$ are each hydrogen, and $R^6$ is $C_1$-$C_6$ alkyl, cycloalkyl or aryl, wherein the cycloalkyl or the aryl may be optionally independently substituted with one or more $C_1$-$C_3$ alkyl, halogen, haloalkyl, amino or cyano.

19. The method of claim 1, wherein Y is —$SO_2NR^4$—, s is 1, m is 1, $R^2$ and $R^3$ are each independently hydrogen and $R^6$ is $C_1$-$C_6$ alkyl or aryl, wherein the aryl may be optionally independently substituted with one or more $C_1$-$C_3$ alkyl, halogen, haloalkyl, amino or cyano.

20. The method of claim 1, wherein Y is —$NR^4C(O)NR^4R^4$, s is 1, m is 1, $R^2$ and $R^3$ are each hydrogen and each $R^4$ is independently hydrogen or $C_1$-$C_3$ alkyl.

21. The method of claim 1, wherein the compound is
1-phenoxy-3-[4-[[trans-2-phenylcyclopropyl] amino]-1-piperidyl] propan-2-ol;
1-(2-methoxy-3-phenoxy-propyl)-N-[trans-2-phenylcyclopropyl]piperidin-4-amine;
2-methyl-1-phenoxy-3-(4-(((trans)-2-phenylcyclopropyl) amino)piperidin-1-yl)propan-2-ol;
1-phenoxy-3-[3-[[[(trans)-2-phenylcyclopropyl] amino]methyl]azetidin-1-yl]propan-2-ol;
(R)-1-phenoxy-3-(4-(((1S,2R)-2-phenylcyclopropyl) amino)piperidin-1-yl)propan-2-ol;
(S)-1-phenoxy-3-(4-(((1S,2R)-2-phenylcyclopropyl) amino)piperidin-1-yl)propan-2-ol;

1-phenoxy-3-[(JR, 5S)-6-[[(trans)-2-phenylcyclopropyl]amino]-3-azabicyclo[3.1.1]heptan-3-yl]propan-2-ol;
(trans)-N-[[1-(2-phenoxyethyl)azetidin-3-yl]methyl]-2-phenyl-cyclopropanamine;
(trans)-N-[[1-(3-phenoxypropyl)azetidin-3-yl]methyl]-2-phenyl-cyclopropanamine;
1-[2-(4-bromophenoxy)ethyl]-N-[(1R,2S)-2-phenylcyclopropyl]piperidin-4-amine;
1-(3-Phenoxypropyl)-N-((trans)-2-phenylcyclopropyl)piperidin-4-amine;
1-(2-Phenoxyethyl)-N-((trans)-2-phenylcyclopropyl)piperidin-4-amine;
2-(4-(2-(4-(((1R,2S)-2-Phenylcyclopropyl)amino)piperidin-1-yl)ethoxy)phenyl)acetic acid;
N-(Methylsulfonyl)-2-(4-(2-(4-(((1R,2 S)-2-phenylcyclopropyl)amino)piperidin-1-yl)ethoxy)phenyl)acetamide;
2-(4-(2-(4-(((1R,2S)-2-phenylcyclopropyl)amino)piperidin-1-yl)ethoxy)phenyl)-N-(phenyl sulfonyl)acetamide;
N,N-Dimethyl-2-(4-(2-(4-(((1R,2 S)-2-phenylcyclopropyl)amino)piperidin-1-yl)ethoxy)phenyl)acetamide;
N-methoxy-2-(4-(2-(4-(((1R,2 S)-2-phenylcyclopropyl)amino)piperidin-1-yl)ethoxy)phenyl)acetamide;
1-[2-(4-morpholinophenoxy)ethyl]-N-[(1R,2S)-2-phenylcyclopropyl]piperidin-4-amine;
1-(2-(4-(4-methylpiperazin-1-yl)phenoxy)ethyl)-N-((1R,2 S)-2-phenylcyclopropyl)piperidin-4-amine;
3-(4-(2-(4-(((1R,2S)-2-phenylcyclopropyl)amino)piperidin-1-yl)ethoxy)phenyl)oxazolidin-2-one;
1-methyl-3-(4-(2-(4-(((1R,2 S)-2-phenylcyclopropyl)amino)piperidin-1-yl)ethoxy)phenyl)imidazolidin-2-one;
3-(4-(2-(4-(((1R,2 S)-2-phenylcyclopropyl)amino)piperidin-1-yl)ethoxy)phenyl)-1,3-oxazinan-2-one;
4-(4-(2-(4-(((1R,2S)-2-phenylcyclopropyl)amino)piperidin-1-yl)ethoxy)phenyl)morpholin-3-one;
1-(4-(4-(2-(4-(((1R,2S)-2-phenylcyclopropyl)amino)piperidin-1-yl)ethoxy)phenyl)piperazin-1-yl)ethan-1-one;
1-(4-(2-(4-(((1R,2S)-2-phenylcyclopropyl)amino)piperidin-1-yl)ethoxy)phenyl)pyrrolidin-2-one;
1-(4-(2-(4-(((1R,2S)-2-phenylcyclopropyl)amino)piperidin-1-yl)ethoxy)phenyl)piperidin-2-one;
N-((1R,2S)-2-phenylcyclopropyl)-1-(2-(4-(piperidin-1-yl)phenoxy)ethyl)piperidin-4-amine;
2-(4-(2-hydroxy-3-(4-(((1R,2S)-2-phenylcyclopropyl)amino)piperidin-1-yl)propoxy)phenyl)acetic acid;
4-(2-hydroxy-3-(4-(((1R,2S)-2-phenylcyclopropyl)amino)piperidin-1-yl)propoxy)benzoic acid;
(E)-3-(4-(2-hydroxy-3-(4-(((1R,2S)-2-phenylcyclopropyl)amino)piperidin-1-yl)propoxy)phenyl)acrylic acid;
2-(4-(3-(4-(((1R,2S)-2-phenylcyclopropyl)amino)piperidin-1-yl)propoxy)phenyl)acetic acid;
4-(3-(4-(((1R,2S)-2-phenylcyclopropyl)amino)piperidin-1-yl)propoxy)benzoic acid;
(E)-3-(4-(3-(4-(((1R,2 S)-2-phenylcyclopropyl)amino)piperidin-1-yl)propoxy)phenyl)acrylic acid;
(1R,2S)—N-((1-(2-(4-bromophenoxy)ethyl)azetidin-3-yl)methyl)-2-phenylcyclopropan-1-amine;
1-(2-(2,4-dichlorophenoxy)ethyl)-N-((1R,2S)-2-phenylcyclopropyl)piperidin-4-amine;
(1R,2S)—N-((1-(2-(2,4-dichlorophenoxy)ethyl)azetidin-3-yl)methyl)-2-phenylcyclopropan-1-amine;
1-(2-(2,4-difluorophenoxy)ethyl)-N-((1R,2S)-2-phenylcyclopropyl)piperidin-4-amine;
(1R,2S)—N-((1-(2-(2,4-difluorophenoxy)ethyl)azetidin-3-yl)methyl)-2-phenylcyclopropan-1-amine;
(E)-3-(4-(2-hydroxy-3-(4-(((1R,2 S)-2-phenylcyclopropyl)amino)piperidin-1-yl)propoxy)phenyl)-N-(methylsulfonyl)acrylamide;
1-(2-((2-methylpyridin-4-yl)oxy)ethyl)-N-((1R,2S)-2-phenylcyclopropyl)piperidin-4-amine;
(1R,2 S)-2-phenyl-N-((1-(2-(p-tolyloxy)ethyl)azetidin-3-yl)methyl)cyclopropan-1-amine;
(1R,2 S)-2-phenyl-N-((1-(2-(pyridin-2-yloxy)ethyl)azetidin-3-yl)methyl)cyclopropan-1-amine;
4-(2-(4-(((1R,2S)-2-phenylcyclopropyl)amino)piperidin-1-yl)ethoxy)benzoic acid;
N-(cyclopropylsulfonyl)-4-(2-(4-(((1R,2 S)-2-phenylcyclopropyl)amino)piperidin-1-yl)ethoxy)benzamide;
4-(2-(4-(((1R,2S)-2-phenylcyclopropyl)amino)piperidin-1-yl)ethoxy)-N-(phenyl sulfonyl)benzamide;
(E)-N-(methylsulfonyl)-3-(4-(3-(4-(((1R,2 S)-2-phenylcyclopropyl)amino)piperidin-1-yl)propoxy)phenyl)acrylamide;
3-(4-(2-(3-(((1R,2 S)-2-phenylcyclopropyl)amino)methyl)azetidin-1-yl)ethoxy)phenyl)-1,3-oxazinan-2-one;
4-(4-(2-(3-((((1R,2 S)-2-phenylcyclopropyl)amino)methyl)azetidin-1-yl)ethoxy)phenyl)morpholin-3-one
1-(4-(2-(3-((((1R,2 S)-2-phenylcyclopropyl)amino)methyl)azetidin-1-yl)ethoxy)phenyl)piperidin-2-one;
(1R,2 S)-2-phenyl-N-((1-(2-(4-(piperazin-1-yl)phenoxy)ethyl)azetidin-3-yl)methyl)cyclopropan-1-amine;
(1R,2 S)—N-((1-(2-(4-(4-methylpiperazin-1-yl)phenoxy)ethyl)azetidin-3-yl)methyl)-2-phenylcyclopropan-1-amine;
1-(4-(4-(2-(3-((((1R,2 S)-2-phenylcyclopropyl)amino)methyl)azetidin-1-yl)ethoxy)phenyl)piperazin-1-yl)ethan-1-one;
1-(2-((5-methylpyridin-2-yl)oxy)ethyl)-N-((1R,2S)-2-phenylcyclopropyl)piperidin-4-amine;
1-(2-((6-methylpyridin-3-yl)oxy)ethyl)-N-((1R,2S)-2-phenylcyclopropyl)piperidin-4-amine;
N-(methyl sulfonyl)-4-(2-(4-(((1R,2 S)-2-phenylcyclopropyl)amino)piperidin-1-yl)ethoxy)benzamide;
N-(ethylsulfonyl)-4-(2-(4-(((1R,2 S)-2-phenylcyclopropyl)amino)piperidin-1-yl)ethoxy)benzamide;
(1S,2R)—N-((1-(2-((5-(4-methylpiperazin-1-yl)pyridin-2-yl)oxy)ethyl)azetidin-3-yl)methyl)-2-phenylcyclopropan-1-amine;
2-(4-(2-(3-((((1S,2R)-2-phenylcyclopropyl)amino)methyl)azetidin-1-yl)ethoxy)phenyl)acetic acid;
4-(2-(3-((((1R,2S)-2-phenylcyclopropyl)amino)methyl)azetidin-1-yl)ethoxy)benzoic acid
2-(4'-(2-(3-((((1S,2R)-2-phenylcyclopropyl)amino)methyl)azetidin-1-yl)ethoxy)-[1,1'-biphenyl]-4-yl)-N-(phenyl sulfonyl)acetamide;
3-(6-(2-(4-(((1R,2 S)-2-phenylcyclopropyl)amino)piperidin-1-yl)ethoxy)pyridin-3-yl)-1,3-oxazinan-2-one;
3-(5-(2-(4-(((1R,2 S)-2-phenylcyclopropyl)amino)piperidin-1-yl)ethoxy)pyridin-2-yl)-1,3-oxazinan-2-one;
N-((1R,2S)-2-phenylcyclopropyl)-1-(2-(p-tolyloxy)ethyl)piperidin-4-amine;
3-(4-(2-(4-(methyl((1R,2 S)-2-phenylcyclopropyl)amino)piperidin-1-yl)ethoxy)phenyl)-1,3-oxazinan-2-one;
2-(4-(2-(1-methyl-3-(((((1R,2S)-2-phenylcyclopropyl)amino)methyl)-,4-azetidin-1-yl)ethoxy)phenyl)-N-(methyl sulfonyl)acetamide;
N-methyl-1-(2-((6-methylpyridin-3-yl)oxy)ethyl)-N-((1R,2S)-2-phenylcyclopropyl)piperidin-4-amine;
(1R,2S)—N-((1-(2-((6-methylpyridin-3-yl)oxy)ethyl)azetidin-3-yl)methyl)-2-phenylcyclopropan-1-amine;

4-(2-(1-methyl-3-(((((1R,2S)-2-phenylcyclopropyl)amino)methyl)-,4-azetidin-1-yl)ethoxy)-N-(methylsulfonyl)benzamide;

3-(5-(2-(3-(((((1R,2S)-2-phenylcyclopropyl)amino)methyl)azetidin-1-yl)ethoxy)pyridin-2-yl)-1,3-oxazinan-2-one;

6-(2-(4-(((1R,2S)-2-phenylcyclopropyl)amino)piperidin-1-yl)ethoxy)-3,4-dihydroquinolin-2(1H)-one;

5-(2-(4-(((1R,2 S)-2-phenylcyclopropyl)amino)piperidin-1-yl)ethoxy)indolin-2-one;

1-(2-(3-fluoro-4-methylphenoxy)ethyl)-N-((1R,2S)-2-phenylcyclopropyl)piperidin-4-amine;

N-((1R,2 S)-2-phenylcyclopropyl)-1-(2-(quinazolin-4-yloxy)ethyl)piperidin-4-amine;

N-((1R,2 S)-2-phenylcyclopropyl)-1-(2-(quinolin-4-yloxy)ethyl)piperidin-4-amine;

N-((1R,2S)-2-phenylcyclopropyl)-1-(2-(pyrimidin-5-yloxy)ethyl)piperidin-4-amine;

1-(2-(3,5-difluorophenoxy)ethyl)-N-((1R,2S)-2-phenylcyclopropyl)piperidin-4-amine;

1-(2-(3,5-dichlorophenoxy)ethyl)-N-((1R,2S)-2-phenylcyclopropyl)piperidin-4-amine;

1-(2-((6-methylpyridazin-3-yl)oxy)ethyl)-N-((1R,2S)-2-phenylcyclopropyl)piperidin-4-amine;

(E)-3-(4-(2-(4-(((1R,2S)-2-phenylcyclopropyl)amino)piperidin-1-yl)ethoxy)phenyl)acrylic acid;

1-(2-(3-fluorophenoxy)ethyl)-N-((1R,2S)-2-phenylcyclopropyl)piperidin-4-amine;

1-(2-((6-methylpyridin-2-yl)oxy)ethyl)-N-((1R,2S)-2-phenylcyclopropyl)piperidin-4-amine;

1-(2-((2-methylpyrimidin-5-yl)oxy)ethyl)-N-((1R,2S)-2-phenylcyclopropyl)piperidin-4-amine;

1-(2-(4-bromophenoxy)ethyl)-4-(((1R,2S)-2-phenylcyclopropyl)amino)piperidin-2-one;

2-(4-(((1R,2 S)-2-phenylcyclopropyl)amino)piperidin-1-yl)ethan-1-ol;

N-(1-(2-(4-(2-oxo-1,3-oxazinan-3-yl)phenoxy)ethyl)piperidin-4-yl)-N-((1R,2S)-2-phenylcyclopropyl)acetamide;

1-(2-methoxyethyl)-N-((1R,2S)-2-phenylcyclopropyl)piperidin-4-amine;

1-(2-((1,3-dimethyl-1H-pyrazol-5-yl)oxy)ethyl)-N-((1R,2S)-2-phenylcyclopropyl)piperidin-4-amine;

1-(2-((1-methyl-1H-pyrazol-3-yl)oxy)ethyl)-N-((1R,2 S)-2-phenylcyclopropyl)piperidin-4-amine;

3-(4-(2-(3-(((((1R,2 S)-2-phenylcyclopropyl)amino)methyl)azetidin-1-yl)ethoxy)phenyl)-1,3-oxazinan-2-one;

1-(2-isopropoxyethyl)-N-((1R,2S)-2-phenylcyclopropyl)piperidin-4-amine;

2-(2-fluoro-4-(2-(4-(((1R,2S)-2-phenylcyclopropyl)amino)piperidin-1-yl)ethoxy)phenyl)acetic acid;

1-(2-(3,5-difluoro-4-methylphenoxy)ethyl)-N-((1R,2S)-2-phenylcyclopropyl)piperidin-4-amine;

1-(2-((5-methyl-1,3,4-thiadiazol-2-yl)oxy)ethyl)-N-((1R,2S)-2-phenylcyclopropyl)piperidin-4-amine;

2-(2-(4-(((1R,2S)-2-phenylcyclopropyl)amino)piperidin-1-yl)ethoxy)isonicotinic acid;

3-(4-(2-(4-(((1R,2S)-2-phenylcyclopropyl)amino)piperidin-1-yl)ethoxy)phenyl)oxazolidin-2-one;

1-(2-(4-bromophenoxy)ethyl)-4-(((1R,2S)-2-phenylcyclopropyl)amino)piperidine-2,6-dione;

N-((1R,2S)-2-phenylcyclopropyl)-1-(2-(pyridin-3-yloxy)ethyl)piperidin-4-amine;

7-(2-(4-(((1R,2S)-2-phenylcyclopropyl)amino)piperidin-1-yl)ethoxy)-2H-benzo[b][1,4]oxazin-3(4H)-one;

6-(2-(4-(((1R,2 S)-2-phenylcyclopropyl)amino)piperidin-1-yl)ethoxy)benzo[d]oxazol-2(3H)-one;

1-(2-((5-methylthiazol-2-yl)oxy)ethyl)-N-((1R,2S)-2-phenylcyclopropyl)piperidin-4-amine;

3-(2-(4-(((1R,2S)-2-phenylcyclopropyl)amino)piperidin-1-yl)ethoxy)isonicotinic acid;

2-(3-chloro-4-(2-(4-(((1R,2S)-2-phenylcyclopropyl)amino)piperidin-1-yl)ethoxy)phenyl)acetic acid;

2-(3-fluoro-4-(2-(4-(((1R,2S)-2-phenylcyclopropyl)amino)piperidin-1-yl)ethoxy)phenyl)acetic acid;

2-(3-methyl-4-(2-(4-(((1R,2 S)-2-phenylcyclopropyl)amino)piperidin-1-yl)ethoxy)phenyl)acetic acid; or 4-(2-(4-(((1R,2S)-2-(3,4-difluorophenyl)cyclopropyl)amino)piperidin-1-yl)ethoxy)benzoic acid;

1-anilino-3-[4-[[trans-2-phenylcyclopropyl]amino]-1-piperidyl] propan-2-ol;

1-(N-methylanilino)-3-[4-[[trans-2-phenylcyclopropyl]amino]-1-piperidyl]propan-2-ol;

1-(2-(phenylamino)ethyl)-N-((1R,2 S)-2-phenylcyclopropyl)piperidin-4-amine;

1-(2-(methyl(phenyl)amino)ethyl)-N-((1R,2S)-2-phenylcyclopropyl)piperidin-4-amine;

1-(2-((4-bromophenyl)amino)ethyl)-N-((1R,2S)-2-phenylcyclopropyl)piperidin-4-amine;

1-(4-((2-(4-(((1R,2 S)-2-phenylcyclopropyl)amino)piperidin-1-yl)ethyl)amino)phenyl)piperidin-2-one;

3-(4-((2-(4-(((1R,2 S)-2-phenylcyclopropyl)amino)piperidin-1-yl)ethyl)amino)phenyl)-1,3-oxazinan-2-one;

4-(4-((2-(4-(((1R,2S)-2-phenylcyclopropyl)amino)piperidin-1-yl)ethyl)amino)phenyl)morpholin-3-one;

N-((1R,2 S)-2-phenylcyclopropyl)-1-(2-((4-(piperidin-1-yl)phenyl)amino)ethyl)piperidin-4-amine;

1-(2-((4-morpholinophenyl)amino)ethyl)-N-((1R,2S)-2-phenylcyclopropyl)piperidin-4-amine;

1-(2-((4-(4-methylpiperazin-1-yl)phenyl)amino)ethyl)-N-((1R,2S)-2-phenylcyclopropyl)piperidin-4-amine;

1-(4-((2-(4-(((1R,2 S)-2-phenylcyclopropyl)amino)piperidin-1-yl)ethyl)amino)phenyl)pyrrolidin-2-one;

3-(4-((2-(4-(((1R,2S)-2-phenylcyclopropyl)amino)piperidin-1-yl)ethyl)amino)phenyl)oxazolidin-2-one;

1-methyl-3-(4-((2-(4-(((1R,2 S)-2-phenylcyclopropyl)amino)piperidin-1-yl)ethyl)amino)phenyl)imidazolidin-2-one;

1-(4-(4-((2-(4-(((1R,2 S)-2-phenylcyclopropyl)amino)piperidin-1-yl)ethyl)amino)phenyl)piperazin-1-yl)ethan-1-one;

3-(4-((2-(3-(((((1R,2 S)-2-phenylcyclopropyl)amino)methyl)azetidin-1-yl)ethyl)amino)phenyl)-1,3-oxazinan-2-one;

N,6-dimethyl-N-(2-(4-(((1R,2 S)-2-phenylcyclopropyl)amino)piperidin-1-yl)ethyl)pyridin-3-amine;

1-(2-((4-bromophenyl)(methyl)amino)ethyl)-N-((1R,2S)-2-phenylcyclopropyl)piperidin-4-amine;

3-(4-(methyl(2-(4-(((1R,2S)-2-phenylcyclopropyl)amino)piperidin-1-yl)ethyl)amino)phenyl)-1,3-oxazinan-2-one;

1-methyl-3-(2-(4-(((1R,2 S)-2-phenylcyclopropyl)amino)piperidin-1-yl)ethyl)urea;

N-methyl-N-(2-(4-(((1R,2 S)-2-phenylcyclopropyl)amino)piperidin-1-yl)ethyl)acetamide;

N,2-dimethyl-N-(2-(4-(((1R,2 S)-2-phenylcyclopropyl)amino)piperidin-1-yl)ethyl)pyridin-4-amine;

1-(2-(4-bromo-2-fluorophenoxy)ethyl)-N-((1R,2S)-2-phenylcyclopropyl)piperidin-4-amine;

2-((2-(4-(((1R,2 S)-2-phenylcyclopropyl)amino)piperidin-1-yl)ethyl)amino)isonicotinic acid; or 3-((2-(4-(((1R,2S)-2-phenylcyclopropyl)amino)piperidin-1-yl)ethyl)amino)isonicotinic acid;
1-morpholino-2-(4-(((1R,2S)-2-phenylcyclopropyl)amino)piperidin-1-yl)propan-1-one;
N-methoxy-2-(4-(((1R,2S)-2-phenylcyclopropyl)amino)piperidin-1-yl)propanamide;
1-morpholino-3-phenyl-2-(4-(((1R,2S)-2-phenylcyclopropyl)amino)piperidin-1-yl)propan-1-one;
1-morpholino-3-(4-(((1R,2S)-2-phenylcyclopropyl)amino)piperidin-1-yl)propan-1-one;
N-(methylsulfonyl)-3-(4-(((1R,2S)-2-phenylcyclopropyl)amino)piperidin-1-yl)propanamide;
3-(4-(((1R,2S)-2-phenylcyclopropyl)amino)piperidin-1-yl)-1-(piperazin-1-yl)propan-1-one;
3-(4-(((1R,2S)-2-phenylcyclopropyl)amino)piperidin-1-yl)-N-(phenyl sulfonyl)propanamide;
1-(4-methylpiperazin-1-yl)-3-(4-(((1R,2S)-2-phenylcyclopropyl)amino)piperidin-1-yl)propan-1-one;
N-(ethylsulfonyl)-3-(4-(((1R,2S)-2-phenylcyclopropyl)amino)piperidin-1-yl)propanamide;
3-(4-(((1R,2S)-2-phenylcyclopropyl)amino)piperidin-1-yl)-1-thiomorpholinopropan-1-one;
1-(4-methylpiperazin-1-yl)-4-(4-(((1R,2S)-2-phenylcyclopropyl)amino)piperidin-1-yl)butan-1-one;
4-(4-(((1R,2S)-2-phenylcyclopropyl)amino)piperidin-1-yl)-1-(piperazin-1-yl)butan-1-one;
1-morpholino-4-(4-(((1R,2S)-2-phenylcyclopropyl)amino)piperidin-1-yl)butan-1-one;
4-(4-(((1R,2S)-2-phenylcyclopropyl)amino)piperidin-1-yl)-N-(phenyl sulfonyl)butanamide;
N-(cyclopropylsulfonyl)-4-(4-(((1R,2S)-2-phenylcyclopropyl)amino)piperidin-1-yl)butanamide;
N-(ethylsulfonyl)-4-(4-(((1R,2S)-2-phenylcyclopropyl)amino)piperidin-1-yl)butanamide;
N-(methylsulfonyl)-4-(4-(((1R,2S)-2-phenylcyclopropyl)amino)piperidin-1-yl)butanamide; or
1-(cis-2,6-dimethylmorpholino)-3-(4-(((1R,2S)-2-phenylcyclopropyl)amino)piperidin-1-yl)propan-1-one;
N-(2-(4-(((1R,2S)-2-phenylcyclopropyl)amino)piperidin-1-yl)ethyl)methanesulfonamide;
N-(2-(4-(((1R,2S)-2-phenylcyclopropyl)amino)piperidin-1-yl)ethyl)benzenesulfonamide;
N-(2-(4-(((1R,2S)-2-phenylcyclopropyl)amino)piperidin-1-yl)ethyl)propane-2-sulfonamide;
N-(2-(4-(((1R,2S)-2-phenylcyclopropyl)amino)piperidin-1-yl)propyl) methanesulfonamide;
N-methyl-N-(2-(3-((((1R,2S)-2-phenylcyclopropyl)amino)methyl)azetidin-1-yl)ethyl)methanesulfonamide;
N-(2-(3-((((1R,2S)-2-phenylcyclopropyl)amino)methyl)azetidin-1-yl)ethyl)methanesulfonamide;
N-methyl-N-(2-(4-(((1R,2S)-2-phenylcyclopropyl)amino)piperidin-1-yl)ethyl)methanesulfonamide;
N-(2-(4-(((1R,2S)-2-phenylcyclopropyl)amino)piperidin-1-yl)ethyl)cyclopropanesulfonamide;
N-phenyl-2-(4-(((1R,2S)-2-phenylcyclopropyl)amino)piperidin-1-yl)ethane-1-sulfonamide; or
N-methyl-2-(4-(((1R,2S)-2-phenylcyclopropyl)amino)piperidin-1-yl)ethane-1-sulfonamide;
1,1-dimethyl-3-(2-(4-(((1R,2S)-2-phenylcyclopropyl)amino)piperidin-1-yl)ethyl)urea;
or a pharmaceutically acceptable salt thereof.

22. A method of treating cancer in a subject in need thereof, the method comprising administering to the subject a therapeutically effective amount of 3-(4-(((1R,2S)-2-phenylcyclopropyl)amino)piperidin-1-yl)propanoic acid, 4-(4-(((1R,2S)-2-phenylcyclopropyl)amino)piperidin-1-yl)butanoic acid, or a pharmaceutically acceptable salt of either, wherein the cancer is Lung, Bone, or Hematologic cancer.

23. The method of claim 22, wherein the cancer is Ewing's sarcoma, myelodysplastic syndrome, or leukemia.

* * * * *

UNITED STATES PATENT AND TRADEMARK OFFICE
CERTIFICATE OF CORRECTION

PATENT NO. : 10,233,152 B2
APPLICATION NO. : 15/725949
DATED : March 19, 2019
INVENTOR(S) : Marx et al.

Page 1 of 1

It is certified that error appears in the above-identified patent and that said Letters Patent is hereby corrected as shown below:

In the Claims

Column 151, Line 50, Claim 1, change "wherein the cancer is Lung, or Hematologic cancer." to --wherein the cancer is Lung, Bone or Hematologic cancer.--

Signed and Sealed this
Thirty-first Day of December, 2019

Andrei Iancu
*Director of the United States Patent and Trademark Office*